(12) United States Patent
Weiner et al.

(10) Patent No.: US 10,428,340 B2
(45) Date of Patent: Oct. 1, 2019

(54) PHYTASES, NUCLEIC ACIDS ENCODING THEM AND METHODS FOR MAKING AND USING THEM

(71) Applicant: Syngenta Participations AG, Basel (CH)

(72) Inventors: David P. Weiner, Del Mar, CA (US); Ame I. Solbak, Jr., San Diego, CA (US); Ryan McCann, San Diego, CA (US)

(73) Assignee: Syngenta Participations AG, Basel (CH)

( * ) Notice: Subject to any disclaimer, the term of this patent is extended or adjusted under 35 U.S.C. 154(b) by 1 day.

(21) Appl. No.: 15/959,991

(22) Filed: Apr. 23, 2018

(65) Prior Publication Data

US 2019/0127712 A1 May 2, 2019

Related U.S. Application Data

(62) Division of application No. 15/627,979, filed on Jun. 20, 2017, now Pat. No. 9,969,992, which is a division of application No. 13/321,465, filed as application No. PCT/US2010/035667 on May 20, 2010, now Pat. No. 9,695,403.

(60) Provisional application No. 61/180,283, filed on May 21, 2009.

(51) Int. Cl.
*C12N 15/82* (2006.01)
*C12N 9/16* (2006.01)

(52) U.S. Cl.
CPC ........... *C12N 15/8242* (2013.01); *C12N 9/16* (2013.01); *Y02E 50/17* (2013.01); *Y10T 428/2982* (2015.01)

(58) Field of Classification Search
None
See application file for complete search history.

(56) References Cited

U.S. PATENT DOCUMENTS

| | | |
|---|---|---|
| 5,284,933 A | 2/1994 | Dobeli et al. |
| 5,366,736 A | 11/1994 | Edwards, Jr. |
| 5,436,156 A | 7/1995 | Van Gorcom et al. |
| 5,492,813 A | 2/1996 | Eisenbeis et al. |
| 5,543,576 A | 8/1996 | van Ooijen et al. |
| 5,593,963 A | 1/1997 | van Ooijen et al. |
| 5,714,474 A | 2/1998 | van Ooijen et al. |
| 5,750,135 A | 5/1998 | Schleicher et al. |
| 5,770,413 A | 6/1998 | van Ooijen et al. |
| 5,830,696 A | 11/1998 | Short |
| 5,830,732 A | 11/1998 | Mochizuki et al. |
| 5,866,118 A | 2/1999 | Berka et al. |
| 5,876,997 A | 3/1999 | Kretz |
| 5,939,303 A | 8/1999 | Cheng et al. |
| 6,013,440 A | 1/2000 | Lipshyutz et al. |
| 6,039,942 A | 3/2000 | Lassen et al. |
| 6,190,897 B1 | 2/2001 | Kretz |
| 7,081,563 B2* | 7/2006 | Lanahan ............... C12N 9/16 435/18 |
| 8,313,937 B2 | 11/2012 | Nguyen et al. |
| 8,420,369 B2 | 4/2013 | Nguyen et al. |
| 8,497,127 B2 | 7/2013 | Basu et al. |
| 2002/0127218 A1 | 9/2002 | Svendsen et al. |
| 2002/0136754 A1 | 9/2002 | Short et al. |
| 2003/0103958 A1 | 6/2003 | Short et al. |
| 2004/0091968 A1 | 5/2004 | Short et al. |
| 2005/0246780 A1 | 11/2005 | Short et al. |
| 2006/0183213 A1 | 8/2006 | Lanahan et al. |

FOREIGN PATENT DOCUMENTS

| | | |
|---|---|---|
| CN | 1706941 | 12/2005 |
| EP | 0441252 B1 | 9/1997 |
| EP | 0897985 B1 | 10/2004 |
| JP | 2005278544 | 10/2005 |
| WO | 1997033976 | 9/1997 |
| WO | 1998044125 | 10/1998 |
| WO | 1999008539 | 2/1999 |
| WO | 2000058481 | 10/2000 |

(Continued)

OTHER PUBLICATIONS

International Search Report for International Patent Application No. PCT/US2010/35667 dated Nov. 18, 2010.

(Continued)

*Primary Examiner* — Cynthia E Collins
(74) *Attorney, Agent, or Firm* — Karen A. Magri

(57) ABSTRACT

This invention relates to phytases, polynucleotides encoding them, uses of the polynucleotides and polypeptides of the invention, as well as the production and isolation of such polynucleotides and polypeptides. In particular, the invention provides polypeptides having phytase activity under high temperature conditions, and phytases that retain activity after exposure to high temperatures. The invention further provides phytases which have increased gastric lability. The phytases of the invention can be used in foodstuffs to improve the feeding value of phytate rich ingredients. The phytases of the invention can be formulated as foods or feeds or supplements for either to, e.g., aid in the digestion of phytate. The foods or feeds of the invention can be in the form of pellets, liquids, powders and the like. In one aspect, phytases of the invention are stabile against thermal denaturation during pelleting; and this decreases the cost of the phytase product while maintaining in vivo efficacy and detection of activity in feed.

20 Claims, 21 Drawing Sheets

Specification includes a Sequence Listing.

(56) References Cited

FOREIGN PATENT DOCUMENTS

| | | |
|---|---|---|
| WO | 2000064247 | 11/2000 |
| WO | 2000071728 | 11/2000 |
| WO | 2001036607 | 5/2001 |
| WO | 2001062947 | 8/2001 |
| WO | 2001090333 | 11/2001 |
| WO | 2003024389 A2 | 3/2003 |
| WO | 2004015084 | 2/2004 |
| WO | 2007112739 | 10/2007 |
| WO | 2008017066 | 2/2008 |
| WO | 2008036916 | 3/2008 |
| WO | 2009073399 | 6/2009 |

OTHER PUBLICATIONS

International Search Report for International Patent Application No. PCT/US2007/079187 dated Oct. 1, 2008.
International Search Report for International Patent Application EP07075392 dated Jul. 9, 2008.
International Search Report for International Patent Application No. PCT/US2002/016482 dated May 24, 2002.
International Search Report for International Patent Application No. PCT/US2005/029621 dated Feb. 28, 2008.
Extended EP Search Report for International Patent Application EP13164378.5 dated Aug. 21, 2013.
Extended EP Search Report for International Patent Application No. EP 10778424.1 dated Oct. 15, 2012.
Extended EP Search Report for EP Application No. EP13163829.8 dated Sep. 12, 2013.
Extended EP Search Report for EP Application No. EP13164079.9 dated Sep. 12, 2013.
Extended EP Search Report for EP Application No. EP13164100.3 dated Sep. 12, 2013.
Extended EP Search Report for EP Application No. EP13164137.5 dated Sep. 12, 2013.
Extended EP Search Report for EP Application No. EP13164210.0 dated Sep. 12, 2013.
Extended EP Search Report for EP Application No. EP13164255.5 dated Sep. 12, 2013.
Extended EP Search Report for EP Application No. EP13164284.5 dated Sep. 12, 2013.
Extended EP Search Report for EP Application No. EP13164324.9 dated Sep. 13, 2013.
Extended EP Search Report for EP Application No. EP13164374.4 dated Sep. 13, 2013.
Extended EP Search Report for EP Application No. EP13175992.0 dated Jan. 16, 2014.
Chinese Notification of Reexamination for Chinese Application No. CN01812774.6 dated Dec. 15, 2010.
Chinese Notification of First Office Action & Translation for Chinese Application No. CN200780043087.9 dated Oct. 26, 2011.
Chinese Second Office Action & Translation for Chinese Application No. CN200810005794.5 dated Dec. 23, 2011.
Fifth Office Action and Translation for Chinese Application No. CN01812774.6 dated Jun. 20, 2013.
Third Office Action and Translation for Chinese Application No. CN200810005794.5 dated Jun. 25, 2013.
Fourth Office Action and Translation for Chinese Application No. CN200780043087.9 dated Aug. 23, 2013.
Third Office Action for Chinese Patent Application No. CN01812774.6 dated Apr. 28, 2012.
Second Office Action for Chinese Application No. CN200780043087.9 dated Jul. 2, 2012.
Decision of Final Rejection for Chinese Application No. CN200810005794.5 dated Oct. 10, 2012.
Fourth Office Action and Translation for Chinese Patent Application No. CN1812774.6 dated Feb. 5, 2013.
Sixth Office Action and Translation for Chinese Patent Application No. CN01812774.6 dated Dec. 4, 2013.
Fifth Office Action and Translation for Chinese Patent Application No. CN200780043087.9 dated Dec. 11, 2013.
First Office Action and Translation for Chinese Patent Application No. 2010800331324 dated Jan. 27, 2014.
Fourth Office Action and Translation for Chinese Patent Application No. CN200810005794.5 dated Feb. 24, 2014.
Second Office Action for Chinese Patent Application 2010800331324 dated Dec. 16, 2014.
Office Action for European Application No. EP07842987.5 dated Apr. 21, 2011.
Office Action for European Application No. EP07842987.5 dated Nov. 4, 2011.
Extended EP Search Report for EP Patent Application No. EP07842987.5 dated Aug. 24, 2010.
94(3) Communication for European Patent Application No. EP05013009.5 dated Apr. 17, 2012.
94(3) Communication for European Patent Application No. EP11181439.8 dated Dec. 5, 2012.
94(3) Communication for European Patent Application No. EP05013009.5 dated Nov. 11, 2013.
94(3) Communication for European Patent Application No. EP13175992.0 dated Nov. 26, 2014.
Office Action and Translation for Brazilian Application No. PI0111124-8 dated Sep. 23, 2013.
Office Action and Translation for Brazilian Patent Application No. PI0010946-0 dated Nov. 10, 2013.
Rejection Decision for Brazilian Patent Application No. PI0010946-0 dated Feb. 17, 2014.
Unfavorable Opinion for Brazilian Patent Application No. PI0208851-7 dated Apr. 21, 2014.
Unfavorable Opinion for Brazilian Patent Application No. PI0208851-7 dated Sep. 29, 2014.
Office Action for Brazilian Patent Application No. BR122012006762-8 dated Jun. 7, 2015.
Second Office Action for India Patent Application No. 3129/DELNP/2004 dated Feb. 24, 2012.
Office Action for Canadian Patent Application No. 2663819 dated Jan. 13, 2014.
Office Action and Translation for Eurasia Patent Application No. 201171450 dated Oct. 9, 2013.
Second Examination Report for New Zealand Patent Application No. 596459 dated Aug. 28, 2013.
Office Action, 892 for U.S. Appl. No. 14/032,578 dated Nov. 13, 2013.
Office Action, 892, IDS Considered for U.S. Appl. No. 12/442,207 dated Jan. 24, 2014.
Final Rejection and Considered IDS for U.S. Appl. No. 12/442,207 dated Jun. 27, 2013.
Decision of Grant and Allowed Claims for Japanese Patent Application JP2009-529415 dated May 27, 2013.
Second Examination Report for Australian Patent Application No. AU2007299612 dated Aug. 2, 2013.
First Examination Report for New Zealand Patent Application No. 596459 dated Jun. 1, 2012.
Office Action and Translation for Japanese Patent Application 2009-529415 dated Nov. 12, 2012.
Office Action and Form 892 and references for U.S. Appl. No. 12/442,207 dated Jul. 19, 2012.
Office Action and Form 892 for U.S. Appl. No. 12/442,207 dated Jan. 28, 2013.
Office Action for Japanese Application No. JP2015-238207 dated Aug. 30, 2016.
Office Action for Japanese Patent Application No. JP2015-238206 dated Aug. 30, 2016.
Office Action for Korean Patent Application No. 2011-7030622 dated Sep. 2, 2016.
First Office Action for Chinese Patent Application No. CN2014106036789 dated Sep. 21, 2016.
First Examination Report for Indian Patent Application No. 993/KOLNP/2009 dated Oct. 21, 2016.
Adeola O., et al., Journal of Animal Science (1995) 73: 3384-3391.
Bork, et al., Genome Research (2000) 10:348-400.

(56) References Cited

OTHER PUBLICATIONS

Branden, et al., Introduction to Protein Structure, Garland Publishing Inc., New York, (1991) p. 247.
Brinch-Petersen, et al., Molecular Breeding (2000), pp. 195-206.
Broun, et al., Science (1998) 282:1315-1317.
Office Action for Canadian Patent Application No. 2565314 dated Apr. 29, 2010.
Dassa, et al., Journal of Bacteriology (1990) 172 pp. 5497-5500.
Dassa et al., Journal of Biological Chemistry (1982) 257(12): pp. 6669-6676.
Delagrave, et al., Nature Biotechnology (1993) 11: pp. 1548-1552.
Delagrave, et al., Protein Eng. (1993) 6: 327-331.
GenBank Accession No. AAX26540 Schistosoma Japonicum (2005).
GenBank Accession No. AR130956 Sequence from U.S. Pat. No. 6,190,897 Kretz (2001).
Golovan, et al., Canadian Journal of Microbiology (2000) 46: 59-71.
Greiner, et al., Archives of Biochemistry and Biophysics (1993) 303: 107-113.
Greiner, et al., Archives of Biochemistry and Biophysics (1997) 341: 201-206.
Guo, et al., PNAS USA (2004) 101(25): 9205-9210.
Jung, et al., J. Athl. Train. 40(2): 71-75 (2005).
Kerovuo, et al., Applied and Environmental Biology (1998) 64: 2079-2085.
Lehmann, et al., Protein Science (2000) 1866-1872.
Lim, et al., Nature Structural Biology (2000) 7: pp. 108-113.
NCBI GenBank Accession No. M58708 (1991).
Nelson, et al., J. Nutrition (1971) 101: 1289-1294.
Oh, et al., Abstracts of the General Meeting of the American Society for Microbiology (2000) 100: pp. 499-500.
Ostanin, et al., GenBank Accession No. L03371 (1992).
Pointillart A., Journal of Animal Science (1991) 69: 1109-1115.
Rodriguez, et al., Biochemical and Biophysical Research Comm. (1999) 257: 117-123.
Seffernick, et al., Journal of Bacteriology (2001) 183: 2405-2410.
Swiss-Prot Accession No. P07102 *Escherichia coli* K-12 DASSA (1988).
Warden and Schaible, Poultry Science (1962) 41: 725-732.
Witkowski, et al., Biochemistry (1999) 38: 11643-11650.
Wu, et al., Poultry Science (2006) 85: 64-69.
Wyss, et al., Applied and Environmental Microbiology (1999) 65: 359-366.
Yi Z., et al., Journal of Animal Science (1996) 74: 1601-1611.
Blattner—Science (1997)—277—1453-1462.
EBI (Geneseq) Accession No. GSP:AE127121—Pichia pastoris phytase appA-t protein Figure 4. SUN (2006).
EBI (Geneseq) Accession No. GSP:AE127122—Pichia pastoris phytase appA-t protein p. 15-18. SUN (2006).
Garrett—Appl. Environ. Microbiol. (2004) 70: 3041-3046.
GenBank Accession No. L03371—*Escherichia coli* periplasmic phosphoanhydride Phosphohydrolase (appA) gene—Ostanin (1992).
Giver—PNAS USA (1998) 95: 12809-12813.
Guo—Plant Journal (2003) 34: 383-392.
Jermutus—Journal of Biotechnology (2001) 85: 15-24.
Ostanin—Journal of Biological Chemistry (1993)—268: 20778-20784.
Pen—Biotechnology (1993) 11: 811-814.
Riley—Nucleic Acids Research (2006)—34: 1-9.
Rodriguez—Archives of Biochemistry and Biophysics (2000) 382: 105-112.
Score Accession No. ADA 19445 *Escherichia coli* B. Short (2003).
Tomschy—Protein Science (2000) 9: 1304-1311.
Vetriani—PNAS USA (1998) 95: 12300-12305.
Dvorakova, et al., Folia Microbiology (1998) 43: 323-338.
Arnold—Current Opinion in Chem. Biology (1999)—3: 54-59.
Berg—Biochemistry Fifth Edition, W.H. Freeman and Company, New York (2002) pp. 134-135.
Kuchner—Tibtech (1997) 15: 523-530.
Lei—Appl. Microbiol. Biotechnol (2001) 57: 474-481.
Hurrell—The American Journal of Clinical Nutrition (2003) 77: 1213-1219.

* cited by examiner

| Phytase No. | Temperature (°C) | | | | | | | | | | | | | | | | | |
|---|---|---|---|---|---|---|---|---|---|---|---|---|---|---|---|---|---|---|
| | 72 | 72.6 | 74 | 75.7 | 78.4 | 80 | 80.5 | 81.7 | 83.2 | 85.7 | 88.6 | 91.9 | 95.9 | 96.9 | 98.6 | 99.6 | 100 |
| 1 | 100 | 100 | 100 | 100 | 100 | 100 | 94.7 | 90.0 | 90.2 | 42.9 | 9.1 | 0.5 | 0.7 | 0.5 | 0.7 | 0.5 | 0.4 |
| 2 | 100 | 100 | 100 | 100 | 100 | 100 | 94.2 | 85.7 | 75.3 | 48.9 | 11.8 | 0.9 | 0.6 | 0.5 | 0.8 | | 0.6 |
| 3 | 100 | 100 | 100 | 100 | 100 | 100 | 94.5 | 87.3 | 91.5 | 48.8 | | | | 0.3 | 0.3 | | |
| 4 | 100 | 100 | 100 | 100 | 100 | 100 | 94.3 | 92.5 | 94.2 | 63.7 | 11.7 | 1.2 | 0.8 | 0.8 | 0.8 | 0.8 | 0.9 |
| 5 | 100 | 100 | 100 | 100 | 100 | 100 | 90.3 | 90.8 | 88.9 | 63.3 | 12.1 | 1.1 | 1.0 | 0.9 | 0.9 | 0.8 | 1.0 |
| 6 | 100 | 100 | 100 | 100 | 100 | 100 | 98.0 | 93.5 | 84.2 | 54.5 | 12.8 | 1.3 | 0.0 | 0.8 | 0.6 | 0.6 | 1.0 |
| 7 | 100 | 100 | 100 | 100 | 100 | 100 | 94.6 | 87.3 | | 71.7 | 17.6 | 0.7 | 0.2 | 0.2 | 0.1 | 0.3 | 0.2 |
| 8 | 100 | 100 | 100 | 100 | 100 | 100 | 99.5 | 99.5 | 100.5 | 75.3 | 14.4 | 0.5 | 0.1 | 0.1 | 0.1 | 0.1 | 0.5 |
| 9 | 100 | 100 | 100 | 100 | 100 | 100 | 91.8 | 82.2 | 77.5 | 58.2 | 12.2 | 1.4 | 1.1 | 1.0 | | | 1.2 |
| 10* | 100 | 100 | 100 | 100 | 100 | 100 | 94.6 | 95.8 | 91.7 | 66.6 | 11.7 | 0.5 | 0.2 | 0.3 | 0.5 | 0.4 | 0.4 |
| 11 | 100 | 100 | 100 | 100 | 100 | 100 | 96.6 | 82.8 | | 64.5 | 15.2 | 1.6 | 1.1 | 1.1 | 1.2 | 1.2 | 1.2 |
| 12 | 100 | 100 | 100 | 100 | 100 | 100 | 93.2 | 88.8 | 83.6 | 53.8 | 11.5 | 0.3 | 0.3 | 0.3 | 0.3 | 0.3 | 0.4 |
| 13 | 100 | 100 | 100 | 100 | 100 | 100 | 92.4 | 82.7 | 70.6 | 53.6 | 11.0 | 0.8 | 0.4 | 0.4 | | 0.5 | 20.8 |
| 14 | 100 | 100 | 100 | 100 | 100 | 100 | 103.0 | 93.4 | 98.8 | 77.4 | 17.3 | 0.2 | 0.2 | 0.1 | 0.1 | 0.2 | 0.1 |
| 15 | 100 | 100 | 100 | 100 | 100 | 100 | 91.7 | 92.2 | 89.4 | 62.2 | 12.9 | | 0.2 | 0.3 | -0.2 | 0.2 | 0.2 |
| 16 | 100 | 100 | 100 | 100 | 100 | 100 | 93.2 | 91.4 | 89.2 | 38.7 | 10.6 | 0.3 | 0.2 | 0.2 | 0.2 | 0.1 | 0.2 |
| 17 | 100 | 100 | 100 | 100 | 100 | 100 | 98.0 | 84.7 | 84.3 | 47.0 | 10.1 | 0.2 | 0.2 | 0.2 | | 0.2 | 0.2 |
| 18 | 100 | 100 | 100 | 100 | 100 | 100 | 89.2 | 85.8 | 88.2 | 48.5 | 9.4 | 0.7 | 0.8 | 0.4 | 0.5 | 0.4 | 0.2 |
| 19** | 100 | 100 | 100 | 100 | 100 | 100 | 99.2 | 92.1 | 85.5 | 54.4 | 11.0 | 0.4 | 0.2 | 0.2 | 0.2 | 0.3 | 0.2 |
| 20** | 100 | 100 | 100 | 100 | 100 | 100 | 89.4 | 88.8 | 76.6 | 70.6 | 12.2 | 0.3 | 0.2 | | 0.2 | 0.2 | 0.2 |
| 21** | 100 | 100 | 100 | 100 | 100 | 100 | 106.1 | 93.9 | | 63.8 | 12.7 | 1.0 | 0.6 | 0.6 | 0.6 | 0.5 | 0.6 |
| WT (SEQ ID NO:2) | 100 | 77.4 | 51.7 | 19.5 | 5.29 | 2.6 | 0.4 | 0.3 | 0.0 | 0.0 | 0.0 | 0.0 | 0.0 | 0.0 | 0.0 | 0.0 | 0.0 |

Figure 3

MKAILIPFLSLLIPLTPQSAFAQSEPELKLESVVIVSRHGVRAPTKATQLMQDVTPDAWPTWPVKLGELT
                                         ↓
                                         F

PRGGELIAYLGHYWRQRLVADGLLPKCGCPQSGQVAIIADVDERTRKTGEAFAAGLAPDCAITVHTQADT
                        ↓                                          ↓
                        E,V                                        H

SSPDPLFNPLKTGVCQLDNANVTDAILERAGGSIADFTGHYQTAFRELERVLNFPQSNLCLKREKQDESC
              ↓        ↓↓                ↓
              E,R,V    RR                R

SLTQALPSELKVSADCVSLTGAVSLASMLTEIFLLQQAGMPEPGWGRITDSHQWNTLLSLHNAQFDLLQ
             ↓          ↓                                       ↓
             D          W                                       V

RTPEVARSRATPLLDLIKTALTPHPPQKQAYGVTLPTSVLFIAGHDTNLANLGGALELNWTLPGQPDNTP
       ↓                                                               ↓
       A                                                               Y

PGGELVFERWRRLSDNSQWIQVSLVFQTLQQMRDKTPLSLNTPPGEVKLTLAGCEERNAQGMCSLAGFTQ

IVNEARIPACSL

| Evolved phytase no. | # Mutations | Possible Mutations | | | | | | | | | | | | | | | |
|---|---|---|---|---|---|---|---|---|---|---|---|---|---|---|---|---|---|
| | | A47F | C97V | C97E | T136H | N159V | N159E | T163R | D164R | E168R | G179R | C226D | V233W | Q275V | R289A | T349Y | L363P |
| 1 | 10X | A47F | | C97E | T136H | N159V | | | | | G179R | C226D | V233W | Q275V | R289A | T349Y | L363P |
| 2 | 10X | A47F | | C97E | | N159V | | T163R | D164R | | | C226D | V233W | Q275V | R289A | T349Y | |
| 3 | 10X | A47F | | | T136H | N159V | | T163R | D164R | | G179R | C226D | V233W | Q275V | | T349Y | |
| 4 | 12X | A47F | | | T136H | N159V | | T163R | D164R | E168R | G179R | C226D | V233W | Q275V | R289A | T349Y | |
| 5 | 12X | A47F | C97V | | T136H | N159V | | T163R | D164R | E168R | G179R | C226D | V233W | Q275V | R289A | T349Y | |
| 6 | 12X | A47F | C97V | | T136H | N159V | | T163R | D164R | E168R | G179R | C226D | V233W | Q275V | | T349Y | |
| 7 | 11X | A47F | | | T136H | N159V | | T163R | D164R | E168R | G179R | | V233W | Q275V | | T349Y | |
| 8 | 11X | A47F | | C97E | T136H | N159V | | T163R | D164R | E168R | G179R | C226D | V233W | Q275V | R289A | T349Y | |
| 9 | 12X | A47F | | C97E | T136H | N159V | | T163R | D164R | E168R | G179R | | V233W | Q275V | R289A | T349Y | |
| 10* | 12X | A47F | | C97E | T136H | | N159E | T163R | D164R | E168R | G179R | | | | | T349Y | L363P |
| 11 | 11X | A47F | C97V | | T136H | | | T163R | D164R | E168R | G179R | C226D | V233W | Q275V | R289A | T349Y | |
| 12 | 13X | A47F | | C97E | T136H | N159V | | T163R | D164R | E168R | G179R | C226D | V233W | Q275V | R289A | T349Y | |
| 13 | 10X | A47F | | C97E | | N159V | | | D164R | | G179R | C226D | V233W | Q275V | R289A | T349Y | |
| 14 | 13X | A47F | | C97E | T136H | N159V | | T163R | D164R | E168R | G179R | C226D | V233W | Q275V | R289A | T349Y | |
| 15 | 13X | A47F | C97V | | T136H | N159V | | T163R | D164R | E168R | G179R | C226D | V233W | Q275V | R289A | T349Y | |
| 16 | 10X | A47F | | C97E | T136H | N159V | | T163R | | | G179R | C226D | V233W | Q275V | R289A | T349Y | |
| 17 | 12X | A47F | | C97E | T136H | N159V | | T163R | D164R | | G179R | C226D | V233W | Q275V | R289A | T349Y | |
| 18 | 11X | A47F | | | T136H | N159V | | T163R | D164R | | G179R | C226D | V233W | Q275V | R289A | T349Y | |
| 19** | 9X | A47F | | | T136H | N159V | | | | | G179R | C226D | V233W | Q275V | R289A | T349Y | |
| 20** | 10X | A47F | C97V | | T136H | N159V | | | D164R | | G179R | C226D | V233W | Q275V | | T349Y | |
| 21** | 9X | A47F | C97V | | T136H | N159V | | | D164R | | G179R | | V233W | Q275V | | T349Y | |
| 22 | 6X | A47F | | | | N159V | | | | | G179R | C226D | V233W | | R289A | T349Y | |

* Possesses an additional (L363P) not introduced by GSSM™ evolution. This mutation was introduced by random chance and may or may not have any relevance to thermal stability.
** Possess an additional C-terminal Histidine tag (RSHHHHHH)

Figure 5

| GSSM™ change | Original Amino Acid | Amino Acid Changed To | Codon Mutation Location | Nucleotide Positions of Changed Codon in SEQ ID NO:1 | Original Codon | Codon Changed To | All Possible Codons For the Mutated Amino Acid |
|---|---|---|---|---|---|---|---|
| A47F | A | F | 47 | 139-141 | GCC | TTT | TTT, TTC |
| C97V | C | V | 97 | 289-291 | TGT | GTT | GTT, GTC, GTA, GTG |
| C97E | C | E | 97 | 289-291 | TGT | GAG | GAA, GAG |
| T136H | T | H | 136 | 406-408 | ACC | CAT GTC or | CAT, CAC |
| N159V | N | V | 159 | 475-477 | AAC | GTG | GTT, GTC, GTA, GTG |
| N159E | N | E | 159 | 475-477 | AAC | GAG | GAA, GAG |
| T163R | T | R | 163 | 487-489 | ACT | CGG | CGT, CGC, CGA, CGG, AGA, AGG |
| D164R | D | R | 164 | 490-492 | GAC | CGG | CGT, CGC, CGA, CGG, AGA, AGG |
| E168R | E | R | 168 | 502-504 | GAG | CGG | CGT, CGC, CGA, CGG, AGA, AGG |
| G179R | G | R | 179 | 535-537 | GGG | CGG | CGT, CGC, CGA, CGG, AGA, AGG |
| C226D | C | D | 226 | 676-678 | TGT | GAT | GAT, GAC |
| V233W | V | W | 233 | 697-699 | GTA | TGG | TGG |
| Q275V | Q | V | 275 | 823-825 | CAA | GTG | GTT, GTC, GTA, GTG |
| R289A | R | A | 289 | 865-867 | CGC | GCT | GCT, GCC, GCA, GCG |
| T349Y | T | Y | 349 | 1045-1047 | ACG | TAT | TAT, TAC |
| L363P | L | P | 363 | 1087-1089 | CTA | CCA | CCA, CCC, CCG, CCT |

Figure 6

PHYTASES, NUCLEIC ACIDS ENCODING THEM AND METHODS FOR MAKING AND USING THEM

RELATED APPLICATIONS

This application is a divisional of U.S. application Ser. No. 15/627,979, filed Jun. 20, 2017 (now U.S. Pat. No. 9,969,992), which is a divisional of U.S. application Ser. No. 13/321,465 (now U.S. Pat. No. 9,695,403), which is a 371 national stage entry of International Application No. PCT/US10/35667 filed May 20, 2010, which claims priority to U.S. Provisional Application No. 61/180,283, filed May 21, 2009, all of which are incorporated herein by reference in their entirety.

REFERENCE TO SEQUENCE LISTING SUBMITTED VIA EFS-WEB

This application is being filed electronically via the USPTO EFS-WEB server, as authorized and set forth in MPEP § 1730 II.B.2(a)(A), and this electronic filing includes an electronically submitted sequence (SEQ ID) listing. The entire content of this sequence listing is herein incorporated by reference for all purposes. The sequence listing is identified on the electronically filed .txt file as follows:

| File Name | Date of Creation | Size (bytes) |
| --- | --- | --- |
| 72743-US-REG-D-P-1_sequence_listing.txt | May 20, 2010 | 58,575 bytes |

FIELD OF THE INVENTION

This invention relates to phytases, polynucleotides encoding them, uses of the polynucleotides and polypeptides of the invention, as well as the production and isolation of such polynucleotides and polypeptides. In particular, the invention provides polypeptides having phytase activity under high temperature conditions, and phytases that retain activity after exposure to high temperatures. The invention further provides phytases which have increased gastric lability. The phytases of the invention can be used in foodstuffs to improve the feeding value of phytate rich ingredients. The phytases of the invention can be formulated as foods or feeds or supplements for either to, e.g., aid in the digestion of phytate. The foods or feeds of the invention can be in the form of pellets, liquids, powders and the like. In one aspect, phytases of the invention are stabile against thermal denaturation during pelleting; and this decreases the cost of the phytase product while maintaining in vivo efficacy and detection of activity in feed.

BACKGROUND

Minerals are essential elements for the growth of all organisms. Dietary minerals can be derived from many source materials, including plants. For example, plant seeds are a rich source of minerals since they contain ions that are complexed with the phosphate groups of phytic acid molecules. These phytate-associated minerals may, in some cases, meet the dietary needs of some species of farmed organisms, such as multi-stomached ruminants. Accordingly, in some cases ruminants require less dietary supplementation with inorganic phosphate and minerals because microorganisms in the rumen produce enzymes that catalyze conversion of phytate (myo-inositol-hexaphosphate) to inositol and inorganic phosphate. In the process, minerals that have been complexed with phytate are released. The majority of species of farmed organisms, however, are unable to efficiently utilize phytate-associated minerals. Thus, for example, in the livestock production of monogastric animals (e.g., pigs, birds, and fish), feed is commonly supplemented with minerals and/or with antibiotic substances that alter the digestive flora environment of the consuming organism to enhance growth rates.

As such, there are many problematic burdens—related to nutrition, ex vivo processing steps, health and medicine, environmental conservation, and resource management—that are associated with an insufficient hydrolysis of phytate in many applications. The following are non-limiting examples of these problems:

1) The supplementation of diets with inorganic minerals is a costly expense.
2) The presence of unhydrolyzed phytate is undesirable and problematic in many ex vivo applications (e.g. by causing the presence of unwanted sludge).
3) The supplementation of diets with antibiotics poses a medical threat to humans and animals alike by increasing the abundance of antibiotic-tolerant pathogens.
4) The discharge of unabsorbed fecal minerals into the environment disrupts and damages the ecosystems of surrounding soils, fish farm waters, and surface waters at large.
5) The valuable nutritional offerings of many potential foodstuffs remain significantly untapped and squandered.

Consequently, phytate-containing foodstuffs require supplementation with exogenous nutrients and/or with a source of phytase activity in order to amend their deficient nutritional offerings upon consumption by a very large number of species of organisms.

Consequently, there is a need for means to achieve efficient and cost effective hydrolysis of phytate in various applications. Particularly, there is a need for means to optimize the hydrolysis of phytate in commercial applications. In a particular aspect, there is a need to optimize commercial treatment methods that improve the nutritional offerings of phytate-containing foodstuffs for consumption by humans and farmed animals.

SUMMARY OF THE INVENTION

This invention provides polypeptides having phytase activity, polynucleotides encoding them, uses of the polynucleotides and polypeptides of the invention, and methods for the production and isolation of such polynucleotides and polypeptides. In one aspect, the invention provides polypeptides having phytase activity under high temperature conditions, and phytases that retain activity after exposure to high temperatures. The phytases of the invention can be used in foodstuffs to improve the feeding value of phytate rich ingredients. The phytases of the invention can be formulated as foods or feeds or supplements for either to, e.g., aid in the digestion of phytate. The foods or feeds of the invention can be in the form of pellets, tablets, pills, liquids, powders, sprays and the like. In one aspect, phytases of the invention are stabile against thermal denaturation during pelleting; and this decreases the cost of the phytase product while maintaining in vivo efficacy and detection of activity in feed.

SUMMARY

The invention provides isolated, synthetic, or recombinant nucleic acids comprising (a) (i) a nucleic acid sequence encoding a polypeptide having a phytase activity and having at least 95%, 96% 97%, 98% or 99% or more sequence identity to SEQ ID NO:1, wherein the polypeptide comprises at least one mutation listed in Table 4, 5, 6, 7, 9, or any combination thereof;

(ii) a polynucleotide encoding a polypeptide having at least 95%, 96% 97%, 98% or 99% or more sequence identity to SEQ ID NO:2, wherein the polypeptide comprises at least one mutation listed in Table 4, 5, 6, 7, 9, or any combination thereof; or (a) (i) a nucleic acid sequence encoding a polypeptide having a phytase activity and having at least 95%, 96% 97%, 98% or 99% or more sequence identity to SEQ ID NO:1, wherein the polypeptide comprises at least one mutation listed in Table 4, 5, 6, 7, 9, or any combination thereof;

(ii) a polynucleotide encoding a polypeptide having at least 95%, 96% 97%, 98% or 99% or more sequence identity to SEQ ID NO:2, wherein the polypeptide comprises at least one mutation listed in Table 4, 5, 6, 7, 9, or any combination thereof; or (iii) the nucleic acid sequence of (i) or (ii), wherein the sequence identities are determined by analysis with a sequence comparison algorithm or by a visual inspection, and optionally the sequence comparison algorithm is a BLAST version 2.2.2 algorithm where a filtering setting is set to blastall -p blastp -d "nr pataa"-F F, and all other options are set to default;

(b) the nucleic acid of (a), wherein the at least one mutation is: A109V, A232P, A236H, A236T, A248L, A248T, A274F, A274I, A274L, A274T, A274V, A429P, C155Y, D139Y, E113P, F147Y, F194L, G171M, G171S, G257A, G257R, G353C, G395E, G395I, G395L, G395Q, G395T, G67A, H263P, H272W, I107H, I107P, I108A, I108Q, I108R, I108S, I108Y, I174F, I174P, I427G, I427S, I427T, K151H, K151P, L126R, L146R, L146T, L150T, L150Y, L157C, L157P, L167S, L192F, L216T, L235I, L244S, L269I, L269T, L296T, L379S, L379V, L50W, M51A, M51G, M51L, N148K, N148M, N148R, N161K, N266P, N339E, N348K, N348W, P100A, P145L, P149L, P149N, P217D, P217G, P217L, P217S, P254S, P269L, P343E, P343I, P343L, P343N, P343R, P343V, Q137F, Q137L, Q137V, Q137Y, Q246W, Q247H, Q275H, Q309P, Q377R, Q381S, Q86H, S102A, S102Y, S173G, S173H, S173V, S197G, S208P, S211H, S218I, S218Y, S389H, S389V, T163P, T282H, T291V, T291W, T341D, T48F, T48H, T48I, T48K, T48L, T48M, T48V, T48W, T48Y, V162L, V162T, V191A, V422M, W265L, Y79H, Y79N, Y79S, or Y79W;

(c) the nucleic acid of (b), wherein the polypeptide further comprises at least one mutation of: C226D, D164R, G179R, N159V, Q275V, T163R, or T349Y; or (d) sequences fully complementary thereto. All of these nucleic acids are "nucleic acids of the invention", encoding "polypeptides of the invention".

In one aspect, the sequence comparison algorithm is a BLAST version 2.2.2 algorithm where a filtering setting is set to blastall -p blastp -d "nr pataa"-F F, and all other options are set to default.

In one aspect, the nucleic acid sequences of the invention lack a homologous nucleic acid sequence encoding a signal sequence, proprotein sequence, or promoter sequence. In another aspect, the nucleic acids of the invention further comprise of a heterologous nucleic acid sequence, wherein optionally the heterologous nucleic acid sequence comprises, or consists of a sequence encoding a heterologous signal sequence, a tag, an epitope, or a promoter sequence. In another aspect, the heterologous nucleic acid sequence encodes a heterologous signal sequence comprising or consisting of an N-terminal and/or C-terminal extension for targeting to an endoplasmic reticulum (ER) or endomembrane, or to a plant endoplasmic reticulum (ER) or endomembrane system, or the heterologous sequence encodes a restriction site. In yet another aspect, the heterologous promoter sequence comprises or consists of a constitutive or inducible promoter, or a cell type specific promoter, or a plant specific promoter, or a maize specific promoter.

In one aspect, the phytase activity comprises catalysis of phytate (myo-inositol-hexaphosphate) to inositol and inorganic phosphate; or, the hydrolysis of phytate (myo-inositol-hexaphosphate). In another aspect, the phytase activity comprises catalyzing hydrolysis of a phytate in a feed, a food product or a beverage, or a feed, food product or beverage comprising a cereal-based animal feed, a wort or a beer, a dough, a fruit or a vegetable; or, catalyzing hydrolysis of a phytate in a microbial cell, a fungal cell, a mammalian cell or a plant cell.

In one aspect, the phytases of the invention are thermotolerant, and optionally the polypeptide retains a phytase activity after exposure to a temperature in the range from about −100° C. to about −80° C., about −80° C. to about −40° C., about −40° C. to about −20° C., about −20° C. to about 0° C., about 0° C. to about 37° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. In one aspect, the phytases of the invention are thermostable, and optionally the phytase retains activity at a temperature in the range from about −100° C. to about −80° C., about −80° C. to about −40° C., about −40° C. to about −20° C., about −20° C. to about 0° C., about 0° C. to about 37° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more.

In another embodiment, the phytases of the inventions are thermotolerant or thermoactive at an acidic pH of about pH 6.5, pH 6, pH 5.5, pH 5, pH 4.5, pH 4.0, pH 3.5, pH 3.0 or less, or the phytase polypeptide is thermotolerant or thermoactive at about pH 7, pH 7.5, pH 8.0, pH 8.5, pH 9, pH 9.5, pH 10, pH 10.5, pH 11.0, pH 11.5, pH 12.0, pH 12.5 or more.

The invention provides expression cassettes, vectors, cloning vehicles, expression vectors, and cloning vectors comprising a nucleic acid of the invention, or having contained therein a nucleic acid of the invention (which include nucleic acids encoding polypeptides of the invention), wherein optionally the expression cassette, cloning vehicle or vector comprises or is a viral vector, a plasmid, a phage, a phagemid, a cosmid, a fosmid, a bacteriophage or an artificial chromosome, the viral vector comprises or is an adenovirus vector, a retroviral vector or an adeno-associated viral vector, or the expression cassette, cloning vehicle or vector comprises or is a bacterial artificial chromosome (BAC), a bacteriophage P1-derived vector (PAC), a yeast artificial chromosome (YAC) or a mammalian artificial chromosome (MAC).

The invention provides transformed cells, transduced cells, host cells and the like comprising a nucleic acid of the invention, or having contained therein a nucleic acid of the invention (which include nucleic acids encoding polypeptides of the invention), or the expression cassette, vector, cloning vehicle, expression vector, or cloning vector of the invention, wherein optionally the cell is a bacterial cell, a mammalian cell, a fungal cell, a yeast cell, an insect cell or a plant cell.

The invention provides transgenic non-human animals comprising a nucleic acid of the invention, or having contained therein a nucleic acid of the invention (which include nucleic acids encoding polypeptides of the invention), or the expression cassette, vector, cloning vehicle, expression vector, or cloning vector of the invention, wherein optionally the animal is a mouse, a rat, a goat, a rabbit, a sheep, a pig or a cow.

The invention provides transgenic plants (including plant parts, e.g., processed, or harvested, e.g., leaves, stems, roots or fruits) or seeds comprising a nucleic acid of the invention, or having contained therein a nucleic acid of the invention (which include nucleic acids encoding polypeptides of the invention), or the expression cassette, vector, cloning vehicle, expression vector, or cloning vector of the invention, wherein optionally the plant is a corn plant, a potato plant, a tomato plant, a wheat plant, an oilseed plant, a rapeseed plant, a soybean plant or a tobacco plant, and optionally the seed is a corn seed, a wheat kernel, an oilseed, a rapeseed, a soybean seed, a palm kernel, a sunflower seed, a sesame seed, a peanut or a tobacco plant seed. In alternative embodiments, the plant or a seed produced from a seed or plant of the invention, or a plant or seed of the invention, can include crop plants, for example, corn, alfalfa, sunflower, Brassica, soybean, sugar cane, cotton, safflower, peanut, sorghum, wheat, oat, rye, millet, barley, rice, conifers, legume crops, e.g., pea, bean and soybean, starchy tuber/roots, e.g., potato, sweet potato, cassava, taro, canna and sugar beet and the like, or the plant can be a corn plant, a potato plant, a tomato plant, a wheat plant, an oilseed plant, a rapeseed plant, a soybean plant or a tobacco plant, or a forage and/or feed plant for an animal, or for a ruminant animal, or the plant can be or comprises the forage or feed plant is hay, corn, millet, soy, wheat, buckwheat, barley, alfalfa, rye, an annual grass, sorghum, sudangrass, veldt grass or buffel grass; or, the seed is a corn seed, a wheat kernel, an oilseed, a rapeseed, a soybean seed, a palm kernel, a sunflower seed, a sesame seed, a peanut or peanut seed, an alfalfa seed, a cotton seed, a safflower seed, a sorghum seed, an oat kernel, a rye seed, a millet seed, a barley seed, a rice kernel, a pea seed, or a tobacco plant seed, or the plant is corn, alfalfa, sunflower, Brassica, soybean, sugar cane, cotton, safflower, peanut, sorghum, wheat, oat, rye, millet, barley, rice, conifers, pea, bean, soybean, potato, sweet potato, cassava, taro, canna or sugar beet.

The invention provides antisense oligonucleotides comprising a nucleic acid which is antisense to a nucleic acid of the invention and encoding at least one mutation listed in Table 4, 5, 6, 7, 9, or any combination thereof, wherein optionally the antisense oligonucleotide is between about 10 to 50, about 20 to 60, about 30 to 70, about 40 to 80, about 60 to 100 or about 50 to 150 bases in length. The invention also provides ribozymes and/or iRNA (e.g., siRNA or miRNA) comprising antisense sequences of the invention.

The invention provides methods of inhibiting the translation of a phytase message in a cell comprising administering to the cell or expressing in the cell an antisense oligonucleotide of the invention.

The invention provides isolated, synthetic, or recombinant polypeptides comprising (a) (i) an amino acid sequence encoded by the nucleic acids of the invention;

(ii) an amino acid sequence having at least 95%, 96% 97%, 98% or 99% sequence identity to SEQ ID NO:2, wherein the polypeptide comprises at least one mutation listed in Table 4, 5, 6, 7, 9, or any combination thereof; or (iii) the polypeptide of (i) or (ii), wherein the sequence identities are determined by analysis with a sequence comparison algorithm or by a visual inspection;

(b) the polypeptide of (a), wherein the at least one mutation is: A109V, A232P, A236H, A236T, A248L, A248T, A274F, A274I, A274L, A274T, A274V, A429P, C155Y, D139Y, E113P, F147Y, F194L, G171M, G171S, G257A, G257R, G353C, G395E, G395I, G395L, G395Q, G395T, G67A, H263P, H272W, I107H, I107P, I108A, I108Q, I108R, I108S, I108Y, I174F, I174P, I427G, I427S, I427T, K151H, K151P, L126R, L146R, L146T, L150T, L150Y, L157C, L157P, L167S, L192F, L216T, L235I, L244S, L269I, L269T, L296T, L379S, L379V, L50W, M51A, M51G, M51L, N148K, N148M, N148R, N161K, N266P, N339E, N348K, N348W, P100A, P145L, P149L, P149N, P217D, P217G, P217L, P217S, P254S, P269L, P343E, P343I, P343L, P343N, P343R, P343V, Q137F, Q137L, Q137V, Q137Y, Q246W, Q247H, Q275H, Q309P, Q377R, Q381S, Q86H, S102A, S102Y, S173G, S173H, S173V, S197G, S208P, S211H, S218I, S218Y, S389H, S389V, T163P, T282H, T291V, T291W, T341D, T48F, T48H, T48I, T48K, T48L, T48M, T48V, T48W, T48Y, V162L, V162T, V191A, V422M, W265L, Y79H, Y79N, Y79S, or Y79W; or (c) the polypeptide of (b), wherein the polypeptide further comprises at least one mutation of: C226D, D164R, G179R, N159V, Q275V, T163R, or T349Y.

In one aspect, the phytase activity comprises catalysis of phytate (myo-inositol-hexaphosphate) to inositol and inorganic phosphate; or, the hydrolysis of phytate (myo-inositol-hexaphosphate). In another aspect, the phytase activity comprises catalyzing hydrolysis of a phytate in a feed, a food product or a beverage, or a feed, food product or beverage comprising a cereal-based animal feed, a wort or a beer, a dough, a fruit or a vegetable; or, catalyzing hydrolysis of a phytate in a microbial cell, a fungal cell, a mammalian cell or a plant cell.

The invention provides polypeptides of the invention that have phytase activity whose activity is thermotolerant, and optionally the polypeptide retains a phytase activity after exposure to a temperature in the range of from about −100° C. to about −80° C., about −80° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75°

C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. The thermotolerant polypeptides according to the invention can retain activity, e.g. a phytase activity, after exposure to a temperature in the range from about −100° C. to about −80° C., about −80° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. In some embodiments, the thermotolerant polypeptides according to the invention retains activity, e.g. a phytase activity, after exposure to a temperature in the ranges described above, at about pH 3.0, about pH 3.5, about pH 4.0, about pH 4.5, about pH 5.0, about pH 5.5, about pH 6.0, about pH 6.5, about pH 7.0, about pH 7.5, about pH 8.0, about pH 8.5, about pH 9.0, about pH 9.5, about pH 10.0, about pH 10.5, about pH 11.0, about pH 11.5, about pH 12.0 or more.

The invention provides polypeptides of the invention that have phytase activity whose activity is thermostable. For example, a polypeptide of the invention can be thermostable. The thermostable polypeptide according to the invention can retain binding and/or enzymatic activity, e.g., a phytase activity, under conditions comprising a temperature range from about −100° C. to about −80° C., about −80° C. to about −40° C., about −40° C. to about −20° C., about −20° C. to about 0° C., about 0° C. to about 37° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. The thermostable polypeptides according to the invention can retain activity, e.g. a phytase activity, in temperatures in the range from about −100° C. to about −80° C., about −80° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. In some embodiments, the thermostable polypeptides according to the invention retains activity, e.g., a phytase activity, at a temperature in the ranges described above, at about pH 3.0, about pH 3.5, about pH 4.0, about pH 4.5, about pH 5.0, about pH 5.5, about pH 6.0, about pH 6.5, about pH 7.0, about pH 7.5, about pH 8.0, about pH 8.5, about pH 9.0, about pH 9.5, about pH 10.0, about pH 10.5, about pH 11.0, about pH 11.5, about pH 12.0 or more.

The invention provides isolated, synthetic or recombinant polypeptides comprising an amino acid sequence of the invention and (a) lacking a homologous signal sequence (leader peptide) or proprotein sequence; (b) lacking a signal sequence (leader peptide) and further comprising a heterologous signal sequence (leader peptide); (c) the amino acid sequence of (a) or (b) and further comprising a heterologous sequence, wherein optionally the heterologous sequence comprises, or consists of a heterologous signal sequence, or a tag or an epitope, or the heterologous sequence comprises an identification peptide. In one aspect, the heterologous signal sequence comprises or consists of an N-terminal and/or C-terminal extension for targeting to an endoplasmic reticulum (ER) or endomembrane, or to a plant endoplasmic reticulum (ER) or endomembrane system, or the heterologous amino acid sequence comprises, or consists of an enzyme target site. In another aspect, the polypeptide of the invention further comprises additional amino acid residues between a signal sequence (leader sequence or leader peptide) and the enzyme.

In one aspect, the phytase activity of any polypeptide of the invention comprises (has) a specific activity: at about 37° C. in the range from about 100 to about 1000 units per milligram of protein; or, from about 500 to about 750 units per milligram of protein; or, at 37° C. in the range from about 500 to about 1200 units per milligram of protein; or, at 37° C. in the range from about 750 to about 1000 units per milligram of protein. In one aspect, the thermotolerant phytase activity comprises a specific activity after exposure to a temperature at about 37° C. in the range from about 100 to about 1000 units per milligram of protein; or, the thermostable phytase activity comprises a specific activity from about 500 to about 750 units per milligram of protein; or, the thermostable phytase activity comprises a specific activity at 37° C. in the range from about 500 to about 1200 units per milligram of protein; or, the thermostable phytase activity comprises a specific activity at 37° C. in the range from about 750 to about 1000 units per milligram of protein. In one aspect, the thermo stable phytase activity comprises a specific activity under conditions comprising a temperature of about 37° C. in the range from about 100 to about 1000 units per milligram of protein; or, the thermostable phytase activity comprises a specific activity from about 500 to about 750 units per milligram of protein; or, the thermostable phytase activity comprises a specific activity at 37° C. in the range from about 500 to about 1200 units per milligram of protein; or, the thermostable phytase activity comprises a specific activity at 37° C. in the range from about 750 to about 1000 units per milligram of protein.

In one aspect, a polypeptide of the invention is glycosylated or comprises at least one glycosylation site, wherein optionally the glycosylation is an N-linked glycosylation, or an 0-linked glycosylation, and optionally the polypeptide is glycosylated after being expressed in a yeast, which optionally is a P. pastoris or a S. pombe.

In one aspect, the polypeptide retains a phytase activity under conditions comprising about pH 6.5, pH 6, pH 5.5, pH 5, pH 4.5, pH 4.0, pH 3.5, pH 3.0 or less (more acidic) pH. Alternatively, a polypeptide of the invention can retain a phytase activity under conditions comprising about pH 7.5, pH 8, pH 8.5, pH 9, pH 9.5, pH 10.0, pH 10.5, pH 11.0, pH 11.5, pH 12, pH 12.5 or more (more basic) pH.

The invention provides protein preparations comprising a polypeptide of the invention, wherein the protein preparation comprises a liquid, a slurry, a powder, a spray, a suspension, a lyophilized composition/formulation, a solid, geltab, pill, implant, a gel; or a pharmaceutical formulation, a food, a feed, a food supplement, a feed supplement, a food additive, a feed additive, a nutritional supplement or a dietary supplement thereof.

The invention provides heterodimers comprising a polypeptide of the invention, and in one aspect the heterodimer comprises a second domain, wherein optionally the second domain is a polypeptide and the heterodimer is a fusion protein, and optionally the second domain is an epitope or a tag.

The invention provides immobilized polypeptides comprising a polypeptide of the invention, wherein the immobilized polypeptide can comprises a homodimer or a heterodimer of the invention, wherein optionally the polypeptide is immobilized on or inside a cell, a vesicle, a liposome, a film, a membrane, a metal, a resin, a polymer, a ceramic, a glass, a microelectrode, a graphitic particle, a bead, a gel, a plate, an array, a capillary tube, a crystal, a tablet, a pill, a capsule, a powder, an agglomerate, a surface, or a porous structure. In one aspect, the invention provides arrays (e.g., microarrays) comprising an immobilized polypeptide, wherein the polypeptide comprises the polypeptide of the invention, or the heterodimer of the invention, or the nucleic acid of the invention, or a combination thereof.

The invention provides isolated, synthetic or recombinant antibodies that specifically bind to a polypeptide of the invention or to a polypeptide encoded by the nucleic acid of the invention, wherein optionally the antibody is a monoclonal or a polyclonal antibody. The invention provides hybridomas comprising the antibody of the invention.

The invention provides methods of producing a recombinant polypeptide comprising: (a) providing a nucleic acid, wherein the nucleic acid comprises a sequence of the invention; and (b) expressing the nucleic acid of (a) under conditions that allow expression of the polypeptide, thereby producing a recombinant polypeptide, and optionally the method further comprises transforming a host cell with the nucleic acid of (a) followed by expressing the nucleic acid of (a), thereby producing the recombinant polypeptide in a transformed host cell. In an alternative embodiment, the nucleic acid is operably linked to a promoter before being transformed into a host cell.

The invention provides methods for identifying a polypeptide having a phytase activity comprising: (a) providing the polypeptide of the invention; (b) providing a phytase substrate; and (c) contacting the polypeptide or a fragment or variant thereof of (a) with the substrate of (b) and detecting an increase in the amount of substrate or a decrease in the amount of reaction product, wherein a decrease in the amount of substrate or an increase in the amount of the reaction product detects a polypeptide having a phytase activity.

The invention provides methods for identifying a phytase substrate comprising: (a) providing the polypeptide of the invention; (b) providing a test substrate; and (c) contacting the polypeptide of (a) with the test substrate of (b) and detecting an increase in the amount of substrate or a decrease in the amount of reaction product, wherein a decrease in the amount of the substrate or an increase in the amount of the reaction product identifies the test substrate as a phytase substrate.

The invention provides methods of determining whether a compound specifically binds to a polypeptide comprising: (a) expressing a nucleic acid or a vector comprising the nucleic acid under conditions permissive for translation of the nucleic acid to a polypeptide, wherein the nucleic acid comprises a sequence of the invention; (b) contacting the polypeptide with the test compound; and (c) determining whether the test compound specifically binds to the polypeptide, thereby determining that the compound specifically binds to the polypeptide.

The invention provides methods for identifying a modulator of a phytase activity comprising: (a) providing the phytase polypeptide of the invention; (b) providing a test compound; (c) contacting the polypeptide of (a) with the test compound of (b) and measuring an activity of the phytase, wherein a change in the phytase activity measured in the presence of the test compound compared to the activity in the absence of the test compound provides a determination that the test compound modulates the phytase activity, wherein optionally the phytase activity is measured by providing a phytase substrate and detecting an increase in the amount of the substrate or a decrease in the amount of a reaction product, and optionally a decrease in the amount of the substrate or an increase in the amount of the reaction product with the test compound as compared to the amount of substrate or reaction product without the test compound identifies the test compound as an activator of phytase activity, and optionally an increase in the amount of the substrate or a decrease in the amount of the reaction product with the test compound as compared to the amount of substrate or reaction product without the test compound identifies the test compound as an inhibitor of phytase activity.

The invention provides methods for hydrolyzing an inositol-hexaphosphate to inositol and inorganic phosphate comprising: (a) providing a polypeptide having a phytase activity, wherein the polypeptide comprises the amino acid sequence of the invention, or, a polypeptide encoded by the nucleic acid of the invention; (b) providing a composition comprising an inositol-hexaphosphate; and (c) contacting the polypeptide of (a) with the composition of (b) under conditions wherein the polypeptide hydrolyzes the inositol-hexaphosphate to produce to inositol and inorganic phosphate, wherein optionally the conditions comprise a temperature of between about 37° C. and about 70° C., between about 50° C. and about 80° C., or between about 60° C. and about 90° C., and optionally the composition comprises a phytic acid.

The invention provides methods for oil degumming comprising: (a) providing a polypeptide having a phytase activity, wherein the polypeptide comprises the amino acid sequence of the invention, or, a polypeptide encoded by the nucleic acid of the invention; (b) providing a composition comprising a vegetable oil; and (c) contacting the polypeptide of (a) and the vegetable oil of (b) under conditions wherein the polypeptide can cleave an inositol-inorganic phosphate linkage, thereby degumming the vegetable oil.

The invention provides methods for producing a feed or a food, or a feed or food supplement, or a food or feed additive, or a nutritional supplement, or a dietary supplement, comprising: (a) transforming a plant, plant part or plant cell with a polynucleotide encoding a phytase enzyme polypeptide, wherein the phytase comprises a polypeptide comprising the amino acid sequence of the invention, or, a polypeptide encoded by the nucleic acid of the invention; (b) culturing the plant, plant part or plant cell under conditions in which the phytase enzyme is expressed; and, (c) converting the plant, plant parts or plant cell into a composition suitable for a food, a feed, a food supplement, a feed supplement, a food additive, a feed additive, a nutritional supplement or a dietary supplement, or adding the cultured plant, plant part or plant cell to a food, a feed, a food supplement, a feed supplement, a food additive, a feed additive, a nutritional supplement or a dietary supplement, thereby producing a food, a feed, a food supplement, a feed supplement, a food additive, a feed additive, a nutritional supplement or a dietary supplement, wherein optionally the polynucleotide is contained in an expression vector, and optionally the vector comprises an expression control sequence capable of expressing the nucleic acid in a plant cell, and optionally the food, feed, food supplement, feed supplement, food additive, feed additive, nutritional supplement or dietary supplement is for an animal, and optionally wherein the animal is a monogastric animal, and optionally the animal is a ruminant, and optionally the food, feed, food supplement, feed supplement, food additive, feed additive, nutritional supplement or dietary supplement, is in the form of a delivery matrix, a pellet, a tablet, a gel, a liquids, a spray, ground grain or a powder. In one aspect, the phytase enzyme is glycosylated to provide thermotolerance or thermostability at pelletizing conditions, and optionally delivery matrix is formed by pelletizing a mixture comprising a grain germ and the phytase enzyme to yield a particle, and optionally the pellets are made under conditions comprising application of steam, optionally the pellets are made under conditions comprising application of a temperature in excess of 80° C. for about 5 minutes, and optionally the pellet comprises a phytase enzyme that comprises a specific activity of at least 350 to about 900 units per milligram of enzyme.

The invention provides methods for delivering a phytase enzyme supplement to an animal or a human, said method comprising: (a) preparing an edible delivery matrix comprising an edible carrier and a phytase enzyme comprising a polypeptide comprising the amino acid sequence of the invention, wherein the matrix readily disperses and releases the phytase enzyme when placed into aqueous media, and, (b) administering the edible enzyme delivery matrix to the animal or human, wherein optionally in the edible delivery matrix comprises a granulate edible carrier, and optionally the edible delivery matrix is in the form of pellets, tablets, gels, liquids, sprays or powders, and optionally the edible carrier comprises a carrier selected from the group consisting of grain germ, hay, alfalfa, timothy, soy hull, sunflower seed meal, corn meal, soy meal and wheat meal, and optionally the edible carrier comprises grain germ that is spent of oil.

The invention provides a food, feed, food supplement, feed supplement, food additive, feed additive, nutritional supplement or dietary supplement, for an animal or a human, comprising the polypeptide of the invention, or a homodimer or heterodimer of the invention; wherein optionally the polypeptide is glycosylated, and optionally the phytase activity is thermotolerant or thermostable. In one aspect, the food, feed, food supplement, feed supplement, food additive, feed additive, nutritional supplement or dietary supplement is manufactured in pellet, pill, tablet, capsule, gel, geltab, spray, powder, lyophilized formulation, pharmaceutical formulation, liquid form, as a suspension or slurry, or produced using polymer-coated additives, or manufactured in granulate form, or produced by spray drying.

The invention provides edible or absorbable enzyme delivery matrix (matrices) comprising the polypeptide of the invention, or a homodimer or heterodimer of the invention; wherein optionally the polypeptide is glycosylated, and optionally the phytase activity is thermotolerant or thermostable. In one aspect, the edible delivery matrix comprises a pellet, or the edible or absorbable enzyme delivery matrix is manufactured in pellet, pill, tablet, capsule, gel, geltab, spray, powder, lyophilized formulation, pharmaceutical formulation, liquid form, as a suspension or slurry, or produced using polymer-coated additives, or manufactured in granulate form, or produced by spray drying.

The invention provides edible or absorbable pellets comprising a granulate edible or absorbable carrier and the polypeptide of the invention, or a homodimer or heterodimer of the invention; wherein optionally the polypeptide is glycosylated, and optionally the phytase activity is thermotolerant or thermostable, and optionally the pellet is manufactured in pellet form, or as a pill, tablet, capsule, gel, geltab, spray, powder, lyophilized formulation, pharmaceutical formulation, liquid form, as a suspension or slurry, or produced using polymer-coated additives, or manufactured in granulate form, or produced by spray drying.

The invention provides meals, e.g., a soybean meal, comprising a polypeptide of the invention, or a homodimer or heterodimer of the invention, and optionally the meal, e.g., soybean meal, is manufactured as a pellet, pill, tablet, capsule, gel, geltab, spray, powder, lyophilized formulation, or liquid form.

The invention provides methods of increasing the resistance of a phytase polypeptide to enzymatic inactivation in a digestive system of an animal, the method comprising glycosylating a phytase polypeptide comprising the polypeptide of the invention, thereby increasing resistance of the phytase polypeptide to enzymatic inactivation in a digestive system of an animal, and optionally the glycosylation is N-linked glycosylation, and, and optionally the phytase polypeptide is glycosylated as a result of in vivo expression of a polynucleotide encoding the phytase in a cell, and optionally the cell is a eukaryotic cell, and optionally the eukaryotic cell is a fungal cell, a plant cell, or a mammalian cell.

The invention provides methods for processing of corn and sorghum kernels comprising: (a) providing a polypeptide having a phytase activity, wherein the polypeptide comprises the polypeptide of the invention; (b) providing a composition comprising a corn steep liquor or a sorghum steep liquor; and (c) contacting the polypeptide of (a) and the composition of (b) under conditions wherein the polypeptide can cleave an inositol-inorganic phosphate linkage.

The invention provides pharmaceuticals or a dietary formulations comprising a polypeptide or heterodimer of the invention; wherein optionally the polypeptide is glycosylated, and optionally the phytase activity is thermotolerant or thermostable; and optionally the pharmaceutical or a dietary formulation is formulated as in pellet, pill, tablet, capsule, geltab, spray, powder, lotion or liquid form, or produced using polymer-coated additives, or as an implant, or manufactured in granulate form, or produced by spray drying.

The invention provides compositions comprising a polypeptide or heterodimer of the invention; and, (b) any product as set forth in Table 2, or any of the compositions listed in Table 1; wherein optionally the polypeptide is glycosylated, and optionally the phytase activity is thermotolerant or thermostable.

The invention provides a self-contained meal Ready-to-Eat unit (MRE), a drink or a hydrating agent comprising a polypeptide or heterodimer of the invention; wherein optionally the polypeptide is glycosylated, and optionally the phytase activity is thermotolerant or thermostable.

The invention provides methods for ameliorating (slowing the progress of, treating or preventing) osteoporosis comprising administering to an individual in need thereof an effective amount (dosage) of a composition comprising a polypeptide or heterodimer of the invention; wherein optionally the polypeptide is glycosylated, and optionally the phytase activity is thermotolerant or thermostable.

The invention provides methods for increasing gastric lability of a phytase comprising providing a polypeptide having a phytase activity, and replacing one or more amino acids in the sequence encoding the polypeptide with arginine, histidine, proline, leucine, serine, threonine, or tyrosine. The invention further provides exemplary phytases for use in the method, e.g. SEQ ID NO:2 or other phytases of the invention, as described in detail in Example 2, below.

The invention provides methods for altering at least two different properties of an enzyme, as described in detail in Example 2, below, comprising (a) providing a polypeptide having an enzymatic activity; (b) creating variants from the polypeptide of (a), wherein each variant has a single amino acid change from the polypeptide of (a); (c) screening the variants of (b) for the two different properties; (d) selecting desired variants of (c), and identifying the single amino acid change in each selected variant; (e) creating new variants comprising different combinations of the selected single amino acid changes of (d); (f) screening the variants of (e) for the two altered properties; and (g) selecting desired variants of (f) with the two altered properties. The invention provides alternative methods for altering at least two different properties of an enzyme comprising (a) providing a polypeptide having an enzymatic activity; (b) creating variants from the polypeptide of (a), wherein each variant has a single amino acid change from the polypeptide of (a); (c) screening the variants of (b) for one altered property; (d) screening the variants (b) for another altered property; (e) selecting desired variants of (c) and (d), and identifying the single amino acid change in each selected variant; (f) creating new variants comprising different combinations of the selected single amino acid changes of (c) and (d); (g) screening the variants of (f) for the two altered properties; and (h) selecting desired variants of (g) with the two altered properties. The invention further provides exemplary methods for creating the variants, e.g. by GSSM evolution, GeneReassembly evolution, and/or TMCA evolution.

The invention provides methods for decoupling gastric stability from thermotolerance of a phytase, as described in detail in Example 2, below, comprising (a) providing a polypeptide having a phytase activity; (b) creating variant phytases from the polypeptide of (a), wherein each variant has a single amino acid change from the polypeptide of (a); (c) screening the variant phytases of (b) for altered gastric stability and altered thermotolerance; (d) selecting the variants of (c) with desired gastric stability and thermotolerance, and identifying the single amino acid change in each selected variant; (e) creating new variant phytases comprising different combinations of the selected single amino acid changes of (d); (f) screening the variants of (e) for altered gastric stability and altered thermotolerance; and (g) selecting the variants of (f) with desired gastric stability and thermotolerance. The invention provides alternative methods for decoupling gastric stability from thermotolerance of a phytase comprising (a) providing a polypeptide having a phytase activity; (b) creating variant phytases from the polypeptide of (a), wherein each variant has a single amino acid change from the polypeptide of (a); (c) screening the variant phytases of (b) for altered gastric stability; (d) screening the variant phytases (b) for altered thermotolerance; (e) selecting the variants of (c) and (d) with desired gastric stability or thermotolerance, and identifying the single amino acid change in each selected variant; (f) creating new variant phytases comprising different combinations of the selected single amino acid changes of (c) and (d); (g) screening the variants of (f) for altered gastric stability and altered thermotolerance; and (h) selecting the variants of (g) with desired gastric stability and thermotolerance. The invention further provides exemplary methods for creating the variants, e.g. by GSSM evolution, GeneReassembly evolution, and/or TMCA evolution. The invention provides exemplary phytases for use in the methods, e.g. SEQ ID NO:2 and other phytases of the invention. The invention provides exemplary mutations which decouple gastric stability from thermotolerance, for example, the mutations listed in Table 4, 5, 6, 7, 9, or any combination thereof.

The invention provides phytases which are gastric labile and thermotolerant, described in detail in Example 2, below, wherein the phytase completely degrades in stimulated gastric fluid (SGF) in less than 10 minutes, less than 8 minutes, less than 6 minutes, less than 4 minutes, or less than 2 minutes, and the phytase retains activity after exposure to a temperature in the range from about 75° C. to about 85° C., about 85° C. to about 90° C., about 90° C. to about 95° C., or about 80° C. to about 86° C., for example, the phytases of the invention as described in detail in Example 2, below. In one aspect, the gastric labile and thermotolerant phytases of the invention completely degrade in stimulated gastric fluid (SGF) in less than 4 minutes, and the phytase retains activity after exposure to a temperature in the range from about 80° C. to about 86° C.

The details of one or more aspects of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

BRIEF DESCRIPTION OF THE DRAWINGS

The following drawings are illustrative of aspects of the invention and are not meant to limit the scope of the invention as encompassed by the claims.

FIG. 3 graphically summarizes the data used to generate the graph of FIG. 1; as described in detail in Example 1, below.

FIG. 4 illustrates the sequence of the parental phytase SEQ ID NO:2 and the gene site saturation mutagenesis (GSSM)-generated sequence modifications selected for GeneReassembly™ library construction; as described in detail, below.

FIG. 5 illustrates exemplary phytases having multiple residue modifications to the parental SEQ ID NO:2; as described in detail herein.

FIG. 6 illustrates exemplary phytases having single residue modifications to the parental SEQ ID NO:2; as described in detail herein.

Like reference symbols in the various drawings indicate like elements.

DETAILED DESCRIPTION OF THE INVENTION

Figure 1:
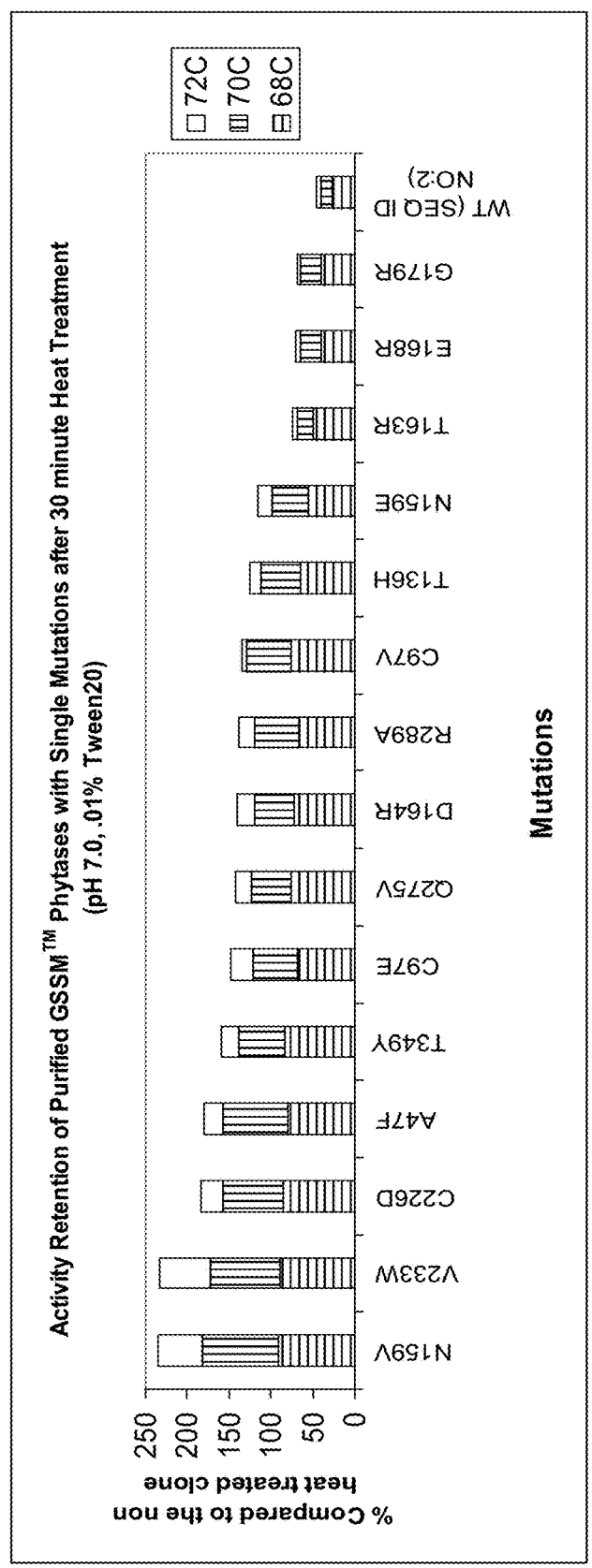
FIG. 1 illustrates a summary of residue activity of purified polypeptides of the invention, single mutation exemplary sequences of the invention, after heat treatment at various temperatures for 30 minutes; where the phytase activity is assayed with a fluorescence substrate, and the rates were compared to the rates of each corresponding non-treated sample; as described in detail in Example 1, below.

The invention relates to phytase polypeptides having comprising the specific residue modifications to SEQ ID NO:2, as described above, and polynucleotides encoding them, (e.g., comprising the specific base pair modifications to SEQ ID NO:1, as described above), as well as methods of use of the polynucleotides and polypeptides. FIG. 6 illustrates exemplary phytases having single residue modifications to the parental SEQ ID NO:2, and FIG. 5 illustrates exemplary phytases having multiple residue modifications to the parental SEQ ID NO:2.

The phytase activity of polypeptides of the invention can encompass enzymes having any phytase activity, for example, enzymes capable of catalyzing the degradation of phytate, e.g., the catalysis of phytate (myo-inositol-hexaphosphate) to inositol and inorganic phosphate. The phytases of the invention include thermotolerant and thermoresistant enzymes.

The phytases and polynucleotides encoding the phytases of the invention are useful in a number of processes, methods, and compositions. For example, as discussed above, a phytase can be used in animal feed, and feed supplements as well as in treatments to degrade or remove excess phytate from the environment or a sample. Other uses will be apparent to those of skill in the art based upon the teachings provided herein, including those discussed above.

In one aspect, phytase molecules of the invention—either alone or in combination with other reagents (including but not limited to enzymes, such as proteases, amylases and the like)—are used in the processing of foodstuffs, e.g., for prevention of the unwanted corn sludge, and in other applications where phytate hydrolysis is desirable.

In one aspect, phytase molecules of the invention are used to eliminate or decrease the presence of unhydrolyzed phytate, especially where unhydrolyzed phytate leads to problematic consequences in ex vivo processes including—but not limited to—the processing of foodstuffs. In one aspect, phytase molecules of the invention are used in procedures as described in EP0321004-B1 (Vaara et al.), including steps in the processing of corn and sorghum kernels whereby the hard kernels are steeped in water to soften them. Water-soluble substances that leach out during this process become part of a corn steep liquor, which is concentrated by evaporation. Unhydrolyzed phytic acid in the corn steep liquor, largely in the form of calcium and magnesium salts, is associated with phosphorus and deposits an undesirable sludge with proteins and metal ions. This sludge is problematic in the evaporation, transportation and storage of the corn steep liquor. Phytase molecules of the invention are used to hydrolyze this sludge.

In one aspect, the phytases of the invention can provide substantially superior commercial performance than previously identified phytase molecules, e.g. phytase molecules of fungal origin. In one aspect, the enzymes of the invention can be approximately 4400 U/mg, or greater than approximately between 50 to 100, or 50 to 1000, or 100 to 4000 U/mg protein.

The invention also provides methods for changing the characteristics of a phytase of the invention by mutagenesis and other method, as discussed in detail, below.

Generating and Manipulating Nucleic Acids

The invention provides nucleic acids encoding the polypeptides and phytases of the invention. The invention also provides expression cassettes, vectors such as expression or cloning vectors, cloning vehicles such as a viral vector, a plasmid, a phage, a phagemid, a cosmid, a fosmid, a bacteriophage or an artificial chromosome, which can comprise, or have contained therein, a nucleic acid of the invention.

The invention also includes methods for discovering new phytase sequences using the nucleic acids of the invention. Also provided are methods for modifying the nucleic acids of the invention by, e.g., synthetic ligation reassembly, optimized directed evolution system and/or saturation mutagenesis.

In one aspect, the invention provides a genus of nucleic acids that are synthetically generated variants of the parent SEQ ID NO:1, wherein these nucleic acids of the invention having at least 95%, 96% 97%, 98% or 99% sequence identity to the "parent" SEQ ID NO:1, and encoding at least one mutation listed in Table 4, 5, 6, 7, 9, or any combination thereof, For reference, the parent SEQ ID NO:1 is:

tides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105: 661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

```
atgaaagcga tcttaatccc attttatct cttctgattc cgttaacccc gcaatctgca      60
ttcgctcaga gtgagccgga gctgaagctg gaaagtgtgg tgattgtcag tcgtcatggt    120
gtgcgtgctc caaccaaggc cacgcaactg atgcaggatg tcaccccaga cgcatggcca    180
acctggccgg taaaactggg tgagctgaca ccgcgcggtg gtgagctaat cgcctatctc    240
ggacattact ggcgtcagcg tctggtagcc gacggattgc tgcctaaatg tggctgcccg    300
cagtctggtc aggtcgcgat tattgctgat gtcgacgagc gtacccgtaa aacaggcgaa    360
gccttcgccg ccgggctggc acctgactgt gcaataaccg tacataccca ggcagatacg    420
tccagtcccg atccgttatt taatcctcta aaaactggcg tttgccaact ggataacgcg    480
aacgtgactg acgcgatcct cgagagggca ggagggtcaa ttgctgactt taccgggcat    540
tatcaaacgg cgtttcgcga actggaacgg gtgcttaatt ttccgcaatc aaacttgtgc    600
cttaaacgtg agaaacagga cgaaagctgt tcattaacgc aggcattacc atcggaactc    660
aaggtgagcg ccgactgtgt ctcattaacc ggtgcggtaa gcctcgcatc aatgctgacg    720
gagatatttc tcctgcaaca agcacaggga atgccggagc cggggtgggg aaggatcacc    780
gattcacacc agtggaacac cttgctaagt ttgcataacg cgcaatttga tttgctacaa    840
cgcacgccag aggttgcccg cagccgcgcc acccccgttat tagatttgat caagacagcg    900
ttgacgcccc atccaccgca aaaacaggcg tatggtgtga cattacccac ttcagtgctg    960
tttatcgccg gacacgatac taatctggca aatctcggcg gcgcactgga gctcaactgg   1020
acgcttcccg gtcagccgga taacacgccg ccaggtggtg aactggtgtt tgaacgctgg   1080
cgtcggctaa gcgataacag ccagtggatt caggtttcgc tggtcttcca gactttacag   1140
cagatgcgtg ataaaacgcc gctgtcatta aatacgccgc ccggagaggt gaaactgacc   1200
ctggcaggat gtgaagagcg aaatgcgcag ggcatgtgtt cgttggcagg ttttacgcaa   1260
atcgtgaatg aagcacgcat accggcgtgc agtttgtaa                          1299
```

The nucleic acids of the invention can be made, isolated and/or manipulated by, e.g., cloning and expression of cDNA libraries, amplification of message or genomic DNA by PCR, and the like. In practicing the methods of the invention, homologous genes can be modified by manipulating a template nucleic acid, as described herein. The invention can be practiced in conjunction with any method or protocol or device known in the art, which are well described in the scientific and patent literature.

General Techniques

The nucleic acids used to practice this invention, whether RNA, iRNA, antisense nucleic acid, cDNA, genomic DNA, vectors, viruses or hybrids thereof, may be isolated from a variety of sources, genetically engineered, amplified, and/or expressed/generated recombinantly. Recombinant polypep- Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

In alternative aspects, the phrases "nucleic acid" or "nucleic acid sequence" refer to an oligonucleotide, nucleotide, polynucleotide, or to a fragment of any of these, to DNA or RNA (e.g., mRNA, rRNA, tRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., iRNPs). The term encompasses nucleic acids, i.e., oligonucleotides, containing known analogues of natural nucleotides. The term also encompasses nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156.

In one aspect, recombinant polynucleotides of the invention comprise sequences adjacent to a "backbone" nucleic acid to which it is not adjacent in its natural environment. In one aspect, nucleic acids represent 5% or more of the number of nucleic acid inserts in a population of nucleic acid "backbone molecules." "Backbone molecules" according to the invention include nucleic acids such as expression vectors, self-replicating nucleic acids, viruses, integrating nucleic acids, and other vectors or nucleic acids used to maintain or manipulate a nucleic acid insert of interest. In one aspect, the enriched nucleic acids represent 15%, 20%, 30%, 40%, 50%, 60%, 70%, 80%, 90% or more of the number of nucleic acid inserts in the population of recombinant backbone molecules.

In one aspect, a nucleic acid encoding a polypeptide of the invention is assembled in appropriate phase with a leader sequence capable of directing secretion of the translated polypeptide or fragment thereof.

The invention provides fusion proteins and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

In one aspect, the term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment. In one aspect, the term "purified" does not require absolute purity; rather, it is intended as a relative definition. Individual nucleic acids obtained from a library have been conventionally purified to electrophoretic homogeneity. The sequences obtained from these clones could not be obtained directly either from the library or from total human DNA. The purified nucleic acids of the invention have been purified from the remainder of the genomic DNA in the organism by at least $10^4$-$10^6$ fold. In alternative aspects, the term "purified" also includes nucleic acids which have been purified from the remainder of the genomic DNA or from other sequences in a library or other environment by at least one order of magnitude, or alternatively, two or three orders, or four or five orders of magnitude.

Transcriptional and Translational Control Sequences

The invention provides nucleic acid (e.g., DNA) sequences of the invention operatively linked to expression (e.g., transcriptional or translational) control sequence(s), e.g., promoters or enhancers, to direct or modulate RNA synthesis/expression. The expression control sequence can be in an expression vector. Exemplary bacterial promoters include lacI, lacZ, T3, T7, gpt, lambda PR, PL and trp. Exemplary eukaryotic promoters include CMV immediate early, HSV thymidine kinase, early and late SV40, LTRs from retrovirus, and mouse metallothionein I.

Promoters suitable for expressing, or over-expressing, a polypeptide in bacteria include the *E. coli* lac or trp promoters, the lad promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), and the acid phosphatase promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Expression Vectors and Cloning Vehicles

The invention provides expression systems, e.g., expression cassettes, vectors, cloning vehicles and the like, comprising nucleic acids of the invention, e.g., sequences encoding the phytases of the invention, for expression, and over-expression, of the polypeptides of the invention (and nucleic acids, e.g., antisense). Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors of the invention can include chromosomal, non-chromosomal and synthetic DNA sequences. Large numbers of suitable vectors are known to those of skill in the art, and are commercially available. Exemplary vectors are include: bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present invention.

As representative examples of expression vectors which may be used there may be mentioned viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present invention.

An exemplary vector for use in the present invention contains an f-factor origin replication. The f-factor (or fertility factor) in *E. coli* is a plasmid which effects high frequency transfer of itself during conjugation and less frequent transfer of the bacterial chromosome itself. One aspect uses cloning vectors, referred to as "fosmids" or bacterial artificial chromosome (BAC) vectors. These are derived from *E. coli* f-factor which is able to stably integrate large segments of genomic DNA. When integrated with DNA from a mixed uncultured environmental sample, this makes it possible to achieve large genomic fragments in the form of a stable "environmental DNA library."

Another type of vector for use in the present invention is a cosmid vector. Cosmid vectors were originally designed to clone and propagate large segments of genomic DNA. Cloning into cosmid vectors is described in detail in "Molecular Cloning: A laboratory Manual" (Sambrook et al., 1989).

The DNA sequence in the expression vector is operatively linked to an appropriate expression control sequence(s) (promoter) to direct RNA synthesis. Particular named bacterial promoters include lacI, lacZ, T3, T7, gpt, lambda PR, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers. In addition, the expression vectors can contain one or more selectable marker genes to provide a phenotypic trait for selection of transformed host cells such as dihydrofolate reductase or neomycin resistance for eukaryotic cell culture, or tetracycline or ampicillin resistance in *E. coli*.

In one aspect, expression cassettes of the invention comprise a sequence of the invention and a nucleotide sequence which is capable of affecting expression of a structural gene (i.e., a protein coding sequence, such as a phytase of the invention) in a host compatible with such sequences. Expression cassettes include at least a promoter operably linked with the polypeptide coding sequence; and, optionally, with other sequences, e.g., transcription termination signals. Additional factors necessary or helpful in effecting expression may also be used, e.g., enhancers. In one aspect, "operably linked" as used herein refers to linkage of a promoter upstream from a DNA sequence such that the promoter mediates transcription of the DNA sequence. Thus, expression cassettes also include plasmids, expression vectors, recombinant viruses, any form of recombinant "naked DNA" vector, and the like. In one aspect, a "vector" comprises a nucleic acid that can infect, transfect, transiently or permanently transduce a cell. A vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). In one aspect, vectors include, but are not limited to, replicons (e.g., RNA replicons, bacteriophages) to which fragments of DNA may be attached and become replicated. In one aspect, vectors include, but are not limited to RNA, autonomous self-replicating circular or linear DNA or RNA (e.g., plasmids, viruses, and the like, see, e.g., U.S. Pat. No. 5,217,879), and includes both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The expression vector may comprise a promoter, a ribosome binding site for translation initiation and a transcription terminator. The vector may also include appropriate sequences for amplifying expression. Mammalian expression vectors can comprise an origin of replication, any necessary ribosome binding sites, a polyadenylation site, splice donor and acceptor sites, transcriptional termination sequences, and 5' flanking non-transcribed sequences. In some aspects, DNA sequences derived from the SV40 splice and polyadenylation sites may be used to provide the required non-transcribed genetic elements.

In one aspect, the expression vectors contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in *E. coli*, and the *S. cerevisiae* TRP1 gene. Promoter regions can be selected from any desired gene using chloramphenicol transferase (CAT) vectors or other vectors with selectable markers.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

A DNA sequence may be inserted into a vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are known in the art, e.g., as described in Ausubel and Sambrook. Such procedures and others are deemed to be within the scope of those skilled in the art.

The vector may be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook.

Particular bacterial vectors which may be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

Host Cells and Transformed Cells

The invention also provides a transformed cell comprising a nucleic acid sequence of the invention, e.g., a sequence encoding a phytase of the invention, or comprising an expression cassette, vector, cloning vehicle, expression vector, or cloning vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include any species within the genera *Escherichia, Bacillus, Streptomyces, Salmonella, Pseudomonas, Lactococcus*, and *Staphylococcus*, including, e.g., *Escherichia coli, Lactococcus lactis, Bacillus subtilis, Bacillus cereus, Salmonella typhimurium, Pseudomonas fluorescens*. Exemplary fungal cells include any species of *Aspergillus*, including *Aspergillus niger*. Exemplary yeast cells include any species of *Pichia, Saccharomyces, Schizosaccharomyces*, or *Schwanniomyces*, including *Pichia pastoris, Saccharomyces cerevisiae*, or *Schizosaccharomyces pombe*. Exemplary insect cells include any species of *Spodoptera* or *Drosophila*, including *Drosophila* S2 and *Spodoptera* Sf9. Exemplary insect cells include *Drosophila* S2 and *Spodoptera* Sf9. Exemplary yeast cells include *Pichia pastoris, Saccharomyces cerevisiae* or *Schizosaccharomyces pombe*. Exemplary animal cells include CHO, COS or Bowes melanoma or any mouse or human cell line. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The nucleic acids of the invention can be expressed, or overexpressed, in any in vitro or in vivo expression system. Any cell culture systems can be employed to express, or overexpress, recombinant protein, including bacterial, insect, yeast, fungal or mammalian cultures. Over-expression can be effected by appropriate choice of promoters, enhancers, vectors (e.g., use of replicon vectors, dicistronic vectors (see, e.g., Gurtu (1996) Biochem. Biophys. Res. Commun. 229:295-8)), media, culture systems and the like. In one aspect, gene amplification using selection markers, e.g., glutamine synthetase (see, e.g., Sanders (1987) Dev. Biol. Stand. 66:55-63), in cell systems are used to overexpress the polypeptides of the invention.

Various mammalian cell culture systems can be employed to express recombinant protein, examples of mammalian expression systems include the COS-7 lines of monkey kidney fibroblasts, described in "SV40-transformed simian cells support the replication of early SV40 mutants" (Gluzman, 1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 splice, and polyadenylation sites may be used to provide the required non-transcribed genetic elements.

Host cells containing the polynucleotides of interest can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan. The clones which are identified as having the specified enzyme activity may then be sequenced to identify the polynucleotide sequence encoding an enzyme having the enhanced activity.

Amplification of Nucleic Acids

In practicing the invention, nucleic acids encoding the polypeptides of the invention, or modified nucleic acids, can be reproduced by, e.g., amplification. The invention provides amplification primer sequence pairs for amplifying nucleic acids encoding polypeptides with a phytase activity, or subsequences thereof, where the primer pairs are capable of amplifying nucleic acid sequences including the exemplary SEQ ID NO:1, and at least one of the specific sequence modifications set forth above. One of skill in the art can design amplification primer sequence pairs for any part of or the full length of these sequences; for example:

The "parent" SEQ ID NO:1 is as shown above. Thus, an amplification primer sequence pair for amplifying this parent sequence, or one of the exemplary sequences of the invention having at least one of the specific sequence modifications set forth herein, can be residues 1 to 21 of SEQ ID NO:1 (i.e., ATGAAAGCGATCTTAATCCCA) and the complementary strand of the last 21 residues of SEQ ID NO:1 (i.e., the complementary strand of TGCAGTTTGAGATCTCATCTA).

Amplification reactions can also be used to quantify the amount of nucleic acid in a sample (such as the amount of message in a cell sample), label the nucleic acid (e.g., to apply it to an array or a blot), detect the nucleic acid, or quantify the amount of a specific nucleic acid in a sample. In one aspect of the invention, message isolated from a cell or a cDNA library are amplified. The skilled artisan can select and design suitable oligonucleotide amplification primers. Amplification methods are also well known in the art, and include, e.g., polymerase chain reaction, PCR (see, e.g., PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477-1491), automated Q-beta replicase amplification assay (see, e.g., Burg (1996) Mol. Cell. Probes 10:257-271) and other RNA polymerase mediated techniques (e.g., NASBA, Cangene, Mississauga, Ontario); see also Berger (1987) Methods Enzymol. 152:307-316; Sambrook; Ausubel; U.S. Pat. Nos. 4,683,195 and 4,683,202; Sooknanan (1995) Biotechnology 13:563-564.

Determining the Degree of Sequence Identity

The invention provides an isolated, synthetic or recombinant nucleic acid comprising a nucleic acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to SEQ ID NO:1, and including at least one of the specifically enumerated modifications to SEQ ID NO:1 discussed above. In one aspect, the extent of sequence identity (homology) may be determined using any computer program and associated parameters, including those described herein, such as BLAST 2.2.2. or FASTA version 3.0t78, with the default parameters.

Homologous sequences also include RNA sequences in which uridines replace the thymines in the nucleic acid sequences. The homologous sequences may be obtained using any of the procedures described herein or may result from the correction of a sequencing error.

Various sequence comparison programs identified herein are used in this aspect of the invention. Protein and/or nucleic acid sequence identities (homologies) may be evaluated using any of the variety of sequence comparison algorithms and programs known in the art. Such algorithms and programs include, but are not limited to, TBLASTN, BLASTP, FASTA, TFASTA, and CLUSTALW (Pearson and Lipman, Proc. Natl. Acad. Sci. USA 85(8):2444-2448, 1988; Altschul et al., J. Mol. Biol. 215(3):403-410, 1990; Thompson et al., Nucleic Acids Res. 22(2):4673-4680, 1994; Higgins et al., Methods Enzymol. 266:383-402, 1996; Altschul et al., J. Mol. Biol. 215(3):403-410, 1990; Altschul et al., Nature Genetics 3:266-272, 1993.

Homology or identity can be measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. For sequence comparison, one sequence can act as a reference sequence (an exemplary sequence of the invention) to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous residues. For example, in alternative aspects of the invention, contiguous residues ranging anywhere from 20 to the full length of exemplary sequences of the invention are compared to a reference sequence of the same number of contiguous positions after the two sequences are optimally aligned. If the reference sequence has the requisite sequence identity to exemplary sequences of the invention, e.g., 98% sequence identity to SEQ ID NO:1, SEQ ID NO:2, and having one of the specific sequence modifications noted above, that sequence is within the scope of the invention. In alternative embodiments, subsequences ranging from about 20 to 600, about 50 to 200, and about 100 to 150 are compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of person & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information, such as BLAST, BLAST2, BLASTN and BLASTX), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FASTA (Pearson and Lipman, Proc. Natl. Acad. Sci. USA, 85: 2444, 1988), FASTDB (Brutlag et al. Comp. App. Biosci. 6:237-245, 1990), FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Other programs and databases used to practice the invention include, but are not limited to: MacPattern (EMBL), DiscoveryBase (Molecular Applications Group), GeneMine (Molecular Applications Group), Look (Molecular Applications Group), MacLook (Molecular Applications Group), Catalyst (Molecular Simulations Inc.), Catalyst/SHAPE (Molecular Simulations Inc.), Cerius2.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwent's World Drug Index database, the BioByteMasterFile database, the GenBank database, the GenSeq database, and the GenomeQuest database. Many other programs and data bases would be apparent to one of skill in the art given the present disclosure. Such alignment programs can also be used to screen genome databases to identify polynucleotide sequences having substantially identical sequences. A number of genome databases are available, for example, through the NCBI (National Center for Biotechnology Information) website. Databases containing genomic information annotated with some functional information are maintained by different organization, and are accessible via the internet.

BLAST, BLAST 2.0 and BLAST 2.2.2 algorithms are also used to practice the invention. They are described, e.g., in Altschul (1977) Nuc. Acids Res. 25:3389-3402; Altschul (1990) J. Mol. Biol. 215:403-410. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff (1989) Proc. Natl. Acad. Sci. USA 89:10915) alignments (B) of 50, expectation (E) of 10, M=5, N=−4, and a comparison of both strands. The BLAST algorithm also performs a statistical analysis of the similarity between two sequences (see, e.g., Karlin & Altschul (1993) Proc. Natl. Acad. Sci. USA 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, less than about 0.01, or less than about 0.001. In one aspect, protein and nucleic acid sequence homologies are evaluated using the Basic Local Alignment Search Tool ("BLAST"). For example, five specific BLAST programs can be used to perform the following task: (1) BLASTP and BLASTS compare an amino acid query sequence against a protein sequence database; (2) BLASTN compares a nucleotide query sequence against a nucleotide sequence database; (3) BLASTX compares the six-frame conceptual translation products of a query nucleotide sequence (both strands) against a protein sequence database; (4) TBLASTN compares a query protein sequence against a nucleotide sequence database translated in all six reading frames (both strands); and, (5) TBLASTX compares the six-frame translations of a nucleotide query sequence against the six-frame translations of a nucleotide sequence database. The BLAST programs identify homologous sequences by identifying similar segments, which are referred to herein as "high-scoring segment pairs," between a query amino or nucleic acid sequence and a test sequence which can be obtained from a protein or nucleic acid sequence database. High-scoring segment pairs can be identified (i.e., aligned) by means of a scoring matrix, many of which are known in the art. An exemplary scoring matrix used is the BLOSUM62 matrix (Gonnet et al., Science 256:1443-1445, 1992; Henikoff and Henikoff, Proteins 17:49-61, 1993). Alternatively, the PAM or PAM250 matrices may be used (see, e.g., Schwartz and Dayhoff, eds., 1978, Matrices for Detecting Distance Relationships: Atlas of Protein Sequence and Structure, Washington: National Biomedical Research Foundation).

In one aspect of the invention, to determine if a nucleic acid has the requisite sequence identity to be within the scope of the invention, the NCBI BLAST 2.2.2 programs is used. default options to blastp. There are about 38 setting options in the BLAST 2.2.2 program. In this exemplary aspect of the invention, all default values are used except for the default filtering setting (i.e., all parameters set to default except filtering which is set to OFF); in its place a "–F F" setting is used, which disables filtering. Use of default filtering often results in Karlin-Altschul violations due to short length of sequence.

The default values used in this exemplary aspect of the invention include:

"Filter for low complexity: ON
>Word Size: 3
>Matrix: Blosum62
>Gap Costs: Existence:11
>Extension:1"
"Filter for low complexity: ON Other default settings are: filter for low complexity OFF, word size of 3 for protein, BLOSUM62 matrix, gap existence penalty of –11 and a gap extension penalty of –1.

In some aspects, a sequence comparison algorithm can be used for comparing a nucleic acid sequence or amino acid sequence of the invention to a reference sequence. For example, the sequence comparison algorithm may compare the nucleotide sequences or amino acid sequences of the invention with the "parent" sequence SEQ ID NO:1 and/or SEQ ID NO:2, or to reference sequences to identify homologies or structural motifs. A comparison of the sequences can be performed to determine if the first sequence is the same as the second sequence. It is important to note that this type of comparison is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the comparison algorithm.

Once a comparison of two sequences has been performed, a determination is made whether the two sequences are the same. Of course, the term "same" is not limited to sequences that are absolutely identical. The sequence comparison may indicate a sequence identity level between the sequences compared or identify structural motifs, or it may identify structural motifs in sequences which are compared to these nucleic acid codes and polypeptide codes. The level of sequence identity is determined by calculating the proportion of characters between the sequences that were the same out of the total number of sequences in the first sequence. Thus, if every character in a first 100 nucleotide sequence aligned with every character in a second sequence, the sequence identity level would be 100%.

Alternatively, the algorithm can compare a reference sequence to a sequence of the invention to determine whether the sequences differ at one or more positions. The result of the comparison may indicate the length and identity of inserted, deleted or substituted nucleotides or amino acid residues with respect to the sequence of either the reference or the invention. In other aspects, the algorithm can be used to identify features within a nucleic acid or polypeptide of the invention. For example, identifier feature may comprise an open reading frame (ORF), an "Initiation Codon" (e.g., the codon "ATG"), a "TAATAA Box", or motifs such as alpha helices, beta sheets, or functional polypeptide motifs such as enzymatic active sites, helix-turn-helix motifs, leucine zippers, glycosylation sites, ubiquitination sites, alpha helices, beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites, as well as other motifs known to those skilled in the art.

Inhibiting Expression of a Phytase

The invention further provides for nucleic acids complementary to (e.g., antisense sequences to) the nucleic acid sequences of the invention, including nucleic acids comprising antisense, iRNA, ribozymes. Antisense sequences are capable of inhibiting the transport, splicing or transcription of phytase-encoding genes. The inhibition can be effected through the targeting of genomic DNA or messenger RNA. The transcription or function of targeted nucleic acid can be inhibited, for example, by hybridization and/or cleavage. One particularly useful set of inhibitors provided by the present invention includes oligonucleotides which are able to either bind phytase gene or message, in either case preventing or inhibiting the production or function of phytase enzyme. The association can be though sequence specific hybridization. Another useful class of inhibitors includes oligonucleotides which cause inactivation or cleavage of phytase message. The oligonucleotide can have enzyme activity which causes such cleavage, such as ribozymes. The oligonucleotide can be chemically modified or conjugated to an enzyme or composition capable of cleaving the complementary nucleic acid. One may screen a pool of many different such oligonucleotides for those with the desired activity.

Antisense Oligonucleotides

The invention provides antisense oligonucleotides comprising the new phytase sequence modifications of the invention, where these antisense oligonucleotides are capable of binding phytase message which can inhibit phytase activity by targeting mRNA. Strategies for designing antisense oligonucleotides are well described in the scientific and patent literature, and the skilled artisan can design such phytase oligonucleotides using the novel reagents of the invention. For example, gene walking/RNA mapping protocols to screen for effective antisense oligonucleotides are well known in the art, see, e.g., Ho (2000) Methods Enzymol. 314:168-183, describing an RNA mapping assay, which is based on standard molecular techniques to provide an easy and reliable method for potent antisense sequence selection. See also Smith (2000) Euro. J. Pharm. Sci. 11:191-198.

Naturally occurring nucleic acids are used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata (1997) Toxicol Appl Pharmacol 144:189-197; Antisense Therapeutics, ed. Agarwal (Humana Press, Totowa, N.J., 1996). Antisense oligonucleotides having synthetic DNA backbone analogues provided by the invention can also include phosphoro-dithioate, methylphosphonate, phosphoramidate, alkyl phosphotriester, sulfamate, 3'-thioacetal, methylene (methylimino), 3'-N-carbamate, and morpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense phytase sequences of the invention (see, e.g., Gold (1995) J. of Biol. Chem. 270:13581-13584).

Inhibitory Ribozymes

The invention provides ribozymes comprising the new phytase sequence modifications of the invention, where the ribozymes of the invention are capable of binding phytase message which can inhibit phytase enzyme activity by targeting mRNA. Strategies for designing ribozymes and selecting the phytase-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it is typically released from that RNA and so can bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

The enzymatic ribozyme RNA molecule can be formed in a hammerhead motif, but may also be formed in the motif of a hairpin, hepatitis delta virus, group I intron or RNaseP-like RNA (in association with an RNA guide sequence). Examples of such hammerhead motifs are described by Rossi (1992) Aids Research and Human Retroviruses 8:183; hairpin motifs by Hampel (1989) Biochemistry 28:4929, and Hampel (1990) Nuc. Acids Res. 18:299; the hepatitis delta virus motif by Perrotta (1992) Biochemistry 31:16; the RNaseP motif by Guerrier-Takada (1983) Cell 35:849; and the group I intron by Cech U.S. Pat. No. 4,987,071. The recitation of these specific motifs is not intended to be limiting; those skilled in the art will recognize that an enzymatic RNA molecule of this invention has a specific substrate binding site complementary to one or more of the target gene RNA regions, and has nucleotide sequence within or surrounding that substrate binding site which imparts an RNA cleaving activity to the molecule.

RNA Interference (RNAi)

In one aspect, the invention provides an RNA inhibitory molecule, a so-called "RNAi" molecule, comprising an enzyme sequence of the invention. The RNAi molecule comprises a double-stranded RNA (dsRNA) molecule. The RNAi molecule, e.g., siRNA and/or miRNA, can inhibit expression of phytase enzyme gene. In one aspect, the RNAi molecule, e.g., siRNA and/or miRNA, is about 15, 16, 17, 18, 19, 20, 21, 22, 23, 24, 25 or more duplex nucleotides in length.

While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi is the breaking of a double-stranded RNA (dsRNA) matching a specific gene sequence into short pieces called short interfering RNA, which trigger the degradation of mRNA that matches its sequence. In one aspect, the RNAi's of the invention are used in gene-silencing therapeutics, see, e.g., Shuey (2002) Drug Discov. Today 7:1040-1046. In one aspect, the invention provides methods to selectively degrade RNA using the RNAi's molecules, e.g., siRNA and/or miRNA, of the invention. In one aspect, the micro-inhibitory RNA (miRNA) inhibits translation, and the siRNA inhibits transcription. The process may be practiced in vitro, ex vivo or in vivo. In one aspect, the RNAi molecules of the invention can be used to generate a loss-of-function mutation in a cell, an organ or an animal. Methods for making and using RNAi molecules, e.g., siRNA and/or miRNA, for selectively degrade RNA are well known in the art, see, e.g., U.S. Pat. Nos. 6,506,559; 6,511,824; 6,515,109; 6,489,127.

Modification of Nucleic Acids

The invention provides methods of generating variants of the nucleic acids of the invention, e.g., those encoding a phytase enzyme. These methods can be repeated or used in various combinations to generate phytase enzymes having an altered or different activity or an altered or different stability from that of a phytase encoded by the template nucleic acid. These methods also can be repeated or used in various combinations, e.g., to generate variations in gene/message expression, message translation or message stability. In another aspect, the genetic composition of a cell is altered by, e.g., modification of a homologous gene ex vivo, followed by its reinsertion into the cell.

The invention also provides methods for changing the characteristics of a phytase of the invention by mutagenesis and other method, including directed evolution, e.g., Diversa Corporation's (San Diego, Calif.) proprietary approaches; e.g., DirectEvolution; (see, e.g., U.S. Pat. No. 5,830,696; Gene Site Saturation Mutagenesis (GSSM) (see, e.g., U.S. Pat. Nos. 6,171,820 and 6,579,258), Exonuclease-Mediated Gene Assembly in Directed Evolution (see, e.g., U.S. Pat. Nos. 6,361,974 and 6,352,842), End Selection in Directed Evolution (see, e.g., U.S. Pat. Nos. 6,358,709 and 6,238,884), Recombination-Based Synthesis Shuffling (see, e.g., U.S. Pat. Nos. 5,965,408 and 6,440,668, and Australian Patent No. AU724521), and Directed Evolution of Thermophilic Enzymes (see, e.g., U.S. Pat. Nos. 5,830,696 and 6,335,179).

In one aspect, the characteristics of a phytase are modified by a DirectEvolution protocol comprising: a) the subjection of one or more molecular templates, e.g., the phytase nucleic acids of the invention, to mutagenesis to generate novel molecules, and b) the selection among these progeny species of novel molecules with more desirable characteristics. The power of directed evolution depends on the starting choice of starting templates (e.g., the "parent" SEQ ID NO:1, or any sequence of this invention), as well as on the mutagenesis process(es) chosen and the screening process(es) used. Thus, the invention provides novel highly active, physiologically effective, and economical sources of phytase activity, including novel phytases that: a) have superior activities under one or more specific applications, such as high temperature manufacture of foodstuffs, and are thus useful for optimizing these specific applications; b) are useful as templates for directed evolution to achieve even further improved novel molecules; and c) are useful as tools for the identification of additional related molecules by means such as hybridization-based approaches.

A nucleic acid of the invention can be altered by any means. For example, random or stochastic methods, or, non-stochastic, or "directed evolution," methods. Methods for random mutation of genes are well known in the art, see, e.g., U.S. Pat. No. 5,830,696. For example, mutagens can be used to randomly mutate a gene. Mutagens include, e.g., ultraviolet light or gamma irradiation, or a chemical mutagen, e.g., mitomycin, nitrous acid, photoactivated psoralens, alone or in combination, to induce DNA breaks amenable to repair by recombination. Other chemical mutagens include, for example, sodium bisulfite, nitrous acid, hydroxylamine, hydrazine or formic acid. Other mutagens are analogues of nucleotide precursors, e.g., nitrosoguanidine, 5-bromouracil, 2-aminopurine, or acridine. These agents can be added to a PCR reaction in place of the nucleotide precursor thereby mutating the sequence. Intercalating agents such as proflavine, acriflavine, quinacrine and the like can also be used.

Any technique in molecular biology can be used, e.g., random PCR mutagenesis, see, e.g., Rice (1992) Proc. Natl. Acad. Sci. USA 89:5467-5471; or, combinatorial multiple cassette mutagenesis, see, e.g., Crameri (1995) Biotechniques 18:194-196. Alternatively, nucleic acids, e.g., genes, can be reassembled after random, or "stochastic," fragmentation, see, e.g., U.S. Pat. Nos. 6,291,242; 6,287,862; 6,287,861; 5,955,358; 5,830,721; 5,824,514; 5,811,238; 5,605,793. In alternative aspects, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturation mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

The following publications describe a variety of recursive recombination procedures and/or methods which can be incorporated into the methods of the invention: Stemmer (1999) "Molecular breeding of viruses for targeting and other clinical properties" Tumor Targeting 4:1-4; Ness (1999) Nature Biotechnology 17:893-896; Chang (1999) "Evolution of a cytokine using DNA family shuffling" Nature Biotechnology 17:793-797; Minshull (1999) "Protein evolution by molecular breeding" Current Opinion in Chemical Biology 3:284-290; Christians (1999) "Directed evolution of thymidine kinase for AZT phosphorylation using DNA family shuffling" Nature Biotechnology 17:259-264; Crameri (1998) "DNA shuffling of a family of genes from diverse species accelerates directed evolution" Nature 391:288-291; Crameri (1997) "Molecular evolution of an arsenate detoxification pathway by DNA shuffling," Nature Biotechnology 15:436-438; Zhang (1997) "Directed evolution of an effective fucosidase from a galactosidase by DNA shuffling and screening" Proc. Natl. Acad. Sci. USA 94:4504-4509; Patten et al. (1997) "Applications of DNA Shuffling to Pharmaceuticals and Vaccines" Current Opinion in Biotechnology 8:724-733; Crameri et al. (1996) "Construction and evolution of antibody-phage libraries by DNA shuffling" Nature Medicine 2:100-103; Crameri et al. (1996) "Improved green fluorescent protein by molecular evolution using DNA shuffling" Nature Biotechnology 14:315-319; Gates et al. (1996) "Affinity selective isolation of ligands from peptide libraries through display on a lac repressor 'headpiece dimer'" Journal of Molecular Biology 255:373-386; Stemmer (1996) "Sexual PCR and Assembly PCR" In: The Encyclopedia of Molecular Biology. VCH Publishers, New York. pp. 447-457; Crameri and Stemmer (1995) "Combinatorial multiple cassette mutagenesis creates all the permutations of mutant and wildtype cassettes" BioTechniques 18:194-195; Stemmer et al. (1995) "Single-step assembly of a gene and entire plasmid form large numbers of oligodeoxyribonucleotides" Gene, 164:49-53; Stemmer (1995) "The Evolution of Molecular Computation" Science 270: 1510; Stemmer (1995) "Searching Sequence Space" Bio/Technology 13:549-553; Stemmer (1994) "Rapid evolution of a protein in vitro by DNA shuffling" Nature 370:389-391; and Stemmer (1994) "DNA shuffling by random fragmentation and reassembly: In vitro recombination for molecular evolution." Proc. Natl. Acad. Sci. USA 91:10747-10751.

Mutational methods of generating diversity include, for example, site-directed mutagenesis (Ling et al. (1997) "Approaches to DNA mutagenesis: an overview" Anal Biochem. 254(2): 157-178; Dale et al. (1996) "Oligonucleotide-directed random mutagenesis using the phosphorothioate method" Methods Mol. Biol. 57:369-374; Smith (1985) "In vitro mutagenesis" Ann. Rev. Genet. 19:423-462; Botstein & Shortle (1985) "Strategies and applications of in vitro mutagenesis" Science 229:1193-1201; Carter (1986) "Site-directed mutagenesis" Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488-492; Kunkel et al. (1987) "Rapid and efficient site-specific mutagenesis without phenotypic selection" Methods in Enzymol. 154, 367-382; and Bass et al. (1988) "Mutant Trp repressors with new DNA-binding specificities" Science 242:240-245); oligonucleotide-directed mutagenesis (Methods in Enzymol. 100: 468-500 (1983); Methods in Enzymol. 154: 329-350 (1987); Zoller & Smith (1982) "Oligonucleotide-directed mutagenesis using M13-derived vectors: an efficient and general procedure for the production of point mutations in any DNA fragment" Nucleic Acids Res. 10:6487-6500; Zoller & Smith (1983) "Oligonucleotide-directed mutagenesis of DNA fragments cloned into M13 vectors" Methods in Enzymol. 100:468-500; and Zoller & Smith (1987) "Oligonucleotide-directed mutagenesis: a simple method using two oligonucleotide primers and a single-stranded DNA template" Methods in Enzymol. 154:329-350); phosphorothioate-modified DNA mutagenesis (Taylor et al. (1985) "The use of phosphorothioate-modified DNA in restriction enzyme reactions to prepare nicked DNA" Nucl. Acids Res. 13: 8749-8764; Taylor et al. (1985) "The rapid generation of oligonucleotide-directed mutations at high frequency using phosphorothioate-modified DNA" Nucl. Acids Res. 13: 8765-8787 (1985); Nakamaye (1986) "Inhibition of restriction endonuclease Nci I cleavage by phosphorothioate groups and its application to oligonucleotide-directed mutagenesis" Nucl. Acids Res. 14: 9679-9698; Sayers et al. (1988) "Y-T Exonucleases in phosphorothioate-based oligonucleotide-directed mutagenesis" Nucl. Acids Res. 16:791-802; and Sayers et al. (1988) "Strand specific cleavage of phosphorothioate-containing DNA by reaction with restriction endonucleases in the presence of ethidium bromide" Nucl. Acids Res. 16: 803-814); mutagenesis using gapped duplex DNA (Kramer et al. (1984) "The gapped duplex DNA approach to oligonucleotide-directed mutation construction" Nucl. Acids Res. 12: 9441-9456; Kramer & Fritz (1987) Methods in Enzymol. "Oligonucleotide-directed construction of mutations via gapped duplex DNA" 154: 350-367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16: 6987-6999).

Additional protocols used in the methods of the invention include point mismatch repair (Kramer (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh (1986) "Use of oligonucleotides to generate large deletions" Nucl. Acids Res. 14: 5115), restriction-selection and restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar and Khorana (1988) "Total synthesis and expression of a gene for the a-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34:315-323; and Grundstrom et al. (1985) "Oligonucleotide-directed mutagenesis by microscale 'shot-gun' gene synthesis" Nucl. Acids Res. 13: 3305-3316), double-strand break repair (Mandecki (1986); Arnold (1993) "Protein engineering for unusual environments" Current Opinion in Biotechnology 4:450-455. "Oligonucleotide-directed double-strand break repair in plasmids of *Escherichia coli*: a method for site-specific mutagenesis" Proc. Natl. Acad. Sci. USA 83:7177-7181).

Additional details or alternative protocols on many of the above methods can be found in Methods in Enzymology Volume 154, which also describes useful controls for trouble-shooting problems with various mutagenesis methods. See also U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library ImLmunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination."

U.S. applications provide additional details or alternative protocols regarding various diversity generating methods, including "SHUFFLING OF CODON ALTERED GENES" by Patten et al. filed Sep. 28, 1999, (U.S. Ser. No. 09/407, 800); "EVOLUTION OF WHOLE CELLS AND ORGANISMS BY RECURSIVE SEQUENCE RECOMBINATION" by del Cardayre et al., filed Jul. 15, 1998 (U.S. Ser. No. 09/166,188), and Jul. 15, 1999 (U.S. Ser. No. 09/354,922); "OLIGONUCLEOTIDE MEDIATED NUCLEIC ACID RECOMBINATION" by Crameri et al., filed Sep. 28, 1999 (U.S. Ser. No. 09/408,392), and "OLIGONUCLEOTIDE MEDIATED NUCLEIC ACID RECOMBINATION" by Crameri et al., filed Jan. 18, 2000 (PCT/US00/01203); "USE OF CODON-VARIED OLIGONUCLEOTIDE SYNTHESIS FOR SYNTHETIC SHUFFLING" by Welch et al., filed Sep. 28, 1999 (U.S. Ser. No. 09/408,393); "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) and, e.g. "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer, filed Jan. 18, 2000 (PCT/US00/01138); and "SINGLE-STRANDED NUCLEIC ACID TEMPLATE-MEDIATED RECOMBINATION AND NUCLEIC ACID FRAGMENT ISOLATION" by Affholter, filed Sep. 6, 2000 (U.S. Ser. No. 09/656,549).

Non-stochastic, or "directed evolution," methods include, e.g., gene site saturation mutagenesis (GSSM), synthetic ligation reassembly (SLR), or a combination thereof are used to modify the nucleic acids of the invention to generate phytases with new or altered properties (e.g., activity under highly acidic or alkaline conditions, high or low temperatures, and the like). Polypeptides encoded by the modified nucleic acids can be screened for an activity before testing for a phytase or other activity. Any testing modality or protocol can be used, e.g., using a capillary array platform. See, e.g., U.S. Pat. Nos. 6,361,974; 6,280,926; 5,939,250.

Saturation Mutagenesis, or, GSSM

The invention also provides methods for making enzyme using Gene Site Saturation mutagenesis, or, GSSM, as described herein, and also in U.S. Pat. Nos. 6,171,820 and 6,579,258.

In one aspect, codon primers containing a degenerate N,N,G/T sequence are used to introduce point mutations into a polynucleotide, e.g., a phytase enzyme or an antibody of the invention, so as to generate a set of progeny polypeptides in which a full range of single amino acid substitutions is represented at each amino acid position, e.g., an amino acid residue in an enzyme active site or ligand binding site targeted to be modified. These oligonucleotides can comprise a contiguous first homologous sequence, a degenerate N,N,G/T sequence, and, optionally, a second homologous sequence. The downstream progeny translational products from the use of such oligonucleotides include all possible amino acid changes at each amino acid site along the polypeptide, because the degeneracy of the N,N,G/T sequence includes codons for all 20 amino acids. In one aspect, one such degenerate oligonucleotide (comprising, e.g., one degenerate N,N,G/T cassette) is used for subjecting each original codon in a parental polynucleotide template to a full range of codon substitutions. In another aspect, at least two degenerate cassettes are used—either in the same oligonucleotide or not, for subjecting at least two original codons in a parental polynucleotide template to a full range of codon substitutions. For example, more than one N,N,G/T sequence can be contained in one oligonucleotide to introduce amino acid mutations at more than one site. This plurality of N,N,G/T sequences can be directly contiguous, or separated by one or more additional nucleotide sequence(s). In another aspect, oligonucleotides serviceable for introducing additions and deletions can be used either alone or in combination with the codons containing an N,N,G/T sequence, to introduce any combination or permutation of amino acid additions, deletions, and/or substitutions.

In one aspect, simultaneous mutagenesis of two or more contiguous amino acid positions is done using an oligonucleotide that contains contiguous N,N,G/T triplets, i.e. a degenerate (N,N,G/T)n sequence. In another aspect, degenerate cassettes having less degeneracy than the N,N,G/T sequence are used. For example, it may be desirable in some instances to use (e.g. in an oligonucleotide) a degenerate triplet sequence comprising only one N, where said N can be in the first second or third position of the triplet. Any other bases including any combinations and permutations thereof can be used in the remaining two positions of the triplet. Alternatively, it may be desirable in some instances to use (e.g. in an oligo) a degenerate N,N,N triplet sequence.

In one aspect, use of degenerate triplets (e.g., N,N,G/T triplets) allows for systematic and easy generation of a full range of possible natural amino acids (for a total of 20 amino acids) into each and every amino acid position in a polypeptide (in alternative aspects, the methods also include generation of less than all possible substitutions per amino acid residue, or codon, position). For example, for a 100 amino acid polypeptide, 2000 distinct species (i.e. 20 possible amino acids per position×100 amino acid positions) can be generated. Through the use of an oligonucleotide or set of oligonucleotides containing a degenerate N,N,G/T triplet, 32 individual sequences can code for all 20 possible natural amino acids. Thus, in a reaction vessel in which a parental polynucleotide sequence is subjected to saturation mutagenesis using at least one such oligonucleotide, there are generated 32 distinct progeny polynucleotides encoding 20 distinct polypeptides. In contrast, the use of a non-degenerate oligonucleotide in site-directed mutagenesis leads to only one progeny polypeptide product per reaction vessel. Nondegenerate oligonucleotides can optionally be used in combination with degenerate primers disclosed; for example, nondegenerate oligonucleotides can be used to generate specific point mutations in a working polynucleotide. This provides one means to generate specific silent point mutations, point mutations leading to corresponding amino acid changes, and point mutations that cause the generation of stop codons and the corresponding expression of polypeptide fragments.

In one aspect, each saturation mutagenesis reaction vessel contains polynucleotides encoding at least 20 progeny polypeptide (e.g., phytase enzymes) molecules such that all 20 natural amino acids are represented at the one specific amino acid position corresponding to the codon position mutagenized in the parental polynucleotide (other aspects use less than all 20 natural combinations). The 32-fold degenerate progeny polypeptides generated from each saturation mutagenesis reaction vessel can be subjected to clonal amplification (e.g. cloned into a suitable host, e.g., E. coli host, using, e.g., an expression vector) and subjected to expression screening. When an individual progeny polypeptide is identified by screening to display a favorable change in property (when compared to the parental polypeptide, such as increased glucan hydrolysis activity under alkaline or acidic conditions), it can be sequenced to identify the correspondingly favorable amino acid substitution contained therein.

In one aspect, upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e. 2 at each of three positions) and no change at any position.

In yet another aspect, site-saturation mutagenesis can be used together with shuffling, chimerization, recombination and other mutagenizing processes, along with screening. This invention provides for the use of any mutagenizing process(es), including saturation mutagenesis, in an iterative manner. In one exemplification, the iterative use of any mutagenizing process(es) is used in combination with screening.

The invention also provides for the use of proprietary codon primers (containing a degenerate N,N,N sequence) to introduce point mutations into a polynucleotide, so as to generate a set of progeny polypeptides in which a full range of single amino acid substitutions is represented at each amino acid position (Gene Site Saturation Mutagenesis (GSSM)). The oligos used are comprised contiguously of a first homologous sequence, a degenerate N,N,N sequence and in one aspect but not necessarily a second homologous sequence. The downstream progeny translational products from the use of such oligos include all possible amino acid changes at each amino acid site along the polypeptide, because the degeneracy of the N,N,N sequence includes codons for all 20 amino acids.

In one aspect, one such degenerate oligo (comprising one degenerate N,N,N cassette) is used for subjecting each original codon in a parental polynucleotide template to a full range of codon substitutions. In another aspect, at least two degenerate N,N,N cassettes are used—either in the same oligo or not, for subjecting at least two original codons in a parental polynucleotide template to a full range of codon substitutions. Thus, more than one N,N,N sequence can be contained in one oligo to introduce amino acid mutations at more than one site. This plurality of N,N,N sequences can be directly contiguous, or separated by one or more additional nucleotide sequence(s). In another aspect, oligos serviceable for introducing additions and deletions can be used either alone or in combination with the codons containing an N,N,N sequence, to introduce any combination or permutation of amino acid additions, deletions and/or substitutions.

In a particular exemplification, it is possible to simultaneously mutagenize two or more contiguous amino acid positions using an oligo that contains contiguous N,N,N triplets, i.e. a degenerate $(N,N,N)_n$ sequence.

In another aspect, the present invention provides for the use of degenerate cassettes having less degeneracy than the N,N,N sequence. For example, it may be desirable in some instances to use (e.g. in an oligo) a degenerate triplet sequence comprising only one N, where the N can be in the first second or third position of the triplet. Any other bases including any combinations and permutations thereof can be used in the remaining two positions of the triplet. Alternatively, it may be desirable in some instances to use (e.g., in an oligo) a degenerate N,N,N triplet sequence, N,N,G/T, or an N,N, G/C triplet sequence.

It is appreciated, however, that the use of a degenerate triplet (such as N,N,G/T or an N,N, G/C triplet sequence) as disclosed in the instant invention is advantageous for several reasons. In one aspect, this invention provides a means to systematically and fairly easily generate the substitution of the full range of possible amino acids (for a total of 20 amino acids) into each and every amino acid position in a polypeptide. Thus, for a 100 amino acid polypeptide, the invention provides a way to systematically and fairly easily generate 2000 distinct species (i.e., 20 possible amino acids per position times 100 amino acid positions). It is appreciated that there is provided, through the use of an oligo containing a degenerate N,N,G/T or an N,N, G/C triplet sequence, 32 individual sequences that code for 20 possible amino acids. Thus, in a reaction vessel in which a parental polynucleotide sequence is subjected to saturation mutagenesis using one such oligo, there are generated 32 distinct progeny polynucleotides encoding 20 distinct polypeptides. In contrast, the use of a non-degenerate oligo in site-directed mutagenesis leads to only one progeny polypeptide product per reaction vessel.

This invention also provides for the use of nondegenerate oligos, which can optionally be used in combination with degenerate primers disclosed. It is appreciated that in some situations, it is advantageous to use nondegenerate oligos to generate specific point mutations in a working polynucleotide. This provides a means to generate specific silent point mutations, point mutations leading to corresponding amino acid changes and point mutations that cause the generation of stop codons and the corresponding expression of polypeptide fragments.

Thus, in one aspect of this invention, each saturation mutagenesis reaction vessel contains polynucleotides encoding at least 20 progeny polypeptide molecules such that all 20 amino acids are represented at the one specific amino acid position corresponding to the codon position mutagenized in the parental polynucleotide. The 32-fold degenerate progeny polypeptides generated from each saturation mutagenesis reaction vessel can be subjected to clonal amplification (e.g., cloned into a suitable E. coli host using an expression vector) and subjected to expression screening. When an individual progeny polypeptide is identified by screening to display a favorable change in property (when compared to the parental polypeptide), it can be sequenced to identify the correspondingly favorable amino acid substitution contained therein.

It is appreciated that upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid and each of two favorable changes) and 3 positions. Thus, there are 3×3×3 or 27 total possibilities, including 7 that were previously examined—6 single point mutations (i.e., 2 at each of three positions) and no change at any position.

Thus, in a non-limiting exemplification, this invention provides for the use of saturation mutagenesis in combination with additional mutagenization processes, such as process where two or more related polynucleotides are introduced into a suitable host cell such that a hybrid polynucleotide is generated by recombination and reductive reassortment.

In addition to performing mutagenesis along the entire sequence of a gene, the instant invention provides that mutagenesis can be use to replace each of any number of bases in a polynucleotide sequence, wherein the number of bases to be mutagenized is in one aspect every integer from 15 to 100,000. Thus, instead of mutagenizing every position along a molecule, one can subject every or a discrete number of bases (in one aspect a subset totaling from 15 to 100,000) to mutagenesis. In one aspect, a separate nucleotide is used for mutagenizing each position or group of positions along a polynucleotide sequence. A group of 3 positions to be mutagenized may be a codon. The mutations can be introduced using a mutagenic primer, containing a heterologous cassette, also referred to as a mutagenic cassette. Exemplary cassettes can have from 1 to 500 bases. Each nucleotide position in such heterologous cassettes be N, A, C, G, T, A/C, A/G, A/T, C/G, C/T, G/T, C/G/T, A/G/T, A/C/T, A/C/G, or E, where E is any base that is not A, C, G, or T (E can be referred to as a designer oligo).

In a general sense, saturation mutagenesis is comprised of mutagenizing a complete set of mutagenic cassettes (wherein each cassette is in one aspect about 1-500 bases in length) in defined polynucleotide sequence to be mutagenized (wherein the sequence to be mutagenized is in one aspect from about 15 to 100,000 bases in length). Thus, a group of mutations (ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons and groupings of particular nucleotide cassettes.

Defined sequences to be mutagenized include a whole gene, pathway, cDNA, an entire open reading frame (ORF) and entire promoter, enhancer, repressor/transactivator, origin of replication, intron, operator, or any polynucleotide functional group. Generally, a "defined sequences" for this purpose may be any polynucleotide that a 15 base-polynucleotide sequence and polynucleotide sequences of lengths between 15 bases and 15,000 bases (this invention specifically names every integer in between). Considerations in choosing groupings of codons include types of amino acids encoded by a degenerate mutagenic cassette.

In one exemplification a grouping of mutations that can be introduced into a mutagenic cassette, this invention specifically provides for degenerate codon substitutions (using degenerate oligos) that code for 2, 3, 4, 5, 6, 7, 8, 9, 10, 11, 12, 13, 14, 15, 16, 17, 18, 19 and 20 amino acids at each position and a library of polypeptides encoded thereby.

Synthetic Ligation Reassembly (SLR)

The invention provides a non-stochastic gene modification system termed "synthetic ligation reassembly," or simply "SLR," a "directed evolution process," to generate polypeptides, e.g., phytase enzymes or antibodies of the invention, with new or altered properties. SLR is a method of ligating oligonucleotide fragments together non-stochastically. This method differs from stochastic oligonucleotide shuffling in that the nucleic acid building blocks are not shuffled, concatenated or chimerized randomly, but rather are assembled non-stochastically. See, e.g., U.S. Pat. Nos. 6,773,900; 6,740,506; 6,713,282; 6,635,449; 6,605,449; 6,537,776.

In one aspect, SLR comprises the following steps: (a) providing a template polynucleotide, wherein the template polynucleotide comprises sequence encoding a homologous gene; (b) providing a plurality of building block polynucleotides, wherein the building block polynucleotides are designed to cross-over reassemble with the template polynucleotide at a predetermined sequence, and a building block polynucleotide comprises a sequence that is a variant of the homologous gene and a sequence homologous to the template polynucleotide flanking the variant sequence; (c) combining a building block polynucleotide with a template polynucleotide such that the building block polynucleotide cross-over reassembles with the template polynucleotide to generate polynucleotides comprising homologous gene sequence variations.

SLR does not depend on the presence of high levels of homology between polynucleotides to be rearranged. Thus, this method can be used to non-stochastically generate libraries (or sets) of progeny molecules comprising over $10^{100}$ different chimeras. SLR can be used to generate libraries comprising over $10^{1000}$ different progeny chimeras. Thus, aspects of the present invention include non-stochastic methods of producing a set of finalized chimeric nucleic acid molecule shaving an overall assembly order that is chosen by design. This method includes the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus the overall assembly order in which the nucleic acid building blocks can be coupled is specified by the design of the ligatable ends. If more than one assembly step is to be used, then the overall assembly order in which the nucleic acid building blocks can be coupled is also specified by the sequential order of the assembly step(s). In one aspect, the annealed building pieces are treated with an enzyme, such as a ligase (e.g. T4 DNA ligase), to achieve covalent bonding of the building pieces. In one aspect, a non-stochastic method termed synthetic ligation reassembly (SLR), that is somewhat related to stochastic shuffling, save that the nucleic acid building blocks are not shuffled or concatenated or chimerized randomly, but rather are assembled non-stochastically can be used to create variants.

The SLR method does not depend on the presence of a high level of homology between polynucleotides to be shuffled. The invention can be used to non-stochastically generate libraries (or sets) of progeny molecules comprising over $10^{100}$ different chimeras. Conceivably, SLR can even be used to generate libraries comprising over $10^{1000}$ different progeny chimeras.

Thus, in one aspect, the invention provides a non-stochastic method of producing a set of finalized chimeric nucleic acid molecules having an overall assembly order that is chosen by design, which method is comprises the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). In one aspect of the invention, the annealed building pieces are treated with an enzyme, such as a ligase (e.g., T4 DNA ligase) to achieve covalent bonding of the building pieces.

In a another aspect, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, i.e. chimerized or shuffled.

In one exemplification, the invention provides for the chimerization of a family of related genes and their encoded family of related products. In a particular exemplification, the encoded products are enzymes. Enzymes and polypeptides for use in the invention can be mutagenized in accordance with the methods described herein.

Thus according to one aspect of the invention, the sequences of a plurality of progenitor nucleic acid templates are aligned in order to select one or more demarcation points, which demarcation points can be located at an area of homology. The demarcation points can be used to delineate the boundaries of nucleic acid building blocks to be generated. Thus, the demarcation points identified and selected in the progenitor molecules serve as potential chimerization points in the assembly of the progeny molecules.

Typically a serviceable demarcation point is an area of homology (comprised of at least one homologous nucleotide base) shared by at least two progenitor templates, but the demarcation point can be an area of homology that is shared by at least half of the progenitor templates, at least two thirds of the progenitor templates, at least three fourths of the progenitor templates, or almost all of the progenitor templates. In one aspect, a serviceable demarcation point is an area of homology that is shared by all of the progenitor templates.

In one aspect, the ligation reassembly process is performed exhaustively in order to generate an exhaustive library. In other words, all possible ordered combinations of the nucleic acid building blocks are represented in the set of finalized chimeric nucleic acid molecules. At the same time, the assembly order (i.e. the order of assembly of each building block in the 5' to 3 sequence of each finalized chimeric nucleic acid) in each combination is by design (or non-stochastic). Because of the non-stochastic nature of the method, the possibility of unwanted side products is greatly reduced.

In another aspect, the method provides that, the ligation reassembly process is performed systematically, for example in order to generate a systematically compartmentalized library, with compartments that can be screened systematically, e.g., one by one. In other words the invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant ligation reassembly invention, the progeny molecules generated can comprise a library of finalized chimeric nucleic acid molecules having an overall assembly order that is chosen by design. In a particularly aspect, such a generated library is comprised of greater than $10^3$ to greater than $10^{1000}$ different progeny molecular species.

In one aspect, a set of finalized chimeric nucleic acid molecules, produced as described is comprised of a polynucleotide encoding a polypeptide. According to one aspect, this polynucleotide is a gene, which may be a man-made gene. According to another aspect, this polynucleotide is a gene pathway, which may be a man-made gene pathway. The invention provides that one or more man-made genes generated by the invention may be incorporated into a man-made gene pathway, such as pathway operable in a eukaryotic organism (including a plant).

In another exemplification, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g., by mutagenesis) or in an in vivo process (e.g., by utilizing the gene splicing ability of a host organism). It is appreciated that in many instances the introduction of these nucleotides may also be desirable for many other reasons in addition to the potential benefit of creating a serviceable demarcation point.

Thus, according to another aspect, the invention provides that a nucleic acid building block can be used to introduce an intron. Thus, the invention provides that functional introns may be introduced into a man-made gene of the invention. The invention also provides that functional introns may be introduced into a man-made gene pathway of the invention. Accordingly, the invention provides for the generation of a chimeric polynucleotide that is a man-made gene containing one (or more) artificially introduced intron(s).

Accordingly, the invention also provides for the generation of a chimeric polynucleotide that is a man-made gene pathway containing one (or more) artificially introduced intron(s). In one aspect, the artificially introduced intron(s) are functional in one or more host cells for gene splicing much in the way that naturally-occurring introns serve functionally in gene splicing. The invention provides a process of producing man-made intron-containing polynucleotides to be introduced into host organisms for recombination and/or splicing.

A man-made gene produced using the invention can also serve as a substrate for recombination with another nucleic acid. Likewise, a man-made gene pathway produced using the invention can also serve as a substrate for recombination with another nucleic acid. In one aspect, the recombination is facilitated by, or occurs at, areas of homology between the man-made intron-containing gene and a nucleic acid with serves as a recombination partner. In one aspect, the recombination partner may also be a nucleic acid generated by the invention, including a man-made gene or a man-made gene pathway. Recombination may be facilitated by or may occur at areas of homology that exist at the one (or more) artificially introduced intron(s) in the man-made gene.

The synthetic ligation reassembly method of the invention utilizes a plurality of nucleic acid building blocks, each of which can have two ligatable ends. The two ligatable ends on each nucleic acid building block may be two blunt ends (i.e. each having an overhang of zero nucleotides), or one blunt end and one overhang, or two overhangs.

A useful overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

In one aspect, a nucleic acid building block is generated by chemical synthesis of two single-stranded nucleic acids (also referred to as single-stranded oligos) and contacting them so as to allow them to anneal to form a double-stranded nucleic acid building block.

A double-stranded nucleic acid building block can be of variable size. The sizes of these building blocks can be small or large. Exemplary sizes for building block range from 1 base pair (not including any overhangs) to 100,000 base pairs (not including any overhangs). Other size ranges are also provided, which have lower limits of from 1 bp to 10,000 bp (including every integer value in between), and upper limits of from 2 bp to 100,000 bp (including every integer value in between).

Many methods exist by which a double-stranded nucleic acid building block can be generated that is serviceable for the invention; and these are known in the art and can be readily performed by the skilled artisan.

According to one aspect, a double-stranded nucleic acid building block is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another aspect, the two strands of a double-stranded nucleic acid building block are complementary at fewer than every nucleotide apart from any that form an overhang. Thus, according to this aspect, a double-stranded nucleic acid building block can be used to introduce codon degeneracy. In one aspect, the codon degeneracy is introduced using the site-saturation mutagenesis described herein, using one or more N,N,G/T cassettes or alternatively using one or more N,N,N cassettes.

The in vivo recombination method of the invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of expression. This approach may also be useful in the study of repetitive DNA sequences. Finally, this approach may be useful to mutate ribozymes or aptamers.

In one aspect variants of the polynucleotides and polypeptides described herein are obtained by the use of repeated cycles of reductive reassortment, recombination and selection which allow for the directed molecular evolution of highly complex linear sequences, such as DNA, RNA or proteins thorough recombination.

In vivo shuffling of molecules is useful in providing variants and can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In another aspect, the invention includes a method for producing a hybrid polynucleotide from at least a first polynucleotide and a second polynucleotide. The invention can be used to produce a hybrid polynucleotide by introducing at least a first polynucleotide and a second polynucleotide which share at least one region of partial sequence homology (e.g., SEQ ID NO:1) into a suitable host cell. The regions of partial sequence homology promote processes that result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

The invention provides methods for generating hybrid polynucleotides which may encode biologically active hybrid polypeptides (e.g., a hybrid phytase). In one aspect, the original polynucleotides encode biologically active polypeptides. The method of the invention produces new hybrid polypeptides by utilizing cellular processes which integrate the sequence of the original polynucleotides such that the resulting hybrid polynucleotide encodes a polypeptide demonstrating activities derived from the original biologically active polypeptides. For example, the original polynucleotides may encode a particular enzyme from different microorganisms. An enzyme encoded by a first polynucleotide from one organism or variant may, for example, function effectively under a particular environmental condition, e.g., high salinity. An enzyme encoded by a second polynucleotide from a different organism or variant may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

In addition to the various methods described above, various methods are known in the art that can be used to obtain hybrid polynucleotides with enhanced enzymatic properties. The following examples illustrate the use of such procedures for obtaining thermostable or thermotolerant enzymes by mutagenesis of a polynucleotide encoding a wild-type enzyme of interest.

For example, in one aspect, the invention uses methods as described by M. Lehmann et al. (in *Biochimica et Biophysica Acta* 1543:408-415, 2000) describes a "consensus approach" wherein sequence alignment of homologous fungal phytases was used to calculate a consensus phytase amino acid sequence. Upon construction of the corresponding consensus gen, recombinant expression and purification, the recombinant phytase obtained displayed an unfolding temperature (Tm) 15-22° C. higher than that of all parent phytases used in the design. Site-directed mutagenesis of the gene encoding the recombinant protein was used to further increase the Tm value to 90.4° C. The thermostabilizing effect was attributed to a combination of multiple amino acid exchanges that were distributed over the entire sequence of the protein and mainly affected surface-exposed residues.

In one aspect, the invention uses methods to obtaining an enzyme with enhanced thermal properties as described by L. Jermutus et al. (J. of Biotechnology 85:15-24, 2001). In this approach ionic interactions and hydrogen bonds on the surface of *Aspergillus terreus* phytase were first restored to correspond to those present in the homologous, but more thermostable enzyme from *A. niger*. Then entire secondary structural elements were replaced in the same region and based on the crystal structure of *A. niger* phytase. The replacement of one helix on the surface of *A. terreus* phytase by the corresponding stretch of *A niger* phytase resulted in a structure-based chimeric enzyme (fusion protein) with improved thermostability and unaltered enzymatic activity.

In one aspect, the invention uses methods as described by L. Giver et al. (*Proc. Natl. Acad. Sci. USA* 95:12809-12813, 1998), who describes a procedure wherein six generations of random mutagenesis introduced during mutagenic PCR of a polynucleotide encoding *Bacillus subtilis* p-nitrobenzyl esterase followed by in vitro recombination based on the method of Stemmer resulted in a recombinant esterase with increased thermostability (greater than 14° C. increase in Tm) without compromising catalytic activity at lower temperatures.

In one aspect, the invention uses methods as described by C. Vetriani et al. (*Proc. Natl. Acad. Sci USA* 95:12300-12305, 1998), who describes a procedure by which homology-based modeling and direct structure comparison of the hexameric glutamate dehydrogenases from the hyperthermophiles *Pyrococcus furiosus* and *Thermococcus litoralis*, with optimal growth temperatures of 100° C. and 88° C., respectively, were used to determine key thermostabilizing features. An intersubunit ion-pair network observed to be substantially reduced in the less stable enzyme was altered by mutagenesis of two residues therein to restore the interactions found in the more stable enzyme. Although either single mutation had adverse effects on the thermostability, with both mutations in place, a four-fold improvement of stability at 104° C. over the wild-type enzyme was observed.

In one aspect, the invention uses methods as described by A. Tomschy et al. (*Protein Science* 9:1304-1311, 2000), who describes a procedure utilizing the crystal structure of *Aspergillus Niger* phytase (at 2.5 angstroms resolution) to specify all active sites of the enzyme. A multiple amino acid sequence alignment was then used to identify non-conserved active site residues that might correlate with a given favorable property of interest. Using this approach, Gln27 of *A. fumigatus* phytase, which differed from Leu27 of *A. niger*, was identified as likely to be involved in substrate binding and/or release and responsible for the lower specific activity of the *A. fumigatus* phytase (26.5 vs. 196 6 U/mg protein at pH 5.0). Site directed mutagenesis of Gln27 of *A. fumigatus* phytase to Leu increased the specific activity of the mutant enzyme to 92.1 U/mg protein.

Transgenic Plants and Seeds

The invention provides transgenic plants and seeds comprising a nucleic acid, a polypeptide, an expression cassette, cloning mechanism or vector of the invention, or a transfected or transformed cell of the invention. The invention also provides plant products, e.g., oils, seeds, leaves, extracts and the like, comprising a nucleic acid and/or a polypeptide of the invention. The transgenic plant can be dicotyledonous (a dicot) or monocotyledonous (a monocot). The invention also provides methods of making and using these transgenic plants and seeds. The transgenic plant or plant cell expressing a polypeptide of the present invention may be constructed in accordance with any method known in the art. See, for example, U.S. Pat. No. 6,309,872.

The recombinant expression, or over-expression, of the phytase molecules of the invention may be achieved in combination with one or more additional molecules such as, for example, other enzymes. This approach is useful for producing combination products, such as a plant or plant part that contains the instant phytase molecules as well as one or more additional molecules. The phytase molecules of this invention and the additional molecules can be used in a combination treatment. The resulting recombinantly expresssed molecules may be used in homogenized and/or purified form or alternatively in relatively unpurified form (e.g. as consumable plant parts that are useful when admixed with other foodstuffs for catalyzing the degradation of phytate).

In a particular aspect, the present invention provides for the expression of phytase in transgenic plants or plant organs and methods for the production thereof. DNA expression constructs are provided for the transformation of plants with a gene encoding phytase under the control of regulatory sequences which are capable of directing the expression of phytase. These regulatory sequences include sequences capable of directing transcription in plants, either constitutively, or in stage and/or tissue specific manners.

The manner of expression depends, in part, on the use of the plant or parts thereof. The transgenic plants and plant organs provided by the present invention may be applied to a variety of industrial processes either directly, e.g. in animal feeds or alternatively, the expressed phytase may be extracted and if desired, purified before application. Alternatively, the recombinant host plant or plant part may be used directly. In a particular aspect, the present invention provides methods of catalyzing phytate-hydrolyzing reactions using seeds containing enhanced amounts of phytase. The method involves contacting transgenic, non-wild type seeds, e.g., in a ground or chewed form, with phytate-containing substrate and allowing the enzymes in the seeds to increase the rate of reaction. By directly adding the seeds to a phytate-containing substrate, the invention provides a solution to the expensive and problematic process of extracting and purifying the enzyme. In one exemplification the present invention provides methods of treatment whereby an organism lacking a sufficient supply of an enzyme is administered the enzyme in the form of seeds containing enhanced amounts of the enzyme. In one aspect, the timing of the administration of the enzyme to an organism is coordinated with the consumption of a phytate-containing foodstuff.

The expression of phytase in plants can be achieved by a variety of means. Specifically, for example, technologies are available for transforming a large number of plant species, including dicotyledonous species (e.g. tobacco, potato, tomato, *Petunia, Brassica*) and monocot species. Additionally, for example, strategies for the expression of foreign genes in plants are available. Additionally still, regulatory sequences from plant genes have been identified that are serviceable for the construction of chimeric genes that can be functionally expressed in plants and in plant cells (e.g. Klee (1987) Ann. Rev. of Plant Phys. 38:467-486; Clark et al. (1990) Virology December; 179(2):640-7; Smith et al. (1990) Mol. Gen. Genet. December; 224(3):477-81.

The introduction of gene constructs into plants can be achieved using several technologies including transformation with *Agrobacterium tumefaciens* or *Agrobacterium rhizogenes*. Non-limiting examples of plant tissues that can be transformed thusly include protoplasts, microspores or pollen, and explants such as leaves, stems, roots, hypocotyls, and cotyls. Furthermore, DNA can be introduced directly into protoplasts and plant cells or tissues by microinjection, electroporation, particle bombardment, and direct DNA uptake.

Proteins may be produced in plants by a variety of expression systems. For instance, the use of a constitutive promoter such as the 35S promoter of Cauliflower Mosaic Virus (Guilley et al., 1982) is serviceable for the accumulation of the expressed protein in virtually all organs of the transgenic plant. Alternatively, the use of promoters that are highly tissue-specific and/or stage-specific are serviceable for this invention (Higgins, 1984; Shotwell, 1989) in order to bias expression towards desired tissues and/or towards a desired stage of development. The invention also uses protocols for expression in plants of phytase molecules of the instant invention as disclosed in, for example, U.S. Pat. No. 5,770,413 (Van Ooijen et al.) and U.S. Pat. No. 5,593,963 (Van Ooijen et al.), that teaches use of fungal phytases.
Modification of Coding Sequences and Adjacent Sequences The transgenic expression in plants of genes derived from heterologous sources may involve the modification of those genes to achieve and optimize their expression in plants. In particular, bacterial ORFs which encode separate enzymes but which are encoded by the same transcript in the native microbe are best expressed in plants on separate transcripts.

Thus, in one aspect, to achieve this, each microbial ORF is isolated individually and cloned within a cassette which provides a plant promoter sequence at the 5' end of the ORF and a plant transcriptional terminator at the 3' end of the ORF. The isolated ORF sequence can includes the initiating ATG codon and the terminating STOP codon but may include additional sequence beyond the initiating ATG and the STOP codon. In addition, the ORF may be truncated, but still retain the required activity; for particularly long ORFs, truncated versions which retain activity may be preferable for expression in transgenic organisms. "Plant promoters" and "plant transcriptional terminators" that can be used to practice this invention include any promoters and/or transcriptional terminators which operate within plant cells. This includes promoters and transcription terminators which may be derived from non-plant sources such as viruses (an example is the Cauliflower Mosaic Virus).

In some cases, modification to the ORF coding sequences and adjacent sequence is not required. It is sufficient to isolate a fragment containing the ORF of interest and to insert it downstream of a plant promoter. For example, Gaffney et. al. (Science 261: 754-756 (1993)) have expressed the *Pseudomonas* nahG gene in transgenic plants under the control of the CaMV 35S promoter and the CaMV tml terminator successfully without modification of the coding sequence and with nucleotides of the *Pseudomonas* gene upstream of the ATG still attached, and nucleotides downstream of the STOP codon still attached to the nahG ORF. Preferably as little adjacent microbial sequence should be left attached upstream of the ATG and downstream of the STOP codon. In practice, such construction may depend on the availability of restriction sites.

In other cases, the expression of genes derived from microbial sources may provide problems in expression. These problems have been well characterized in the art and are particularly common with genes derived from certain microbial sources. These problems may apply to the nucleotide sequence of this invention and the modification of these genes can be undertaken using techniques now well known in the art. The following problems may be encountered:
Codon Usage The invention provides nucleic acids having codons modified for usage in plants; in some cases preferred codon usage in plants differs from the preferred codon usage in certain microorganisms. Comparison of the usage of codons within a cloned microbial ORF to usage in plant genes (and in particular genes from the target plant) will enable an identification of the codons within the ORF which should preferably be changed. Typically plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome.
GC/AT Content The invention provides nucleic acids having their GC content modified, e.g., for usage in plants; plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as splice sites (see below).

Sequences Adjacent to the Initiating Methionine

The invention provides nucleic acids having nucleotides adjacent to the ATG modified and/or added; plants differ from microorganisms in that their messages do not possess a defined ribosome binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be enhanced by the inclusion of a eukaryotic consensus translation initiator at the ATG. Clontech (1993/1994 catalog, page 210, incorporated herein by reference) have suggested one sequence as a consensus translation initiator for the expression of the *E. coli* uidA gene in plants. Further, Joshi (*N.A.R.* 15: 6643-6653 (1987), incorporated herein by reference) has compared many plant sequences adjacent to the ATG and suggests another consensus sequence. In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. In some aspects, preferred sequences adjacent to the initiating methionine may differ between different plant species. A survey of 14 maize genes located in the GenBank database provided the following results:

Position Before the Initiating ATG in 14 Maize Genes

|   | -10 | -9 | -8 | -7 | -6 | -5 | -4 | -3 | -2 | -1 |
|---|-----|----|----|----|----|----|----|----|----|-----|
| C | 3 | 8 | 4 | 6 | 2 | 5 | 6 | 0 | 10 | 7 |
| T | 3 | 0 | 3 | 4 | 3 | 2 | 1 | 1 | 1 | 0 |
| A | 2 | 3 | 1 | 4 | 3 | 2 | 3 | 7 | 2 | 3 |
| G | 6 | 3 | 6 | 0 | 6 | 5 | 4 | 6 | 1 | 5 |

This analysis can be done for the desired plant species into which the nucleotide sequence is being incorporated, and the sequence adjacent to the ATG modified to incorporate the preferred nucleotides.

Removal of Illegitimate Splice Sites

The invention provides nucleic acids having illegitimate splice sites modified or removed or functionally "knocked out"; genes cloned from non-plant sources and not optimized for expression in plants may also contain motifs which may be recognized in plants as 5' or 3' splice sites, and be cleaved, thus generating truncated or deleted messages. These sites can be removed using the techniques well known in the art.

Techniques for the modification of coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. These are, for example, described in the published patent disclosures EP 0 385 962 (to Monsanto), EP 0 359 472 (to Lubrizol) and WO 93/07278 (to Ciba-Geigy), all of which are incorporated herein by reference. In most cases it is preferable to assay the expression of gene constructions using transient assay protocols (which are well known in the art) prior to their transfer to transgenic plants.

Plant Promoters

The compositions of the invention may contain nucleic acid sequences, e.g., promoters, e.g., for transformation and expression in a plant of interest. The nucleic acid sequences may be present in DNA constructs or expression cassettes. Nucleic acids of the invention can be, or comprise, "expression cassettes", including any nucleic acid molecule capable of directing expression of a particular nucleotide sequence in an appropriate host cell comprising a promoter operatively linked to the nucleotide sequence of interest which is operatively linked to termination signals.

The compositions (e.g., nucleic acid sequences) of the invention also can comprise sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. Additionally, the promoter can also be specific to a particular tissue or organ or stage of development.

The present invention encompasses the transformation of plants with expression cassettes capable of expressing polynucleotides. The expression cassette will include in the 5'-3' direction of transcription, a transcriptional and translational initiation region (i.e., a promoter) and a polynucleotide of interest. The expression cassette may optionally comprise a transcriptional and translational termination region (i.e. termination region) functional in plants. In some embodiments, the expression cassette comprises a selectable marker gene to allow for selection for stable transformants. Expression constructs of the invention may also comprise a leader sequence and/or a sequence allowing for inducible expression of the polynucleotide of interest. See, Guo et. al. (2003) *Plant J.* 34:383-92 and Chen et. al. (2003) *Plant J.* 36:731-40 for examples of sequences allowing for inducible expression.

The regulatory sequences of the expression construct are operably linked to the polynucleotide of interest. By "operably linked" is intended a functional linkage between a promoter and a second sequence wherein the promoter sequence initiates and mediates transcription of the DNA sequence corresponding to the second sequence. Generally, operably linked means that the nucleotide sequences being linked are contiguous.

Any promoter capable of driving expression in the plant of interest may be used in the practice of the invention. The promoter may be native or analogous or foreign or heterologous to the plant host. The terms "heterologous" and "exogenous" when used herein to refer to a nucleic acid sequence (e.g. a DNA or RNA sequence) or a gene, refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. In alternative embodiments, a "homologous" nucleic acid (e.g. DNA) sequence is a nucleic acid (e.g. DNA or RNA) sequence naturally associated with a host cell into which it is introduced.

The choice of promoters to be included depends upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to that sequence.

Some suitable promoters initiate transcription only, or predominantly, in certain cell types. Thus, as used herein a cell type- or tissue-preferential promoter is one that drives expression preferentially in the target tissue, but may also lead to some expression in other cell types or tissues as well. Methods for identifying and characterizing promoter regions in plant genomic DNA include, for example, those described in the following references: Jordano, et. al., Plant Cell, 1:855-866 (1989); Bustos, et. al., Plant Cell, 1:839-854 (1989); Green, et. al., EMBO J. 7, 4035-4044 (1988); Meier, et. al., Plant Cell, 3, 309-316 (1991); and Zhang, et. al., Plant Physiology 110: 1069-1079 (1996).

Several tissue preferred regulated genes and/or promoters have been reported in plants. Some reported tissue preferred genes include the genes encoding the seed storage proteins (such as napin, cruciferin, beta-conglycinin, and phaseolin, prolamines, glutelins, globulins, and zeins) zeins or oil body proteins (such as oleosin), or genes involved in fatty acid biosynthesis (including acyl carrier protein, stearoyl-ACP desaturase, and fatty acid desaturases (fad 2-1)), and other genes expressed during embryo development (such as Bce4, see, for example, EP 255378 and Kridl et. al., (1991) Seed Science Research, 1:209).

Examples of tissue-specific promoters, which have been described, include the lectin (Vodkin, Prog. Clin. Biol. Res., 138; 87 (1983); Lindstrom et. al., (1990) Der. Genet., 11:160), corn alcohol dehydrogenase 1 (Dennis et. al., Nucleic Acids Res., 12:3983 (1984)), corn light harvesting complex (see, e.g., Simpson, (1986) Science, 233:34; Bansal (1992) Proc. Natl. Acad. Sci. USA 89:3654), corn heat shock protein (see, e.g., Odell et. al., (1985) Nature, 313:810; pea small subunit RuBP carboxylase (see, e.g., Poulsen et. al., (1986) Mol. Gen. Genet., 205:193-200; Cashmore et. al., (1983) Gen. Eng. of Plants, Plenum Press, New York, 29-38); Ti plasmid mannopine synthase (see, e.g., Langridge et. al., (1989) Proc. Natl. Acad. Sci. USA, 86:3219-3223), Ti plasmid nopaline synthase (Langridge et. al., (1989) Proc. Natl. Acad. Sci. USA, 86:3219-3223), petunia chalcone isomerase (see, e.g., vanTunen (1988) EMBO J. 7:1257); bean glycine rich protein 1 (see, e.g., Keller (1989) Genes Dev. 3:1639); truncated CaMV 35s (see, e.g., Odell (1985) Nature 313:810); potato patatin (see, e.g., Wenzler (1989) Plant Mol. Biol. 13:347; root cell (see, e.g., Yamamoto (1990) Nucleic Acids Res. 18:7449); maize zein (see, e.g., Reina (1990) Nucleic Acids Res. 18:6425; Lopes et. al. (1995) Mol. Gen. Genet. 247: 603-613; Kriz (1987) Mol. Gen. Genet. 207:90; Wandelt (1989) Nucleic Acids Res., 17:2354; Langridge (1983) Cell, 34:1015; Reina (1990) Nucleic Acids Res., 18:7449), ADP-gpp promoter (see, e.g., U.S. Pat. No. 7,102,057); globulin-1 (see, e.g., Belanger (1991) Genetics 129:863); α-globulin (Sunilkumar, et. al. (2002), Transgenic Res. 11: 347-359); α-tubulin; cab (see, e.g., Sullivan (1989) Mol. Gen. Genet., 215:431); PEPCase (see e.g., Hudspeth & Grula, (1989) Plant Molec. Biol., 12:579-589); R gene complex-associated promoters (Chandler et. al., (1989) Plant Cell, 1:1175); pea vicilin promoter (Czako et. al., (1992) Mol. Gen. Genet., 235:33; U.S. Pat. No. 5,625,136); GTL1 promoter (Takaiwa et. al. (1991) Plant Mol. Biol. 16 (1), 49-58); chalcone synthase promoters (Franken et. al., (1991) EMBO J., 10:2605); GY1 promoter (Sims & Goldburg (1989) Nuc. Acid Res. 17(11) 4368) and the like; all of which are herein incorporated by reference.

The invention can use fruit-preferred promoters, including any class of fruit-preferred promoters, e.g., as expressed at or during antithesis through fruit development, at least until the beginning of ripening, e.g., as discussed in U.S. Pat. No. 4,943,674, the disclosure of which is hereby incorporated by reference. The promoter for polygalacturonase gene is active in fruit ripening. The invention can use the polygalacturonase gene as described, e.g., in U.S. Pat. Nos. 4,535,060, 4,769,061, 4,801,590, and 5,107,065, which disclosures are incorporated herein by reference.

The invention can use any tissue-preferred promoters, including those that direct expression in leaf cells following damage to the leaf (for example, from chewing insects), in tubers (for example, patatin gene promoter), and in fiber cells (an example of a developmentally-regulated fiber cell protein is E6 (John & Crow (1992) PNAS 89:5769-5773). The E6 gene is most active in fiber, although low levels of transcripts are found in leaf, ovule and flower.

The invention can use promoters active in photosynthetic tissue, e.g., in order to drive transcription in green tissues such as leaves and stems, are suitable when they drive expression only or predominantly in such tissues. Alternatively, the invention can use promoters to confer expression constitutively throughout the plant, or differentially with respect to the green tissues, or differentially with respect to the developmental stage of the green tissue in which expression occurs, or in response to external stimuli. Exemplary promoters used to practice this invention include the ribulose-1,5-bisphosphate carboxylase (RbcS) promoters such as the RbcS promoter from eastern larch (*Larix laricina*), the pine cab6 promoter (Yamamoto et. al. (1994) Plant Cell Physiol. 35:773-778), the Cab-1 gene promoter from wheat (Fejes et. al. (1990) Plant Mol. Biol. 15:921-932), the CAB-1 promoter from spinach (Lubberstedt et. al. (1994) Plant Physiol. 104:997-1006), the cab1R promoter from rice (Luan et. al. (1992) Plant Cell 4:971-981), the pyruvate orthophosphate dikinase (PPDK) promoter from corn (Matsuoka et. al. (1993) Proc Natl Acad Sci USA 90:9586-9590), the tobacco Lhcb1*2 promoter (Cerdan et. al. (1997) Plant Mol. Biol. 33:245-255), the *Arabidopsis thaliana* SUC2 sucrose-H+ symporter promoter (Truernit et. al. (1995) Planta 196:564-570), and thylakoid membrane protein promoters from spinach (psaD, psaF, psaE, PC, FNR, atpC, atpD, cab, rbcS. Other promoters that drive transcription in stems, leafs and green tissue are described in U.S. Patent Publication No. 2007/0006346, herein incorporated by reference in its entirety.

In some embodiments, the tissue specificity of some "tissue preferred" promoters may not be absolute and may be tested reporter genes such as Gus or green fluorescent protein, cyan fluorescent protein, yellow fluorescent protein or red fluorescent protein. One can also achieve tissue preferred expression with "leaky" expression by a combination of different tissue-preferred promoters. Other tissue preferred promoters can be isolated by one skilled in the art (see U.S. Pat. No. 5,589,379).

In one aspect, plant promoters which are inducible upon exposure to plant hormones, such as auxins, are used to express the nucleic acids of the invention. For example, the invention can use the auxin-response elements E1 promoter fragment (AuxREs) in the soybean (*Glycine max* L.) (Liu (1997) Plant Physiol. 115:397-407); the auxin-responsive *Arabidopsis* GST6 promoter (also responsive to salicylic acid and hydrogen peroxide) (Chen (1996) Plant J. 10: 955-966); the auxin-inducible parC promoter from tobacco (Sakai (1996) 37:906-913); a plant biotin response element (Streit (1997) Mol. Plant Microbe Interact. 10:933-937); and, the promoter responsive to the stress hormone abscisic acid (Sheen (1996) Science 274:1900-1902).

The nucleic acids of the invention can also be operably linked to plant promoters which are inducible upon exposure to chemicals reagents which can be applied to the plant, such as herbicides or antibiotic. For example, gene expression systems that are activated in the presence of a chemical ligand, including ethanol, such as can be found in WO 96/27673; WO 93/01294; WO 94/03619; WO 02/061102, all of which are hereby incorporated by reference. The maize In2-2 promoter, activated by benzenesulfonamide herbicide safeners, can be used (De Veylder (1997) Plant Cell Physiol. 38:568-577); application of different herbicide safeners induces distinct gene expression patterns, including expression in the root, hydathodes, and the shoot apical meristem. Coding sequence can be under the control of, e.g., a tetracycline-inducible promoter, e.g., as described with transgenic tobacco plants containing the *Avena sativa* L. (oat) arginine decarboxylase gene (Masgrau (1997) Plant J. 11:465-473); estrogen, such as, the ecdysone receptor (WO 01/52620) or, a salicylic acid-responsive element (Stange (1997) Plant J. 11:1315-1324). Using chemically- (e.g., hormone- or pesticide-) induced promoters, i.e., promoter responsive to a chemical which can be applied to the transgenic plant in the field, expression of a polypeptide of the invention can be induced at a particular stage of development of the plant.

Exemplary constitutive promoters which can be used to practice this invention, and which have been described, include rice actin 1 (Wang et. al. (1992) Mol. Cell. Biol., 12:3399; U.S. Pat. No. 5,641,876); other actin isoforms (McElroy et. al. (1990) Plant Cell 2: 163-171 and McElroy et. al. (1991) Mol. Gen. Genet. 231: 150-160); CaMV 35S (Odell et. al. (1985) Nature, 313:810); CaMV 19S (Lawton et. al. (1987) Plant Mol. Biol. 9:315-324; U.S. Pat. No. 5,639,949); nos (Ebert et. al. (1987) PNAS USA 84:5745-5749); Adh (Walker et. al. (1987) PNAS USA 84:6624-6628), sucrose synthase (Yang & Russell (1990) PNAS USA 87:4144-4148); and the ubiquitin promoters (e.g. sunflower—Binet et. al. (1991) Plant Science 79: 87-94; maize—Christensen et. al. (1989) Plant Molec. Biol. 12: 619-632; and *Arabidopsis*—Callis et. al., J. Biol. Chem. (1990) 265:12486-12493; and Norris et. al., Plant Mol. Biol. (1993) 21:895-906.

Any transcriptional terminator can be used to practice this invention, e.g., can be used in vectors, expression cassettes and the like. These are responsible for the termination of transcription beyond the transgene and correct mRNA polyadenylation. The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Appropriate transcriptional terminators are those that are known to function in plants and include the CAMV 35S terminator, the tml terminator, the nopaline synthase terminator and the pea rbcs E9 terminator. These can be used in both monocotyledons and dicotyledons. In addition, a gene's native transcription terminator may be used.

The invention can use any sequence to enhance gene expression from within the transcriptional unit; and these sequences can be used in conjunction with the genes of this invention to increase their expression in transgenic plants. For example, various intron sequences have been shown to enhance expression, particularly in monocotyledonous cells. For example, the introns of the maize Adhl gene have been found to significantly enhance the expression of the wild-type gene under its cognate promoter when introduced into maize cells.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et. al. Nucl. Acids Res. 15: 8693-8711 (1987); Skuzeski et. al. Plant Molec. Biol. 15: 65-79 (1990)).

Targeting of the Gene Product within the Cell

Any mechanism for targeting gene products, e.g., in plants, can be used to practice this invention, and such mechanisms are known to exist in plants and the sequences controlling the functioning of these mechanisms have been characterized in some detail. Sequences have been characterized which cause the targeting of gene products to other cell compartments. Amino terminal sequences can be responsible for targeting a protein of interest to any cell compartment, such as, a vacuole, mitochondrion, peroxisome, protein bodies, endoplasmic reticulum, chloroplast, starch granule, amyloplast, apoplast or cell wall of a plant (e.g. Unger et. al. Plant Molec. Biol. 13: 411-418 (1989); Rogers et. al. (1985) Proc. Natl. Acad. Sci. USA 82: 6512-651; U.S. Pat. No. 7,102,057; WO 2005/096704, all of which are hereby incorporated by reference). Optionally, the signal sequence may be an N-terminal signal sequence from waxy, an N-terminal signal sequence from γ-zein, a starch binding domain, a C-terminal starch binding domain, a chloroplast targeting sequence, which imports the mature protein to the chloroplast (Comai et. al. (1988) J. Biol. Chem. 263: 15104-15109; van den Broeck, et. al. (1985) Nature 313: 358-363; U.S. Pat. No. 5,639,949) or a secretion signal sequence from aleurone cells (Koehler & Ho, Plant Cell 2: 769-783 (1990)). Additionally, amino terminal sequences in conjunction with carboxy terminal sequences are responsible for vacuolar targeting of gene products (Shinshi et. al. (1990) Plant Molec. Biol. 14: 357-368).

In one aspect, the signal sequence selected should include the known cleavage site, and the fusion constructed should take into account any amino acids after the cleavage site(s), which are required for cleavage. In some cases this requirement may be fulfilled by the addition of a small number of amino acids between the cleavage site and the transgene ATG or, alternatively, replacement of some amino acids within the transgene sequence. These construction techniques are well known in the art and are equally applicable to any cellular compartment.

In one aspect, the above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

In sum, a variety of means can be used to practice this invention, including any means to achieve the recombinant expression of phytase in a transgenic plant, seed, organ or any plant part. Such a transgenic plants and plant parts are serviceable as sources of recombinantly expressed phytase, which can be added directly to phytate-containing sources. Alternatively, the recombinant plant-expressed phytase can be extracted away from the plant source and, if desired, purified prior to contacting the phytase substrate.

Within the context of the present invention, plants that can be selected (used to practice this invention) include, but are not limited to crops producing edible flowers such as cauliflower (*Brassica oleracea*), artichoke (*Cynara scolymus*), fruits such as apple (*Malus*, e.g. *domesticus*), banana (*Musa*, e.g. *acuminata*), berries (such as the currant, *Ribes*, e.g. *rubrum*), cherries (such as the sweet cherry, *Prunus*, e.g. *avium*), cucumber (*Cucumis*, e.g. *sativus*), grape (*Vitis*, e.g. *vinifera*), lemon (*Citrus limon*), melon (*Cucumis melo*), nuts (such as the walnut, *Juglans*, e.g. *regia*; peanut, *Arachis hypogeae*), orange (*Citrus*, e.g. *maxima*), peach (*Prunus*, e.g. *persica*), pear (*Pyra*, e.g. *communis*), plum (*Prunus*, e.g. *domestica*), strawberry (*Fragaria*, e.g. *moschata*), tomato (*Lycopersicon*, e.g. *esculentum*), leafs, such as alfalfa (*Medicago*, e.g. *sativa*), cabbages (e.g. *Brassica oleracea*), endive (*Cichoreum*, e.g. *endivia*), leek (*Allium*, e.g. *porrum*), lettuce (*Lactuca*, e.g. *sativa*), spinach (*Spinacia*, e.g. *oleraceae*), tobacco (*Nicotiana*, e.g. *tabacum*), roots, such as arrowroot (*Maranta*, e.g. *arundinacea*), beet (Beta, e.g. vulgaris), carrot (*Daucus*, e.g. *carota*), cassava (*Manihot*, e.g. *esculenta*), turnip (*Brassica*, e.g. *rapa*), radish (*Raphanus*, e.g. *sativus*), yam (*Dioscorea*, e.g. *esculenta*), sweet potato (*Ipomoea batatas*) and seeds, such as bean (*Phaseolus*, e.g. vulgaris), pea (*Pisum*, e.g. *sativum*), soybean (*Glycin*, e.g. *max*), wheat (*Triticum*, e.g. *aestivum*), barley (*Hordeum*, e.g. *vulgare*), corn (*Zea*, e.g. *mays*), rice (*Oryza*, e.g. *sativa*), rapeseed (*Brassica napus*), millet (*Panicum* L.), sunflower (*Helianthus annus*), oats (*Avena sativa*), tubers, such as kohlrabi (*Brassica*, e.g. *oleraceae*), potato (*Solanum*, e.g. *tuberosum*) and the like.

In one aspect, the nucleic acids and polypeptides of the invention are expressed in or inserted in any plant or seed. Transgenic plants of the invention can be dicotyledonous or monocotyledonous. Examples of monocot transgenic plants of the invention are grasses, such as meadow grass (blue grass, Poa), forage grass such as *festuca*, *lolium*, temperate grass, such as *Agrostis*, and cereals, e.g., wheat, oats, rye, barley, rice, sorghum, and maize (corn). Examples of dicot transgenic plants of the invention are tobacco, legumes, such as lupins, potato, sugar beet, pea, bean and soybean, and cruciferous plants (family Brassicaceae), such as cauliflower, rape seed, and the closely related model organism *Arabidopsis thaliana*. Thus, the transgenic plants and seeds of the invention include a broad range of plants, including, but not limited to, species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna*, and *Zea*.

In alternative embodiments, the nucleic acids of the invention are expressed in plants which contain fiber cells, including, e.g., cotton, silk cotton tree (Kapok, *Ceiba pentandra*), desert willow, creosote bush, winterfat, balsa, ramie, kenaf, hemp, roselle, jute, sisal abaca and flax. In alternative embodiments, the transgenic plants of the invention can be members of the genus *Gossypium*, including members of any *Gossypium* species, such as *G. arboreum; G. herbaceum, G. barbadense*, and *G. hirsutum*.

Additional plants as well as non-plant expression systems can be used to practice this invention. The choice of the plant species is primarily determined by the intended use of the plant or parts thereof and the amenability of the plant species to transformation.

Several techniques are available for the introduction of the expression construct containing the phytase-encoding DNA sequence into the target plants. Techniques for transforming a wide variety of higher plant species are well known and described in the technical and scientific literature. See, e.g., Weising (1988) Ann. Rev. Genet. 22:421-477; U.S. Pat. No. 5,750,870. Such techniques also can include but are not limited to transformation of protoplasts using the calcium/polyethylene glycol method, electroporation and microinjection or (coated) particle bombardment (Potrykus, 1990). In addition to these so-called direct DNA transformation methods, transformation systems involving vectors are widely available, such as viral vectors (e.g. from the Cauliflower Mosaic Cirus (CaMV) and bacterial vectors (e.g. from the genus *Agrobacterium*) (Potrykus, 1990). After selection and/or screening, the protoplasts, cells or plant parts that have been transformed can be regenerated into whole plants, using methods known in the art (Horsch et al., 1985). The choice of the transformation and/or regeneration techniques is not critical for this invention.

Nucleic acids and expression constructs of the invention can be introduced into a plant cell by any means. In alternative aspects of practicing this invention, the term "introducing" in the context of a polynucleotide, for example, a nucleotide construct of interest, is intended to mean presenting to the plant the polynucleotide in such a manner that the polynucleotide gains access to the interior of a cell of the plant. Where more than one polynucleotide is to be introduced, these polynucleotides can be assembled as part of a single nucleotide construct, or as separate nucleotide constructs, and can be located on the same or different transformation vectors. Accordingly, these polynucleotides can be introduced into the host cell of interest in a single transformation event, in separate transformation events, or, for example, in plants, as part of a breeding protocol. The methods of the invention do not depend on a particular method for introducing one or more polynucleotides into a plant, only that the polynucleotide(s) gains access to the interior of at least one cell of the plant. Methods for introducing polynucleotides into plants are known in the art including, but not limited to, transient transformation methods, stable transformation methods, and virus-mediated methods.

"Transient transformation" can be used to practice this invention, and in some aspects in the context of a polynucleotide is intended to mean that a polynucleotide is introduced into the plant and does not integrate into the genome of the plant. "Stably introducing" or "stably introduced" in the context of a polynucleotide introduced into a plant can be used to practice this invention, and in some aspects it is intended that the introduced polynucleotide is stably incorporated into the plant genome, and thus the plant is stably transformed with the polynucleotide.

"Stable transformation" or "stably transformed" in the context of a polynucleotide introduced into a plant can be used to practice this invention, and in some aspects it is intended that a polynucleotide, for example, a nucleotide construct described herein, is introduced into a plant integrates into the genome of the plant and is capable of being inherited by the progeny thereof, more particularly, by the progeny of multiple successive generations. Introduction into the genome of a desired plant can be such that the enzyme is regulated by endogenous transcriptional or translational control elements. Transformation techniques for both monocotyledons and dicotyledons are well known in the art.

The nucleic acids of the invention can be used to confer desired traits on essentially any plant. In one embodiment, the enzyme of the invention may be expressed in such a way that the enzyme will not come in contact with it's substrate until desired. For example, an enzyme of the invention may be targeted and retained in the endoplasmic reticulum of a plant cell. Retention of the enzyme, in the endoplasmic reticulum of the cell, will prevent the enzyme from coming in contact with its substrate. The enzyme and substrate may then be brought into contact through any means able to disrupt the subcellular architecture, such as, grinding, milling, heating, and the like. See, WO 98/11235, WO 2003/18766, and WO 2005/096704, all of which are hereby incorporated by reference.

Selectable marker genes can be added to the gene construct in order to identify plant cells or tissues that have successfully integrated the transgene. This may be necessary because achieving incorporation and expression of genes in plant cells is a rare event, occurring in just a few percent of the targeted tissues or cells. Selectable marker genes encode proteins that provide resistance to agents that are normally toxic to plants, such as antibiotics or herbicides. Only plant cells that have integrated the selectable marker gene will survive when grown on a medium containing the appropriate antibiotic or herbicide. Selection markers used routinely in transformation include the nptII gene, which confers resistance to kanamycin and related antibiotics (Messing & Vierra. Gene 19: 259-268 (1982); Bevan et. al., Nature 304:184-187 (1983)), the bar gene, which confers resistance to the herbicide phosphinothricin (White et. al., Nucl. Acids Res 18: 1062 (1990), Spencer et. al. Theor. Appl. Genet 79: 625-631 (1990)), the hph gene, which confers resistance to the antibiotic hygromycin (Blochinger & Diggelmann, Mol Cell Biol 4: 2929-2931), the dhfr gene, which confers resistance to methotrexate (Bourouis et. al., EMBO J. 2(7): 1099-1104 (1983)), the EPSPS gene, which confers resistance to glyphosate (U.S. Pat. Nos. 4,940,935 and 5,188,642), Alternatively, transgenic plant material can be identified through a positive selection system, such as, the system utilizing the mannose-6-phosphate isomerase gene, which provides the ability to metabolize mannose (U.S. Pat. Nos. 5,767,378 and 5,994,629).

In one aspect, making transgenic plants or seeds comprises incorporating sequences of the invention and, optionally, marker genes into a target expression construct (e.g., a plasmid), along with positioning of the promoter and the terminator sequences. This can involve transferring the modified gene into the plant through a suitable method. One or more of the sequences of the invention may be combined with sequences that confer resistance to insect, disease, drought, increase yield, improve nutritional quality of the grain, improve ethanol yield and the like.

For example, a construct may be introduced directly into the genomic DNA of the plant cell using techniques such as electroporation and microinjection of plant cell protoplasts, or the constructs can be introduced directly to plant tissue using ballistic methods, such as DNA particle bombardment. For example, see, e.g., Christou (1997) Plant Mol. Biol. 35:197-203; Pawlowski (1996) Mol. Biotechnol. 6:17-30; Klein (1987) Nature 327:70-73; Takumi (1997) Genes Genet. Syst. 72:63-69, discussing use of particle bombardment to introduce transgenes into wheat; and Adam (1997) supra, for use of particle bombardment to introduce YACs into plant cells. For example, Rinehart (1997) supra, used particle bombardment to generate transgenic cotton plants. Apparatus for accelerating particles is described U.S. Pat. No. 5,015,580; and, the commercially available BioRad (Biolistics) PDS-2000 particle acceleration instrument; see also, John, U.S. Pat. No. 5,608,148; and Ellis, U.S. Pat. No. 5,681,730, describing particle-mediated transformation of gymnosperms.

In one aspect, protoplasts can be immobilized and injected with a nucleic acids, e.g., an expression construct. Although plant regeneration from protoplasts is not easy with cereals, plant regeneration is possible in legumes using somatic embryogenesis from protoplast derived callus. Organized tissues can be transformed with naked DNA using gene gun technique, where DNA is coated on tungsten microprojectiles, shot 1/100th the size of cells, which carry the DNA deep into cells and organelles. Transformed tissue is then induced to regenerate, usually by somatic embryogenesis. This technique has been successful in several cereal species including maize and rice.

Nucleic acids, e.g., expression constructs, can also be introduced in to plant cells using recombinant viruses. Plant cells can be transformed using viral vectors, such as, e.g., tobacco mosaic virus derived vectors (Rouwendal (1997) Plant Mol. Biol. 33:989-999), see Porta (1996) "Use of viral replicons for the expression of genes in plants," Mol. Biotechnol. 5:209-221.

Alternatively, nucleic acids, e.g., an expression construct, can be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, e.g., Horsch (1984) *Science* 233:496-498; Fraley (1983) *Proc. Natl. Acad. Sci. USA* 80:4803 (1983); Gene Transfer to Plants, Potrykus, ed. (Springerlag, Berlin 1995). The DNA in an *A. tumefaciens* cell is contained in the bacterial chromosome as well as in another structure known as a Ti (tumor-inducing) plasmid. The Ti plasmid contains a stretch of DNA termed T-DNA (~20 kb long) that is transferred to the plant cell in the infection process and a series of vir (virulence) genes that direct the infection process. *A. tumefaciens* can only infect a plant through wounds: when a plant root or stem is wounded it gives off certain chemical signals, in response to which, the vir genes of *A. tumefaciens* become activated and direct a series of events necessary for the transfer of the T-DNA from the Ti plasmid to the plant's chromosome. The T-DNA then enters the plant cell through the wound. One speculation is that the T-DNA waits until the plant DNA is being replicated or transcribed, then inserts itself into the exposed plant DNA. In order to use *A. tumefaciens* as a transgene vector, the tumor-inducing section of T-DNA have to be removed, while retaining the T-DNA border regions and the vir genes. The transgene is then inserted between the T-DNA border regions, where it is transferred to the plant cell and becomes integrated into the plant's chromosomes.

The invention provides for the transformation of monocotyledonous plants using the nucleic acids of the invention, including important cereals, see Hiei (1997) Plant Mol. Biol. 35:205-218. See also, e.g., Horsch, Science (1984) 233:496; Fraley (1983) Proc. Natl. Acad. Sci USA 80:4803; Thykjaer (1997) supra; Park (1996) Plant Mol. Biol. 32:1135-1148, discussing T-DNA integration into genomic DNA. See also D'Halluin, U.S. Pat. No. 5,712,135, describing a process for the stable integration of a DNA comprising a gene that is functional in a cell of a cereal, or other monocotyledonous plant.

In one aspect, the third step can involve selection and regeneration of whole plants capable of transmitting the incorporated target gene to the next generation. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee (1987) Ann. Rev. of Plant Phys. 38:467-486. To obtain whole plants from transgenic tissues such as immature embryos, they can be grown under controlled environmental conditions in a series of media containing nutrients and hormones, a process known as tissue culture. Once whole plants are generated and produce seed, evaluation of the progeny begins.

In one aspect, after the expression cassette is stably incorporated in transgenic plants, it can be introduced into other plants by sexual crossing. Any of a number of standard breeding techniques can be used, depending upon the species to be crossed. See, for example, Welsh J. R., *Fundamentals of Plant Genetics and Breeding*, John Wiley & Sons, N Y (1981); Crop Breeding, Wood D. R. (Ed.) American Society of Agronomy Madison, Wis. (1983); Mayo O., *The Theory of Plant Breeding*, Second Edition, Clarendon Press, Oxford (1987); Singh, D. P., *Breeding for Resistance to Diseases and Insect Pests*, Springer-Verlag, N.Y. (1986); and Wricke and Weber, *Quantitative Genetics and Selection Plant Breeding*, Walter de Gruyter and Co., Berlin (1986).

In one aspect, since transgenic expression of the nucleic acids of the invention leads to phenotypic changes, plants comprising the recombinant nucleic acids of the invention can be sexually crossed with a second plant to obtain a final product. Thus, the seed of the invention can be derived from a cross between two transgenic plants of the invention, or a cross between a plant of the invention and another plant. The desired effects (e.g., expression of the polypeptides of the invention to produce a plant in which flowering behavior is altered) can be enhanced when both parental plants express the polypeptides (e.g., phytase) of the invention. The desired effects can be passed to future plant generations by standard propagation means.

For dicots, a binary vector system can be used (Hoekema et al., 1983; EP 0120516 Schilperoort et al.). For example, *Agrobacterium* strains can be used which contain a vir plasmid with the virulence genes and a compatible plasmid containing the gene construct to be transferred. This vector can replicate in both *E. coli* and in *Agrobacterium*, and is derived from the binary vector Bin19 (Bevan, 1984) that is altered in details that are not relevant for this invention. The binary vectors as used in this example contain between the left- and right-border sequences of the T-DNA, an identical NPTII-gene coding for kanamycin resistance (Bevan, 1984) and a multiple cloning site to clone in the required gene constructs.

The transformation and regeneration of monocotyledonous crops can be practiced using any method or standard procedure; monocots are amenable to transformation and fertile transgenic plants can be regenerated from transformed cells. In an alternative aspect, monocots are transformed by *Agrobacterium* transformation.

In one aspect, transgenic rice plants can be obtained using the bacterial hph gene, encoding hygromycin resistance, as a selection marker; the gene can be introduced by electroporation. In one aspect, transgenic maize plants can be obtained by introducing the *Streptomyces hygroscopicus* bar gene, which encodes phosphinothricin acetyltransferase (an enzyme which inactivates the herbicide phosphinothricin), into embryogenic cells of a maize suspension culture by microparticle bombardment. In one aspect, genetic material can be introduced into aleurone protoplasts of monocot crops such as wheat and barley. In one aspect, wheat plants are regenerated from embryogenic suspension culture by selecting only the aged compact and nodular embryogenic callus tissues for the establishment of the embryogenic suspension cultures. In one aspect, the combination with transformation systems for these crops enables the application of the present invention to monocots. These methods and other methods may also be applied for the transformation and regeneration of dicots.

In practicing this invention, expression of the phytase construct involves such details as transcription of the gene by plant polymerases, translation of mRNA, etc. that are known to persons skilled in the art of recombinant DNA techniques. Some details relevant for the practicing some embodiments of this invention are discussed herein. Regulatory sequences which are known or are found to cause expression of phytase may be used in the present invention. The choice of the regulatory sequences used can depend on the target crop and/or target organ of interest. Such regulatory sequences may be obtained from plants or plant viruses, or may be chemically synthesized. Such regulatory sequences are promoters active in directing transcription in plants, either constitutively or stage and/or tissue specific, depending on the use of the plant or parts thereof. These promoters include, but are not limited to promoters showing constitutive expression, such as the 35S promoter of Cauliflower Mosaic Virus (CaMV) (Guilley et al., 1982), those for leaf-specific expression, such as the promoter of the ribulose bisphosphate carboxylase small subunit gene (Coruzzi et al., 1984), those for root-specific expression, such as the promoter from the glutamine synthase gene (Tingey et al., 1987), those for seed-specific expression, such as the cruciferin A promoter from *Brassica napus* (Ryan et al., 1989), those for tuber-specific expression, such as the class-I patatin promoter from potato (Koster-Topfer et al., 1989; Wenzler et al., 1989) or those for fruit-specific expression, such as the polygalacturonase (PG) promoter from tomato (Bird et al., 1988).

Other regulatory sequences such as terminator sequences and polyadenylation signals can be used to practice this invention, and they can include any such sequence functioning as such in plants, the choice of which is within the level of the skilled artisan. An example of such sequences is the 3' flanking region of the nopaline synthase (nos) gene of *Agrobacterium tumefaciens* (Bevan, supra). The regulatory sequences may also include enhancer sequences, such as found in the 35S promoter of CaMV, and mRNA stabilizing sequences such as the leader sequence of Alfalfa Mosaic Cirus (A1MV) RNA4 (Brederode et al., 1980) or any other sequences functioning in a like manner.

In some embodiments, a phytase of the invention is expressed in an environment that allows for stability of the expressed protein. The choice of cellular compartments, such as cytosol, endoplasmic reticulum, vacuole, protein body or periplasmic space can be used in the present invention to create such a stable environment, depending on the biophysical parameters of the phytase. Such parameters include, but are not limited to pH-optimum, sensitivity to proteases or sensitivity to the molarity of the preferred compartment.

In some embodiments, a phytase of the invention is expressed in cytoplasm; in some aspect, to obtain expression in the cytoplasm of the cell, the expressed enzyme should not contain a secretory signal peptide or any other target sequence. For expression in chloroplasts and mitochondria the expressed enzyme should contain specific so-called transit peptide for import into these organelles. Targeting sequences that can be attached to the enzyme of interest in order to achieve this are known (Smeekens et al., 1990; van den Broeck et al., 1985; Wolter et al., 1988). If the activity of the enzyme is desired in the vacuoles a secretory signal peptide has to be present, as well as a specific targeting sequence that directs the enzyme to these vacuoles (Tague et al., 1990). The same is true for the protein bodies in seeds. The DNA sequence encoding the enzyme of interest should be modified in such a way that the enzyme can exert its action at the desired location in the cell.

In some embodiments, to achieve extracellular expression of the phytase, the expression construct of the present invention utilizes a secretory signal sequence. Although signal sequences which are homologous (native) to the plant host species may be preferred, heterologous signal sequences, i.e. those originating from other plant species or of microbial origin, may be used as well. Such signal sequences are known to those skilled in the art. Appropriate signal sequences which may be used within the context of the present invention are disclosed in Blobel et al., 1979; Von Heijne, 1986; Garcia et al., 1987; Sijmons et al., 1990; Ng et al., 1994; and Powers et al., 1996).

In some embodiments, all parts of the relevant DNA constructs (promoters, regulatory-, secretory-, stabilizing-, targeting-, or termination sequences) of the present invention are modified, if desired, to affect their control characteristics using methods known to those skilled in the art. Plants containing phytase obtained via the present invention may be used to obtain plants or plant organs with yet higher phytase levels. For example, it may be possible to obtain such plants or plant organs by the use of somoclonal variation techniques or by cross breeding techniques. Such techniques are well known to those skilled in the art.

In one aspect, the instant invention provides a method (and products thereof) of achieving a highly efficient overexpression system for phytase and other molecules. In one aspect, the invention provides a method (and products thereof) of achieving a highly efficient overexpression system for phytase and pH 2.5 acid phosphatase in *Trichoderma*. This system results in enzyme compositions that have particular utility in the animal feed industry. Additional details regarding this approach are in the public literature and/or are known to the skilled artisan. In a particular non-limiting exemplification, such publicly available literature includes EP 0659215 (WO 9403612 A1) (Nevalainen et al.), although these reference do not teach the inventive molecules of the instant application.

In some embodiments, the invention uses in vivo reassortment, which can be focused on "inter-molecular" processes collectively referred to as "recombination", which in bacteria can be a "RecA-dependent" phenomenon. The invention can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process.

Therefore, in another aspect of the invention, variant polynucleotides can be generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of novel molecular species. Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

The invention can use repeated or "quasi-repeated" sequences; these sequence can play a role in genetic instability. In the present invention, "quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. The constructs containing the quasi-repeats thus effectively provide sufficient molecular elasticity that deletion (and potentially insertion) events can occur virtually anywhere within the quasi-repetitive units.

In some aspects, when the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, in one aspect of the invention the sequences are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it can still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following:
(a) Primers that include a poly-A head and poly-T tail which when made single-stranded provide orientation can be utilized. This is accomplished by having the first few bases of the primers made from RNA and hence easily removed RNAse H.
(b) Primers that include unique restriction cleavage sites can be utilized. Multiple sites, a battery of unique sequences, and repeated synthesis and ligation steps would be required.
(c) The inner few bases of the primer can be thiolated and an exonuclease used to produce properly tailed molecules.

In some aspects, the recovery of the re-assorted sequences relies on the identification of cloning vectors with a reduced RI. The re-assorted encoding sequences can then be recovered by amplification. The products are re-cloned and expressed. The recovery of cloning vectors with reduced RI can be effected by:
1) The use of vectors only stably maintained when the construct is reduced in complexity;
2) The physical recovery of shortened vectors by physical procedures. In this case, the cloning vector is recovered using standard plasmid isolation procedures and size fractionated on either an agarose gel, or column with a low molecular weight cut off utilizing standard procedures;
3) The recovery of vectors containing interrupted genes which can be selected when insert size decreases; and
4) The use of direct selection techniques with an expression vector and the appropriate selection.

Encoding sequences (for example, genes) from related organisms can be used to practice this invention, and they can demonstrate a high degree of homology and encode quite diverse protein products. These types of sequences are particularly useful in the present invention as quasi-repeats. However, while the exemplary protocols discussed below demonstrate the reassortment of nearly identical original encoding sequences (quasi-repeats), this process is not limited to such nearly identical repeats.

Once formed, the constructs may or may not be size fractionated on an agarose gel according to published protocols, inserted into a cloning vector, and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intra-molecular" mechanism, or mediated by recombination-like events through "inter-molecular" mechanisms is immaterial. The end result is a reassortment of the molecules into all possible combinations.

In one aspect, methods of this invention comprise the additional step of screening the library members of the shuffled pool to identify individual shuffled library members having the ability to bind or otherwise interact, or catalyze a particular reaction (e.g., such as catalyzing the hydrolysis of a phytate).

In one aspect, the polypeptides that are identified from such libraries can be used for therapeutic, diagnostic, research and related purposes (e.g., catalysts, solutes for increasing osmolarity of an aqueous solution, and the like), and/or can be subjected to one or more additional cycles of shuffling and/or selection.

In another aspect, prior to or during recombination or reassortment, polynucleotides of the invention or polynucleotides generated by the method described herein can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N3-Adenine, see Sun and Hurley, 1992); an N-acetylated or deacetylated 4'-fluro-4-aminobiphenyl adduct capable of inhibiting DNA synthesis (see, for example, van de Poll et al., 1992); or a N-acetylated or deacetylated 4-aminobiphenyl adduct capable of inhibiting DNA synthesis (see also, van de Poll et al., 1992, pp. 751-758); trivalent chromium, a trivalent chromium salt, a polycyclic aromatic hydrocarbon ("PAH") DNA adduct capable of inhibiting DNA replication, such as 7-bromomethyl-benz[a]anthracene ("BMA"), tris(2,3-dibromopropyl)phosphate ("Tris-BP"), 1,2-dibromo-3-chloropropane ("DBCP"), 2-bromoacrolein (2BA), benzo[a]pyrene-7,8-dihydrodiol-9-10-epoxide ("BPDE"), a platinum(II) halogen salt, N-hydroxy-2-amino-3-methylimidazo[4,5-f]-quinoline ("N-hydroxy-IQ"), and N-hydroxy-2-amino-1-methyl-6-phenylimidazo[4,5-f]-pyridine ("N-hydroxy-PhIP"). An exemplary means for slowing or halting PCR amplification consist of UV light (+)-CC-1065 and (+)-CC-1065-(N3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

In another aspect, the invention is directed to a method of producing recombinant proteins having biological activity by treating a sample comprising double-stranded template polynucleotides encoding a wild type protein under conditions according to the invention which provide for the production of hybrid or re-assorted polynucleotides.

The invention also provides for the use of proprietary codon primers (containing a degenerate N,N,G/T sequence) to introduce point mutations into a polynucleotide, so as to generate a set of progeny polypeptides in which a full range of single amino acid substitutions is represented at each amino acid position (gene site saturated mutagenesis (GSSM)). The oligos used are comprised contiguously of a first homologous sequence, a degenerate N,N,G/T sequence, and optionally a second homologous sequence. The downstream progeny translational products from the use of such oligos include all possible amino acid changes at each amino acid site along the polypeptide, because the degeneracy of the N,N,G/T sequence includes codons for all 20 amino acids.

In one aspect, one such degenerate oligo (comprised of one degenerate N,N,G/T cassette) is used for subjecting each original codon in a parental polynucleotide template to a full range of codon substitutions. In another aspect, at least two degenerate N,N,G/T cassettes are used—either in the same oligo or not, for subjecting at least two original codons in a parental polynucleotide template to a full range of codon substitutions. Thus, more than one N,N,G/T sequence can be contained in one oligo to introduce amino acid mutations at more than one site. This plurality of N,N,G/T sequences can be directly contiguous, or separated by one or more additional nucleotide sequence(s). In another aspect, oligos serviceable for introducing additions and deletions can be used either alone or in combination with the codons containing an N,N,G/T sequence, to introduce any combination or permutation of amino acid additions, deletions, and/or substitutions.

In one aspect, it is possible to simultaneously mutagenize two or more contiguous amino acid positions using an oligo that contains contiguous N,N,G/T triplets, i.e. a degenerate $(N,N,G/T)_n$ sequence.

In another aspect, the present invention provides for the use of degenerate cassettes having less degeneracy than the N,N,G/T sequence. For example, it may be desirable in some instances to use (e.g. in an oligo) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g., in an oligo) a degenerate N,N,N triplet sequence, or an N,N, G/C triplet sequence.

It is appreciated, however, that the use of a degenerate triplet (such as N,N,G/T or an N,N, G/C triplet sequence) as disclosed in the instant invention is advantageous for several reasons. In one aspect, this invention provides a means to systematically and fairly easily generate the substitution of the full range of possible amino acids (for a total of 20 amino acids) into each and every amino acid position in a polypeptide. Thus, for a 100 amino acid polypeptide, the invention provides a way to systematically and fairly easily generate 2000 distinct species (i.e., 20 possible amino acids per position times 100 amino acid positions). It is appreciated that there is provided, through the use of an oligo containing a degenerate N,N,G/T or an N,N, G/C triplet sequence, 32 individual sequences that code for 20 possible amino acids. Thus, in a reaction vessel in which a parental polynucleotide sequence is subjected to saturation mutagenesis using one such oligo, there are generated 32 distinct progeny polynucleotides encoding 20 distinct polypeptides. In contrast, the use of a non-degenerate oligo in site-directed mutagenesis leads to only one progeny polypeptide product per reaction vessel.

This invention also provides for the use of nondegenerate oligos, which can optionally be used in combination with degenerate primers disclosed. It is appreciated that in some situations, it is advantageous to use nondegenerate oligos to generate specific point mutations in a working polynucleotide. This provides a means to generate specific silent point mutations, point mutations leading to corresponding amino acid changes, and point mutations that cause the generation of stop codons and the corresponding expression of polypeptide fragments.

Thus, in one aspect, each saturation mutagenesis reaction vessel contains polynucleotides encoding at least 20 progeny polypeptide molecules such that all 20 amino acids are represented at the one specific amino acid position corresponding to the codon position mutagenized in the parental polynucleotide. The 32-fold degenerate progeny polypeptides generated from each saturation mutagenesis reaction vessel can be subjected to clonal amplification (e.g., cloned into a suitable E. coli host using an expression vector) and subjected to expression screening. When an individual progeny polypeptide is identified by screening to display a favorable change in property (when compared to the parental polypeptide), it can be sequenced to identify the correspondingly favorable amino acid substitution contained therein.

It is appreciated that upon mutagenizing each and every amino acid position in a parental polypeptide using gene site saturation mutagenesis (GSSM) as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e., 2 at each of three positions) and no change at any position.

In yet another aspect, site-saturation mutagenesis can be used together with shuffling, chimerization, recombination and other mutagenizing processes, along with screening. This invention provides for the use of any mutagenizing process(es), including saturation mutagenesis, in an iterative manner. In one exemplification, the iterative use of any mutagenizing process(es) is used in combination with screening.

Thus, in a non-limiting exemplification, polynucleotides and polypeptides of the invention can be derived by gene site saturation mutagenesis (GSSM) in combination with additional mutagenization processes, such as process where two or more related polynucleotides are introduced into a suitable host cell such that a hybrid polynucleotide is generated by recombination and reductive reassortment.

In addition to performing mutagenesis along the entire sequence of a gene, mutagenesis can be used to replace each of any number of bases in a polynucleotide sequence, wherein the number of bases to be mutagenized can be every integer from 15 to 100,000. Thus, instead of mutagenizing every position along a molecule, one can subject every or a discrete number of bases (can be a subset totaling from 15 to 100,000) to mutagenesis. A separate nucleotide can be used for mutagenizing each position or group of positions along a polynucleotide sequence. A group of 3 positions to be mutagenized may be a codon. The mutations can be introduced using a mutagenic primer, containing a heterologous cassette, also referred to as a mutagenic cassette. Exemplary cassettes can have from 1 to 500 bases. Each nucleotide position in such heterologous cassettes be N, A, C, G, T, A/C, A/G, A/T, C/G, C/T, G/T, C/G/T, A/G/T, A/C/T, A/C/G, or E, where E is any base that is not A, C, G, or T (E can be referred to as a designer oligo).

In a general sense, saturation mutagenesis comprises mutagenizing a complete set of mutagenic cassettes (wherein each cassette can be about 1-500 bases in length) in defined polynucleotide sequence to be mutagenized (wherein the sequence to be mutagenized can be from about 15 to 100,000 bases in length). Thus, a group of mutations (ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons, and groupings of particular nucleotide cassettes.

Defined sequences to be mutagenized include a whole gene, pathway, cDNA, an entire open reading frame (ORF), and entire promoter, enhancer, repressor/transactivator, origin of replication, intron, operator, or any polynucleotide functional group. Generally, a "defined sequences" for this purpose may be any polynucleotide that a 15 base-polynucleotide sequence, and polynucleotide sequences of lengths between 15 bases and 15,000 bases (this invention specifically names every integer in between). Considerations in choosing groupings of codons include types of amino acids encoded by a degenerate mutagenic cassette.

In one aspect, a grouping of mutations that can be introduced into a mutagenic cassette, this invention specifically provides for degenerate codon substitutions (using degenerate oligos) that code for 2, 3, 4, 5, 6, 7, 8, 9, 10, 11, 12, 13, 14, 15, 16, 17, 18, 19, and 20 amino acids at each position, and a library of polypeptides encoded thereby.

In alternative aspects nucleic acids of the invention comprise DNA, including cDNA, genomic DNA, and synthetic DNA. The DNA may be double-stranded or single-stranded, and if single stranded may be the coding strand or non-coding (anti-sense) strand. Alternatively, the nucleic acids of the invention may comprise RNA.

As discussed in more detail below, the isolated nucleic acid sequences of the invention may be used to prepare the polypeptides of the invention.

Accordingly, another aspect of the invention is an isolated nucleic acid sequence which encodes a polypeptide of the invention. A nucleic acid sequence of the invention can comprise additional coding sequences, such as leader sequences or proprotein sequences and non-coding sequences, such as introns or non-coding sequences 5' and/or 3' of the coding sequence. Thus, as used herein, the term "polynucleotide encoding a polypeptide" encompasses a polynucleotide which includes only coding sequence for the polypeptide as well as a polynucleotide which includes additional coding and/or non-coding sequence.

Alternatively, the nucleic acid sequences of the invention may be mutagenized using conventional techniques, such as site directed mutagenesis, or other techniques familiar to those skilled in the art, to introduce silent changes into the polynucleotide of the invention. As used herein, "silent changes" include, for example, changes that do not alter the amino acid sequence encoded by the polynucleotide. Such changes may be desirable in order to increase the level of the polypeptide produced by host cells containing a vector encoding the polypeptide by introducing codons or codon pairs that occur frequently in the host organism.

The invention also relates to polynucleotides that have nucleotide changes which result in amino acid substitutions, additions, deletions, fusions and truncations in the polypeptides of the invention. Such nucleotide changes may be introduced using techniques such as site directed mutagenesis, random chemical mutagenesis, exonuclease III deletion, and other recombinant DNA techniques.

Where necessary, conditions which permit the probe to specifically hybridize to complementary sequences may be determined by placing the probe in contact with complementary sequences from samples known to contain the complementary sequence as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids.

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product.

Many methods for using the labeled probes to detect the presence of complementary nucleic acids in a sample are familiar to those skilled in the art. These include Southern Blots, Northern Blots, colony hybridization procedures, and dot blots. Protocols for each of these procedures are provided in Ausubel et al. Current Protocols in Molecular Biology, John Wiley 503 Sons, Inc. 1997 and Sambrook et al., Molecular Cloning: A Laboratory Manual, 2d Ed., Cold Spring Harbor Laboratory Press, 1989.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). Typically, the probes comprise oligonucleotides. In one aspect, the amplification reaction may comprise a PCR reaction. PCR protocols are described in Ausubel and Sambrook, supra. Alternatively, the amplification may comprise a ligase chain reaction, 3SR, or strand displacement reaction. (See Barmy, F., "The Ligase Chain Reaction in a PCR World," *PCR Methods and Applications* 1:5-16, 1991; E. Fahy et al., "Self-sustained Sequence Replication (3SR): An Isothermal Transcription-based Amplification System Alternative to PCR", *PCR Methods and Applications* 1:25-33, 1991; and Walker G. T. et al., "Strand Displacement Amplification—an Isothermal in vitro DNA Amplification Technique", *Nucleic Acid Research* 20:1691-1696, 1992). In such procedures, the nucleic acids in the sample are contacted with the probes, the amplification reaction is performed, and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the ends of a sequence of the invention may also be used in chromosome walking procedures to identify clones containing genomic sequences located adjacent to the nucleic acid sequences as set forth above. Such methods allow the isolation of genes which encode additional proteins from the host organism.

A nucleic acid sequence of the invention can be used as a probe to identify and isolate related nucleic acids. In some aspects, the related nucleic acids may be cDNAs or genomic DNAs from organisms other than the one from which the nucleic acid was isolated. For example, the other organisms may be related organisms. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10×Denhardt's, and 0.5 mg/ml polyriboadenylic acid. Approximately $2 \times 10^7$ cpm (specific activity $4-9 \times 10^8$ cpm/ug) of $^{32}P$ end-labeled oligonucleotide probe are then added to the solution. After 12-16 hours of incubation, the membrane is washed for 30 minutes at room temperature in 1×SET (150 mM NaCl, 20 mM Tris hydrochloride, pH 7.8, 1 mM $Na_2EDTA$) containing 0.5% SDS, followed by a 30 minute wash in fresh 1×SET at Tm−10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, $T_m$, is the temperature (under defined ionic strength and pH) at which 50% of the target sequence hybridizes to a perfectly complementary probe. Very stringent conditions are selected to be equal to or about 5° C. lower than the $T_m$ for a particular probe. The melting temperature of the probe may be calculated using the following formulas: For probes between 14 and 70 nucleotides in length the melting temperature ($T_m$) is calculated using the formula: $T_m=81.5+16.6$ (log [Na+])+0.41(fraction G+C)−(600/N), where N is the length of the probe. If the hybridization is carried out in a solution containing formamide, the melting temperature may be calculated using the equation: $T_m=81.5+16.6$(log [Na+])+0.41(fraction G+C)−(0.63% formamide)−(600/N), where N is the length of the probe. Prehybridization may be carried out in 6×SSC, 5×Denhardt's reagent, 0.5% SDS, 100 □g/ml denatured fragmented salmon sperm DNA or 6×SSC, 5×Denhardt's reagent, 0.5% SDS, 100 □g/ml denatured fragmented salmon sperm DNA, 50% formamide. The formulas for SSC and Denhardt's solutions can be found, e.g., in Sambrook et al., supra.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the Tm. For shorter probes, such as oligonucleotide probes, the hybridization may be conducted at 5-10° C. below the $T_m$. Typically, for hybridizations in 6×SSC, the hybridization is conducted at approximately 68° C. Usually, for hybridizations in 50% formamide containing solutions, the hybridization is conducted at approximately 42° C. All of the foregoing hybridizations are considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes. Some other examples are given below.

Nucleic acids which have hybridized to the probe can be identified by autoradiography or other conventional techniques.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1 M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

For example, the preceding methods may be used to isolate nucleic acids having a sequence with at least about 99%, at least 98%, at least 97%, at least 95%, at least 90%, or at least 80% homology to a nucleic acid sequence as set forth in SEQ ID NO:1, sequences substantially identical thereto, or fragments comprising at least about 10, 15, 20, 25, 30, 35, 40, 50, 75, 100, 150, 200, 300, 400, or 500 consecutive bases thereof, and the sequences complementary to any of the foregoing sequences. Homology may be measured using an alignment algorithm. For example, the homologous polynucleotides may have a coding sequence which is a naturally occurring allelic variant of one of the coding sequences described herein. Such allelic variants may have a substitution, deletion or addition of one or more nucleotides when compared to a nucleic acid sequence as set forth in SEQ ID NO:1, or sequences complementary thereto.

Additionally, the above procedures may be used to isolate nucleic acids which encode polypeptides having at least about 99%, at least 95%, at least 90%, at least 85%, at least 80%, or at least 70% homology to a polypeptide having a sequence as set forth in SEQ ID NO:2, sequences substantially identical thereto, or fragments comprising at least 5, 10, 15, 20, 25, 30, 35, 40, 50, 75, 100, or 150 consecutive amino acids thereof as determined using a sequence alignment algorithm (e.g., such as the FASTA version 3.0t78 algorithm with the default parameters).

Another aspect of the invention is an isolated or purified polypeptide comprising a sequence as set forth in SEQ ID NO:1, sequences substantially identical thereto, or fragments comprising at least about 5, 10, 15, 20, 25, 30, 35, 40, 50, 75, 100, or 150 consecutive amino acids thereof. As discussed above, such polypeptides may be obtained by inserting a nucleic acid encoding the polypeptide into a vector such that the coding sequence is operably linked to a sequence capable of driving the expression of the encoded polypeptide in a suitable host cell. For example, the expression vector may comprise a promoter, a ribosome binding site for translation initiation and a transcription terminator. The vector may also include appropriate sequences for amplifying expression.

Promoters suitable for expressing the polypeptide or fragment thereof in bacteria include the *E. coli* lac or trp promoters, the lac' promoter, the lacZ promoter, the T3 promoter, the T7 promoter, the gpt promoter, the lambda $P_R$ promoter, the lambda $P_L$ promoter, promoters from operons encoding glycolytic enzymes such as 3-phosphoglycerate kinase (PGK), and the acid phosphatase promoter. Fungal promoters include the ∀ factor promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Mammalian expression vectors may also comprise an origin of replication, any necessary ribosome binding sites, a polyadenylation site, splice donor and acceptor sites, transcriptional termination sequences, and 5' flanking non-transcribed sequences. In some aspects, DNA sequences derived from the SV40 splice and polyadenylation sites may be used to provide the required non-transcribed genetic elements.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

In addition, the expression vectors typically contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in *E. coli*, and the *S. cerevisiae* TRP1 gene.

The probe DNA used for selectively isolating the target DNA of interest from the DNA derived from at least one microorganism can be a full-length coding region sequence or a partial coding region sequence of DNA for an enzyme of known activity. The original DNA library can be probed using mixtures of probes comprising at least a portion of the DNA sequence encoding an enzyme having the specified enzyme activity. These probes or probe libraries can be single-stranded and the microbial DNA which is probed can be converted into single-stranded form. The probes that are suitable are those derived from DNA encoding enzymes having an activity similar or identical to the specified enzyme activity which is to be screened.

The probe DNA can be at least about 10 bases or at least 15 bases. In one aspect, the entire coding region may be employed as a probe. Conditions for the hybridization in which target DNA is selectively isolated by the use of at least one DNA probe will be designed to provide a hybridization stringency of at least about 50% sequence identity, more particularly a stringency providing for a sequence identity of at least about 70%.

The probe DNA can be "labeled" with one partner of a specific binding pair (i.e. a ligand) and the other partner of the pair is bound to a solid matrix to provide ease of separation of target from its source. The ligand and specific binding partner can be selected from, in either orientation, the following: (1) an antigen or hapten and an antibody or specific binding fragment thereof; (2) biotin or iminobiotin and avidin or streptavidin; (3) a sugar and a lectin specific therefor; (4) an enzyme and an inhibitor therefor; (5) an apoenzyme and cofactor; (6) complementary homopolymeric oligonucleotides; and (7) a hormone and a receptor therefor. The solid phase can be selected from: (1) a glass or polymeric surface; (2) a packed column of polymeric beads; and (3) magnetic or paramagnetic particles.

The appropriate DNA sequence may be inserted into the vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are disclosed in Ausubel et al. *Current Protocols in Molecular Biology*, John Wiley 503 Sons, Inc. 1997 and Sambrook et al., *Molecular Cloning: A Laboratory Manual*, 2d Ed., Cold Spring Harbor Laboratory Press, 1989. Such procedures and others are deemed to be within the scope of those skilled in the art.

The vector may be, for example, in the form of a plasmid, a viral particle, or a phage. Other vectors include chromosomal, nonchromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by Sambrook, et al., *Molecular Cloning: A Laboratory Manual*, Second Edition, Cold Spring Harbor, N.Y., (1989).

Particular bacterial vectors which may be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

The host cell may be any of the host cells familiar to those skilled in the art, including prokaryotic cells, eukaryotic cells, mammalian cells, insect cells, or plant cells. As representative examples of appropriate hosts, there may be mentioned: bacterial cells, such as *E. coli, Streptomyces, Bacillus subtilis Bacillus cereus, Salmonella typhimurium* and various species within the genera *Pseudomonas, Strep-*

*tomyces* and *Staphylococcus*, fungal cells, such as *Aspergillus*, yeast such as any species of *Pichia, Saccharomyces, Schizosaccharomyces, Schwanniomyces*, including *Pichia pastoris, Saccharomyces cerevisiae*, or *Schizosaccharomyces pombe*, insect cells such as *Drosophila* S2 and *Spodoptera* Sf9, animal cells such as CHO, COS or Bowes melanoma, and adenoviruses. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells are typically harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts (described by Gluzman, *Cell*, 23:175, 1981), and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue. Additional details relating to the recombinant expression of proteins are available to those skilled in the art. For example, *Protein Expression: A Practical Approach* (Practical Approach Series by S. J. Higgins (Editor), B. D. Hames (Editor) (July 1999) Oxford University Press; ISBN: 0199636249 provides ample guidance to the those skilled in the art for the expression of proteins in a wide variety of organisms.

Alternatively, the polypeptides of the invention can be synthetically produced by conventional peptide synthesizers. In other aspects, fragments or portions of the polypeptides may be employed for producing the corresponding full-length polypeptide by peptide synthesis; therefore, the fragments may be employed as intermediates for producing the full-length polypeptides.

As known by those skilled in the art, the nucleic acid sequences of the invention can be optimized for expression in a variety of organisms. In one aspect, sequences of the invention are optimized for codon usage in an organism of interest, e.g., a fungus such as *S. cerevisiae* or a bacterium such as *E. coli*. Optimization of nucleic acid sequences for the purpose of codon usage is well understood in the art to refer to the selection of a particular codon favored by an organism to encode a particular amino acid. Optimized codon usage tables are known for many organisms. For example, see *Transfer RNA in Protein Synthesis* by Dolph L. Hatfield, Byeong J. Lee, Robert M. Pirtle (Editor) (July 1992) CRC Press; ISBN: 0849356989. Thus, the invention also includes nucleic acids of the invention adapted for codon usage of an organism.

Optimized expression of nucleic acid sequences of the invention also refers to directed or random mutagenesis of a nucleic acid to effect increased expression of the encoded protein. The mutagenesis of the nucleic acids of the invention can directly or indirectly provide for an increased yield of expressed protein. By way of non-limiting example, mutagenesis techniques described herein may be utilized to effect mutation of the 5' untranslated region, 3' untranslated region, or coding region of a nucleic acid, the mutation of which can result in increased stability at the RNA or protein level, thereby resulting in an increased yield of protein.

Cell-free translation systems can also be employed to produce one of the polypeptides of the invention, using mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The invention also relates to variants of the polypeptides of the invention. The term "variant" includes derivatives or analogs of these polypeptides. In particular, the variants may differ in amino acid sequence from the polypeptides of the invention, and sequences substantially identical thereto, by one or more substitutions, additions, deletions, fusions and truncations, which may be present in any combination.

The variants may be naturally occurring or created in vitro. In particular, such variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures.

Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. Typically, these nucleotide differences result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described in Leung, D. W., et al., *Technique*, 1:11-15, 1989) and Caldwell, R. C. and Joyce G. F., *PCR Methods Applic.*, 2:28-33, 1992. Briefly, in such procedures, nucleic acids to be mutagenized are mixed with PCR primers, reaction buffer, $MgCl_2$, $MnCl_2$, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids is evaluated.

Variants may also be created using oligonucleotide directed mutagenesis to generate site-specific mutations in any cloned DNA of interest. Oligonucleotide mutagenesis is described in Reidhaar-Olson, J. F. and Sauer, R. T., et al., *Science*, 241:53-57, 1988. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in pending U.S. patent application Ser. No. 08/677,112 filed Jul. 9, 1996, entitled, Method of "DNA Shuffling with Polynucleotides Produced by Blocking or interrupting a Synthesis or Amplification Process".

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described in Stemmer, W. P., *PNAS*, USA, 91:10747-10751, 1994. Briefly, in such procedures a plurality of nucleic acids to be recombined are digested with DNase to generate fragments having an average size of 50-200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10-30 ng/:1 in a solution of 0.2 mM of each dNTP, 2.2 mM MgCl2, 50 mM KCL, 10 mM Tris HCl, pH 9.0, and 0.1% Triton X-100. 2.5 units of Taq polymerase per 100:1 of reaction mixture is added and PCR is performed using the following regime: 94° C. for 60 seconds, 94° C. for 30 seconds, 50-55° C. for 30 seconds, 72° C. for 30 seconds (30-45 times) and 72° C. for 5 minutes. However, it will be appreciated that these parameters may be varied as appropriate. In some aspects, oligonucleotides may be included in the PCR reactions. In other aspects, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some aspects, random mutations in a sequence of interest are generated by propagating the sequence of interest in a bacterial strain, such as an *E. coli* strain, which carries mutations in one or more of the DNA repair pathways. Such "mutator" strains have a higher random mutation rate than that of a wild type parent. Propagating the DNA in one of these strains will eventually generate random mutations within the DNA. Mutator strains suitable for use for in vivo mutagenesis are described in PCT Publication No. WO 91/16427, published Oct. 31, 1991, entitled "Methods for Phenotype Creation from Multiple Gene Populations".

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described in Arkin, A. P. and Youvan, D.C., *PNAS*, USA, 89:7811-7815, 1992.

In some aspects, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in Delegrave, S. and Youvan, D.C., *Biotechnol. Res.*, 11:1548-1552, 1993. Random and site-directed mutagenesis are described in Arnold, F. H., *Current Opinion in Biotechnology*, 4:450-455, 1993.

In some aspects, the variants are created using shuffling procedures wherein portions of a plurality of nucleic acids which encode distinct polypeptides are fused together to create chimeric nucleic acid sequences which encode chimeric polypeptides as described in pending U.S. patent application Ser. No. 08/677,112 filed Jul. 9, 1996, entitled, "Method of DNA Shuffling with Polynucleotides Produced by Blocking or interrupting a Synthesis or Amplification Process", and pending U.S. patent application Ser. No. 08/651,568 filed May 22, 1996, entitled, "Combinatorial Enzyme Development."

The variants of the polypeptides of the invention may be variants in which one or more of the amino acid residues of the polypeptides of the invention are substituted with a conserved or non-conserved amino acid residue (e.g., a conserved amino acid residue) and such substituted amino acid residue may or may not be one encoded by the genetic code.

Conservative substitutions are those that substitute a given amino acid in a polypeptide by another amino acid of like characteristics. Typically seen as conservative substitutions are the following replacements: replacements of an aliphatic amino acid such as Ala, Val, Leu and Ile with another aliphatic amino acid; replacement of a Ser with a Thr or vice versa; replacement of an acidic residue such as Asp and Glu with another acidic residue; replacement of a residue bearing an amide group, such as Asn and Gln, with another residue bearing an amide group; exchange of a basic residue such as Lys and Arg with another basic residue; and replacement of an aromatic residue such as Phe, Tyr with another aromatic residue.

Other variants are those in which one or more of the amino acid residues of the polypeptides of the invention includes a substituent group.

Still other variants are those in which the polypeptide is associated with another compound, such as a compound to increase the half-life of the polypeptide (for example, polyethylene glycol).

Additional variants are those in which additional amino acids are fused to the polypeptide, such as a leader sequence, a secretory sequence, a proprotein sequence or a sequence which facilitates purification, enrichment, or stabilization of the polypeptide. In some aspects, derivatives and analogs retain the same biological function or activity as the polypeptides of the invention, and can include a proprotein, such that the fragment, derivative, or analog can be activated by cleavage of the proprotein portion to produce an active polypeptide.

Optimizing Codons to Achieve High Levels of Protein Expression in Host Cells

The invention provides methods for modifying phytase-encoding nucleic acids to modify codon usage. In one aspect, the invention provides methods for modifying codons in a nucleic acid encoding a phytase to increase or decrease its expression in a host cell. The invention also provides nucleic acids encoding a phytase modified to increase its expression in a host cell, phytase enzymes so modified, and methods of making the modified phytase enzymes. The method comprises identifying a "non-preferred" or a "less preferred" codon in phytase-encoding nucleic acid and replacing one or more of these non-preferred or less preferred codons with a "preferred codon" encoding the same amino acid as the replaced codon and at least one non-preferred or less preferred codon in the nucleic acid has been replaced by a preferred codon encoding the same amino acid. A preferred codon is a codon over-represented in coding sequences in genes in the host cell and a non-preferred or less preferred codon is a codon under-represented in coding sequences in genes in the host cell.

Host cells for expressing the nucleic acids, expression cassettes and vectors of the invention include bacteria, yeast, fungi, plant cells, insect cells and mammalian cells. Thus, the invention provides methods for optimizing codon usage in all of these cells, codon-altered nucleic acids and polypeptides made by the codon-altered nucleic acids. Exemplary host cells include gram negative bacteria, such as *Escherichia coli* and *Pseudomonas fluorescens*; gram positive bacteria, such as *Lactobacillus gasseri, Lactococcus lactis, Lactococcus cremoris, Bacillus subtilis*. Exemplary host cells also include eukaryotic organisms, e.g., various yeast, such as *Saccharomyces* sp., including *Saccharomyces cerevisiae, Schizosaccharomyces pombe, Pichia pastoris*, and *Kluyveromyces lactis, Hansenula polymorpha, Aspergillus niger*, and mammalian cells and cell lines and insect cells and cell lines. Thus, the invention also includes nucleic acids and polypeptides optimized for expression in these organisms and species.

For example, the codons of a nucleic acid encoding an phytase isolated from a bacterial cell are modified such that the nucleic acid is optimally expressed in a bacterial cell different from the bacteria from which the phytase was derived, a yeast, a fungi, a plant cell, an insect cell or a mammalian cell. Methods for optimizing codons are well known in the art, see, e.g., U.S. Pat. No. 5,795,737; Baca (2000) Int. J. Parasitol. 30:113-118; Hale (1998) Protein Expr. Purif. 12:185-188; Narum (2001) Infect. Immun. 69:7250-7253. See also Narum (2001) Infect. Immun. 69:7250-7253, describing optimizing codons in mouse systems; Outchkourov (2002) Protein Expr. Purif. 24:18-24, describing optimizing codons in yeast; Feng (2000) Biochemistry 39:15399-15409, describing optimizing codons in *E. coli*; Humphreys (2000) Protein Expr. Purif. 20:252-264, describing optimizing codon usage that affects secretion in *E. coli*.

Transgenic Non-Human Animals

The invention provides transgenic non-human animals comprising a nucleic acid, a polypeptide, an expression cassette or vector or a transfected or transformed cell of the invention. The transgenic non-human animals can be, e.g., goats, rabbits, sheep, pigs, cows, rats and mice, comprising the nucleic acids of the invention. These animals can be used, e.g., as in vivo models to study phytase activity, or, as models to screen for modulators of phytase activity in vivo. The coding sequences for the polypeptides to be expressed in the transgenic non-human animals can be designed to be constitutive, or, under the control of tissue-specific, developmental-specific or inducible transcriptional regulatory factors. Transgenic non-human animals can be designed and generated using any method known in the art; see, e.g., U.S. Pat. Nos. 6,211,428; 6,187,992; 6,156,952; 6,118,044; 6,111,166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs and cows. See also, e.g., Pollock (1999) J. Immunol. Methods 231:147-157, describing the production of recombinant proteins in the milk of transgenic dairy animals; Baguisi (1999) Nat. Biotechnol. 17:456-461, demonstrating the production of transgenic goats. U.S. Pat. No. 6,211,428, describes making and using transgenic non-human mammals which express in their brains a nucleic acid construct comprising a DNA sequence. U.S. Pat. No. 5,387,742, describes injecting cloned recombinant or synthetic DNA sequences into fertilized mouse eggs, implanting the injected eggs in pseudopregnant females, and growing to term transgenic mice whose cells express proteins related to the pathology of Alzheimer's disease. U.S. Pat. No. 6,187,992, describes making and using a transgenic mouse whose genome comprises a disruption of the gene encoding amyloid precursor protein (APP).

"Knockout animals" can also be used to practice the methods of the invention. For example, in one aspect, the transgenic or modified animals of the invention comprise a "knockout animal," e.g., a "knockout mouse," engineered not to express or to be unable to express a phytase.

In another aspect, transgenic non-human organisms are provided which contain a heterologous sequence encoding a phytase of the invention (e.g., the specifically enumerated sequence modifications of SEQ ID NO:2). Various methods to make the transgenic animals of the subject invention can be employed. Generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another such method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191.

In yet another exemplary method, embryonic cells are infected with a retrovirus containing the transgene whereby the germ cells of the embryo have the transgene chromosomally integrated therein. When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If micro-injection is to be used with avian species, however, a published procedure by Love et al., (Biotechnol., 12, January 1994) can be utilized whereby the embryo is obtained from a sacrificed hen approximately two and one-half hours after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

In one aspect, the "non-human animals" of the invention include bovine, porcine, ovine and avian animals (e.g., cow, pig, sheep, chicken). The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for micro-injection. The use of zygotes as is target for gene transfer has a major advantage in that in most cases the injected DNA will be incorporated into the host gene before the first cleavage (Brinster et al., *Proc. Natl. Acad. Sci.* USA 82:4438-4442, 1985). As a consequence, all cells of the transgenic non-human animal will carry the incorporated transgene. This will in general also be reflected in the efficient transmission of the transgene to offspring of the founder since 50% of the germ cells will harbor the transgene.

In one aspect, the term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles, 50% of the resulting animals will include the exogenous genetic material within one allele and 25% will include no exogenous genetic material.

In one aspect, a microinjection method is used to practice the invention. The transgene is digested and purified free from any vector DNA, e.g., by gel electrophoresis. In one aspect, the transgene includes an operatively associated promoter which interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionin, skeletal actin, P-enolpyruvate carboxylase (PEPCK), phosphoglycerate (PGK), DHFR, and thymidine kinase. Promoters for viral long terminal repeats (LTRs) such as Rous Sarcoma Virus can also be employed. When the animals to be made transgenic are avian, preferred promoters may include those for the chicken β-globin gene, chicken lysozyme gene, and avian leukosis virus. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retroviral infection (Jaenich, R., *Proc. Natl. Acad. Sci.* USA 73:1260-1264, 1976). Efficient infection of the blastomeres is obtained by enzymatic treatment to remove the zona pellucida (Hogan, et al. (1986) in *Manipulating the Mouse Embryo*, Cold Spring Harbor Laboratory Press, Cold Spring Harbor, N.Y.). The viral vector system used to introduce the transgene is typically a replication-defective retro virus carrying the transgene (Jahner, et al., *Proc. Natl. Acad. Sci.* USA 82: 6927-6931, 1985; Van der Putten, et al., *Proc. Natl. Acad. Sci.* USA 82: 6148-6152, 1985). Transfection is easily and efficiently obtained by culturing the blastomeres on a monolayer of virus-producing cells (Van der Putten, supra; Stewart, et al., *EMBO J.* 6: 383-388, 1987). Alternatively, infection can be performed at a later stage. Virus or virus-producing cells can be injected into the blastocoele (D. Jahner et al., *Nature* 298: 623-628, 1982). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retroviral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al., *Nature* 292:154-156, 1981; M. O. Bradley et al., *Nature* 309:255-258, 1984; Gossler, et al., *Proc. Natl. Acad. Sci.* USA 83:9065-9069, 1986; and Robertson et al., *Nature* 322:445-448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., *Science* 240:1468-1474, 1988).

In one aspect, the "transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

In one aspect, the "transgene" means any piece of DNA which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode phytases or polypeptides having phytase activity, and include polynucleotides, which may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one aspect, transgenic animals having gene knockouts are those in which the target gene has been rendered nonfunctional by an insertion targeted to the gene to be rendered non-functional by homologous recombination.

In one aspect, the term "transgenic" includes any transgenic technology familiar to those in the art which can produce an organism carrying an introduced transgene or one in which an endogenous gene has been rendered non-functional or "knocked out."

The transgene to be used in the practice of the subject invention is a DNA sequence comprising a sequence coding for a phytase or a polypeptide having phytase activity. In one aspect, a polynucleotide having a sequence as set forth in SEQ ID NO:1 or a sequence encoding a polypeptide having a sequence as set forth in SEQ ID NO:2 is the transgene as the term is defined herein. Where appropriate, DNA sequences that encode proteins having phytase activity but differ in nucleic acid sequence due to the degeneracy of the genetic code may also be used herein, as may truncated forms, allelic variants and interspecies homologues.

In one aspect, after an embryo has been microinjected, colonized with transfected embryonic stem cells or infected with a retrovirus containing the transgene (except for practice of the subject invention in avian species which is addressed elsewhere herein), the embryo is implanted into the oviduct of a pseudopregnant female. The consequent progeny are tested for incorporation of the transgene by Southern blot analysis of blood or tissue samples using transgene specific probes. PCR is particularly useful in this regard. Positive progeny (GO) are crossbred to produce offspring (G1) which are analyzed for transgene expression by Northern blot analysis of tissue samples.

In one aspect, the methods comprise increasing the phosphorous uptake in the transgenic animal and/or decreasing the amount of pollutant in the manure of the transgenic organism by about 15%, about 20%, or about 20%, to about 50% or more.

In one aspect, the animals contemplated for use in the practice of the subject invention are those animals generally regarded as domesticated animals including pets (e.g., canines, felines, avian species etc.) and those useful for the processing of food stuffs, i.e., avian such as meat bred and egg laying chicken and turkey, ovine such as lamb, bovine such as beef cattle and milk cows, piscine and porcine. In one aspect, these animals are referred to as "transgenic" when such animal has had a heterologous DNA sequence, or one or more additional DNA sequences normally endogenous to the animal (collectively referred to herein as "transgenes") chromosomally integrated into the germ cells of the animal. The transgenic animal (including its progeny) will also have the transgene fortuitously integrated into the chromosomes of somatic cells.

Screening Methodologies and "On-Line" Monitoring Devices

In practicing the methods of the invention, a variety of apparatus and methodologies can be used to in conjunction with the polypeptides and nucleic acids of the invention, e.g., to screen polypeptides for phytaseactivity, to screen compounds as potential modulators of activity (e.g., potentiation or inhibition of enzyme activity), for antibodies that bind to a polypeptide of the invention, for nucleic acids that hybridize to a nucleic acid of the invention, and the like.

Immobilized Enzyme Solid Supports

The phytase enzymes, fragments thereof and nucleic acids that encode the enzymes and fragments can be affixed to a solid support. This is often economical and efficient in the use of the phytases in industrial processes. For example, a consortium or cocktail of phytase enzymes (or active fragments thereof), which are used in a specific chemical reaction, can be attached to a solid support and dunked into a process vat. The enzymatic reaction can occur. Then, the solid support can be taken out of the vat, along with the enzymes affixed thereto, for repeated use. In one embodiment of the invention, an isolated nucleic acid of the invention is affixed to a solid support. In another embodiment of the invention, the solid support is selected from the group of a gel, a resin, a polymer, a ceramic, a glass, a microelectrode and any combination thereof.

For example, solid supports useful in this invention include gels. Some examples of gels include Sepharose, gelatin, glutaraldehyde, chitosan-treated glutaraldehyde, albumin-glutaraldehyde, chitosan-Xanthan, toyopearl gel (polymer gel), alginate, alginate-polylysine, carrageenan, agarose, glyoxyl agarose, magnetic agarose, dextran-agarose, poly(Carbamoyl Sulfonate) hydrogel, BSA-PEG hydrogel, phosphorylated polyvinyl alcohol (PVA), mono-aminoethyl-N-aminoethyl (MANA), amino, or any combination thereof.

Another solid support useful in the present invention are resins or polymers. Some examples of resins or polymers include cellulose, acrylamide, nylon, rayon, polyester, anion-exchange resin, AMBERLITE™ XAD-7, AMBERLITE™ XAD-8, AMBERLITE™ IRA-94, AMBERLITE™ IRC-50, polyvinyl, polyacrylic, polymethacrylate, or any combination thereof. another type of solid support useful in the present invention is ceramic. Some examples include non-porous ceramic, porous ceramic, $SiO_2$, $Al_2O_3$. Another type of solid support useful in the present invention is glass. Some examples include non-porous glass, porous glass, aminopropyl glass or any combination thereof. Another type of solid support that can be used is a microelectrode. An example is a polyethyleneimine-coated magnetite. Graphitic particles can be used as a solid support. Another example of a solid support is a cell, such as a red blood cell.

Methods of Immobilization

There are many methods that would be known to one of skill in the art for immobilizing enzymes or fragments thereof, or nucleic acids, onto a solid support. Some examples of such methods include, e.g., electrostatic droplet generation, electrochemical means, via adsorption, via covalent binding, via cross-linking, via a chemical reaction or process, via encapsulation, via entrapment, via calcium alginate, or via poly (2-hydroxyethyl methacrylate). Like methods are described in Methods in Enzymology, Immobilized Enzymes and Cells, Part C. 1987. Academic Press. Edited by S. P. Colowick and N. O. Kaplan. Volume 136; and Immobilization of Enzymes and Cells. 1997. Humana Press. Edited by G. F. Bickerstaff. Series: Methods in Biotechnology, Edited by J. M. Walker.

Capillary Arrays

Capillary arrays, such as the GIGAMATRIX™, Diversa Corporation, San Diego, Calif., can be used to in the methods of the invention. Nucleic acids or polypeptides of the invention can be immobilized to or applied to an array, including capillary arrays. Arrays can be used to screen for or monitor libraries of compositions (e.g., small molecules, antibodies, nucleic acids, etc.) for their ability to bind to or modulate the activity of a nucleic acid or a polypeptide of the invention. Capillary arrays provide another system for holding and screening samples. For example, a sample screening apparatus can include a plurality of capillaries formed into an array of adjacent capillaries, wherein each capillary comprises at least one wall defining a lumen for retaining a sample. The apparatus can further include interstitial material disposed between adjacent capillaries in the array, and one or more reference indicia formed within of the interstitial material. A capillary for screening a sample, wherein the capillary is adapted for being bound in an array of capillaries, can include a first wall defining a lumen for retaining the sample, and a second wall formed of a filtering material, for filtering excitation energy provided to the lumen to excite the sample.

A polypeptide or nucleic acid, e.g., a ligand, can be introduced into a first component into at least a portion of a capillary of a capillary array. Each capillary of the capillary array can comprise at least one wall defining a lumen for retaining the first component. An air bubble can be introduced into the capillary behind the first component. A second component can be introduced into the capillary, wherein the second component is separated from the first component by the air bubble. A sample of interest can be introduced as a first liquid labeled with a detectable particle into a capillary of a capillary array, wherein each capillary of the capillary array comprises at least one wall defining a lumen for retaining the first liquid and the detectable particle, and wherein the at least one wall is coated with a binding material for binding the detectable particle to the at least one wall. The method can further include removing the first liquid from the capillary tube, wherein the bound detectable particle is maintained within the capillary, and introducing a second liquid into the capillary tube.

The capillary array can include a plurality of individual capillaries comprising at least one outer wall defining a lumen. The outer wall of the capillary can be one or more walls fused together. Similarly, the wall can define a lumen that is cylindrical, square, hexagonal or any other geometric shape so long as the walls form a lumen for retention of a liquid or sample. The capillaries of the capillary array can be held together in close proximity to form a planar structure. The capillaries can be bound together, by being fused (e.g., where the capillaries are made of glass), glued, bonded, or clamped side-by-side. The capillary array can be formed of any number of individual capillaries, for example, a range from 100 to 4,000,000 capillaries. A capillary array can form a microtiter plate having about 100,000 or more individual capillaries bound together.

Arrays, or "BioChips"

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of a phytase gene. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. "Polypeptide arrays" can also be used to simultaneously quantify a plurality of proteins.

In alternative aspects, "arrays" or "microarrays" or "biochips" or "chips" of the invention comprise a plurality of target elements in addition to a nucleic acid and/or a polypeptide or peptide of the invention; each target element can comprises a defined amount of one or more polypeptides (including antibodies) or nucleic acids immobilized onto a defined area of a substrate surface, as discussed in further detail, below.

The present invention can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts.

In practicing the methods of the invention, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent applications Nos. 20010018642; 20010019827; 20010016322; 20010014449; 20010014448; 20010012537; 20010008765.

Polypeptides and Peptides

The invention provides isolated, synthetic or recombinant polypeptides having an amino acid sequence at least 95%, 96% 97%, 98% or 99% sequence identity to SEQ ID NO:2, and comprising at least one of the mutations listed in Table 4, 5, 6, 7, 9, or any combination thereof. The invention further provides isolated, synthetic or recombinant nucleic acids encoding polypeptides having an amino acid sequence at least 95%, 96% 97%, 98% or 99% sequence identity to SEQ ID NO:2, and comprising at least one of the mutations listed in Table 4, 5, 6, 7, 9, or any combination thereof. For reference, the synthetically generated "parent" SEQ ID NO:2 is:

```
Met Lys Ala Ile Leu Ile Pro Phe Leu Ser Leu Leu Ile Pro Leu Thr
1               5                   10                  15

Pro Gln Ser Ala Phe Ala Gln Ser Glu Pro Glu Leu Lys Leu Glu Ser
                20                  25                  30

Val Val Ile Val Ser Arg His Gly Val Arg Ala Pro Thr Lys Ala Thr
            35                  40                  45

Gln Leu Met Gln Asp Val Thr Pro Asp Ala Trp Pro Thr Trp Pro Val
50                  55                  60

Lys Leu Gly Glu Leu Thr Pro Arg Gly Gly Leu Ile Ala Tyr Leu
65                  70                  75                  80

Gly His Tyr Trp Arg Gln Arg Leu Val Ala Asp Gly Leu Leu Pro Lys
                85                  90                  95

Cys Gly Cys Pro Gln Ser Gly Gln Val Ala Ile Ile Ala Asp Val Asp
                100                 105                 110

Glu Arg Thr Arg Lys Thr Gly Glu Ala Phe Ala Ala Gly Leu Ala Pro
                115                 120                 125

Asp Cys Ala Ile Thr Val His Thr Gln Ala Asp Thr Ser Ser Pro Asp
130                 135                 140

Pro Leu Phe Asn Pro Leu Lys Thr Gly Val Cys Gln Leu Asp Asn Ala
145                 150                 155                 160

Asn Val Thr Asp Ala Ile Leu Glu Arg Ala Gly Gly Ser Ile Ala Asp
                165                 170                 175

Phe Thr Gly His Tyr Gln Thr Ala Phe Arg Glu Leu Glu Arg Val Leu
                180                 185                 190

Asn Phe Pro Gln Ser Asn Leu Cys Leu Lys Arg Glu Lys Gln Asp Glu
                195                 200                 205

Ser Cys Ser Leu Thr Gln Ala Leu Pro Ser Glu Leu Lys Val Ser Ala
                210                 215                 220

Asp Cys Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
                260                 265                 270

Asn Ala Gln Phe Asp Leu Leu Gln Arg Thr Pro Glu Val Ala Arg Ser
                275                 280                 285

Arg Ala Thr Pro Leu Leu Asp Leu Ile Lys Thr Ala Leu Thr Pro His
                290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
                340                 345                 350

Gly Glu Leu Val Phe Glu Arg Trp Arg Arg Leu Ser Asp Asn Ser Gln
                355                 360                 365

Trp Ile Gln Val Ser Leu Val Phe Gln Thr Leu Gln Gln Met Arg Asp
                370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
                420                 425                 430
```

The sequence of the parental phytase SEQ ID NO:2, encoded by, e.g., SEQ ID NO:1, showing the gene site saturation mutagenesis (GSSM)-generated sequence modifications selected for GeneReassembly™ library construction, as described in Example 1, are shown in FIG. 4. Parental phytase SEQ ID NO:2, encoded by, e.g., SEQ ID NO:1 was subjected to further gene site saturation mutagenesis (GSSM) sequence modifications, site directed mutagenesis (SDM) and TMCA library construction, as described in Example 2.

In one aspect, polypeptide and peptides of the invention have phytase activity. In alternative aspects, they also can be useful as, e.g., labeling probes, antigens, toleragens, motifs, phytase active sites.

In alternative aspects, polypeptides and peptides of the invention are synthetic or are recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3 □13) and automated synthesis may be achieved, e.g., using the ABI 431A Peptide Synthesizer (Perkin Elmer) in accordance with the instructions provided by the manufacturer.

The enzymes and polynucleotides of the present invention can be provided in an isolated form or purified to homogeneity. The phytase polypeptide of the invention can be obtained using any of several standard methods. For example, phytase polypeptides can be produced in a standard recombinant expression system (as described herein), chemically synthesized (although somewhat limited to small phytase peptide fragments), or purified from organisms in which they are naturally expressed. Useful recombinant expression methods include mammalian hosts, microbial hosts, and plant hosts.

In alternative aspects, polypeptides and peptides of the invention comprise "amino acids" or "amino acid sequences" that are oligopeptides, peptides, polypeptides or protein sequences, or alternatively, are fragments, portions or subunits of any of these, and to naturally occurring or synthetic molecules.

In alternative aspects, "recombinant" polypeptides or proteins of the invention include (refer to) polypeptides or proteins produced by recombinant DNA techniques; e.g., produced from cells transformed by an exogenous DNA construct encoding the desired polypeptide or protein. "Synthetic" nucleic acids (including oligonucleotides), polypeptides or proteins of the invention include those prepared by chemical synthesis, as described in detail herein. In alternative aspects, polypeptides or proteins of the invention comprise amino acids joined to each other by peptide bonds or modified peptide bonds, i.e., peptide isosteres, and may contain modified amino acids other than the 20 gene-encoded amino acids. The polypeptides may be modified by either natural processes, such as post-translational processing, or by chemical modification techniques that are well known in the art. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation.

In alternative aspects, "synthetic" polypeptides or protein are those prepared by chemical synthesis. Solid-phase chemical peptide synthesis methods can also be used to synthesize the polypeptide or fragments of the invention. Such method have been known in the art since the early 1960's (Merrifield, R. B., *J. Am. Chem. Soc.,* 85:2149-2154, 1963) (See also Stewart, J. M. and Young, J. D., Solid Phase Peptide Synthesis, 2 ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, *Proc. Natl. Acad. Sci., USA,* 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A automated peptide synthesizer. Such equipment provides ready access to the peptides of the invention, either by direct synthesis or by synthesis of a series of fragments that can be coupled using other known techniques.

In alternative aspects, peptides and polypeptides of the invention are glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked, or, a combination thereof.

In alternative aspects, peptides and polypeptides of the invention, as defined above, comprise "mimetic" and "peptidomimetic" forms, either in part or completely. In one aspect, the terms "mimetic" and "peptidomimetic" refer to a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Thus, in one aspect, a mimetic composition is within the scope of the invention if it has a phytase activity.

In alternative aspects, peptides and polypeptides of the invention have sequences comprising the specific modification to SEQ ID NO:2, as defined above, and also conservative substitutions that may or may not modify activity, e.g., enzymatic activity. In alternative aspects, conservative substitutions are those that substitute a given amino acid in a polypeptide by another amino acid of like characteristics. In alternative aspects, conservative substitutions are the following replacements: replacements of an aliphatic amino acid such as Ala, Val, Leu and Ile with another aliphatic amino acid; replacement of a Ser with a Thr or vice versa; replacement of an acidic residue such as Asp and Glu with another acidic residue; replacement of a residue bearing an amide group, such as Asn and Gln, with another residue bearing an amide group; exchange of a basic residue such as Lys and Arg with another basic residue; and replacement of an aromatic residue such as Phe, Tyr with another aromatic residue.

Polypeptide mimetic compositions of the invention can contain any combination of non-natural structural components. In alternative aspect, mimetic compositions of the invention include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the invention can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH2- for —C(=O)—NH—), aminomethylene (CH2-NH), ethylene, olefin (CH=CH), ether (CH2-O), thioether (CH2-S), tetrazole (CN4-), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, N.Y.).

A polypeptide of the invention can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; K- or L-p-methoxy-biphenylphenylalanine; D- or L-2-indole(alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N—C—N—R') such as, e.g., 1-cyclohexyl-3 (2-morpholinyl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, which for these reagents it may be preferable to use alkaline conditions. Tyrosine residue mimetics can be generated by reacting tyrosyl with, e.g., aromatic diazonium compounds or tetranitromethane. N-acetylimidizol and tetranitromethane can be used to form 0-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A residue, e.g., an amino acid, of a polypeptide of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

The invention also provides methods for modifying the polypeptides of the invention by either natural processes, such as post-translational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1-12 (1983).

Solid-phase chemical peptide synthesis methods can also be used to synthesize the polypeptide or fragments of the invention. Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A™ automated peptide synthesizer. Such equipment provides ready access to the peptides of the invention, either by direct synthesis or by synthesis of a series of fragments that can be coupled using other known techniques.

In one aspect, peptides and polypeptides of the invention have sequences comprising the specific modification to SEQ ID NO:2, as defined above, and also "substantially identical" amino acid sequences, i.e., a sequence that differs by one or more conservative or non-conservative amino acid substitutions, deletions, or insertions, particularly when such a substitution occurs at a site that is not the active site of the molecule, and provided that the polypeptide essentially retains its functional properties. In one aspect, peptides and polypeptides of the invention have sequences comprising the specific modification to SEQ ID NO:2, as defined above, and conservative amino acid substitutions that substitute one amino acid for another of the same class, for example, substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine. In one aspect, one or more amino acids can be deleted, for example, from a phytase polypeptide of the invention to result in modification of the structure of the polypeptide without significantly altering its biological activity, or alternative, to purposely significantly alter its biological activity. For example, amino- or carboxyl-terminal amino acids that are required, or alternatively are not required, for phytase biological activity can be removed and/or added. Modified polypeptide sequences of the invention can be assayed for phytase biological activity by any number of methods, including contacting the modified polypeptide sequence with a phytase substrate and determining whether the modified polypeptide decreases the amount of specific substrate in the assay or increases the bioproducts of the enzymatic reaction of a functional phytase polypeptide with the substrate.

Another aspect of the invention comprises polypeptides having about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to SEQ ID NO:2 and having one of the specific enumerated sequence modifications, as discussed (set forth) above.

These amino acid sequence variants of the invention can be characterized by a predetermined nature of the variation, a feature that sets them apart from a naturally occurring form, e.g., an allelic or interspecies variation of a phytase sequence. In one aspect, the variants of the invention exhibit the same qualitative biological activity as the naturally occurring analogue. Alternatively, the variants can be selected for having modified characteristics. In one aspect, while the site or region for introducing an amino acid sequence variation is predetermined, the mutation per se need not be predetermined. For example, in order to optimize the performance of a mutation at a given site, random mutagenesis may be conducted at the target codon or region and the expressed phytase variants screened for the optimal combination of desired activity. Techniques for making substitution mutations at predetermined sites in DNA having a known sequence are well known, as discussed herein for example, M13 primer mutagenesis and PCR mutagenesis. Screening of the mutants can be done using, e.g., assays of catalysis of phytate (myo-inositol-hexaphosphate) to inositol and inorganic phosphate; or, the hydrolysis of phytate (myo-inositol-hexaphosphate). In alternative aspects, amino acid substitutions can be single residues; insertions can be on the order of from about 1 to 20 amino acids, although considerably larger insertions can be done. Deletions can range from about 1 to about 20, 30, 40, 50, 60, 70 residues or more. To obtain a final derivative with the optimal properties, substitutions, deletions, insertions or any combination thereof may be used. Generally, these changes are done on a few amino acids to minimize the alteration of the molecule. However, larger changes may be tolerated in certain circumstances.

Polypeptides of the invention may be obtained through biochemical enrichment or purification procedures. The sequence of potentially homologous polypeptides or fragments may be determined by proteolytic digestion, gel electrophoresis and/or microsequencing.

Another aspect of the invention is an assay for identifying fragments or variants of polypeptides of the invention. Polypeptides of the invention may be used to catalyze biochemical reactions to indicate that said fragment or variant retains the enzymatic activity of a polypeptides of the invention.

An exemplary assay for determining if fragments of variants retain the enzymatic activity of the polypeptides of the invention comprises: contacting the polypeptide fragment or variant with a substrate molecule under conditions which allow the polypeptide fragment or variant to function, and detecting either a decrease in the level of substrate or an increase in the level of the specific reaction product of the reaction between the polypeptide and substrate.

Polypeptides of the invention may be used to catalyze biochemical reactions. In accordance with one aspect of the invention, there is provided a process for utilizing a polypeptide of the invention as a phytase.

The invention provides phytases having no or modified signal sequences (also called signal peptides (SPs), or leader peptides), or heterologous signal sequences. The polypeptides of the invention also can have no or modified or heterologous prepro domains and/or catalytic domains (CDs). The modified or heterologous SPs, prepro domains and/or CDs incorporated in a polypeptide the invention can be part of a fusion protein, e.g., as a heterologous domain in a chimeric protein, or added by a chemical linking agent. For example, an enzyme of the invention can comprise a heterologous SP and/or prepro in a vector, e.g., a pPIC series vector (Invitrogen, Carlsbad, Calif.).

Additionally, polypeptides of the invention can further comprise heterologous sequences, either sequences from other phytases, or from non-phytase sources, or entirely synthetic sequences. Thus, in one aspect, a nucleic acid of the invention comprises coding sequence for an endogenous, modified or heterologous signal sequence (SP), prepro domain and/or catalytic domain (CD) and a heterologous sequence (i.e., a sequence not naturally associated with the a signal sequence (SP), prepro domain and/or catalytic domain (CD) of the invention). The heterologous sequence can be on the 3' terminal end, 5' terminal end, and/or on both ends of the SP, prepro domain and/or CD coding sequence.

Methods for identifying "prepro" domain sequences and signal sequences are well known in the art, see, e.g., Van de Ven (1993) Crit. Rev. Oncog. 4(2):115-136. For example, to identify a prepro sequence, the protein is purified from the extracellular space and the N-terminal protein sequence is determined and compared to the unprocessed form. Various methods of recognition of signal sequences are known to those of skill in the art. For example, in one aspect, signal peptides for use with polypeptides of the invention are identified by a method referred to as SignalP. SignalP uses a combined neural network which recognizes both signal peptides and their cleavage sites; see, e.g., Nielsen (1997) "Identification of prokaryotic and eukaryotic signal peptides and prediction of their cleavage sites" Protein Engineering 10:1-6.

The invention provides phytase enzymes where the structure of the polypeptide backbone, the secondary or the tertiary structure, e.g., an alpha-helical or beta-sheet structure, has been modified. In one aspect, the charge or hydrophobicity has been modified. In one aspect, the bulk of a side chain has been modified. Substantial changes in function or immunological identity are made by selecting substitutions that are less conservative. For example, substitutions can be made which more significantly affect: the structure of the polypeptide backbone in the area of the alteration, for example an alpha-helical or a beta-sheet structure; a charge or a hydrophobic site of the molecule, which can be at an active site; or a side chain. The invention provides substitutions in polypeptide of the invention where (a) a hydrophilic residues, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine. The variants can exhibit the same qualitative biological activity (i.e., phytase enzyme activity) although variants can be selected to modify the characteristics of the phytase as needed.

In one aspect, phytases of the invention comprise epitopes or purification tags, signal sequences or other fusion sequences, etc. In one aspect, phytases of the invention can be fused to a random peptide to form a fusion polypeptide. By "fused" or "operably linked" herein is meant that the random peptide and the phytase are linked together, in such a manner as to minimize the disruption to the stability of phytase activity. The fusion polypeptide (or fusion polynucleotide encoding the fusion polypeptide) can comprise further components as well, including multiple peptides at multiple loops.

In one aspect, phytases of the invention are chimeric polypeptides, e.g., comprising heterologous SPs, carbohydrate binding modules, phytase enzyme catalytic domains, linkers and/or non-phytase catalytic domains. The invention provides a means for generating chimeric polypeptides which may encode biologically active hybrid polypeptides (e.g., hybrid phytase enzymes). In one aspect, the original polynucleotides encode biologically active polypeptides. The method of the invention produces new hybrid polypeptides by utilizing cellular processes which integrate the sequence of the original polynucleotides such that the resulting hybrid polynucleotide encodes a polypeptide demonstrating activities derived from the original biologically active polypeptides. For example, the original polynucleotides may encode a particular enzyme from different microorganisms. An enzyme encoded by a first polynucleotide from one organism or variant may, for example, function effectively under a particular environmental condition, e.g. high salinity. An enzyme encoded by a second polynucleotide from a different organism or variant may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

Thus, a hybrid polypeptide resulting from this method of the invention may exhibit specialized enzyme activity not displayed in the original enzymes. For example, following recombination and/or reductive reassortment of polynucleotides encoding phytase enzymes, the resulting hybrid polypeptide encoded by a hybrid polynucleotide can be screened for specialized enzyme activities, e.g., hydrolase, peptidase, phosphorylase, etc., activities, obtained from each of the original enzymes. Thus, for example, the hybrid polypeptide may be screened to ascertain those chemical functionalities which distinguish the hybrid polypeptide from the original parent polypeptides, such as the temperature, pH or salt concentration at which the hybrid polypeptide functions.

A hybrid polypeptide resulting from the method of the invention may exhibit specialized enzyme activity not displayed in the original enzymes. For example, following recombination and/or reductive reassortment of polynucleotides encoding hydrolase activities, the resulting hybrid polypeptide encoded by a hybrid polynucleotide can be screened for specialized hydrolase activities obtained from each of the original enzymes, i.e., the type of bond on which the hydrolase acts and the temperature at which the hydrolase functions. Thus, for example, a phytase may be screened to ascertain those chemical functionalities which distinguish the hybrid phytase from the original phytases, such as: (a) amide (peptide bonds), i.e., proteases; (b) ester bonds, i.e., esterases and lipases; (c) acetals, i.e., glycosidases and, for example, the temperature, pH or salt concentration at which the hybrid polypeptide functions.

In one aspect, the invention relates to a method for producing a biologically active hybrid polypeptide and screening such a polypeptide for enhanced activity by:

(1) introducing at least a first polynucleotide in operable linkage and a second polynucleotide in operable linkage, said at least first polynucleotide and second polynucleotide sharing at least one region of partial sequence homology, into a suitable host cell;

(2) growing the host cell under conditions which promote sequence reorganization resulting in a hybrid polynucleotide in operable linkage;

(3) expressing a hybrid polypeptide encoded by the hybrid polynucleotide;

(4) screening the hybrid polypeptide under conditions which promote identification of enhanced biological activity; and (5) isolating the a polynucleotide encoding the hybrid polypeptide.

Methods for screening for various enzyme activities are known to those of skill in the art and are discussed throughout the present specification. Such methods may be employed when isolating the polypeptides and polynucleotides of the invention.

In one aspect, the instant invention provides a method (and products thereof) of producing stabilized aqueous liquid formulations having phytase activity that exhibit increased resistance to heat inactivation of the enzyme activity and which retain their phytase activity during prolonged periods of storage. The liquid formulations are stabilized by means of the addition of urea and/or a polyol such as sorbitol and glycerol as stabilizing agent. Also provided are feed preparations for monogastric animals and methods for the production thereof that result from the use of such stabilized aqueous liquid formulations. Additional details regarding this approach are in the public literature and/or are known to the skilled artisan. In a particular non-limiting exemplification, such publicly available literature includes EP 0626010 (WO 9316175 A1) (Barendse et al.), although references in the publicly available literature do not teach the inventive molecules of the instant application.

Antibodies and Antibody-Based Screening Methods

The invention provides isolated, synthetic or recombinant antibodies that specifically bind to a phytase of the invention. These antibodies can be used to isolate, identify or quantify the phytases of the invention or related polypeptides. These antibodies can be used to inhibit the activity of an enzyme of the invention. These antibodies can be used to isolated polypeptides related to those of the invention, e.g., related phytase enzymes.

Antibodies of the invention can comprise a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

The antibodies can be used in immunoprecipitation, staining (e.g., FACS), immunoaffinity columns, and the like. If desired, nucleic acid sequences encoding for specific antigens can be generated by immunization followed by isolation of polypeptide or nucleic acid, amplification or cloning and immobilization of polypeptide onto an array of the invention. Alternatively, the methods of the invention can be used to modify the structure of an antibody produced by a cell to be modified, e.g., an antibody's affinity can be increased or decreased. Furthermore, the ability to make or modify antibodies can be a phenotype engineered into a cell by the methods of the invention.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, N Y (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

The polypeptides can be used to generate antibodies which bind specifically to the polypeptides of the invention. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the invention.

In immunoaffinity procedures, the antibody is attached to a solid support, such as a bead or other column matrix. The protein preparation is placed in contact with the antibody under conditions in which the antibody specifically binds to one of the polypeptides of the invention. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of the invention can be obtained by direct injection of the polypeptides into an animal or by administering the polypeptides to an animal, for example, a nonhuman. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77-96).

Techniques described for the production of single chain antibodies (see, e.g., U.S. Pat. No. 4,946,778) can be adapted to produce single chain antibodies to the polypeptides of the invention. Alternatively, transgenic mice may be used to express humanized antibodies to these polypeptides or fragments thereof.

Antibodies generated against the polypeptides of the invention may be used in screening for similar polypeptides from other organisms and samples. In such techniques, polypeptides from the organism are contacted with the antibody and those polypeptides which specifically bind the antibody are detected. Any of the procedures described above may be used to detect antibody binding.

Kits

The invention provides kits comprising the compositions, e.g., nucleic acids, expression cassettes, vectors, cells, polypeptides (e.g., phytases) and/or antibodies of the invention. The kits also can contain instructional material teaching the methodologies and industrial uses of the invention, as described herein.

The polypeptides of the invention may also be used to generate antibodies which bind specifically to the enzyme polypeptides or fragments. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of a polypeptide of SEQ ID NO:2, sequences substantially identical thereto, or fragments of the foregoing sequences.

In immunoaffinity procedures, the antibody is attached to a solid support, such as a bead or other column matrix. The protein preparation is placed in contact with the antibody under conditions in which the antibody specifically binds to one of the polypeptides of SEQ ID NO:2, sequences substantially identical thereto, or fragment thereof. After a wash to remove non-specifically bound proteins, the specifically bound polypeptides are eluted.

The isolated polynucleotide sequences, polypeptide sequence, variants and mutants thereof can be measured for retention of biological activity characteristic to the enzyme of the present invention, for example, in an assay for detecting enzymatic phytase activity (Food Chemicals Codex, $4^{th}$ Ed.). Such enzymes include truncated forms of phytase, and variants such as deletion and insertion variants of the polypeptide sequence as set forth in SEQ ID NO:2. These phytases have thermotolerance. That is, the phytase has a residual specific activity of about 90% after treatment at 70° C. for 30 minutes and about 50% after treatment at 75° C. for 30 minutes. The thermotolerance of the invention phytases is advantageous in using the enzyme as a feed additive as the feed can be molded, granulated, or pelletized at a high temperature.

For example, in one aspect, the invention provides an edible pelletized enzyme delivery matrix and method of use for delivery of phytase to an animal, for example as a nutritional supplement. The enzyme delivery matrix readily releases a phytase enzyme, such as one having the amino acid sequence of SEQ ID NO:2 or at least 30 contiguous amino acids thereof, in aqueous media, such as, for example, the digestive fluid of an animal. The invention enzyme delivery matrix is prepared from a granulate edible carrier selected from such components as grain germ that is spent of oil, hay, alfalfa, timothy, soy hull, sunflower seed meal, wheat meal, and the like, that readily disperse the recombinant enzyme contained therein into aqueous media. In use, the edible pelletized enzyme delivery matrix is administered to an animal to delivery of phytase to the animal. Suitable grain-based substrates may comprise or be derived from any suitable edible grain, such as wheat, corn, soy, sorghum, alfalfa, barley, and the like. An exemplary grain-based substrate is a corn-based substrate. The substrate may be derived from any suitable part of the grain, e.g., a grain germ, approved for animal feed use, such as corn germ that is obtained in a wet or dry milling process. The grain germ can comprise spent germ, which is grain germ from which oil has been expelled, such as by pressing or hexane or other solvent extraction. Alternatively, the grain germ is expeller extracted, that is, the oil has been removed by pressing.

The enzyme delivery matrix of the invention is in the form of discrete plural particles, pellets or granules. By "granules" is meant particles that are compressed or compacted, such as by a pelletizing, extrusion, or similar compacting to remove water from the matrix. Such compression or compacting of the particles also promotes intraparticle cohesion of the particles. For example, the granules can be prepared by pelletizing the grain-based substrate in a pellet mill. The pellets prepared thereby are ground or crumbled to a granule size suitable for use as an adjuvant in animal feed. Since the matrix is itself approved for use in animal feed, it can be used as a diluent for delivery of enzymes in animal feed.

The enzyme delivery matrix can be in the form of granules having a granule size ranging from about 4 to about 400 mesh (USS); or about 8 to about 80 mesh; or about 14 to about 20 mesh. If the grain germ is spent via solvent extraction, use of a lubricity agent such as corn oil may be necessary in the pelletizer, but such a lubricity agent ordinarily is not necessary if the germ is expeller extracted. In other aspects of the invention, the matrix is prepared by other compacting or compressing processes such as, for example, by extrusion of the grain-based substrate through a die and grinding of the extrudate to a suitable granule size.

The enzyme delivery matrix may further include a polysaccharide component as a cohesiveness agent to enhance the cohesiveness of the matrix granules. The cohesiveness agent is believed to provide additional hydroxyl groups, which enhance the bonding between grain proteins within the matrix granule. It is further believed that the additional hydroxyl groups so function by enhancing the hydrogen bonding of proteins to starch and to other proteins. The cohesiveness agent may be present in any amount suitable to enhance the cohesiveness of the granules of the enzyme delivery matrix. Suitable cohesiveness agents include one or more of dextrins, maltodextrins, starches, such as corn starch, flours, cellulosics, hemicellulosics, and the like. For example, the percentage of grain germ and cohesiveness agent in the matrix (not including the enzyme) is 78% corn germ meal and 20% by weight of corn starch.

Because the enzyme-releasing matrix of the invention is made from biodegradable materials, the matrix may be subject to spoilage, such as by molding. To prevent or inhibit such molding, the matrix may include a mold inhibitor, such as a propionate salt, which may be present in any amount sufficient to inhibit the molding of the enzyme-releasing matrix, thus providing a delivery matrix in a stable formulation that does not require refrigeration.

The phytase enzyme contained in the invention enzyme delivery matrix and methods is in one aspect a thermotolerant phytase, as described herein, so as to resist inactivation of the phytase during manufacture where elevated temperatures and/or steam may be employed to prepare the pelletized enzyme delivery matrix. During digestion of feed containing the invention enzyme delivery matrix, aqueous digestive fluids will cause release of the active enzyme. Other types of thermotolerant enzymes and nutritional supplements that are thermotolerant can also be incorporated in the delivery matrix for release under any type of aqueous conditions.

A coating can be applied to the invention enzyme matrix particles for many different purposes, such as to add a flavor or nutrition supplement to animal feed, to delay release of animal feed supplements and enzymes in gastric conditions, and the like. Or, the coating may be applied to achieve a functional goal, for example, whenever it is desirable to slow release of the enzyme from the matrix particles or to control the conditions under which the enzyme will be released. The composition of the coating material can be such that it is selectively broken down by an agent to which it is susceptible (such as heat, acid or base, enzymes or other chemicals). Alternatively, two or more coatings susceptible to different such breakdown agents may be consecutively applied to the matrix particles.

The invention is also directed towards a process for preparing an enzyme-releasing matrix. In accordance with the invention, the process comprises providing discrete plural particles of a grain-based substrate in a particle size suitable for use as an enzyme-releasing matrix, wherein the particles comprise a phytase enzyme of the invention. The process can include compacting or compressing the particles of enzyme-releasing matrix into granules, which can be accomplished by pelletizing. The mold inhibitor and cohesiveness agent, when used, can be added at any suitable time, and can be mixed with the grain-based substrate in the desired proportions prior to pelletizing of the grain-based substrate. Moisture content in the pellet mill feed can be in the ranges set forth above with respect to the moisture content in the finished product, or about 14% to 15%, or about 10% to 20%. Moisture can be added to the feedstock in the form of an aqueous preparation of the enzyme to bring the feedstock to this moisture content. The temperature in the pellet mill can be brought to about 82° C. with steam. The pellet mill may be operated under any conditions that impart sufficient work to the feedstock to provide pellets. The pelleting process itself is a cost-effective process for removing water from the enzyme-containing composition.

In one aspect, the pellet mill is operated with a ⅛ in. by 2 in. die at 100 lb./min. pressure at 82° C. to provide pellets, which then are crumbled in a pellet mill crumbler to provide discrete plural particles having a particle size capable of passing through an 8 mesh screen but being retained on a 20 mesh screen.

The thermotolerant phytases described herein can have high optimum temperatures and can have high heat resistance or heat tolerance. Thus, the phytases of the invention can carry out enzymatic reactions at temperatures normally considered above optimum. The phytases of the invention also can carry out enzymatic reactions after being exposed to high temperatures (thermotolerance being the ability to retain enzymatic activity at temperatures where the wild type phytase is active after previously being exposed to high temperatures, even if the high temperature can inactivate or diminish the enzyme's activity, see also definition of thermotolerance, above). The gene encoding the phytase according to the present invention can be used in preparation of phytases (e.g. using GSSM and/or TMCA technology, as described herein) having characteristics different from those of the phytase of SEQ ID NO:2 (in terms of optimum pH, optimum temperature, heat resistance, stability to solvents, specific activity, affinity to substrate, secretion ability, translation rate, transcription control and the like). Furthermore, the polynucleotides of the invention may be employed for screening of variant phytases prepared by the methods described herein to determine those having a desired activity, such as improved or modified thermostability or thermotolerance. For example, U.S. Pat. No. 5,830,732, describes a screening assay for determining thermotolerance of a phytase.

An in vitro example of such a screening assay is the following assay for the detection of phytase activity: Phytase activity can be measured by incubating 150 µl of the enzyme preparation with 600 µl of 2 mM sodium phytate in 100 mM Tris HCl buffer, pH 7.5, supplemented with 1 mM $CaCl_2$) for 30 minutes at 37° C. After incubation the reaction is stopped by adding 750 µl of 5% trichloroacetic acid. Phosphate released was measured against phosphate standard spectrophotometrically at 700 nm after adding 1500 µl of the color reagent (4 volumes of 1.5% ammonium molybdate in 5.5% sulfuric acid and 1 volume of 2.7% ferrous sulfate; Shimizu, 1992). One unit of enzyme activity is defined as the amount of enzyme required to liberate one µmol Pi per min under assay conditions. Specific activity can be expressed in units of enzyme activity per mg of protein. The enzyme of the present invention has enzymatic activity with respect to the hydrolysis of phytate to inositol and free phosphate.

In one aspect, the instant invention provides a method of hydrolyzing phytate comprised of contacting the phytate with one or more of the novel phytase molecules disclosed herein (e.g., proteins having the specific modifications of SEQ ID NO:2). Accordingly, the invention provides a method for catalyzing the hydrolysis of phytate to inositol and free phosphate with release of minerals from the phytic acid complex. The method includes contacting a phytate substrate with a degrading effective amount of an enzyme of the invention. The term "degrading effective" amount refers to the amount of enzyme which is required to degrade at least 50% of the phytate, as compared to phytate not contacted with the enzyme. 80% of the phytate can be degraded.

In another aspect, the invention provides a method for hydrolyzing phospho-mono-ester bonds in phytate. The method includes administering an effective amount of phytase molecules of the invention, to yield inositol and free phosphate. In one aspect, an "effective" amount refers to the amount of enzyme which is required to hydrolyze at least 50% of the phospho-mono-ester bonds, as compared to phytate not contacted with the enzyme. In one aspect, at least 80% of the bonds are hydrolyzed.

In a particular aspect, when desired, the phytase molecules may be used in combination with other reagents, such as other catalysts; in order to effect chemical changes (e.g. hydrolysis) in the phytate molecules and/or in other molecules of the substrate source(s). According to this aspect, the phytase molecules and the additional reagent(s) will not inhibit each other. The phytase molecules and the additional reagent(s) can have an overall additive effect, or, alternatively, phytase molecules and the additional reagent(s) can have an overall synergistic effect.

Relevant sources of the substrate phytate molecules include foodstuffs, potential foodstuffs, byproducts of foodstuffs (both in vitro byproducts and in vivo byproducts, e.g. ex vivo reaction products and animal excremental products), precursors of foodstuffs, and any other material source of phytate.

In a non-limiting aspect, the recombinant phytase can be consumed by organisms and retains activity upon consumption. In another exemplification, transgenic approaches can be used to achieve expression of the recombinant phytase— e.g., in a controlled fashion (methods are available for controlling expression of transgenic molecules in time-specific and tissue specific manners).

In one aspect, the phytase activity in the source material (e.g. a transgenic plant source or a recombinant prokaryotic host) may be increased upon consumption; this increase in activity may occur, for example, upon conversion of a precursor phytase molecule in pro-form to a significantly more active enzyme in a more mature form, where said conversion may result, for example, from the ingestion and digestion of the phytase source. Hydrolysis of the phytate substrate may occur at any time upon the contacting of the phytase with the phytate; for example, this may occur before ingestion or after ingestion or both before and after ingestion of either the substrate or the enzyme or both. It is additionally appreciated that the phytate substrate may be contacted with—in addition to the phytase—one or more additional reagents, such as another enzyme, which may be also be applied either directly or after purification from its source material.

It is appreciated that the phytase source material(s) can be contacted directly with the phytate source material(s); e.g. upon in vitro or in vivo grinding or chewing of either or both the phytase source(s) and the phytate source(s). Alternatively the phytase enzyme may be purified away from source material(s), or the phytate substrate may be purified away from source material(s), or both the phytase enzyme and the phytate substrate may be purified away from source material(s) prior to the contacting of the phytase enzyme with the phytate substrate. It is appreciated that a combination of purified and unpurified reagents—including enzyme(s) or substrates(s) or both—may be used.

It is appreciated that more than one source material may be used as a source of phytase activity. This is serviceable as one way to achieve a timed release of reagent(s) from source material(s), where release from different reagents from their source materials occur differentially, for example as ingested source materials are digested in vivo or as source materials are processed in in vitro applications. The use of more than one source material of phytase activity is also serviceable to obtain phytase activities under a range of conditions and fluctuations thereof, that may be encountered—such as a range of pH values, temperatures, salinities, and time intervals—for example during different processing steps of an application. The use of different source materials is also serviceable in order to obtain different reagents, as exemplified by one or more forms or isomers of phytase and/or phytate and/or other materials.

It is appreciated that a single source material, such a transgenic plant species (or plant parts thereof), may be a source material of both phytase and phytate; and that enzymes and substrates may be differentially compartmentalized within said single source—e.g. secreted vs. non-secreted, differentially expressed and/or having differential abundances in different plant parts or organs or tissues or in subcellular compartments within the same plant part or organ or tissue. Purification of the phytase molecules contained therein may comprise isolating and/or further processing of one or more desirable plant parts or organs or tissues or subcellular compartments.

In one aspect, this invention provides a method of catalyzing in vivo and/or in vitro reactions using seeds containing enhanced amounts of enzymes. The method comprises adding transgenic, non-wild type seeds, e.g., in a ground form, to a reaction mixture and allowing the enzymes in the seeds to increase the rate of reaction. By directly adding the seeds to the reaction mixture the method provides a solution to the more expensive and cumbersome process of extracting and purifying the enzyme. Methods of treatment are also provided whereby an organism lacking a sufficient supply of an enzyme is administered the enzyme in the form of seeds from one or more plant species, e.g., transgenic plant species, containing enhanced amounts of the enzyme. Additional details regarding this approach are in the public literature and/or are known to the skilled artisan. In a particular non-limiting exemplification, such publicly available literature includes U.S. Pat. No. 5,543,576 (Van Ooijen et al.) and U.S. Pat. No. 5,714,474 (Van Ooijen et al.), although these reference do not teach the inventive molecules of the instant application and instead teach the use of fungal phytases.

In one aspect, the instant phytase molecules are serviceable for generating recombinant digestive system life forms (or microbes or flora) and for the administration of said recombinant digestive system life forms to animals. Administration may be optionally performed alone or in combination with other enzymes and/or with other life forms that can provide enzymatic activity in a digestive system, where said other enzymes and said life forms may be may recombinant or otherwise. For example, administration may be performed in combination with xylanolytic bacteria.

In one aspect, the present invention provides a method for steeping corn or sorghum kernels in warm water containing sulfur dioxide in the presence of an enzyme preparation comprising one or more phytin-degrading enzymes, e.g., in such an amount that the phytin present in the corn or sorghum is substantially degraded. The enzyme preparation may comprise phytase and/or acid phosphatase and optionally other plant material degrading enzymes. The steeping time may be 12 to 18 hours. The steeping may be interrupted by an intermediate milling step, reducing the steeping time. In one aspect, corn or sorghum kernels are steeped in warm water containing sulfur dioxide in the presence of an enzyme preparation including one or more phytin-degrading enzymes, such as phytase and acid phosphatases, to eliminate or greatly reduce phytic acid and the salts of phytic acid. Additional details regarding this approach are in the public literature and/or are known to the skilled artisan, e.g., U.S. Pat. No. 4,914,029, (Caransa et al.) and EP 0321004 (Vaara et al.).

In one aspect, the present invention provides a method to obtain a bread dough having desirable physical properties such as non-tackiness and elasticity and a bread product of superior quality such as a specific volume comprising adding phytase molecules to the bread dough. In one aspect, phytase molecules of the instant invention are added to a working bread dough preparation that is subsequently formed and baked. Additional details regarding this approach are in the public literature and/or are known to the skilled artisan, for example, JP 03076529 (Hara et al.).

In one aspect, the present invention provides a method to produce improved soybean foodstuffs. Soybeans are combined with phytase molecules of the instant invention to remove phytic acid from the soybeans, thus producing soybean foodstuffs that are improved in their supply of trace nutrients essential for consuming organisms and in its digestibility of proteins. In one aspect, in the production of soybean milk, phytase molecules of the instant invention are added to or brought into contact with soybeans in order to reduce the phytic acid content. In a non-limiting exemplification, the application process can be accelerated by agitating the soybean milk together with the enzyme under heating or by a conducting a mixing-type reaction in an agitation container using an immobilized enzyme. Additional details regarding this approach are in the public literature and/or are known to the skilled artisan, for example, JP 59166049 (Kamikubo et al.).

In one aspect, the instant invention provides a method of producing an admixture product for drinking water or animal feed in fluid form, and which comprises using mineral mixtures and vitamin mixtures, and also novel phytase molecules of the instant invention. In a one aspect, there is achieved a correctly dosed and composed mixture of necessary nutrients for the consuming organism without any risk of precipitation and destruction of important minerals/vitamins, while at the same time optimum utilization is made of the phytin-bound phosphate in the feed. Additional details regarding this approach are in the public literature and/or are known to the skilled artisan, e.g., EP 0772978 (Bendixen et al.).

It is appreciated that the phytase molecules of the instant invention may also be used to produce other alcoholic and non-alcoholic drinkable foodstuffs (or drinks) based on the use of molds and/or on grains and/or on other plants. These drinkable foodstuffs include liquors, wines, mixed alcoholic drinks (e.g. wine coolers, other alcoholic coffees such as Irish coffees, etc.), beers, near-beers, juices, extracts, homogenates, and purees. In one aspect, the instantly disclosed phytase molecules are used to generate transgenic versions of molds and/or grains and/or other plants serviceable for the production of such drinkable foodstuffs. In another aspect, the instantly disclosed phytase molecules are used as additional ingredients in the manufacturing process and/or in the final content of such drinkable foodstuffs. Additional details regarding this approach are in the public literature and/or are known to the skilled artisan.

In one aspect, the present invention provides a means to obtain refined sake having a reduced amount of phytin and an increased content of inositol. Such a sake may have—through direct and/or psychogenic effects—a preventive action on hepatic disease, arteriosclerosis, and other diseases. In one aspect, a sake is produced from rice Koji by multiplying a rice Koji mold having high phytase activity as a raw material. It is appreciated that the phytase molecules of the instant invention may be used to produce a serviceable mold with enhanced activity (e.g., a transgenic mold) and/or added exogenously to augment the effects of a Koji mold. The strain is added to boiled rice and Koji is produced by a conventional procedure. In one exemplification, the prepared Koji is used, the whole rice is prepared at two stages and Sake is produced at constant Sake temperature of 15° C. to give the objective refined Sake having a reduced amount of phytin and an increased content of inositol. Additional details regarding this approach are in the public literature and/or are known to the skilled artisan, for example, JP 06153896 (Soga et al.) and JP 06070749 (Soga et al.).

In one aspect, the present invention provides a method to obtain an absorbefacient capable of promoting the absorption of minerals including ingested calcium without being digested by gastric juices or intestinal juices at a low cost. In one aspect, the mineral absorbefacient contains a partial hydrolysate of phytic acid as an active ingredient. A partial hydrolysate of the phytic acid can be produced by hydrolyzing the phytic acid or its salts using novel phytase molecules of the instant invention. The treatment with the phytase molecules may occur either alone and/or in a combination treatment (to inhibit or to augment the final effect), and is followed by inhibiting the hydrolysis within a range so as not to liberate all the phosphate radicals. Additional details regarding this approach are in the public literature and/or are known to the skilled artisan, e.g., JP 04270296 (Hoshino).

In one aspect, the present invention provides a method (and products therefrom) to produce an enzyme composition having an additive or a synergistic phytate hydrolyzing activity; said composition comprises novel phytase molecules of the instant invention and one or more additional reagents to achieve a composition that is serviceable for a combination treatment. In one aspect, the combination treatment of the present invention is achieved with the use of at least two phytases of different position specificity, i.e. any combinations of 1-, 2-, 3-, 4-, 5-, and 6-phytases. By combining phytases of different position specificity an additive or synergistic effect is obtained. Compositions such as food and feed or food and feed additives comprising such phytases in combination are also included in this invention as are processes for their preparation. Additional details regarding this approach are in the public literature and/or are known to the skilled artisan, e.g., WO 30681 (Ohmann et al.).

In another aspect, the combination treatment of the present invention is achieved with the use of an acid phosphatase having phytate hydrolyzing activity at a pH of 2.5, in a low ratio corresponding to a pH 2.5:5.0 activity profile of from about 0.1:1.0 to 10:1, or of from about 0.5:1.0 to 5:1, or from about 0.8:1.0 to 3:1, or from about 0.8:1.0 to 2:1. The enzyme composition can display a higher synergetic phytate hydrolyzing efficiency through thermal treatment. The enzyme composition is serviceable in the treatment of foodstuffs (drinkable and solid food, feed and fodder products) to improve phytate hydrolysis. Additional details or alternative protocols regarding this approach are in the public literature and/or are known to the skilled artisan, e.g., U.S. Pat. No. 5,554,399 (Vanderbeke et al.) and U.S. Pat. No. 5,443,979 (Vanderbeke et al.), teaching the use of fungal (in particular *Aspergillus*) phytases.

In another aspect, the present invention provides a method (and products therefrom) to produce a composition comprising the instant novel phytate-acting enzyme in combination with one or more additional enzymes that act on polysaccharides. Such polysaccharides can be selected from the group consisting of arabinans, fructans, fucans, galactans, galacturonans, glucans, mannans, xylans, levan, fucoidan, carrageenan, galactocarolose, pectin, pectic acid, amylose, pullulan, glycogen, amylopectin, cellulose, carboxylmethylcellulose, hydroxypropylmethylcellulose, dextran, pustulan, chitin, agarose, keratan, chondroitin, dermatan, hyaluronic acid, alginic acid, and polysaccharides containing at least one aldose, ketose, acid or amine selected from the group consisting of erythrose, threose, ribose, arabinose, xylose, lyxose, allose, altrose, glucose, mannose, gulose, idose, galactose, talose, erythrulose, ribulose, xylulose, psicose, fructose, sorbose, tagatose, glucuronic acid, gluconic acid, glucaric acid, galacturonic acid, mannuronic acid, glucosamine, galactosamine and neuraminic acid.

In one aspect, the present invention provides a method (and products therefrom) to produce a composition having a synergistic phytate hydrolyzing activity comprising one or more novel phytase molecules of the instant invention, a cellulase (can also include a xylanase), optionally a protease, and optionally one or more additional reagents. In alternative aspects, such combination treatments are serviceable in the treatment of foodstuffs, wood products, such as paper products, and as cleansing solutions and solids.

In one aspect, phytases of the invention are serviceable in combination with cellulose components. It is known that cellulases of many cellulolytic bacteria are organized into discrete multi-enzyme complexes, called cellulosomes. The multiple subunits of cellulosomes are composed of numerous functional domains, which interact with each other and with the cellulosic substrate. One of these subunits comprises a distinctive new class of non-catalytic scaffolding polypeptide, which selectively integrates the various cellulase and xylanase subunits into the cohesive complex. Intelligent application of cellulosome hybrids and chimeric constructs of cellulosomal domains should enable better use of cellulosic biomass and may offer a wide range of novel applications in research, medicine and industry.

In one aspect, phytases of the invention are serviceable—either alone or in combination treatments—in areas of biopulping and biobleaching where a reduction in the use of environmentally harmful chemicals traditionally used in the pulp and paper industry is desired. Waste water treatment represents another vast application area where biological enzymes have been shown to be effective not only in color removal but also in the bioconversion of potentially noxious substances into useful bioproducts.

In one aspect, phytases of the invention are serviceable for generating life forms that can provide at least one enzymatic activity—either alone or in combination treatments—in the treatment of digestive systems of organisms. Particularly relevant organisms to be treated include non-ruminant organisms, although ruminant organisms may also benefit from such treatment. Specifically, it is appreciated that this approach may be performed alone or in combination with other biological molecules (for example, xylanases) to generate a recombinant host that expresses a plurality of biological molecules. It is also appreciated that the administration of the instant phytase molecules and/or recombinant hosts expressing the instant phytase molecules may be performed either alone or in combination with other biological molecules, and/or life forms that can provide enzymatic activities in a digestive system—where said other enzymes and said life forms may be may recombinant or otherwise. For example, administration may be performed in combination with xylanolytic bacteria.

For example, in addition to phytate, many organisms are also unable to adequately digest hemicelluloses. Hemicelluloses or xylans are major components (35%) of plant materials. For ruminant animals, about 50% of the dietary xylans are degraded, but only small amounts of xylans are degraded in the lower gut of non-ruminant animals and humans. In the rumen, the major xylanolytic species are *Butyrivibrio fibrisolvens* and *Bacteroides ruminicola*. In the human colon, *Bacteroides ovatus* and *Bacteroides fragilis* subspecies "a" are major xylanolytic bacteria. Xylans are chemically complex, and their degradation requires multiple enzymes. Expression of these enzymes by gut bacteria varies greatly among species. *Butyrivibrio fibrisolvens* makes extracellular xylanases but *Bacteroides* species have cell-bound xylanase activity. Biochemical characterization of xylanolytic enzymes from gut bacteria has not been done completely. A xylosidase gene has been cloned from *B. fibrosolvens*. The data from DNA hybridizations using a xylanase gene cloned from *B. fibrisolvens* indicate this gene may be present in other *B. fibrisolvens* strains. A cloned xylanase from *Bact. ruminicola* was transferred to and highly expressed in *Bact. fragilis* and *Bact. uniformis*. Arabinosidase and xylosidase genes from *Bact. ovatus* have been cloned and both activities appear to be catalyzed by a single, bifunctional, novel enzyme.

In one aspect, phytases of the invention are serviceable for 1) transferring into a suitable host (such as *Bact. fragilis* or *Bact. uniformis*); 2) achieving adequate expression in a resultant recombinant host; and 3) administering said recombinant host to organisms to improve the ability of the treated organisms to degrade phytate. Continued research in genetic and biochemical areas will provide knowledge and insights for manipulation of digestion at the gut level and improved understanding of colonic fiber digestion.

Additional details or alternative protocols regarding this approach are in the public literature and/or are known to the skilled artisan, for example, the invention can incorporate procedures as described in U.S. Pat. No. 5,624,678 (Bedford et al.), U.S. Pat. No. 5,683,911 (Bodie et al.), U.S. Pat. No. 5,720,971 (Beauchemin et al.), U.S. Pat. No. 5,759,840 (Sung et al.), U.S. Pat. No. 5,770,012 (Cooper), U.S. Pat. No. 5,786,316 (Baeck et al.), U.S. Pat. No. 5,817,500 (Hansen et al.).

The instant invention teaches that phytase molecules of the instant invention may be added to the reagent(s) disclosed in order to obtain preparations having an additional phytase activity. In one aspect, reagent(s) and the additional phytase molecules will not inhibit each other. In one aspect, the reagent(s) and the additional phytase molecules may have an overall additive effect. In one aspect, the reagent(s) and the additional phytase molecules may have an overall synergistic effect.

In one aspect, the present invention provides a method (and products therefrom) for enhancement of phytate phosphorus utilization and treatment and prevention of tibial dyschondroplasia in animals, particularly poultry, by administering to animals a feed composition containing a hydroxylated vitamin D3 derivative. The vitamin D3 derivative can be administered to animals in feed containing reduced levels of calcium and phosphorus for enhancement of phytate phosphorus utilization. Accordingly, the vitamin D3 derivative can be administered in combination with novel phytase molecules of the instant invention for further enhancement of phytate phosphorus utilization. Additional details or alternative protocols regarding this approach are in the public literature and/or are known to the skilled artisan, e.g., U.S. Pat. No. 5,516,525 (Edwards et al.) and U.S. Pat. No. 5,366,736 (Edwards et al.), U.S. Pat. No. 5,316,770 (Edwards et al.).

In one aspect, the present invention provides a method (and products therefrom) to obtain foodstuff that 1) comprises phytin that is easily absorbed and utilized in a form of inositol in a body of an organism; 2) that is capable of reducing phosphorus in excrementary matter; and 3) that is accordingly useful for improving environmental pollution. Said foodstuff is comprised of an admixture of a phytin-containing grain, a lactic acid-producing microorganism, and a novel phytase molecule of the instant invention. In one aspect, said foodstuff is produced by compounding a phytin-containing grain (e.g. rice bran) with an effective microbial group having an acidophilic property, producing lactic acid, without producing butyric acid, free from pathogenicity, and a phytase. Examples of an effective microbial group include e.g. *Streptomyces* sp. (American Type Culture Collection No. ATCC 3004) belonging to the group of actinomyces and *Lactobacillus* sp. (IFO 3070) belonging to the group of lactobacilli.

An exemplary amount of addition of an effective microbial group is 0.2 wt. % in terms of bacterial body weight based on a grain material. In one aspect, the amount of the addition of the phytase is about 1-2 wt. % based on the phytin in the grain material. Additional details or alternative protocols regarding this approach are in the public literature and/or are known to the skilled artisan, e.g., JP 08205785 (Akahori et al.).

In one aspect, the present invention provides a method for improving the solubility of vegetable proteins. More specifically, the invention relates to methods for the solubilization of proteins in vegetable protein sources, which methods comprise treating the vegetable protein source with an efficient amount of one or more phytase enzymes of the invention and treating the vegetable protein source with an efficient amount of one or more proteolytic enzymes. In another aspect, the invention provides animal feed additives comprising a phytase of the invention and one or more proteolytic enzymes. Additional details or alternative protocols regarding this approach are in the public literature and/or are known to the skilled artisan, e.g., EP 0756457 (WO 9528850 A1) (Nielsen and Knap).

In one aspect, the present invention provides a method of producing a plant protein preparation comprising dispersing vegetable protein source materials in water at a pH in the range of 2 to 6 and admixing phytase molecules of the instant invention therein. The acidic extract containing soluble protein is separated and dried to yield a solid protein of desirable character. One or more proteases can also be used to improve the characteristics of the protein. Additional details or alternative protocols regarding this approach are in the public literature and/or are known to the skilled artisan, e.g., U.S. Pat. No. 3,966,971.

In one aspect, the present invention provides a method (and products thereof) to activate inert phosphorus in soil and/or compost, to improve the utilization rate of a nitrogen compound, and to suppress propagation of pathogenic molds by adding three reagents, phytase, saponin and chitosan, to the compost.

In one aspect, the method can comprise treating the compost by 1) adding phytase-containing microorganisms in media, e.g., recombinant hosts that overexpress the novel phytase molecules of the instant invention, for example, at 100 ml media/100 kg wet compost; 2) alternatively also adding a phytase-containing plant source—such as wheat bran—e.g. at 0.2 to 1 kg/100 kg wet compost; 3) adding a saponin-containing source—such as peat, mugworts and yucca plants—e.g. at 0.5 to 3.0 g/kg; 4) adding chitosan-containing materials—such as pulverized shells of shrimps, crabs, etc.—e.g. at 100 to 300 g/kg wet compost.

In one aspect, recombinant sources the three reagents, phytase, saponin, and chitosan, are used. Additional details or alternative protocols regarding this approach are in the public literature and/or are known to the skilled artisan, e.g., JP 07277865 (Toya Taisuke).

In some instances it may be advantageous to deliver and express a phytase sequence of the invention locally (e.g., within a particular tissue or cell type). For example, local expression of a phytase or digestive enzyme in the gut of an animal will assist in the digestion and uptake of, for example, phytate and phosporous, respectively. The nucleic sequence may be directly delivered to the salivary glands, tissue and cells and/or to the epithelial cells lining the gut, for example. Such delivery methods are known in the art and include electroporation, viral vectors and direct DNA uptake. Any polypeptide having phytase activity can be utilized in the methods of the invention (e.g., those specifically described under this subsection 6.3.18, as well as those described in other sections of the invention).

For example, a nucleic acid constructs of the present invention will comprise nucleic acid molecules in a form suitable for uptake into target cells within a host tissue. The nucleic acids may be in the form of bare DNA or RNA molecules, where the molecules may comprise one or more structural genes, one or more regulatory genes, antisense strands, strands capable of triplex formation, or the like. Commonly, the nucleic acid construct will include at least one structural gene under the transcriptional and translational control of a suitable regulatory region. More usually, nucleic acid constructs of the present invention will comprise nucleic acids incorporated in a delivery vehicle to improve transfection efficiency, wherein the delivery vehicle will be dispersed within larger particles comprising a dried hydrophilic excipient material.

One such delivery vehicles comprises viral vectors, such as retroviruses, adenoviruses, and adeno-associated viruses, which have been inactivated to prevent self-replication but which maintain the native viral ability to bind a target host cell, deliver genetic material into the cytoplasm of the target host cell, and promote expression of structural or other genes which have been incorporated in the particle. Suitable retrovirus vectors for mediated gene transfer are described in Kahn et al. (1992) *Circ. Res.* 71:1508-1517. A suitable adenovirus gene delivery is described in Rosenfeld et al.

(1991) *Science* 252:431-434. Both retroviral and adenovirus delivery systems are described in Friedman (1989) *Science* 244:1275-1281.

A second type of nucleic acid delivery vehicle comprises liposomal transfection vesicles, including both anionic and cationic liposomal constructs. The use of anionic liposomes requires that the nucleic acids be entrapped within the liposome. Cationic liposomes do not require nucleic acid entrapment and instead may be formed by simple mixing of the nucleic acids and liposomes. The cationic liposomes avidly bind to the negatively charged nucleic acid molecules, including both DNA and RNA, to yield complexes which give reasonable transfection efficiency in many cell types. See, Farhood et al. (1992) *Biochem. Biophys. Acta.* 1111:239-246. An exemplary material for forming liposomal vesicles is lipofectin which is composed of an equimolar mixture of dioleylphosphatidyl ethanolamine (DOPE) and dioleyloxypropyl-triethylammonium (DOTMA), as described in Felgner and Ringold (1989) *Nature* 337:387-388.

It is also possible to combine these two types of delivery systems. For example, Kahn et al. (1992), supra., teaches that a retrovirus vector may be combined in a cationic DEAE-dextran vesicle to further enhance transformation efficiency. It is also possible to incorporate nuclear proteins into viral and/or liposomal delivery vesicles to even further improve transfection efficiencies. See, Kaneda et al. (1989) *Science* 243:375-378.

In another aspect, a digestive aid containing an enzyme either as the sole active ingredient or in combination with one or more other agents and/or enzymes is provided. The use of enzymes and other agents in digestive aids of livestock or domesticated animals not only improves the animal's health and life expectancy but also assists in increasing the health of livestock and in the production of foodstuffs from livestock.

The invention also can use feeds for livestock (e.g., certain poultry feed) that are highly supplemented with numerous minerals (e.g., inorganic phosphorous), enzymes, growth factors, drugs, and other agents for delivery to the livestock. These supplements replace many of the calories and natural nutrients present in grain, for example. By reducing or eliminating the inorganic phosphorous supplement and other supplements (e.g., trace mineral salts, growth factors, enzymes, antibiotics) from the feed itself, the feed is able to carry more nutrient and energy. Accordingly, the remaining diet would contain more usable energy. For example, grain-oilseed meal diets generally contain about 3,200 kcal metabolizable energy per kilogram of diet, and mineral salts supply no metabolizable energy. Removal of the unneeded minerals and substitution with grain therefore increase the usable energy in the diet. Thus, the invention is differentiated over commonly used phytase containing feed. For example, in one aspect, a biocompatible material is used that is resistant to digestion by the gastrointestinal tract of an organism.

In many organisms, including, for example, poultry or birds such as, for example, chickens, turkeys, geese, ducks, parrots, peacocks, ostriches, pheasants, quail, pigeons, emu, kiwi, loons, cockatiel, cockatoo, canaries, penguins, flamingoes, and dove, the digestive tract includes a gizzard which stores and uses hard biocompatible objects (e.g., rocks and shells from shell fish) to help in the digestion of seeds or other feed consumed by a bird. A typical digestive tract of this general family of organisms, includes the esophagus which contains a pouch, called a crop, where food is stored for a brief period of time. From the crop, food moves down into the true stomach, or proventriculus, where hydrochloric acid and pepsin starts the process of digestion. Next, food moves into the gizzard, which is oval shaped and thick walled with powerful muscles. The chief function of the gizzard is to grind or crush food particles—a process which is aided by the bird swallowing small amounts of fine gravel or grit. From the gizzard, food moves into the duodenum. The small intestine of birds is similar to mammals. There are two blind pouches or ceca, about 4-6 inches in length at the junction of the small and large intestine. The large intestine is short, consisting mostly of the rectum about 3-4 inches in length. The rectum empties into the cloaca and feces are excreted through the vent.

Hard, biocompatible objects consumed (or otherwise introduced) and presented in the gizzard provide a useful vector for delivery of various enzymatic, chemical, therapeutic and antibiotic agents. These hard substances have a life span of a few hours to a few days and are passed after a period of time. Accordingly, the invention provides coated, impregnated (e.g., impregnated matrix and membranes) modified dietary aids for delivery of useful digestive or therapeutic agents to an organism. Such dietary aids include objects which are typically ingested by an organism to assist in digestion within the gizzard (e.g., rocks or grit). The invention provides biocompatible objects that have coated thereon or impregnated therein agents useful as a digestive aid for an organism or for the delivery of a therapeutic or medicinal agent or chemical.

In one aspect, the invention provides a dietary aid, having a biocompatible composition designed for release of an agent that assists in digestion, wherein the biocompatible composition is designed for oral consumption and release in the digestive tract (e.g., the gizzard) of an organism. "Biocompatible" means that the substance, upon contact with a host organism (e.g., a bird), does not elicit a detrimental response sufficient to result in the rejection of the substance or to render the substance inoperable. Such inoperability may occur, for example, by formation of a fibrotic structure around the substance limiting diffusion of impregnated agents to the host organism therein or a substance which results in an increase in mortality or morbidity in the organism due to toxicity or infection. A biocompatible substance may be non-biodegradable or biodegradable. In one aspect, the biocompatible composition is resistant to degradation or digestion by the gastrointestinal tract. In another aspect, the biocompatible composition has the consistency of a rock or stone.

A non-biodegradable material useful in the invention is one that allows attachment or impregnation of a dietary agent. Such non-limiting non-biodegradable materials include, for example, thermoplastics, such as acrylic, modacrylic, polyamide, polycarbonate, polyester, polyethylene, polypropylene, polystyrene, polysulfone, polyethersulfone, and polyvinylidene fluoride. Elastomers are also useful materials and include, for example, polyamide, polyester, polyethylene, polypropylene, polystyrene, polyurethane, polyvinyl alcohol and silicone (e.g., silicone based or containing silica). The invention provides that the biocompatible composition can contain a plurality of such materials, which can be, e.g., admixed or layered to form blends, copolymers or combinations thereof.

In one aspect, a "biodegradable" material means that the composition will erode or degrade in vivo to form smaller chemical species. Degradation may occur, for example, by enzymatic, chemical or physical processes. Suitable biodegradable materials contemplated for use in the invention include, but are not limited to, poly(lactide)s, poly(glycolide)s, poly(lactic acid)s, poly(glycolic acid)s, polyanhydrides, polyorthoesters, polyetheresters, polycaprolactone, polyesteramides, polycarbonate, polycyanoacrylate, polyurethanes, polyacrylate, and the like. Such materials can be admixed or layered to form blends, copolymers or combinations thereof.

In one aspect, a number different biocompatible substances of the invention may be given to the animal and ingested sequentially, or otherwise provided to the same organism simultaneously, or in various combinations (e.g., one material before the other). In addition, the biocompatible substances of the invention may be designed for slow passage through the digestive tract. For example, large or fatty substances tend to move more slowly through the digestive tract, accordingly, a biocompatible material having a large size to prevent rapid passing in the digestive tract can be used. Such large substances can be a combination of non-biodegradable and biodegradable substances. For example, a small non-biodegradable substance can be encompassed by a biodegradable substance of the invention such that over a period of time the biodegradable portion will be degraded allowing the non-biodegradable portion to pass through the digestive trace. In addition, it is recognized that any number of flavorings can be provided to a biocompatible substance of the invention to assist in consumption.

Any number of agents alone or in combination with other agents can be coated on the biocompatible substances of the invention, including polypeptides (e.g., enzymes, antibodies, cytokines or therapeutic small molecules), and antibiotics, for example. Examples of particular useful agents are listed in Table 1 and 2, below. It is also contemplated that cells can be encapsulated into the biocompatible material of the invention and used to deliver the enzymes or therapeutics. For example, porous substances can be designed that have pores large enough for cells to grow in and through and that these porous materials can then be taken into the digestive tract. For example, the biocompatible substance of the invention can comprise a plurality of microfloral environments (e.g., different porosity, pH etc.) that provide support for a plurality of cell types. The cells can be genetically engineered to deliver a particular drug, enzyme or chemical to the organism. The cells can be eukaryotic or prokaryotic.

TABLE 1

| Treatment Class | Chemical | Description |
| --- | --- | --- |
| Antibiotics | Amoxycillin and Its Combination Mastox Injection (Amoxycillin and Cloxacillin) | Treatment Against Bacterial Diseases Caused By Gram + and Gram − Bacteria |
| | Ampicillin and Its Combination Biolox Injection (Ampicillin and Cloxacillin) | Treatment Against Bacterial Diseases Caused By Gram + And Gram − Bacteria. |
| | Nitrofurazone + Urea Nefrea Bolus | Treatment Of Genital Infections |
| | Trimethoprim + Sulphamethoxazole Trizol Bolus | Treatment Of Respiratory Tract Infections, Gastro Intestinal Tract Infections, Urino- Genital Infections. |
| | Metronidazole and Furazolidone Metofur Bolus | Treatment Of Bacterial And Protozoal Diseases. |
| | Phthalylsulphathiazole, Pectin and Kaolin Pectolin Bolus Suspension | Treatment Of Bacterial And Non-Specific Diarrhoea, Bacillary Dysentery And Calf Scours. |
| Antihelmintics | Ectoparasiticide Germex Ointment (Gamma Benzene Hexachloride, Proflavin Hemisulphate and Cetrimide) | Ectoparasiticide and Antiseptic |
| | Endoparasiticides > Albendazole and Its Combination Alben (Albendazole) Suspension (Albendazole 2.5%) Plus Suspension (Albendazole 5%) Forte Bolus (Albendazole 1.5 Gm.) Tablet (Albendazole 600 Mg.) Powder(Albendazole 5%, 15%) | Prevention And Treatment Of Roundworm, Tapeworm and Fluke Infestations |
| | Alpraz (Albendazole and Praziquantel)Tablet | Prevention And Treatment Of Roundworm and Tapeworm Infestation In Canines and Felines. |
| | Oxyclozanide and Its Combination Clozan (Oxyclozanide) Bolus, Suspension | Prevention and Treatment Of Fluke Infestations |

TABLE 1-continued

| Treatment Class | Chemical | Description |
|---|---|---|
| | Tetzan (Oxyclozanide and Tetramisole Hcl) Bolus, Suspension | Prevention and Treatment Of Roundworm and Fluke Infestations |
| | Fluzan (Oxyclozanide and Levamisole Hcl) Bolus, Suspension | Prevention and Treatment Of Roundworm Infestations and Increasing Immunity |
| | Levamisole Nemasol Injection Wormnil Powder | Prevention and Treatment Of Roundworm Infestations and Increasing Immunity. |
| | Fenbendazole Fenzole Tablet (Fenbendazole 150 Mg.) Bolus (Fenbendazole 1.5 Gm.) Powder (Fenbendazole 2.5% W/W) | Prevention And Treatment of Roundworm and Tapeworm Infestations |
| Tonics | Vitamin B Complex, Amino Acids and Liver Extract Heptogen Injection | Treatment Of Anorexia, Hepatitis, Debility, Neuralgic Convulsions Emaciation and Stunted Growth. |
| | Calcium Levulinate With Vit. $B_{12}$ and Vit $D_3$ Hylactin Injection | Prevention and treatment of hypocalcaemia, supportive therapy in sick conditions (especially hypothermia) and treatment of early stages of rickets. |
| Animal Feed Supplements | Essential Minerals, Selenium and Vitamin E Gynolactin Bolus | Treatment Of Anoestrus Causing Infertility and Repeat Breeding In Dairy Animals and Horses. |
| | Essential Minerals, Vitamin E, and Iodine Hylactin Powder | Infertility, Improper Lactation, Decreased Immunity, Stunted Growth and Debility. |
| | Essential Electrolytes With Vitamin C Electra – C Powder | Diarrhoea, Dehydration, Prior to and after Transportation, In Extreme temperatures (High Or Low) and other Conditions of stress. |
| | Pyrenox Plus (Diclofenac Sodium + Paracetamol) Bolus, Injection. | Treatment Of Mastitis, Pyrexia Post Surgical Pain and Inflammation, Prolapse Of Uterus, Lameness and Arthritis. |

TABLE 2

Therapeutic Formulations

| Product | Description |
|---|---|
| Acutrim ® (phenylpropanolamine) | Once-daily appetite suppressant tablets. |
| The Baxter ® Infusor | For controlled intravenous delivery of anticoagulants, antibiotics, chemotherapeutic agents, and other widely used drugs. |
| Catapres-TTS ® (clonidine transdermal therapeutic system) | Once-weekly transdermal system for the treatment of hypertension. |
| Covera HS3 (verapamil hydrochloride) | Once-daily Controlled-Onset Extended-Release (COER-24) tablets for the treatment of hypertension and angina pectoris. |
| DynaCirc CR ® (isradipine) | Once-daily extended release tablets for the treatment of hypertension. |
| Efidac 24 ® (chlorpheniramine maleate) | Once-daily extended release tablets for the relief of allergy symptoms. |
| Estraderm ® (estradiol transdermal system) | Twice-weekly transdermal system for treating certain postmenopausal symptoms and preventing osteoporosis |
| Glucotrol XL ® (glipizide) | Once-daily extended release tablets used as an adjunct to diet for the control of hyperglycemia in patients with non-insulin-dependent diabetes mellitus. |
| IVOMEC SR ® Bolus (ivermectin) | Ruminal delivery system for season-long control of major internal and external parasites in cattle. |
| Minipress XL ® (prazosin) | Once-daily extended release tablets for the treatment of hypertension. |
| NicoDerm ® CQ ™ (nicotine transdermal system) | Transdermal system used as a once-daily aid to smoking cessation for relief of nicotine withdrawal symptoms. |

TABLE 2-continued

Therapeutic Formulations

| Product | Description |
| --- | --- |
| Procardia XL ® (nifedipine) | Once-daily extended release tablets for the treatment of angina and hypertension. |
| Sudafed ® 24 Hour (pseudoephedrine) | Once-daily nasal decongestant for relief of colds, sinusitis, hay fever and other respiratory allergies. |
| Transderm-Nitro ® (nitroglycerin transdermal system) | Once-daily transdermal system for the prevention of angina pectoris due to coronary artery disease. |
| Transderm Scop ® (scopolamin transdermal system) | Transdermal system for the prevention of nausea and vomiting associated with motion sickness. |
| Volmax (albuterol) | Extended release tablets for relief of bronchospasm in patients with reversible obstructive airway disease. |
| Actisite ® | (tetracycline hydrochloride) Periodontal fiber used as an adjunct to scaling and root planing for reduction of pocket depth and bleeding on probing in patients with adult periodontitis. |
| ALZET ® | Osmotic pumps for laboratory research. |
| Amphotec ® (amphotericin B cholesteryl sulfate complex for injection) | AMPHOTEC ® is a fungicidal treatment for invasive aspergillosis in patients where renal impairment or unacceptable toxicity precludes use of amphotericin B in effective doses and in patients with invasive aspergillosis where prior amphotericin B therapy has failed. |
| BiCitra ® (sodium citrate and citric acid) | Alkalinizing agent used in those conditions where long-term maintenance of alkaline urine is desirable. |
| Ditropan ® (oxybutynin chloride) | For the relief of symptoms of bladder instability associated with uninhibited neurogenic or reflex neurogenic bladder (i.e., urgency, frequency, urinary leakage, urge incontinence, dysuria). |
| Ditropan ® XL (oxybutynin chloride) | is a once-daily controlled-release tablet indicated for the treatment of overactive bladder with symptoms of urge urinary incontinence, urgency and frequency. |
| DOXIL ® (doxorubicin HCl liposome injection) | |
| Duragesic ® (fentanyl transdermal system) CII | 72-hour transdermal system for management of chronic pain in patients who require continuous opioid analgesia for pain that cannot be managed by lesser means such as acetaminophen-opioid combinations, non-steroidal analgesics, or PRN dosing with short-acting opioids. |
| Elmiron ® (pentosan polysulfate sodium) | Indicated for the relief of bladder pain or discomfort associated with interstitial cystitis. |
| ENACT AirWatch ™ | An asthma monitoring and management system. |
| Ethyol ® (amifostine) | Indicated to reduce the cumulative renal toxicity associated with repeated administration of cisplatin in patients with advanced ovarian cancer or non-small cell lung cancer. Indicated to reduce the incidence of moderate to severe xerostomia in patients undergoing post-operative radiation treatment for head and neck cancer, where the radiation port includes a substantial portion of the parotid glands. |
| Mycelex ® Troche (clotrimazole) | For the local treatment of oropharyngeal candidiasis. Also indicated prophylactically to reduce the incidence of oropharyngeal candidiasis in patients immunocompromised by conditions that include chemotherapy, radiotherapy, or steroid therapy utilized in the treatment of leukemia, solid tumors, or renal transplantation. |
| Neutra-Phos ® (potassium and sodium phosphate) | a dietary/nutritional supplement |
| PolyCitra ® -K Oral Solution and PolyCitra ® - K Crystals (potassium citrate and citric acid) | Alkalinizing agent useful in those conditions where long-term maintenance of an alkaline urine is desirable, such as in patents with uric acid and cystine calculi of the urinary tract, especially when the administration of sodium salts is undesirable or contraindicated |
| PolyCitra ® -K Syrup and LC (tricitrates) | Alkalinizing agent useful in those conditions where long-term maintenance of an alkaline urine is desirable, such as in patients with uric acid and cystine calculi of the urinary tract. |
| Progestasert ® (progesterone) | Intrauterine Progesterone Contraceptive System |

TABLE 2-continued

Therapeutic Formulations

| Product | Description |
| --- | --- |
| Testoderm ® Testoderm ® with Adhesive and Testoderm ® TTS CIII | Testosterone Transdermal System The Testoderm ® products are indicated for replacement therapy in males for conditions associated with a deficiency or absence of endogenous testosterone: (1) Primary hypogonadism (congenital or acquired) or (2) Hypogonadotropic hypogonadism (congenital or acquired). |
| Viadur ™ (leuprolide acetate implant) | Once-yearly implant for the palliative treatment of prostate cancer |

Certain agents can be designed to become active or in activated under certain conditions (e.g., at certain pH's, in the presence of an activating agent etc.). In addition, it may be advantageous to use pro-enzymes in the compositions of the invention. For example, a pro-enzymes can be activated by a protease (e.g., a salivary protease that is present in the digestive tract or is artificially introduced into the digestive tract of an organism). It is contemplated that the agents delivered by the biocompatible compositions of the invention are activated or inactivated by the addition of an activating agent which may be ingested by, or otherwise delivered to, the organism. Another mechanism for control of the agent in the digestive tract is an environment sensitive agent that is activated in the proper digestive compartment. For example, an agent may be inactive at low pH but active at neutral pH. Accordingly, the agent would be inactive in the gut but active in the intestinal tract. Alternatively, the agent can become active in response to the presence of a microorganism specific factor (e.g., microorganisms present in the intestine).

In one aspect, the potential benefits of the present invention include, for example, (1) reduction in or possible elimination of the need for mineral supplements (e.g., inorganic phosphorous supplements), enzymes, or therapeutic drugs for animal (including fish) from the daily feed or grain thereby increasing the amount of calories and nutrients present in the feed, and (2) increased health and growth of domestic and non-domestic animals including, for example, poultry, porcine, bovine, equine, canine, and feline animals.

A large number of enzymes can be used in the methods and compositions of the present invention in addition to the phytases of the invention. These enzymes include enzymes necessary for proper digestion of consumed foods, or for proper metabolism, activation or derivation of chemicals, prodrugs or other agents or compounds delivered to the animal via the digestive tract. Examples of enzymes that can be delivered or incorporated into the compositions of the invention, include, for example, feed enhancing enzymes selected from the group consisting of α-galactosidases, β-galactosidases, in particular lactases, phytases, β-glucanases, in particular endo-β-1,4-glucanases and endo-β-1,3 (4)-glucanases, cellulases, xylosidases, galactanases, in particular arabinogalactan endo-1,4-β-galactosidases and arabinogalactan endo-1,3-β-galactosidases, endoglucanases, in particular endo-1,2-β-glucanase, endo-1,3-α-glucanase, and endo-1,3-β-glucanase, pectin degrading enzymes, in particular pectinases, pectinesterases, pectin lyases, polygalacturonases, arabinanases, rhamnogalacturonases, rhamnogalacturonan acetyl esterases, rhamnogalacturonan-α-rhamnosidase, pectate lyases, and α-galacturonisidases, mannanases, β-mannosidases, mannan acetyl esterases, xylan acetyl esterases, proteases, xylanases, arabinoxylanases and lipolytic enzymes such as lipases, phytases and cutinases. Phytases in addition to the phytases having an amino acid sequence as set forth in SEQ ID NO:2 can be used in the methods and compositions of the invention.

In one aspect, the enzyme used in the compositions (e.g., a dietary aid) of the present invention is a phytase enzyme which is stable to heat and is heat resistant and catalyzes the enzymatic hydrolysis of phytate, i.e., the enzyme is able to renature and regain activity after a brief (i.e., 5 to 30 seconds), or longer period, for example, minutes or hours, exposure to temperatures of above 50 C.

A "feed" and a "food," respectively, means any natural or artificial diet, meal or the like or components of such meals intended or suitable for being eaten, taken in, digested, by an animal and a human being, respectively. "Dietary Aid," as used herein, denotes, for example, a composition containing agents that provide a therapeutic or digestive agent to an animal or organism. A "dietary aid," typically is not a source of caloric intake for an organism, in other words, a dietary aid typically is not a source of energy for the organism, but rather is a composition which is taken in addition to typical "feed" or "food".

In various aspects of the invention, feed composition are provided that comprise a recombinant phytase protein having at least thirty contiguous amino acids of a protein having an amino acid sequence of SEQ ID NO:2; and a phytate-containing foodstuff. As will be known to those skilled in the art, such compositions may be prepared in a number of ways, including but not limited to, in pellet form with or without polymer coated additives, in granulate form, and by spray drying. By way of non-limiting example, teachings in the art directed to the preparation of feed include International Publication Nos. WO0070034 A1, WO0100042 A1, WO0104279 A1, WO0125411 A1, WO0125412 A1, and EP 1073342A.

An agent or enzyme (e.g., a phytase) may exert its effect in vitro or in vivo, i.e. before intake or in the stomach or gizzard of the organism, respectively. Also a combined action is possible.

Although any enzyme may be incorporated into a dietary aid, reference is made herein to phytase as an exemplification of the methods and compositions of the invention. A dietary aid of the invention includes an enzyme (e.g., a phytase). Generally, a dietary aid containing a phytase composition is liquid or dry.

Liquid compositions need not contain anything more than the enzyme (e.g. a phytase), preferably in a highly purified form. Usually, however, a stabilizer such as glycerol, sorbitol or mono propylene glycol is also added. The liquid composition may also comprise other additives, such as salts, sugars, preservatives, pH-adjusting agents, proteins, phytate (a phytase substrate). Typical liquid compositions are aqueous or oil-based slurries. The liquid compositions can be added to a biocompatible composition for slow release. Preferably the enzyme is added to a dietary aid composition that is a biocompatible material (e.g., biodegradable or non-biodegradable) and includes the addition of recombinant cells into, for example, porous microbeads.

Dry compositions may be spray dried compositions, in which case the composition need not contain anything more than the enzyme in a dry form. Usually, however, dry compositions are so-called granulates which may readily be mixed with a food or feed components, or more preferably, form a component of a pre-mix. The particle size of the enzyme granulates preferably is compatible with that of the other components of the mixture. This provides a safe and convenient means of incorporating enzymes into animal feed. Granulates of the invention can be biocompatible, or they can be biocompatible granulates that are non-biodegradable.

Agglomeration granulates of the invention coated by an enzyme can be prepared using agglomeration technique in a high shear mixer. Absorption granulates are prepared by having cores of a carrier material to absorb/be coated by the enzyme. In one aspect, the carrier material is a biocompatible non-biodegradable material that simulates the role of stones or grit in the gizzard of an animal. Typical filler materials used in agglomeration techniques include salts, such as disodium sulphate. Other fillers are kaolin, talc, magnesium aluminum silicate and cellulose fibers. Optionally, binders such as dextrins are also included in agglomeration granulates. The carrier materials can be any biocompatible material including biodegradable and non-biodegradable materials (e.g., rocks, stones, ceramics, various polymers). In one aspect, the granulates are coated with a coating mixture. Such mixture comprises coating agents, e.g., hydrophobic coating agents, such as hydrogenated palm oil and beef tallow, and if desired other additives, such as calcium carbonate or kaolin.

In one aspect, the dietary aid compositions (e.g., phytase dietary aid compositions) may contain other substituents such as coloring agents, aroma compounds, stabilizers, vitamins, minerals, other feed or food enhancing enzymes etc. In one aspect, an additive used in a composition of the invention comprises one or more compounds such as vitamins, minerals or feed enhancing enzymes and suitable carriers and/or excipients.

In one aspect, the dietary aid compositions of the invention additionally comprise an effective amount of one or more feed enhancing enzymes, in particular feed enhancing enzymes selected from the group consisting of α-galactosidases, β-galactosidases, in particular lactases, other phytases, β-glucanases, in particular endo-β-1,4-glucanases and endo-β-1,3(4)-glucanases, cellulases, xylosidases, galactanases, in particular arabinogalactan endo-1,4-β-galactosidases and arabinogalactan endo-1,3-β-galactosidases, endoglucanases, in particular endo-1,2-β-glucanase, endo-1,3-α-glucanase, and endo-1,3-β-glucanase, pectin degrading enzymes, in particular pectinases, pectinesterases, pectin lyases, polygalacturonases, arabinanases, rhamnogalacturonases, rhamnogalacturonan acetyl esterases, rhamnogalacturonan-α-rhamnosidase, pectate lyases, and α-galacturonisidases, mannanases, β-mannosidases, mannan acetyl esterases, xylan acetyl esterases, proteases, xylanases, arabinoxylanases and lipolytic enzymes such as lipases, phytases and cutinases.

The animal dietary aid of the invention is supplemented to the mono-gastric animal before or simultaneously with the diet. In one aspect, the dietary aid of the invention is supplemented to the mono-gastric animal simultaneously with the diet. In another aspect, the dietary aid is added to the diet in the form of a granulate or a stabilized liquid.

An effective amount of an enzyme in a dietary aid of the invention is from about 10-20,000; from about 10 to 15,000, from about 10 to 10,000, from about 100 to 5,000, or from about 100 to about 2,000 FYT/kg dietary aid.

Non-limiting examples of other specific uses of the phytase of the invention is in soy processing and in the manufacture of inositol or derivatives thereof.

The invention also relates to a method for reducing phytate levels in animal manure, wherein the animal is fed a dietary aid containing an effective amount of the phytase of the invention. As stated in the beginning of the present application one important effect thereof is to reduce the phosphate pollution of the environment.

In another aspect, the dietary aid is a magnetic carrier. For example, a magnetic carrier containing an enzyme (e.g., a phytase) distributed in, on or through a magnetic carrier (e.g., a porous magnetic bead), can be distributed over an area high in phytate and collected by magnets after a period of time. Such distribution and recollection of beads reduces additional pollution and allows for reuse of the beads. In addition, use of such magnetic beads in vivo allows for the localization of the dietary aid to a point in the digestive tract where, for example, phytase activity can be carried out. For example, a dietary aid of the invention containing digestive enzymes (e.g., a phytase) can be localized to the gizzard of the animal by juxtapositioning a magnet next to the gizzard of the animal after the animal consumes a dietary aid of magnetic carriers. The magnet can be removed after a period of time allowing the dietary aid to pass through the digestive tract. In addition, the magnetic carriers are suitable for removal from the organism after sacrificing or to aid in collection.

When the dietary aid is a porous particle, such particles are typically impregnated by a substance with which it is desired to release slowly to form a slow release particle. Such slow release particles may be prepared not only by impregnating the porous particles with the substance it is desired to release, but also by first dissolving the desired substance in the first dispersion phase. In this case, slow release particles prepared by the method in which the substance to be released is first dissolved in the first dispersion phase are also within the scope and spirit of the invention. The porous hollow particles may, for example, be impregnated by a slow release substance such as a medicine, agricultural chemical or enzyme. In particular, when porous hollow particles impregnated by an enzyme are made of a biodegradable polymers, the particles themselves may be used as an agricultural chemical or fertilizer, and they have no adverse effect on the environment. In one aspect the porous particles are magnetic in nature.

The porous hollow particles may be used as a bioreactor support, in particular an enzyme support. Therefore, it is advantageous to prepare the dietary aid utilizing a method of a slow release, for instance by encapsulating the enzyme of agent in a microvesicle, such as a liposome, from which the dose is released over the course of several days, preferably between about 3 to 20 days. Alternatively, the agent (e.g., an enzyme) can be formulated for slow release, such as incorporation into a slow release polymer from which the dosage of agent (e.g., enzyme) is slowly released over the course of several days, for example from 2 to 30 days and can range up to the life of the animal.

In one aspect, liposomes of the invention are derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The compositions of the invention in liposome form can contain stabilizers, preservatives, excipients, and the like in addition to the agent. Some exemplary lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

Also within the scope of the invention is the use of a phytase of the invention during the preparation of food or feed preparations or additives, i.e., the phytase exerts its phytase activity during the manufacture only and is not active in the final food or feed product. This aspect is relevant for instance in dough making and baking. Accordingly, phytase or recombinant yeast expressing phytase can be impregnated in, on or through a magnetic carriers, distributed in the dough or food medium, and retrieved by magnets.

The dietary aid of the invention may be administered alone to animals in a biocompatible (e.g., a biodegradable or non-biodegradable) carrier or in combination with other digestion additive agents. The dietary aid of the invention thereof can be readily administered as a top dressing or by mixing them directly into animal feed or provided separate from the feed, by separate oral dosage, by injection or by transdermal means or in combination with other growth related edible compounds, the proportions of each of the compounds in the combination being dependent upon the particular organism or problem being addressed and the degree of response desired. It should be understood that the specific dietary dosage administered in any given case will be adjusted in accordance with the specific compounds being administered, the problem to be treated, the condition of the subject and the other relevant facts that may modify the activity of the effective ingredient or the response of the subject, as is well known by those skilled in the art. In general, either a single daily dose or divided daily dosages may be employed, as is well known in the art.

If administered separately from the animal feed, forms of the dietary aid can be prepared by combining them with non-toxic pharmaceutically acceptable edible carriers to make either immediate release or slow release formulations, as is well known in the art. Such edible carriers may be either solid or liquid such as, for example, corn starch, lactose, sucrose, soy flakes, peanut oil, olive oil, sesame oil and propylene glycol. If a solid carrier is used the dosage form of the compounds may be tablets, capsules, powders, troches or lozenges or top dressing as micro-dispersible forms. If a liquid carrier is used, soft gelatin capsules, or syrup or liquid suspensions, emulsions or solutions may be the dosage form. The dosage forms may also contain adjuvants, such as preserving, stabilizing, wetting or emulsifying agents, solution promoters, etc. They may also contain other therapeutically valuable substances. A process for preparing a granulate edible carrier at high temperature for release of enzyme when ingested is described in copending U.S. patent application Ser. No. 09/910,579, filed Jul. 20, 2001.

In alternative embodiments, significant advantages of the invention may include 1) ease of manufacture of the active ingredient loaded biocompatible compositions; 2) versatility as it relates to the class of polymers and/or active ingredients which may be utilized; 3) higher yields and loading efficiencies; and 4) the provision of sustained release formulations that release active, intact active agents in vivo, thus providing for controlled release of an active agent over an extended period of time. In one embodiment, an advantage may be due to the local delivery of the agent with in the digestive tract (e.g., the gizzard) of the organism. In one aspect, the phrase "contained within" denotes a method for formulating an agent into a composition useful for controlled release, over an extended period of time of the agent.

In alternative embodiments of the sustained-release or slow release compositions of the invention an effective amount of an agent (e.g., an enzyme or antibiotic) is utilized. In one aspect, sustained release or slow release refers to the gradual release of an agent from a biocompatible material, over an extended period of time. The sustained release can be continuous or discontinuous, linear or non-linear, and this can be accomplished using one or more biodegradable or non-biodegradable compositions, drug loadings, selection of excipients, or other modifications. However, it is to be recognized that it may be desirable to provide for a "fast" release composition that provides for rapid release once consumed by the organism. It is also to be understood that "release" does not necessarily mean that the agent is released from the biocompatible carrier. Rather in one aspect, the slow release encompasses slow activation or continual activation of an agent present on the biocompatible composition. For example, a phytase need not be released from the biocompatible composition to be effective. In this aspect, the phytase is immobilized on the biocompatible composition.

The animal feed may be any protein-containing organic meal normally employed to meet the dietary requirements of animals. Many of such protein-containing meals are typically primarily composed of corn, soybean meal or a corn/soybean meal mix. For example, typical commercially available products fed to fowl include Egg Maker Complete, a poultry feed product of Land O'Lakes AG Services, as well as Country Game and Turkey Grower a product of Agwa, Inc. (see also The Emu Farmer's Handbook by Phillip Minnaar and Maria Minnaar). Both of these commercially available products are typical examples of animal feeds with which the present dietary aid and/or the enzyme phytase may be incorporated to reduce or eliminate the amount of supplemental phosphorus, zinc, manganese and iron intake required in such compositions.

The invention provides novel formulations and dietary supplements and additives, and methods for diet supplementation for certain diets, e.g., Atkins' diet, vegetarian diet, macrobiotic diet, vegan diet or regional diets, e.g., developing world diets. Foods associated with certain elective diets, such as Atkins, vegetarian, macrobiotic, vegan or regional diets (for example, developing world diets) emphasize certain food categories, such as proteins and fats, soy, etc., or they rely on indigenous crops, e.g., cereals, rice, beans, and the like as substantial or sole contributors to individual nutrition. Many of these cereal based crops have elevated (3 to 10 fold) levels of phytic acid. Processed food products such as soy protein hydrolysate and others appear to retain elevated levels of phytic acid and their inclusion as a protein source to nutrient bars, powders and other foods or food supplements and ingredients increases the phytic acid load experienced by individuals who practice these diets.

Preventing and Reversing Bone Loss

The invention also provides novel pharmaceutical and dietary formulations to be used as supplements and additives, and methods for dietary supplementation, comprising phytases, e.g., any phytase, including a phytase of the invention, for individuals predisposed to bone loss, individuals with bone loss, and individuals with certain medical conditions, e.g., osteoporosis, cachexia, and medical treatments, such as chemotherapies, which can compromise the proper uptake or utilization of essential nutrients. The methods and compositions of the invention can be used alone or in combination with other supplements or treatment regimens, including with medications and the like. For example, the formulations, dietary supplements and methods for diet supplementation can be administered with other dietary supplements or medications for the treatment or prevention of osteoporosis, e.g., with vitamin D3 and/or calcium (which are proven in preventing bone loss). In one aspect, the invention provides a formulation comprising a phytase, e.g., any phytase or a phytase of the invention, and vitamin D3 and/or calcium. In one aspect, the invention provides a formulation comprising a phytase, e.g., any phytase or a phytase of the invention, for preventing bone loss. In one aspect, the invention provides a formulation comprising a phytase, e.g., any phytase or a phytase of the invention, for reversing bone loss.

The formulation can be in the form of a pharmaceutical composition, or, can be an additive to a pharmaceutical, either of which can be in liquid, solid, powder, lotion, spray or aerosol forms. Pharmaceutical compositions and formulations of the invention for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethylcellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

The invention provides aqueous suspensions comprising a phytase, e.g., a phytase of the invention, in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest edition of Remington, The Science and Practice of Pharmacy $20^{th}$ Ed. Lippincott Williams & Wilkins). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention (e.g., reversing bone loss, or, preventing bone loss) are appropriate and correct.

Physical Training Supplements

The invention also provides novel dietary supplements and additives, and methods of using them, comprising phytases, e.g., any phytase, or, a phytase of the invention, for individuals undergoing athletic or other intense physical training, e.g., training for soldiers. Athletic training and hyperexertion can deplete essential nutrients and require dietary supplementation. These diets and conditions have in common a lack of essential micronutrients such as metals (K, Ca, Fe, Zn, Mn, Se) and ions ($PO_4$) necessary for optimal nutrition. Diets rich in phytic acid exacerbate this problem and may also lead to both chronic and acute conditions that result from either voluntary or economically enforced dependence on diets rich in high phytic acid foods.

For example, individuals following various low carbohydrate ("low carb") diets are often plagued with muscle, e.g., leg muscle, cramps. Typical advice for this is to add additional potassium, calcium and other nutrients to their diet. This invention provides compositions for dietary supplementation, dietary aids and supplements and methods for diet supplementation to enhance otherwise compromised nutrition via the mobilization of macro and micronutrients using phytase supplementation to the diet (including use of any phytase, or, a phytase of the invention).

In one aspect of the invention, the use of a phytase (e.g., use of any phytase, or, a phytase of the invention) is optimized to demonstrate thermo labile or pH-stability profiles that will make it suitable for addition directly to the food and supplement process and/or demonstrate enhanced stability and activity in the human or animal gastro intestinal tract.

The invention also provides novel dietary supplements and additives, and methods of using them, comprising phytases, e.g., any phytase, or, a phytase of the invention, for individuals undergoing mineral supplementation. Mineral supplementation for people on foods with high phytic acid content may actually exacerbate problems with nutrient availability. Literature references suggest that complexes of phytic acid, calcium and zinc are much more insoluble that complexes of phytic acid and calcium. People often take multi mineral supplements. The addition of phytase to a scheme devised to combine mineral supplements in the presence of high phytic acid foods could make these supplements much more effective.

In alternative aspects, the compositions and methods of the invention (comprising any phytase, or, a phytase of the invention) are used as supplements or additives to
  Weight-loss programs which limit intake of particular food groups, vegetarian, macrobiotic or vegan diets which limit or preclude intake of meats, nightshade vegetables, breads, etc and other diets which focus on intake of nuts, Specific supplement for individuals on low carb diets rich in high phytic acid foods to ease physiological symptoms based on reduced mineral uptake, Athletic training regimens which seek to enhance performance through dietary intake, including military training regimens, Hospital diets tailored to specific needs of patients compromised in uptake or restricted to food groups Micronutrient-poor cereal and legume diets in the developing world, School lunch programs.

The invention also provides kits comprising compositions of the invention (comprising any phytase, or, a phytase of the invention) and instructions on incorporating the composition or method of the invention into these diets. The kits can comprise any packaging, labeling, product inserts and the like.

In one aspect, the invention provides a natural phytase or an optimized phytase of the invention, formulated for or optimized for (e.g., sequence optimized for) production, processing or passage thru human or animal system, e.g., digestive tract. The phytase enzyme can be optimized using alternative formulations.

Alternatively, a phytase enzyme of the invention, or, any phytase, can be optimized by engineering of its sequence, e.g., using for example, directed evolution, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, ligation reassembly, GSSM™ and any combination thereof, to retain activity during processing, ingestion and in the human gut.

The compositions (e.g., dietary formulations comprising any phytase enzyme, or a phytase enzyme of the invention) can be delivered in a number of ways to provide dietary efficacy. For example, the invention provides compositions (e.g., dietary formulations or additives comprising any phytase enzyme, or a phytase enzyme of the invention) and methods comprising use of:

In packaged food supplements such as chewable tablets or nutritional bars,

As a lyophilized product available for hydration prior to ingestion,

Co-packaged with dietary products, eg., processed soy product or sold as a formulation with soybean protein hydrolysate and other processing fractions from whole foods that are sold as ingredients to the processed food industry, In commercial baked goods, Spray-on to breakfast cereals, Spray-administered (e.g., nasal spray) formulations, As a transgenic product expressed in indigenous crops, ie., cereals and legumes (e.g., as a transgenic product of a microorganism, such as a bacterium)

As a transgenic organism, e.g., a microorganism; for example, a human or animal is fed a bacteria or other microorganism capable of making (and, in an alternative embodiment, secreting) a recombinant phytase, such as a phytase of the invention, after ingestion or implantation, e.g., into the gut of the human or animal.

Phytase-containing products and methods of the invention can be branded as nutrient enhanced, nutrient compatible or otherwise noted for an ability to enhance nutrient performance and relieve various symptoms associated with nutrient deficiency.

Phytase-containing products and methods of the invention are used to mitigate the anti-nutritive effects of phytate, which chelates important dietary minerals such as zinc, copper, iron, magnesium, tin, and calcium. According, phytase-containing products and methods of the invention are used as dietary supplements to prevent the precipitation of metal-binding enzymes and proteins in ingested foods. In one aspect, the phytase-containing products and methods of the invention are used to mitigate the anti-nutritive effects of phytate in human diets, in particular those rich in legumes and cereals, to increase mineral bioavailability. In one aspect, a phytase in a dietary supplement of the invention catalyzes the partial or complete hydrolytic removal of orthophosphate from a phytate, where complete hydrolysis of phytate results in the production of 1 molecule of inositol and 6 molecules of inorganic phosphate.

Phytase-containing products and methods of the invention are applicable to the diet of humans and numerous animals, including fowl and fish. For example, phytase-containing dietary supplement products and dietary supplement methods of the invention can be practiced with commercially significant species, e.g., pigs, cattle, sheep, goats, laboratory rodents (rats, mice, hamsters and gerbils), fur-bearing animals such as mink and fox, and zoo animals such as monkeys and apes, as well as domestic mammals such as cats and dogs. Typical commercially significant avian species include chickens, turkeys, ducks, geese, pheasants, emu, ostrich, loons, kiwi, doves, parrots, cockatiel, cockatoo, canaries, penguins, flamingoes, and quail. Commercially farmed fish such as trout would also benefit from the dietary aids disclosed herein. Other fish that can benefit include, for example, fish (especially in an aquarium or aquaculture environment, e.g., tropical fish), goldfish and other ornamental carp, catfish, trout, salmon, shark, ray, flounder, sole, tilapia, medaka, guppy, molly, platyfish, swordtail, zebrafish, and loach.

Phytase-containing products and methods of the invention are also used in various agars, gels, medias, and solutions used in tissue and/or cell culturing. Inconsistent soy hydrolysates can be a problem encountered when using tissue and/or cell culturing. In one aspect, phytase-containing products and methods of the invention are used as cell culture media additives or as treatments to, e.g., increase cell culture yield and performance consistency. In one aspect, the invention provides hydrolysate for cell culturing comprising phytases, e.g., phytases of the invention.

In one aspect, to provide a consistent product, the invention provide methods for making hydrolysates, supplements or other additives for cell culturing comprising phytases by using phytase biomarkers. For example, the method would comprise "scoring" or "marking" several molecules of phytase in batches of hydrolysate, supplement or other additive, and then blending the batches in the hydrolysate, supplement or other additive to achieve a consistent biomarker pattern. In one aspect, culture performance with each batch is measured in a mini-bioreactor(s) and performance with each biomarker and batch is correlated. In one aspect, a blend is made to generate a higher performance product that is consistent or better than average. In one aspect, thioredoxin (TRX) is added to increase the bioavailability of many proteins by eliminating secondary structure caused by disulfide bonds. In one aspect, proteases are also added to the hydrolysates, supplements or additives of the invention.

The proteases can be "scored" or quality controlled with other biomarkers (as with phytase, as discussed above) to direct the blending process.

In one aspect, the invention provides methods for adding phytases to grains to provide a consistent product using a biomarker "scoring" or quality control process analogous to that described above for the hydrolysates, supplements or additives of the invention.

Enzyme Enhanced Diets for Increased Warfighter Efficiency and Morale

In one aspect, the invention provides novel dietary supplements and additives and methods for diet supplementation comprising phytases, e.g., any phytase, or, a phytase of the invention, for enzyme-enhanced diets for increased warfighter efficiency and morale. In one aspect, these dietary supplement compositions of the invention work, in situ, to enhance energy, stamina and morale in a stable, easily usable and desirable format while limiting food waste.

In one aspect, these dietary supplement compositions and methods of the invention address the military operational challenge comprising efficient delivery of nutrients and the associated health, morale and operational effectiveness of soldiers. The invention provides enzymes optimized to function efficiently in the human gut. These enzymes can enhance extraction of nutrients and generation of energy as well as prolong maintenance of nutritional sufficiency and individual satiety.

In addition to phytase, other enzymes, e.g., amylases, xylanases, proteases, lipases, are used to practice the dietary supplement compositions and methods of the invention. In one aspect, the invention provides formulations, food supplements, foods, self-contained meal Ready-to-Eat units (MREs), drinks, hydrating agents and the like, comprising phytase, e.g., a phytase of the invention, and another enzyme, e.g., amylases, xylanases, proteases, lipases or a combination thereof. When ingested with food, these enzymes have been shown to enhance the release of critical nutrients, e.g., phosphorus, essential metals and ions, amino acids, and sugars. Furthermore, co-ingestion of these enzymes increases gastrointestinal mechanics and absorption by depolymerizing plant-derived cellulose, hemicellulose and starch. This white paper proposes the development of these enzymes as supplements to military diets to provide enhanced nutrient utilization for warfighter.

In one aspect, the food supplement of the invention causes the release of essential phosphate from normally anti-nutritive, plant-derived phytate to increase food energy yield and bone $CaPO_4$ deposition. In one aspect, phytases and other potential nutritional supplement enzymes can withstand gut pH and endogenous protease activities.

In one aspect, the invention provides enzyme supplements to rations, drinks, foods, MREs, hydrating agents and the like to significantly improve nutritional value, digestibility and energy content of military meals (or any meal, including general consumer meal and diet supplementation products) served to warfighters in training, battle or any stressful situation. The supplement can be formulated for ease of use and personal transport (in or with MREs, hydrating agents, etc). In one aspect, the enzyme supplement will not compromise food appearance, taste and/or consistency. In one aspect, the product improve health and increases the stamina of warfighters.

In alternative aspects, the enzyme supplement is delivered in a number of ways to provide dietary efficacy; for example, the invention provides phytases, including phytases of the invention, and in some aspects, additional enzymes, in:

Packaged food or drink supplements such as MREs, rations, survival kits, hydrating agents, chewable tablets or nutritional bars;

As a lyophilized product (e.g., a powder) available for hydration prior to ingestion;

Co-packaged with dietary products, foods, drinks, e.g., processed soy product or a formulation with soybean protein hydrolysate and other processing fractions from whole foods that are sold as ingredients to the processed food industry;

In baked goods;

Spray-on to cereals;

Formulations such as tablets, geltabs, capsules, sprays and the like.

In one aspect, the compositions and methods of the invention provide nutritional supplementation that rapidly releases calories and macro- and micronutrients from ingested meals. In one aspect, the compositions and methods of the invention provides energy and body strength to individuals in stressful situations, e.g., involving hyperexertion and discontinuous periods of depravation. In one aspect, the compositions and methods of the invention provide enzymes optimized and formulated to work effectively in human gut while maintaining stability, shelf life and transportability in a desired environment, e.g., a military setting.

In one aspect, the compositions and methods of the invention provide formulations for increased taste characteristics, dissolvability, chewability and personal transport efficiency of the product. In one aspect, the compositions and methods of the invention further comprise other components, such as potassium, glucose, $CaCl_2$. $CaCl_2$ in the formulation can combine with released phosphate and, in turn, enhance bone deposition and weight gain. In one aspect, the compositions and methods of the invention further comprise formulations of other enzymes, such as proteases, cellulases, hemicellulases, for protein, cellulose and hemicellulose digestion, respectively. These enzymes can improve protein and starch availability and further increase iron absorption from many iron-rich foods.

In one aspect, the compositions and methods of the invention further comprise enzymes for hydrolyzing foods derived from plant material, which is rich in the glucose and xylose-based polymers, cellulose, hemicellulose and starch, as well as in the amino acid polymer, protein. In one aspect, the compositions and methods of the invention facilitate hydrolysis of polymeric materials in foods; i.e., to facilitate complete digestion polymers to monomers, e.g., polysaccharides to monomeric sugars, or proteins to amino acid moieties. Thus, in this aspect, the compositions and methods of the invention allow a food, drink or ration to realize its full caloric and nutritional value. In one aspect, enzyme supplementation comprises use of stabile enzymes, e.g., hydrolases of various kinds, cellulases, hemicellulases, amylases, lipases, amidases, proteases and other enzymes. In one aspect, enzymes used in the compositions and methods of the invention can withstand ambient gut conditions, i.e., stability at low pH and in the presence of gastric proteases.

Industrial Uses of Phytases

In addition to those described above, the invention provides novel industrial uses for phytases, including use of the novel phytases of the invention.

Reducing Phosphate Pollution in the Environment

In one aspect, the invention provides compositions comprising phytases (including the phytases of the invention) for addition to waste or manure piles to convert "environmental" phytic acid. In one aspect, this serves the purposes of reducing pollution and increasing nutrient availability. The invention also provides compositions and methods for adding a phytase to soil, natural or artificial bodies of water (e.g., lakes, ponds, wells, manure ponds, and the like), municipal sewage, any sewage effluent, and the like. As described above, the invention provides compositions and methods for reducing phytate levels in waste or sewage, e.g., an animal manure, wherein the animal is fed a dietary aid containing an effective amount of a phytase, e.g., a phytase of the invention. An exemplary application of the compositions and methods of the invention is to reduce the phosphate pollution in the environment. Thus, the compositions and methods of the invention can be used in any application that reduces pollution by degrading phytic acids.

Farming and Plant Growth Applications

In one aspect, the invention provides compositions comprising phytases (including the phytases of the invention) and methods for farming applications or other plant growth applications, e.g., adding phytases to fertilizers or plant food additives (e.g., MIRACLEGROW™) for plants, e.g., house plants. In using the compositions and methods of the invention for farming applications, users include organic farmers. The compositions and methods of the invention can be used for adding phytases to any soil deficient in phosphorous or needing supplementary phosphorous for a particular crop or application. Because phosphorous release helps plants grow, compositions and methods of the invention can be used for adding phytases to anything that has algae or plant material in it.

Products of Manufacture

The invention provides a variety of products of manufacture comprising one or more phytases of this invention. For example, in one aspect, the invention provides compositions comprising phytases (including the phytases of the invention) and methods for cosmetic applications, e.g., shampoos, lotions or soaps containing plant products.

In one aspect, the invention provides compositions comprising phytases (including the phytases of the invention) and methods for immobilizing the phytase. In one aspect, the immobilized phytase acts as a controlled release mechanism. For example, in one aspect, the invention provides control released (time release) formulations of phytases for application to soil, e.g., clay, to house plants, etc. In one aspect, the phytases are immobilized to beads, e.g., polysorb beads. These beads can be delivered to soil, e.g., for agricultural or house plants. In another aspect, control released (time release) formulations of phytases of the invention are used in dietary supplements and additives.

Biofuels and Biomass Conversion

The invention provides methods for making fuels, e.g., biofuels, comprising use of one or more phytases of this invention; including providing fuels, e.g., biofuels, comprising one or more phytases of this invention. The invention provides methods for biomass conversion comprising use of one or more phytases of this invention.

In one aspect, the invention provides compositions comprising phytases (including the phytases of the invention) and methods for using the phytase in a fermentation or alcohol production process, e.g. ethanol production. For example, the compositions and methods of the invention can be used to provide effective and sustainable alternatives or adjuncts to use of petroleum-based products, e.g., as a mixture of bioethanol and gasoline.

The invention provides organisms expressing enzymes of the invention for participation in chemical cycles involving natural biomass conversion. In addition, the combination of phytase (e.g., an enzyme of this invention) with one or more starch degrading enzymes, such as amylase or glucoamylase, improves the production of ethanol from starch. The invention provides methods for discovering and implementing the most effective of enzymes to enable these important new "biomass conversion" and alternative energy industrial processes.

Biomass Conversion and Production of Clean Bio Fuels

The invention provides polypeptides, including enzymes (phytases of the invention) and antibodies, and methods for the processing of a biomass or any lignocellulosic material (e.g., any composition comprising a cellulose, hemicellulose and lignin), to a fuel (e.g., a bioethanol, biopropanol, biobutanol, biopropanol, biomethanol, biodiesel), in addition to feeds, foods and chemicals. For example, in one aspect, an enzyme of the invention breaks down undigestable phytic acid (phytate) in a biomass (e.g., a lignocellulosic material, a grain or an oil seed) to release digestible phosphorus; thus, in one embodiment, phytases of this invention are used to treat or pretreat a biomass.

Thus, the compositions and methods of the invention can be used in the production and/or processing of biofuels, e.g., to provide effective and sustainable alternatives and/or adjuncts to use of petroleum-based products; for example, compositions and methods of the invention can be used with a mixture of enzymes to produce a biofuel—such as biomethanol, bioethanol, biopropanol, biobutanol, biodiesel and the like; which can be added to a diesel fuel, a gasoline, a kerosene and the like. The invention provides organisms expressing enzymes of the invention for participation in chemical cycles involving natural biomass conversion. In one aspect, enzymes and methods for the conversion are used in enzyme ensembles for the efficient processing of biomass in conjunction with the depolymerization of polysaccharides, cellulosic and/or hemicellulosic polymers to metabolizeable (e.g., fermentable) carbon moieties. The invention provides methods for discovering and implementing the most effective of enzymes to enable these important new "biomass conversion" and alternative energy industrial processes.

The compositions and methods of the invention can be used to provide effective and sustainable alternatives or adjuncts to use of petroleum-based products, e.g., as a mixture of bioethanol, biopropanol, biobutanol, biopropanol, biomethanol and/or biodiesel and gasoline. The invention provides organisms expressing enzymes of the invention for participation in chemical cycles involving natural biomass conversion. The invention provides methods for discovering and implementing the most effective of enzymes to enable these important new "biomass conversion" and alternative energy industrial processes.

The invention provides methods, enzymes and mixtures of enzymes or "cocktails" of the invention, for processing a material, e.g. a biomass material, e.g., compositions comprising a cellooligsaccharide, an arabinoxylan oligomer, a lignin, a lignocellulose, a xylan, a glucan, a cellulose and/or a fermentable sugar; e.g., including methods comprising contacting the composition with a polypeptide of the invention, or a polypeptide encoded by a nucleic acid of the invention, wherein optionally the material is derived from an agricultural crop (e.g., wheat, barley, potatoes, switchgrass, poplar wood), is a byproduct of a food or a feed production, is a lignocellulosic waste product, or is a plant residue or a waste paper or waste paper product, and optionally the plant residue comprise stems, leaves, hulls, husks, corn or corn cobs, corn stover, corn fiber, hay, straw (e.g. rice straw or wheat straw), sugarcane bagasse, sugar beet pulp, citrus pulp, and citrus peels, wood, wood thinnings, wood chips, wood pulp, pulp waste, wood waste, wood shavings and sawdust, construction and/or demolition wastes and debris (e.g. wood, wood shavings and sawdust), and optionally the paper waste comprises discarded or used photocopy paper, computer printer paper, notebook paper, notepad paper, typewriter paper, newspapers, magazines, cardboard and paper-based packaging materials, and recycled paper materials. In addition, urban wastes, e.g. the paper fraction of municipal solid waste, municipal wood waste, and municipal green waste, along with other materials containing sugar, starch, and/or cellulose can be used. In alternative embodiments, the processing of the material, e.g. the biomass material, generates a bioalcohol, e.g., a biodiesel, bioethanol, biomethanol, biobutanol or biopropanol.

Alternatively, the polypeptide of the invention may be expressed in the biomass plant material or feedstock itself.

The methods of the invention also include taking the converted lignocellulosic material (processed by enzymes of the invention) and making it into a fuel (e.g. a bioalcohol, e.g., a bioethanol, biomethanol, biobutanol or biopropanol, or biodiesel) by fermentation and/or by chemical synthesis. In one aspect, the produced sugars are fermented and/or the non-fermentable products are gasified.

The methods of the invention also include converting algae, virgin vegetable oils, waste vegetable oils, animal fats and greases (e.g. tallow, lard, and yellow grease), or sewage, using enzymes of the invention, and making it into a fuel (e.g. a bioalcohol, e.g., a bioethanol, biomethanol, biobutanol or biopropanol, or biodiesel) by fermentation and/or by chemical synthesis or conversion.

The enzymes of the invention (including, for example, organisms, such as microorganisms, e.g., fungi, yeast or bacteria, making and in some aspects secreting recombinant enzymes of the invention) can be used in or included/integrated at any stage of any biomass conversion process, e.g., at any one step, several steps, or included in all of the steps, or all of the following methods of biomass conversion processes, or all of these biofuel alternatives:

Direct combustion: the burning of material by direct heat and is the simplest biomass technology; can be very economical if a biomass source is nearby.

Pyrolysis: is the thermal degradation of biomass by heat in the absence of oxygen. In one aspect, biomass is heated to a temperature between about 800 and 1400 degrees Fahrenheit, but no oxygen is introduced to support combustion resulting in the creation of gas, fuel oil and charcoal.

Gasification: biomass can be used to produce methane through heating or anaerobic digestion. Syngas, a mixture of carbon monoxide and hydrogen, can be derived from biomass.

Landfill Gas: is generated by the decay (anaerobic digestion) of buried garbage in landfills. When the organic waste decomposes, it generates gas consisting of approximately 50% methane, the major component of natural gas.

Anaerobic digestion: converts organic matter to a mixture of methane, the major component of natural gas, and carbon dioxide. In one aspect, biomass such as waterwaste (sewage), manure, or food processing waste, is mixed with water and fed into a digester tank without air.

Fermentation

Alcohol Fermentation: fuel alcohol is produced by converting cellulosic mass and/or starch to sugar, fermenting the sugar to alcohol, then separating the alcohol water mixture by distillation. Feedstocks such as dedicated crops (e.g., corn, wheat, barley, potatoes, switchgrass, Miscanthus, poplar wood), agricultural residues and wastes (e.g. rice straw, corn stover, wheat straw, sugarcane bagasse, rice hulls, corn fiber, sugar beet pulp, citrus pulp, and citrus peels), forestry wastes (e.g. hardwood and softwood thinnings, hardwood and softwood residues from timber operations, wood shavings, and sawdust), urban wastes (e.g. paper fraction of municipal solid waste, municipal wood waste, municipal green waste), wood wastes (e.g. saw mill waste, pulp mill waste, construction waste, demolition waste, wood shavings, and sawdust), and waste paper or other materials containing sugar, starch, and/or cellulose can be converted to sugars and then to alcohol by fermentation with yeast. Alternatively, materials containing sugars can be converted directly to alcohol by fermentation.

Transesterification: An exemplary reaction for converting oil to biodiesel is called transesterification. The transesterification process reacts an alcohol (like methanol) with the triglyceride oils contained in vegetable oils, animal fats, or recycled greases, forming fatty acid alkyl esters (biodiesel) and glycerin. The reaction requires heat and a strong base catalyst, such as sodium hydroxide or potassium hydroxide.

Biodiesel: Biodiesel is a mixture of fatty acid alkyl esters made from vegetable oils, animal fats or recycled greases. Biodiesel can be used as a fuel for vehicles in its pure form, but it is usually used as a petroleum diesel additive to reduce levels of particulates, carbon monoxide, hydrocarbons and air toxics from diesel-powered vehicles.

Hydrolysis: includes hydrolysis of a compound, e.g., a biomass, such as a lignocellulosic material, catalyzed using an enzyme of the instant invention.

Congeneration: is the simultaneous production of more than one form of energy using a single fuel and facility. In one aspect, biomass cogeneration has more potential growth than biomass generation alone because cogeneration produces both heat and electricity.

In one aspect, the polypeptides of the invention can be used in conjunction with other enzymes, e.g., hydrolases or enzymes having cellulolytic activity, e.g., a glucanase, endoglucanase, mannase and/or other enzyme, for generating a fuel such as a bioalcohol, e.g., a bioethanol, biomethanol, biobutanol or biopropanol, or biodiesel, from any organic material, e.g., a biomass, such as compositions derived from plants and animals, including any agricultural crop or other renewable feedstock, an agricultural residue or an animal waste, the organic components of municipal and industrial wastes, or construction or demolition wastes or debris, or microorganisms such as algae or yeast.

In one aspect, polypeptides of the invention are used in processes for converting lignocellulosic biomass to a fuel (e.g. a bioalcohol, e.g., a bioethanol, biomethanol, biobutanol or biopropanol, or biodiesel), or otherwise are used in processes for hydrolyzing or digesting biomaterials such that they can be used as a fuel (e.g. a bioalcohol, e.g., a bioethanol, biomethanol, biobutanol or biopropanol, or biodiesel), or for making it easier for the biomass to be processed into a fuel.

In an alternative aspect, polypeptides of the invention, including the mixture of enzymes or "cocktails" of the invention, are used in processes for a transesterification process reacting an alcohol (like ethanol, propanol, butanol, propanol, methanol) with a triglyceride oil contained in a vegetable oil, animal fat or recycled greases, forming fatty acid alkyl esters (biodiesel) and glycerin. In one aspect, biodiesel is made from soybean oil or recycled cooking oils. Animal's fats, other vegetable oils, and other recycled oils can also be used to produce biodiesel, depending on their costs and availability. In another aspect, blends of all kinds of fats and oils are used to produce a biodiesel fuel of the invention.

Enzymes of the invention, including the mixture of enzymes or "cocktails" of the invention, can also be used in glycerin refining. The glycerin by-product contains unreacted catalyst and soaps that are neutralized with an acid. Water and alcohol are removed to produce 50% to 80% crude glycerin. The remaining contaminants include unreacted fats and oils, which can be processes using the polypeptides of the invention. In a large biodiesel plants of the invention, the glycerin can be further purified, e.g., to 99% or higher purity, for the pharmaceutical and cosmetic industries.

Fuels (including bioalcohols such as bioethanols, biomethanols, biobutanols or biopropanols, or biodiesels) made using the polypeptides of the invention, including the mixture of enzymes or "cocktails" of the invention, can be used with fuel oxygenates to improve combustion characteristics. Adding oxygen results in more complete combustion, which reduces carbon monoxide emissions. This is another environmental benefit of replacing petroleum fuels with biofuels (e.g., a fuel of the invention). A biofuel made using the compositions and/or methods of this invention can be blended with gasoline to form an E10 blend (about 5% to 10% ethanol and about 90% to 95% gasoline), but it can be used in higher concentrations such as E85 or in its pure form. A biofuel made using the compositions and/or methods of this invention can be blended with petroleum diesel to form a B20 blend (20% biodiesel and 80% petroleum diesel), although other blend levels can be used up to B100 (pure biodiesel).

The invention also provides processes using enzymes of this invention for making biofuels (including bioalcohols such as bioethanols, biomethanols, biobutanols or biopropanols, or biodiesels) from compositions comprising a biomass, e.g., a plant-derived source, such as a lignocellulosic biomass. The biomass material can be obtained from agricultural crops, as a byproduct of food or feed production, or as waste products, including lignocellulosic waste products, such as plant residues, waste paper or construction and/or demolition wastes or debris. Examples of suitable plant sources or plant residues for treatment with polypeptides of the invention include kelp, algae, grains, seeds, stems, leaves, hulls, husks, corn cobs, corn stover, straw, sugar cane, sugar cane bagasse, grasses (e.g., Indian grass, such as *Sorghastrum nutans*; or, switch grass, e.g., *Panicum* species, such as *Panicum virgatum*), and the like, as well as wood, wood chips, wood pulp, and sawdust. Examples of paper waste suitable for treatment with polypeptides of the invention include discard photocopy paper, computer printer paper, notebook paper, notepad paper, typewriter paper, and the like, as well as newspapers, magazines, cardboard, and paper-based packaging materials. Examples of construction and demolition wastes and debris include wood, wood scraps, wood shavings and sawdust.

In one embodiment, the enzymes, including the mixture of enzymes or "cocktails" of the invention, and methods of the invention can be used in conjunction with more "traditional" means of making ethanol, methanol, propanol, butanol, propanol and/or diesel from biomass, e.g., as methods comprising hydrolyzing lignocellulosic materials by subjecting dried lignocellulosic material in a reactor to a catalyst comprised of a dilute solution of a strong acid and a metal salt; this can lower the activation energy, or the temperature, of cellulose hydrolysis to obtain higher sugar yields; see, e.g., U.S. Pat. Nos. 6,660,506 and 6,423,145.

Another exemplary method that incorporates use of enzymes of the invention, including the mixture of enzymes or "cocktails" of the invention, comprises hydrolyzing a biomass, including any lignocellulosic material, e.g., containing hemicellulose, cellulose and lignin, or any other polysaccharide that can be hydrolyzed, by subjecting the material to a first stage hydrolysis step in an aqueous medium at a temperature and a pressure chosen to effect primarily depolymerization of hemicellulose without major depolymerization of cellulose to glucose. This step results in a slurry in which the liquid aqueous phase contains dissolved monosaccharides resulting from depolymerization of hemicellulose and a solid phase containing cellulose and lignin. A second stage hydrolysis step can comprise conditions such that at least a major portion of the cellulose is depolymerized, such step resulting in a liquid aqueous phase containing dissolved/soluble depolymerization products of cellulose. See, e.g., U.S. Pat. No. 5,536,325. Enzymes of the invention (including the invention's mixtures, or "cocktails" of enzymes) can be added at any stage of this exemplary process.

Another exemplary method that incorporated use of enzymes of the invention, including the mixture of enzymes or "cocktails" of the invention, comprises processing a lignocellulose-containing biomass material by one or more stages of dilute acid hydrolysis with about 0.4% to 2% strong acid; and treating an unreacted solid lignocellulosic component of the acid hydrolyzed biomass material by alkaline delignification to produce precursors for biodegradable thermoplastics and derivatives. See, e.g., U.S. Pat. No. 6,409,841. Enzymes of the invention can be added at any stage of this exemplary process.

Another exemplary method that incorporated use of enzymes of the invention, including the mixture of enzymes or "cocktails" of the invention, comprises prehydrolyzing lignocellulosic material in a prehydrolysis reactor; adding an acidic liquid to the solid lignocellulosic material to make a mixture; heating the mixture to reaction temperature; maintaining reaction temperature for time sufficient to fractionate the lignocellulo sic material into a solubilized portion containing at least about 20% of the lignin from the lignocellulosic material and a solid fraction containing cellulose; removing a solubilized portion from the solid fraction while at or near reaction temperature wherein the cellulose in the solid fraction is rendered more amenable to enzymatic digestion; and recovering a solubilized portion. See, e.g., U.S. Pat. No. 5,705,369. Enzymes of the invention can be added at any stage of this exemplary process.

The invention provides methods for making motor fuel compositions (e.g., for spark ignition motors) based on liquid hydrocarbons blended with a fuel grade alcohol made by using an enzyme or a method of the invention. In one aspect, the fuels made by use of an enzyme of the invention comprise, e.g., coal gas liquid- or natural gas liquid-ethanol blends. In one aspect, a co-solvent is biomass-derived 2-methyltetrahydrofuran (MTHF). See, e.g., U.S. Pat. No. 6,712,866.

In one aspect, methods of the invention for the enzymatic degradation of lignocellulose, e.g., for production of biofuels (including bioalcohols such as bioethanols, biomethanols, biobutanols or biopropanols, or biodiesels) from lignocellulosic material, can also comprise use of ultrasonic treatment of the biomass material; see, e.g., U.S. Pat. No. 6,333,181.

In another aspect, methods of the invention for producing biofuels (including bioalcohols such as bioethanols, biomethanols, biobutanols or biopropanols, or biodiesels) from a cellulosic substrate comprise providing a reaction mixture in the form of a slurry comprising cellulosic substrate, an enzyme of this invention and a fermentation agent (e.g., within a reaction vessel, such as a semi-continuously solids-fed bioreactor), and the reaction mixture is reacted under conditions sufficient to initiate and maintain a fermentation reaction (as described, e.g., in U.S. Pat. App. No. 20060014260). In one aspect, experiment or theoretical calculations can determine an optimum feeding frequency. In one aspect, additional quantities of the cellulosic substrate and the enzyme are provided into the reaction vessel at an interval(s) according to the optimized feeding frequency.

One exemplary process for making biofuels (including bioalcohols such as bioethanols, biomethanols, biobutanols or biopropanols, or biodiesels) of the invention is described in U.S. Pat. App. Pub. Nos. 20050069998; 20020164730; and in one aspect comprises stages of grinding the lignocellulosic biomass (e.g., to a size of 15-30 mm), subjecting the product obtained to steam explosion pre-treatment (e.g., at a temperature of 190-230° C.) for between 1 and 10 minutes in a reactor; collecting the pre-treated material in a cyclone or related product of manufacture; and separating the liquid and solid fractions by filtration in a filter press, introducing the solid fraction in a fermentation deposit and adding one or more enzymes of the invention, e.g., a cellulase and/or beta-glucosidase enzyme (e.g., dissolved in citrate buffer pH 4.8).

Another exemplary process for making biofuels (including bioalcohols such as bioethanols, biomethanols, biobutanols or biopropanols, or biodiesels) of the invention comprising bioethanols, biomethanols, biobutanols or biopropanols using enzymes of the invention comprises pretreating a starting material comprising a lignocellulosic feedstock comprising at least hemicellulose and cellulose. In one aspect, the starting material comprises potatoes, soybean (rapeseed), barley, rye, corn, oats, wheat, beets or sugar cane or a component or waste or food or feed production byproduct. The starting material ("feedstock") is reacted at conditions which disrupt the plant's fiber structure to effect at least a partial hydrolysis of the hemicellulose and cellulose. Disruptive conditions can comprise, e.g., subjecting the starting material to an average temperature of 180° C. to 270° C. at pH 0.5 to 2.5 for a period of about 5 seconds to 60 minutes; or, temperature of 220° C. to 270° C., at pH 0.5 to 2.5 for a period of 5 seconds to 120 seconds, or equivalent. This generates a feedstock with increased accessibility to being digested by an enzyme, e.g., a cellulase enzyme of the invention. U.S. Pat. No. 6,090,595.

Exemplary conditions for using enzymes of the invention in the hydrolysis of lignocellulosic material include reactions at temperatures between about 30° C. and 48° C., and/or a pH between about 4.0 and 6.0. Other exemplary conditions include a temperature between about 30° C. and 60° C. and a pH between about 4.0 and 8.0.

Glucanases, (or cellulases), mannanases, xylanases, amylases, xanthanases and/or glycosidases, e.g., cellobiohydrolases, mannanases and/or beta-glucosidases can be used in the conversion of biomass to fuels, and in the production of ethanol, e.g., as described in PCT Application Nos. WO0043496 and WO8100857. Glucanases (or cellulases), mannanases, xylanases, amylases, xanthanases and/or glycosidases, e.g., cellobiohydrolases, mannanases and/or beta-glucosidases, can be used in combination with phytase (e.g., enzymes of the invention) to produce fermentable sugars and glucan-containing biomass that can be converted into fuel ethanol. Amylases, glucoamylases, pullanases, glucoisomerase, alpha-glucosidase, and the like can be used in combination with phytase (e.g., enzymes of the invention) to convert starch to fermentable sugars or ethanol. Please see PCT Application No. WO2005/096804.

Distillers Dried Grain Processing

In another aspect, the enzymes of the invention can be used to treat/process "distillers dried solubles (DDS)", "distillers dried grains (DDS)", "condensed distillers solubles (CDS)", "distillers wet grains (DWG)", and "distillers dried grains with solubles (DDGS)"; distillers dried grains can be a cereal byproduct of a distillation process, and can include solubles. These processes can comprise dry-grinding plant by-products, e.g. for feed applications, e.g., for poultry, bovine, swine and other domestic animals. Thus, the enzymes of the invention can be used to treat/process grains, e.g., cereals, that are byproducts of any distillation process, including processes using any source of grain, for example, the traditional sources from brewers, or alternatively, from an ethanol-producing plant (factory, mill or the like). Enzymes of the invention can be used to treat/process drying mash from distilleries; this mash can be subsequently used for a variety of purposes, e.g., as fodder for livestock, especially ruminants; thus the invention provides methods for processing fodder for livestock such as ruminants, and enzyme-processed fodder comprising phytases of this invention.

Figure 10:
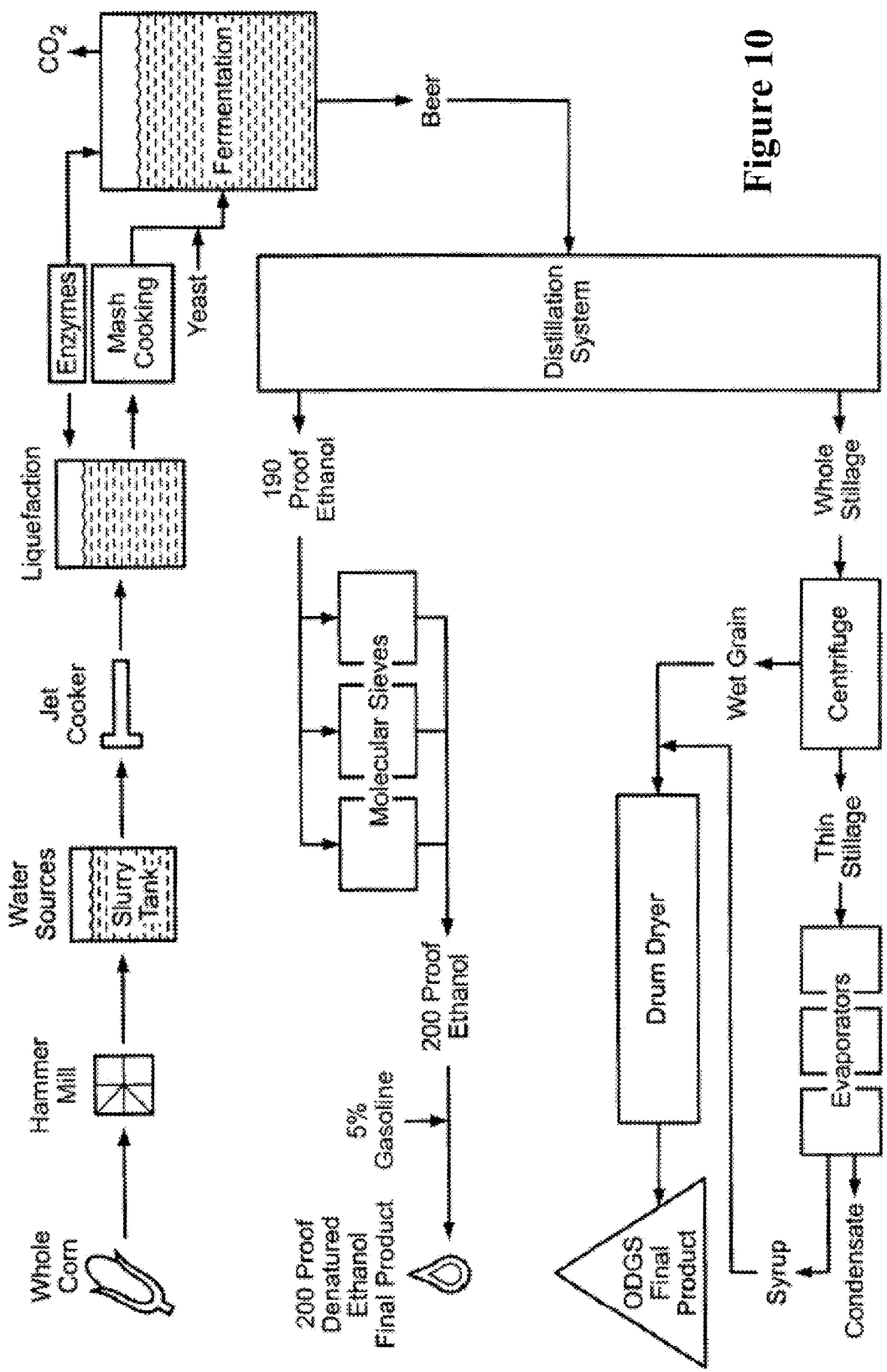
FIG. 10 illustrates an exemplary alcohol process that can incorporate use of phytases of this invention.

Phytases of this invention can be used alone or with other enzymes to process "distillers dried solubles (DDS)", "distillers dried grains (DDS)", "condensed distillers solubles (CDS)", "distillers wet grains (DWG)", and "distillers dried grains with solubles (DDGS)". For example, phytases of this invention can be used in any step of an alcohol product process as illustrated in FIG. 10. Phytases of this invention can be used to increase the bioavailability of phosphorus in any biofuel, or potential biofuel, including phosphorus found in "distillers dried solubles (DDS)", "distillers dried grains (DDS)", "condensed distillers solubles (CDS)", "distillers wet grains (DWG)", and "distillers dried grains with solubles (DDGS)" (see, e.g., C. Martinez Amezcua, 2004 Poultry Science 83:971-976).

Spirit, or Drinkable Alcohol Production

Phytases of this invention of this invention also can be used in processing distillers dried grains for alcohol production—alcohol as in "spirits", e.g., beer or whiskey production (in addition to use in processing biomass for making biofuels). Phytases of this invention of this invention can be used in ethanol plants, e.g. for processing grains such as corn. Distillers dried grains can be made by first grinding a grain (e.g., corn) to a coarse consistency and adding to hot water. After cooling, yeast is added and the mixture ferments for several days to a week. The solids remaining after fermentation are the distillers grains. Phytases of this invention of this invention can be used at any step of this process.

Formulations

The invention provides novel formulations comprising phytases, e.g., as those described herein, and formulations for phytases, including formulations which include the novel phytases of the invention. The phytases of the invention can be used or formulated alone or as mixture of phytases or phytases and other enzymes such as xylanases, cellulases, proteases, lipases, amylases, or redox enzymes such as laccases, peroxidases, catalases, oxidases, or reductases.

They can be used formulated in a solid form such as a powder, a lyophilized preparation, a granule, a tablet, a bar, a crystal, a capsule, a pill, a pellet, or in a liquid form such as in an aqueous solution, an aerosol, a gel, a paste, a slurry, an aqueous/oil emulsion, a cream, a capsule, or in a vesicular or micellar suspension. The formulations of the invention can comprise any or a combination of the following ingredients: polyols such as a polyethylene glycol, a polyvinylalcohol, a glycerol, a sugar such as a sucrose, a sorbitol, a trehalose, a glucose, a fructose, a maltose, a mannose, a gelling agent such as a guar gum, a carageenan, an alginate, a dextrans, a cellulosic derivative, a pectin, a salt such as a sodium chloride, a sodium sulfate, an ammonium sulfate, a calcium chloride, a magnesium chloride, a zinc chloride, a zinc sulfate, a salt of a fatty acid and a fatty acid derivative, a metal chelator such as an EDTA, an EGTA, a sodium citrate, an antimicrobial agent such as a fatty acid or a fatty acid derivative, a paraben, a sorbate, a benzoate, an additional modulating compound to block the impact of an enzyme such as a protease, a bulk proteins such as a BSA, a wheat hydrolysate, a borate compound, an amino acid or a peptide, an appropriate pH or temperature modulating compound, an emulsifier such as a non-ionic and/or an ionic detergent, a redox agent such as a cystine/cysteine, a glutathione, an oxidized glutathione, a reduced or an antioxidant compound such as an ascorbic acid, a wax or oil, or a dispersant. Cross-linking and protein modification such as pegylation, fatty acid modification, glycosylation can also be used to improve enzyme stability.

Measuring Metabolic Parameters

The methods of the invention involve whole cell evolution, or whole cell engineering, of a cell to develop a new cell strain having a new phenotype by modifying the genetic composition of the cell, where the genetic composition is modified by addition to the cell of a nucleic acid of the invention. To detect the new phenotype, at least one metabolic parameter of a modified cell is monitored in the cell in a "real time" or "on-line" time frame. In one aspect, a plurality of cells, such as a cell culture, is monitored in "real time" or "on-line." In one aspect, a plurality of metabolic parameters is monitored in "real time" or "on-line."

Metabolic flux analysis (MFA) is based on a known biochemistry framework. A linearly independent metabolic matrix is constructed based on the law of mass conservation and on the pseudo-steady state hypothesis (PSSH) on the intracellular metabolites. In practicing the methods of the invention, metabolic networks are established, including the:
  identity of all pathway substrates, products and intermediary metabolites
  identity of all the chemical reactions interconverting the pathway metabolites, the stoichiometry of the pathway reactions,
  identity of all the enzymes catalyzing the reactions, the enzyme reaction kinetics,
  the regulatory interactions between pathway components, e.g. allosteric interactions, enzyme-enzyme interactions etc,
  intracellular compartmentalization of enzymes or any other supramolecular organization of the enzymes, and,
  the presence of any concentration gradients of metabolites, enzymes or effector molecules or diffusion barriers to their movement.

Once the metabolic network for a given strain is built, mathematic presentation by matrix notion can be introduced to estimate the intracellular metabolic fluxes if the on-line metabolome data is available.

Metabolic phenotype relies on the changes of the whole metabolic network within a cell. Metabolic phenotype relies on the change of pathway utilization with respect to environmental conditions, genetic regulation, developmental state and the genotype, etc. In one aspect of the methods of the invention, after the on-line MFA calculation, the dynamic behavior of the cells, their phenotype and other properties are analyzed by investigating the pathway utilization. For example, if the glucose supply is increased and the oxygen decreased during the yeast fermentation, the utilization of respiratory pathways will be reduced and/or stopped, and the utilization of the fermentative pathways will dominate. Control of physiological state of cell cultures will become possible after the pathway analysis. The methods of the invention can help determine how to manipulate the fermentation by determining how to change the substrate supply, temperature, use of inducers, etc. to control the physiological state of cells to move along desirable direction. In practicing the methods of the invention, the MFA results can also be compared with transcriptome and proteome data to design experiments and protocols for metabolic engineering or gene shuffling, etc.

In practicing the methods of the invention, any modified or new phenotype can be conferred and detected, including new or improved characteristics in the cell. Any aspect of metabolism or growth can be monitored.

Monitoring Expression of an mRNA Transcript

In one aspect of the invention, the engineered phenotype comprises increasing or decreasing the expression of an mRNA transcript or generating new transcripts in a cell. mRNA transcript, or message can be detected and quantified by any method known in the art, including, e.g., Northern blots, quantitative amplification reactions, hybridization to arrays, and the like. Quantitative amplification reactions include, e.g., quantitative PCR, including, e.g., quantitative reverse transcription polymerase chain reaction, or RT-PCR; quantitative real time RT-PCR, or "real-time kinetic RT-PCR" (see, e.g., Kreuzer (2001) Br. J. Haematol. 114:313-318; Xia (2001) Transplantation 72:907-914).

In one aspect of the invention, the engineered phenotype is generated by knocking out expression of a homologous gene. The gene's coding sequence or one or more transcriptional control elements can be knocked out, e.g., promoters or enhancers. Thus, the expression of a transcript can be completely ablated or only decreased.

In one aspect of the invention, the engineered phenotype comprises increasing the expression of a homologous gene. This can be effected by knocking out of a negative control element, including a transcriptional regulatory element acting in cis- or trans-, or, mutagenizing a positive control element.

As discussed below in detail, one or more, or, all the transcripts of a cell can be measured by hybridization of a sample comprising transcripts of the cell, or, nucleic acids representative of or complementary to transcripts of a cell, by hybridization to immobilized nucleic acids on an array.

Monitoring Expression of a Polypeptides, Peptides and Amino Acids

In one aspect of the invention, the engineered phenotype comprises increasing or decreasing the expression of a polypeptide or generating new polypeptides in a cell. Polypeptides, peptides and amino acids can be detected and quantified by any method known in the art, including, e.g., nuclear magnetic resonance (NMR), spectrophotometry, radiography (protein radiolabeling), electrophoresis, capillary electrophoresis, high performance liquid chromatography (HPLC), thin layer chromatography (TLC), hyperdiffusion chromatography, various immunological methods, e.g. immunoprecipitation, immunodiffusion, immuno-electrophoresis, radioimmunoassays (RIAs), enzyme-linked immunosorbent assays (ELISAs), immuno-fluorescent assays, gel electrophoresis (e.g., SDS-PAGE), staining with antibodies, fluorescent activated cell sorter (FACS), pyrolysis mass spectrometry, Fourier-Transform Infrared Spectrometry, Raman spectrometry, GC-MS, and LC-Electrospray and cap-LC-tandem-electrospray mass spectrometries, and the like. Novel bioactivities can also be screened using methods, or variations thereof, described in U.S. Pat. No. 6,057,103. Furthermore, as discussed below in detail, one or more, or, all the polypeptides of a cell can be measured using a protein array.

Biosynthetically directed fractional $^{13}C$ labeling of proteinogenic amino acids can be monitored by feeding a mixture of uniformly $^{13}C$-labeled and unlabeled carbon source compounds into a bioreaction network. Analysis of the resulting labeling pattern enables both a comprehensive characterization of the network topology and the determination of metabolic flux ratios of the amino acids; see, e.g., Szyperski (1999) Metab. Eng. 1:189-197.

The following examples are intended to illustrate, but not to limit, the invention. While the procedures described in the examples are typical of those that can be used to carry out certain aspects of the invention, other procedures known to those skilled in the art can also be used.

EXAMPLES

Example 1: Activity Characterization of Exemplary Phytases of the Invention

This example describes characterizing the phytase activity of polypeptides of the invention, which are sequence modifications (the so-called "evolved" phytases) of the parental phytase SEQ ID NO:2, and an exemplary phytase activity assay. This phytase activity assay can be used to determine if a polypeptide has sufficient activity to be within the scope of the claimed invention.

After generating the polypeptides of the invention by expressing the GSSM-modified nucleic acid sequences of the invention, the "evolved" phytase polypeptides—only single residue mutation exemplary species in this study—were purified and then heat treated (pH 7.0, 0.01% Tween) at various temperatures for 30 minutes. After the heat treatment step, the samples (20 uL) were assayed with the fluorescence substrate (180 uL) 4 mM DiFMUP at pH 5.5. The rates were compared to the rates of each corresponding non-treated sample. Results are illustrated in FIG. 1.

Figure 2:
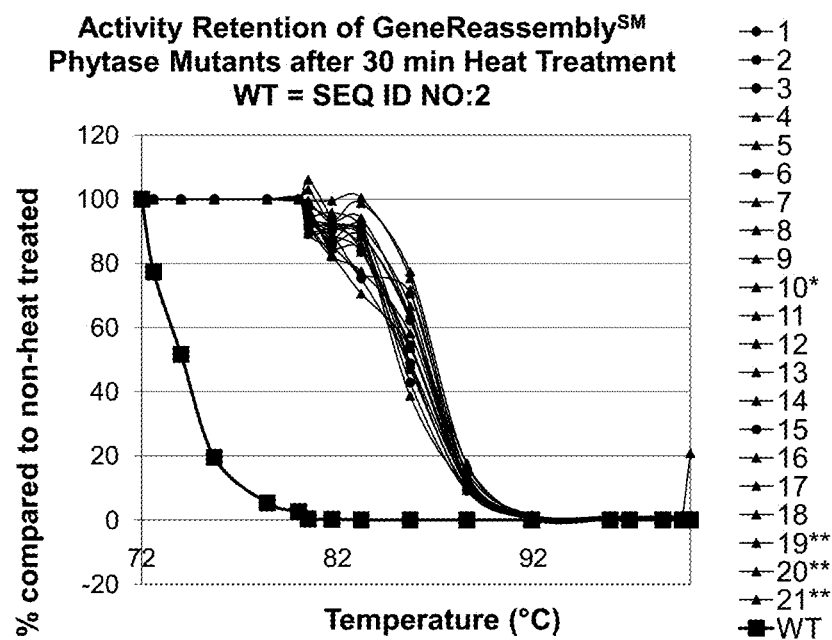
FIG. 2 illustrates a summary of residue activity of purified polypeptides of the invention comprising "blended" single residue mutations (phytases containing multiple mutations), after heat treatment on a thermocycler; where the phytase activity is assayed with a fluorescence substrate, and the rates were compared to the rates of each corresponding non-treated sample; as summarized in FIG. 1; as described in detail in Example 1, below.

In another study, the "evolved" phytases of the invention comprising "blended" single mutations, i.e. phytases containing multiple mutations, were grown overnight in LBCARB100™ (LBcarb100) at 30° C. 100 uL of the each culture (blended mutant) was heat treated on a thermocycler from 72° C. to 100° C. 20 uL of the heat treated culture was mixed with 180 uL of 4 mM DiFMUP at pH 5.5. The rates were compared to the rates of each corresponding non-treated sample; as summarized in FIG. 2. The table illustrated in FIG. 3 graphically summarizes the data (rounded to the nearest tenth) used to generate the graph of FIG. 2.

Sample 1 to 21 correspond to the "blended" single mutations of the parental SEQ ID NO:2, as illustrated in the chart of FIG. 5; note that "evolved" phytase number 10 has a sequence residue modification (from SEQ ID NO:2) that was not introduced by GSSM; this mutation was introduced by random chance and may or may not have any relevance to thermal stability of this exemplary phytase of the invention. Also, note the ** marked exemplary phytases 19, 20 and 21 have C-terminal histidine (6×His) tags (-RSHHH-HHH). FIG. 5 illustrates exemplary phytases having multiple residue modifications to the parental SEQ ID NO:2; as described in detail herein. FIG. 6 illustrates exemplary phytases having single residue modifications to the parental SEQ ID NO:2; as described in detail herein.

Figure 7:
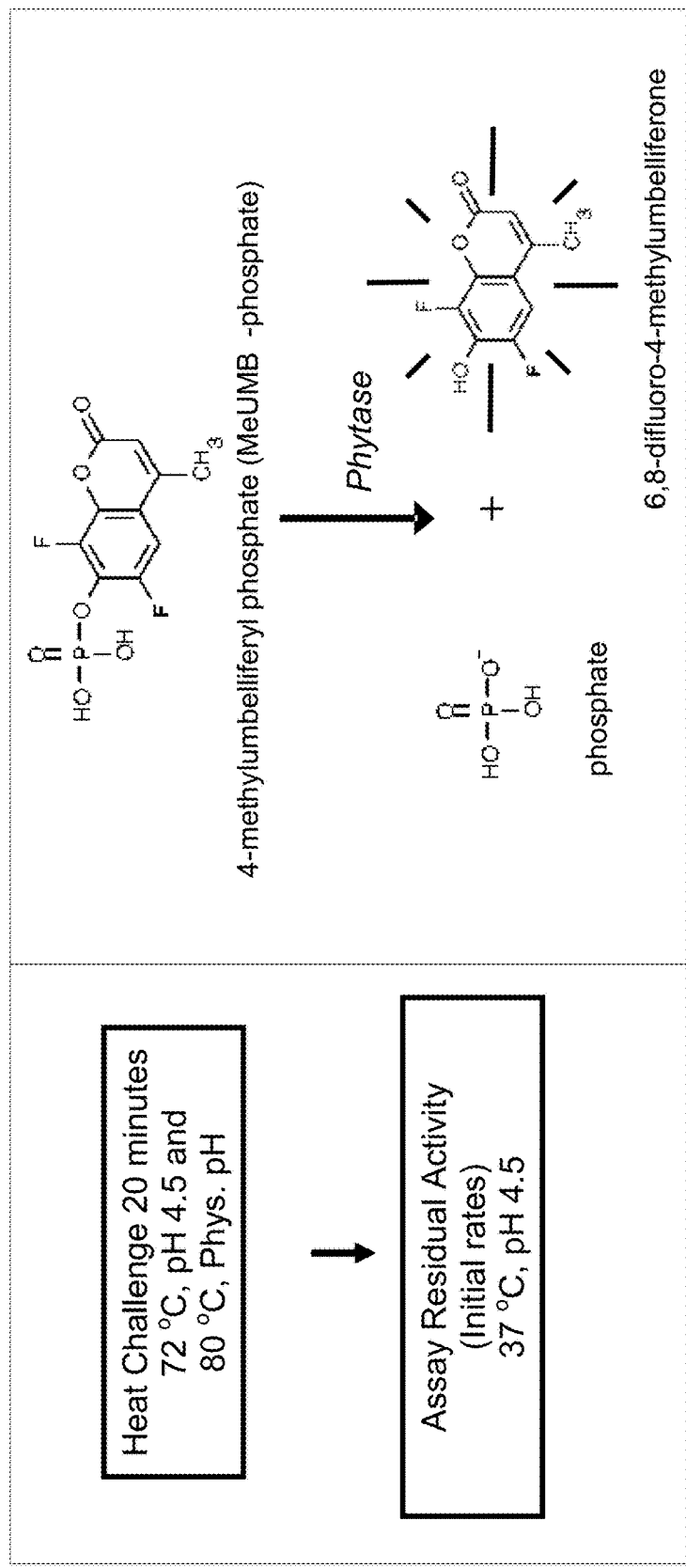
FIG. 7 schematically illustrates an exemplary phytase assay of the invention using the fluorescence substrate 4-methylumbelliferyl phosphate (MeUMB-phosphate); as described in detail in Example 1, below.

FIG. 7 schematically illustrates an exemplary phytase assay of the invention using the fluorescence substrate 4-methylumbelliferyl phosphate (MeUMB-phosphate, whose structure is also illustrated): (i) the phytase is heat challenged for 20 minutes, 72° C., pH 4.5; and, at 80° C. at physiological pH (pH 7.4); and (ii) residual activity is tested at 37° C., pH 4.5:

Measure residual activity both high and low pH,
Calculate residual activity relative to wild-type following heat treatment.

Figure 8:
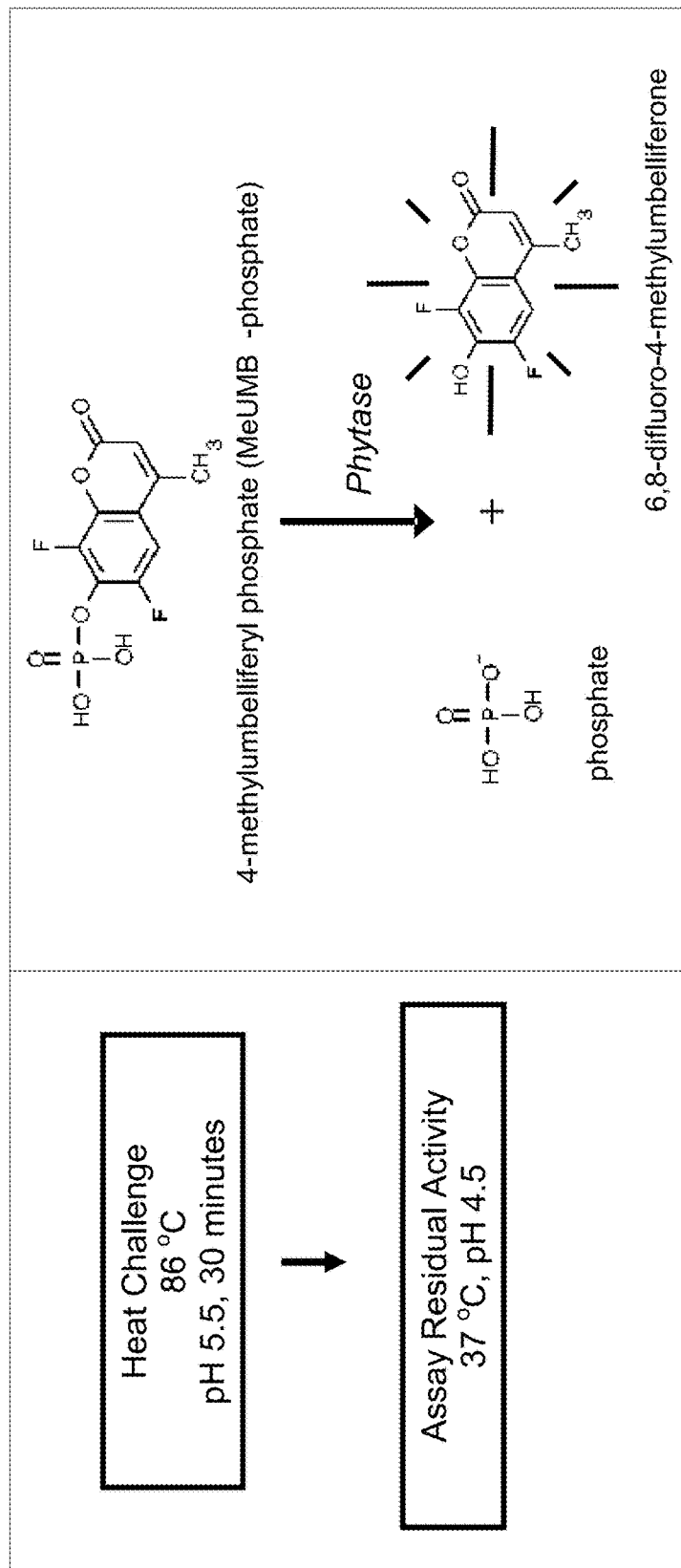
FIG. 8 schematically illustrates an exemplary phytase assay of the invention that uses the fluorescence substrate MeUMB-phosphate; as described in detail in Example 1, below.

FIG. 8 schematically illustrates another exemplary phytase assay of the invention that also uses the fluorescence substrate MeUMB-phosphate: (i) the phytase is heat challenged for 30 minutes, 86° C., pH 5.5; and (ii) residual activity is tested at 37° C., pH 4.5:

Measure residual activity relative to 6× variant control,
Select hits and re-assay at higher stringency to select top variants.

Figure 9:
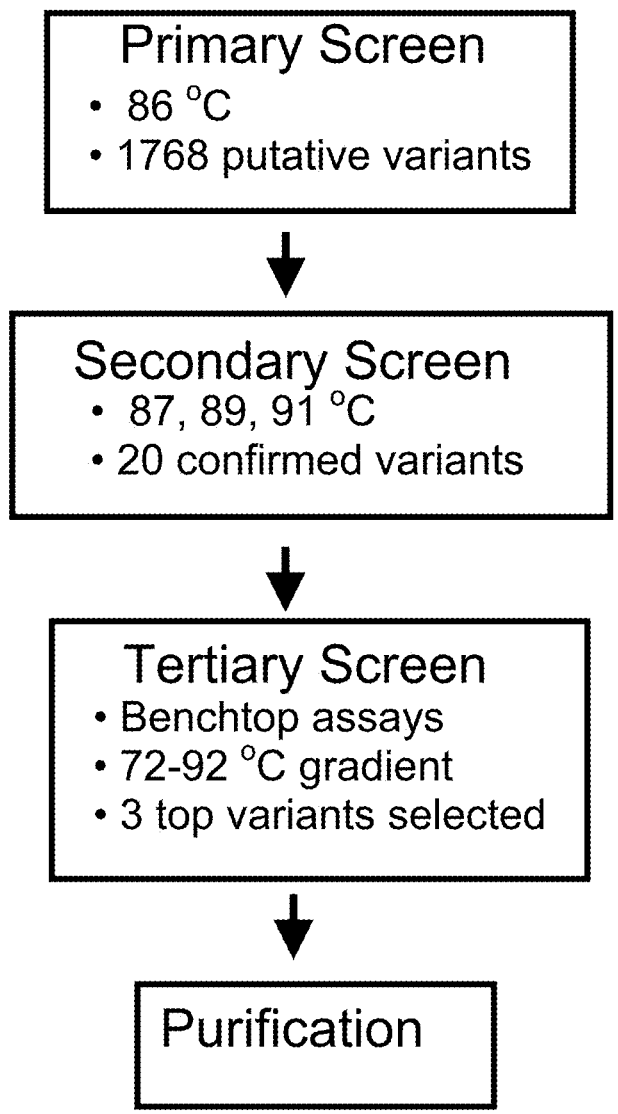
FIG. 9 schematically illustrates the protocol for an exemplary library screen, as described in FIG. 8, as described in detail in Example 1, below.

This assay was used to screen libraries of GSSM variants (of SEQ ID NO:1), by assaying for the phytase activity of the polypeptides they encoded. FIG. 9 schematically illustrates the protocol for this library screen (as described in FIG. 8), where the library size screened is 24,576 variants.

Example 2: Development of a Phytase with Increased Thermotolerance and Increased Gastric Liability This example describes development and characterization of the phytase activity of polypeptides of the invention, which are further sequence modifications (the "evolved" phytases) of the parental phytase SEQ ID NO:2. The evolved phytases described herein have been optimized for plant expression and for broad-acreage commercialization. The phytases have better or equal thermal tolerance relative to the parental phytase (SEQ ID NO:2, encoded by SEQ ID NO:1) and decreased in vitro gastric stability (increased gastric lability).

Template Selection:

The selected GSSM backbone has both thermotolerance and evidence of SGF degradation. The evaluation began with testing the SGF properties of thirteen thermotolerant phytase molecules (as described in Example 1, above and Table 3, below). The SGF data on the purified phytases shows that all thermotolerant variants, including the single-site thermotolerant parental phytase mutation N159V (SEQ ID NO:2-N159V), were very stable, showing minimal degradation over two hours.

Figures 11A, 11B:
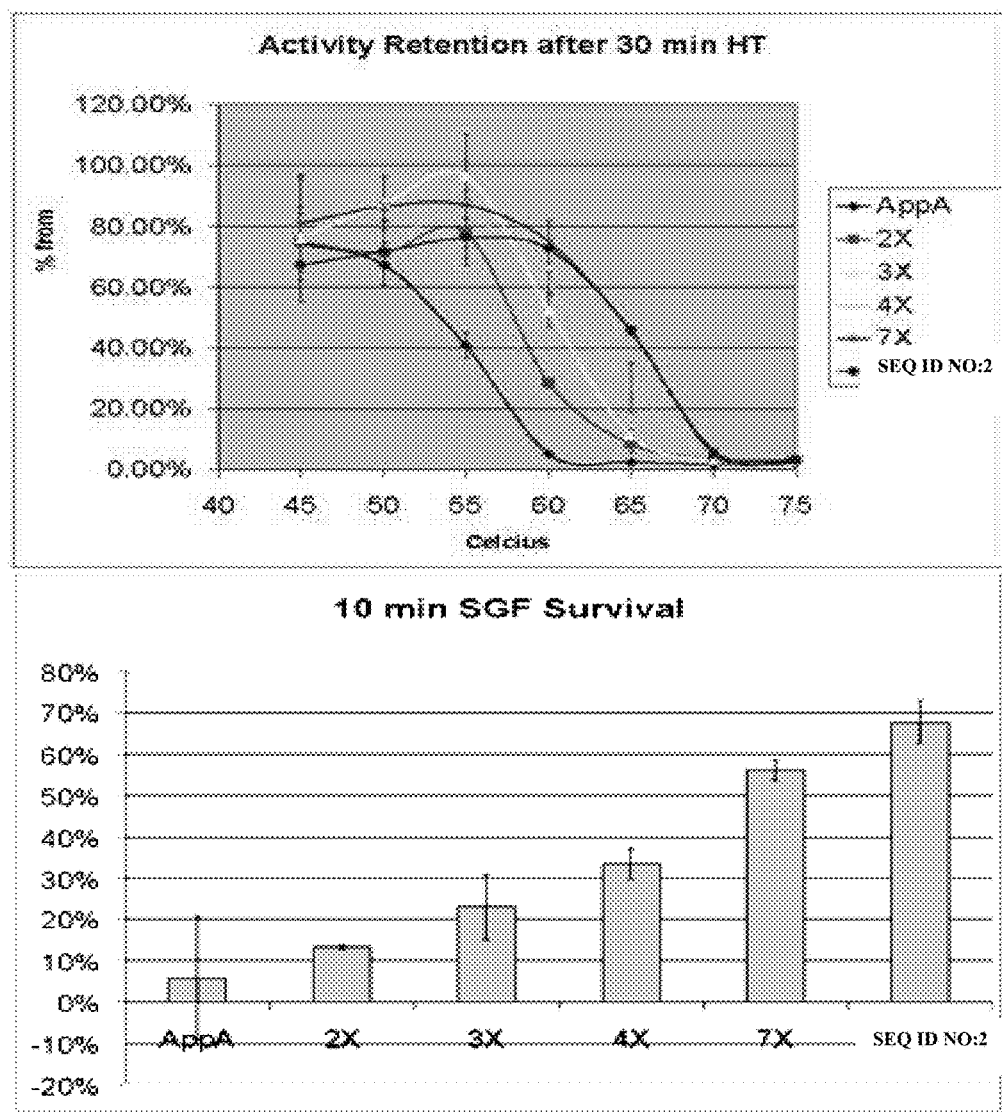
FIGS. 11A and 11B illustrate summaries of thermostability and SGF lability of appA phytase (GenBank accession no. M58708), appA-SEQ ID NO:2 intermediates, and SEQ ID NO:2, as described in detail in Example 2, below.

Previous work/literature suggest that the E. coli phytase appA gene (from strain K12, (GenBank accession no. M58708) was more susceptible to SGF degradation than the parental phytase (SEQ ID NO:2). In an effort to understand the SGF stability phenomenon, five of the intermediate variants between appA and the parental phytase (SEQ ID NO:2) were investigated for SGF lability. The data suggest a strong correlation between thermotolerance and SGF lability (FIGS. 11A and 11B). More importantly, appA -7X which is one amino acid different than the parental phytase (SEQ ID NO:2), showed ~10% more loss in activity in SGF after 10 minute incubation compared to the parental phytase (SEQ ID NO:2). This new data implies that one single mutation change in SEQ ID NO:2 could impact changes in SGF tolerance and more importantly, be differentiated from the parental phytase (SEQ ID NO:2) in the SGF assay. Based on this new evidence, appA −7X was selected as a benchmark control for the SGF evolution and SEQ ID NO:2 was selected as the GSSM backbone for the evolution.

Figure 12:
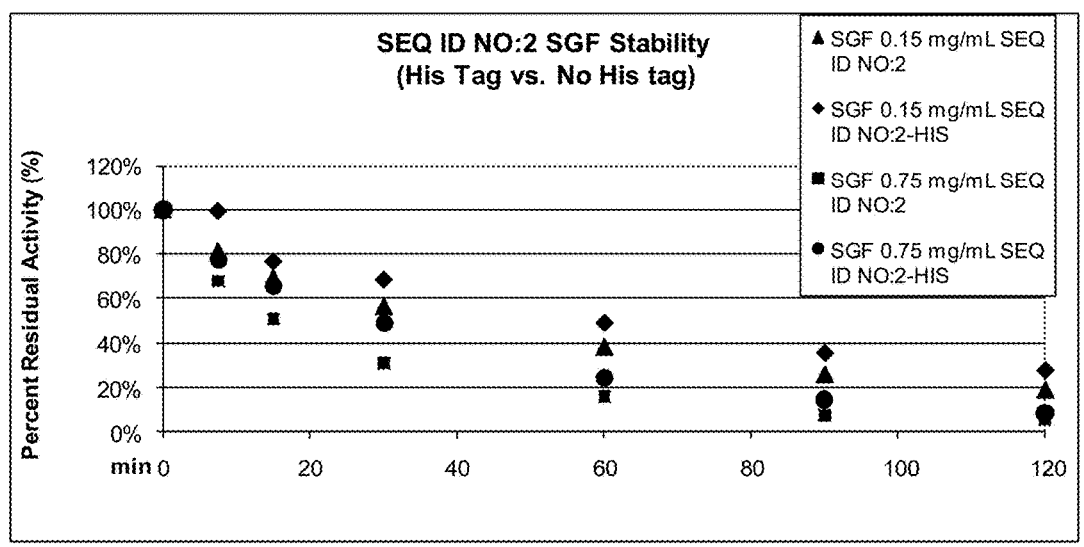
FIG. 12 illustrates the effect of a his-tag on SGF stability, as determined by SGF assays of purified his-tag and non his-tag versions of the parental phytase (SEQ ID NO:2), as described in detail in Example 2, below.

Since protein purification would be an integral part of the characterization process, SEQ ID NO:2 was evaluated as both a his-tag (SEQ ID NO:2-HIS) and non-his tag (SEQ ID NO:2) molecule. SGF assays were performed for both the purified his-tagged and non his-tag versions of the parental phytase (SEQ ID NO:2). The SGF assays were performed with two different pepsin doses (0.15 mg/mL and 0.75 mg/mL). The residual activity was determined at various time points (7.5, 15, 30, 60, 90, and 120 minutes). There was no significant difference in SGF profiles between the two versions (FIG. 12).

TABLE 3

Phytase variants characterized for potential GSSM SGF backbone.

| Parent | Variant | A47F | W68E | Q84W | A95P | C97E | K97C | T136H | S168E | N159V | T163R | D164R |
|---|---|---|---|---|---|---|---|---|---|---|---|---|
| appA | appA 2X | | | Q84W | A95P | | | | | | | |
| appA | appA 3X | | | Q84W | A95P | | | | | | | |
| appA | appA 4X | | | Q84W | A95P | | | | | | | |
| appA | appA 7X | | W68E | Q84W | A95P | | K97C | | | | | |
| SEQ ID NO: 2 | SEQ ID NO: 2 (no mutations) | | W68E | Q84W | A95P | | K97C | | S168E | | | |
| SEQ ID NO: 2 | SEQ ID NO: 2-N159V | | W68E | Q84W | A95P | | K97C | | S168E | N159V | | |
| SEQ ID NO: 2 | SEQ ID NO: 2-3X | A47F | W68E | Q84W | A95P | | K97C | T136H | S168E | | | |
| SEQ ID NO: 2 | SEQ ID NO: 2-5Xa | | W68E | Q84W | A95P | | K97C | T136H | S168E | N159V | | |
| SEQ ID NO: 2 | SEQ ID NO: 2-5Xb | A47F | W68E | Q84W | A95P | | K97C | | S168E | N159V | | |
| SEQ ID NO: 2 | SEQ ID NO: 2-5Xc | A47F | W68E | Q84W | A95P | | K97C | T136H | S168E | | | |
| SEQ ID NO: 2 | SEQ ID NO: 2-5Xd | A47F | W68E | Q84W | A95P | | K97C | T136H | S168E | N159V | | |
| SEQ ID NO: 2 | SEQ ID NO: 2-5Xe | A47F | W68E | Q84W | A95P | | K97C | T136H | S168E | N159V | | |
| SEQ ID NO: 2 | SEQ ID NO: 2-5Xf | A47F | W68E | Q84W | A95P | | K97C | T136H | S168E | N159V | | |
| SEQ ID NO: 2 | SEQ ID NO: 2-6X | A47F | W68E | Q84W | A95P | | K97C | T136H | S168E | N159V | | |
| SEQ ID NO: 2 | SEQ ID NO: 2-9X | A47F | W68E | Q84W | A95P | | K97C | T136H | S168E | N159V | | D164R |
| SEQ ID NO: 2 | SEQ ID NO: 2-10Xa | A47F | W68E | Q84W | A95P | C97E | | T136H | S168E | N159V | T163R | |
| SEQ ID NO: 2 | SEQ ID NO: 2-10Xb | A47F | W68E | Q84W | A95P | | K97C | T136H | S168E | N159V | T163R | D164R |
| SEQ ID NO: 2 | SEQ ID NO: 2-13X | A47F | W68E | Q84W | A95P | C97E | K97C | T136H | S168E | N159V | T163R | D164R |

| Parent | Variant | E168R | G179R | R181Y | N226C | C226D | V233W | Q275V | Y277D | R289A | T349Y |
|---|---|---|---|---|---|---|---|---|---|---|---|
| appA | appA 2X | | | | | | | | | | |
| appA | appA 3X | | | | | | | | Y277D | | |
| appA | appA 4X | | | | | | | | Y277D | | |
| appA | appA 7X | | | R181Y | N226C | | | | Y277D | | |
| SEQ ID NO: 2 | SEQ ID NO: 2 (no mutations) | | | R181Y | N226C | | | | Y277D | | |
| SEQ ID NO: 2 | SEQ ID NO: 2-N159V | | | R181Y | N226C | | | | Y277D | | |
| SEQ ID NO: 2 | SEQ ID NO: 2-3X | | | R181Y | N226C | | V233W | | Y277D | | |
| SEQ ID NO: 2 | SEQ ID NO: 2-5Xa | | | R181Y | | C226D | V233W | | Y277D | | T349Y |
| SEQ ID NO: 2 | SEQ ID NO: 2-5Xb | | | R181Y | | C226D | V233W | | Y277D | | T349Y |
| SEQ ID NO: 2 | SEQ ID NO: 2-5Xc | | | R181Y | | C226D | V233W | | Y277D | | T349Y |
| SEQ ID NO: 2 | SEQ ID NO: 2-5Xd | | | R181Y | N226C | | V233W | | Y277D | | T349Y |
| SEQ ID NO: 2 | SEQ ID NO: 2-5Xe | | | R181Y | | C226D | | | Y277D | | T349Y |
| SEQ ID NO: 2 | SEQ ID NO: 2-5Xf | | | R181Y | | C226D | V233W | | Y277D | | |
| SEQ ID NO: 2 | SEQ ID NO: 2-6X | | | R181Y | | C226D | V233W | | Y277D | | T349Y |
| SEQ ID NO: 2 | SEQ ID NO: 2-9X | | G179R | R181Y | | C226D | V233W | Q275V | Y277D | | T349Y |
| SEQ ID NO: 2 | SEQ ID NO: 2-10Xa | | G179R | R181Y | | C226D | V233W | Q275V | Y277D | | T349Y |

TABLE 3-continued

Phytase variants characterized for potential GSSM SGF backbone.

| SEQ ID NO: 2 | SEQ ID NO: 2-10Xb | | G179R | R181Y | C226D | V233W | Q275V | Y277D | | T349Y |
|---|---|---|---|---|---|---|---|---|---|---|
| SEQ ID NO: 2 | SEQ ID NO: 2-13X | E168R | G179R | R181Y | C226D | V233W | Q275V | Y277D | R289A | T349Y |

Purified phytase fractions of SEQ ID NO:2 and variants SEQ ID NO:2-N159V through SEQ ID NO:2-6× were tested for SGF stability at pepsin doses of 0.75 mg/mL and 0.15 mg/mL; data not shown. Residual activity at various time points (7.5, 15, 30, 60, 90, and 120 minutes) was determined. At both dosages, no significant difference in SGF stability between the variant phytases was observed. SEQ ID NO:2 was the least stable in SGF at both dosages.

SGF assays by SDS-PAGE analysis: All variants listed in Table 3 were tested for SGF stability by SDS-PAGE (data not shown). SDS-PAGE gels were dyed with Simply Blue™ SafeStain. In the SGF assay, SEQ ID NO:2 denatured over a 60 minute timecourse while SEQ ID NO:2-N159V and the other variants did not show significant degradation over a two hour period.

N-Glycosylation Removal:

Previous studies suggested that N-glycosylation might improve SGF stability. Therefore, in order to reduce SFG stability, saturated directed mutagenesis (SDM) was performed to remove the two N-glycosylation sites on the parental SEQ ID NO:2 molecule. The first N-glycosylation recognition site can be removed by either changing the Asparagine (N) at 161 or Threonine (T) at 163 to any other amino acid. The second N-glycosylation recognition site can be eliminated by changing the N at 339 or the T at 341 by the same process.

SDM was conducted by constructing a primer with the desired codon change and then utilizing PCR with the primer and the template (parent sequence) to create a new template with the desired codon change. During SDM all other 19 possible amino acids were substituted at each of the four residues responsible for N-glycosylation recognition: sites 161, 163, 339, and 341. The mutations showing the most similar characteristics (specific activity, thermotolerance, and pH profile) to SEQ ID NO:2 at the four positions were then combined to create a variant that would not have any N-glycosylation recognition sites. The four top mutations that preserved the parental phytase's (SEQ ID NO:2) properties were N161K, T163R, N339E, and T341D. These mutations were combined in a manner which would remove both N-glycosylation recognition sites on the same molecule (Table 4).

TABLE 4

N-glycosylation minus variants

| Name | Mutations |
|---|---|
| Variant GLY1 | N161K and N339E |
| Variant GLY2 | N161K and T341D |
| Variant GLY3 | T163R and N339E |
| Variant GLY4 | T163R and T341D |

Figure 13:
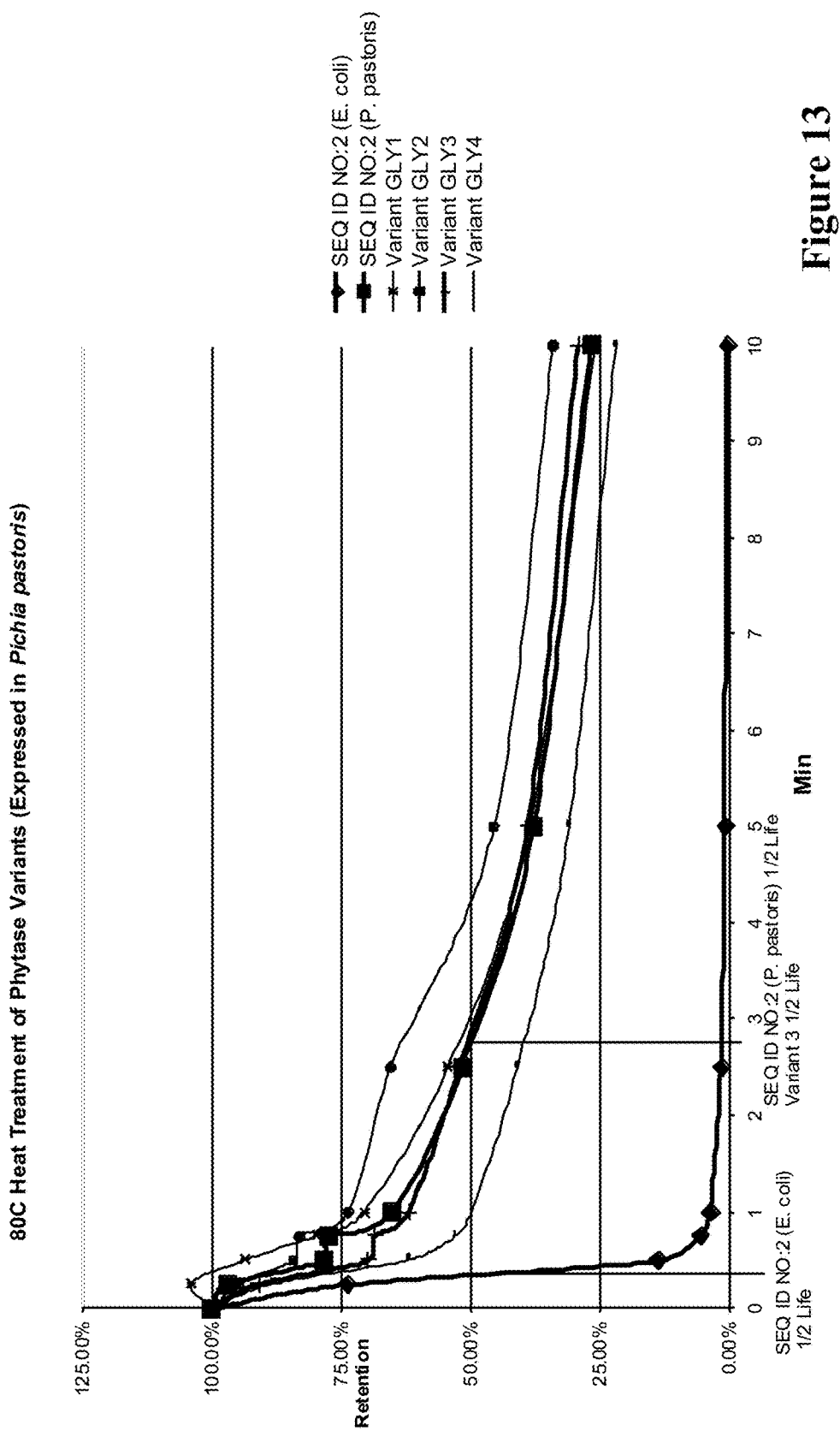
FIG. 13 illustrates the thermotolerance of glycosylation-minus SEQ ID NO:2 variants (Variants GLY1-GLY4) and two SEQ ID NO:2 controls, as described in detail in Example 2, below.

The four glycosylation minus variants were constructed, expressed in *Pichia pastoris*, and characterized. The thermotolerance (½ Life) of glycosylation-minus the variants of SEQ ID NO:2 (Variants GLY1-GLY4) and two SEQ ID NO:2 controls were determined by heat treatment at 80° C. over a ten minute time course. *Pichia*-expressed SEQ ID NO:2 and N-glycosylation-minus variants (Variants GLY1-GLY4) have approximately the same thermotolerance. However, SEQ ID NO:2 (expressed in *Pichia pastoris*) had greater thermotolerance than the same gene expressed in *E. coli* (SEQ ID NO:2-HIS). The lead glycosylation-minus variant, Variant GLY3, has the same thermotolerance, pH profile, and specific activity as SEQ ID NO:2 (FIG. 13). The thermotolerance data was a surprise, a hypothesis from previous work suggested that glycosylation improved thermotolerance, therefore it was expected that the glycosylation-minus variants would have reduced the thermotolerance. As expected, there was a significant difference in thermotolerance between the *E. coli* and *Pichia pastoris* expressed SEQ ID NO:2. However, if glycosylation is not the factor, perhaps of the thermotolerance difference can be attributed to the different protein folding environments of the two expression host; *Pichia*-intracellular protein folding, *E. coli*-periplasm protein folding.

The T163R and N339E mutations were incorporated into the top SGF labile variants later in the project (see TMCA$^{SM}$ Evolution, below).

Phytase activity and pH profiles of glycosylation-minus variants (Variants GLY1-GLY4), as well as for purified *Pichia* expressed SEQ ID NO:2 were determined on phytate at pH 2, 2.5, 3, 4, 5, and 6 at 37° C. The data (not shown) indicates that the glycosylation-minus variants have similar activity and pH profile to SEQ ID NO:2.

SEQ ID NO:2 SGF GSSM$^{SM}$ Screen

SEQ ID NO:2-HIS was chosen as the GSSM template. GSSM$^{SM}$ (Gene Site Saturation Mutagenesis$^{SM}$) evolution was performed (see, for example, U.S. Pat. No. 6,171,820).

Figure 14:
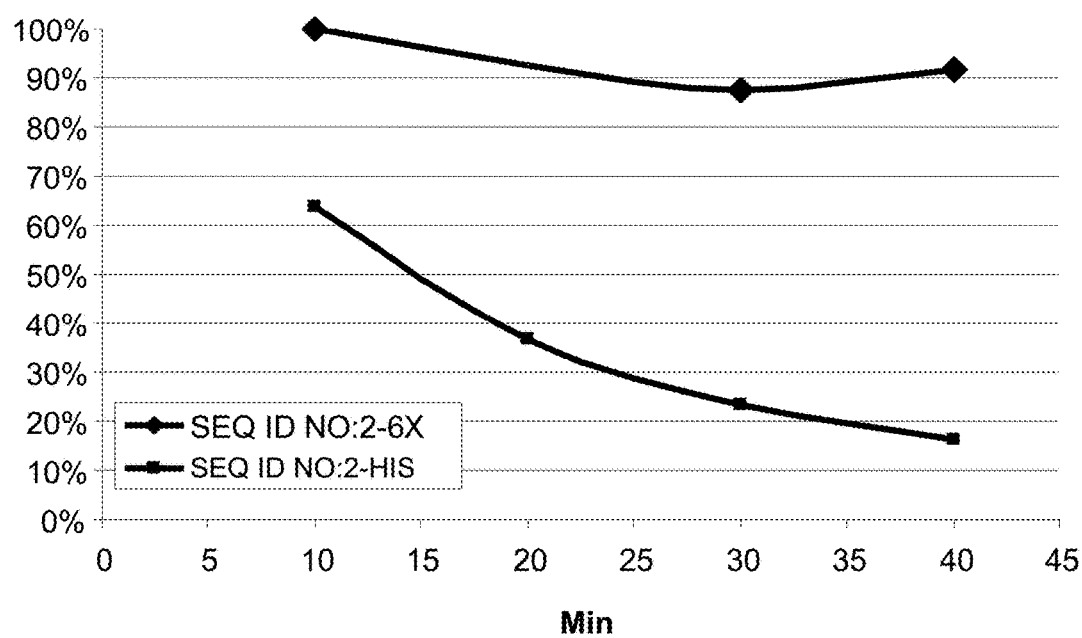
FIG. 14 illustrates the SGF stability of SEQ ID NO:2-HIS and the SEQ ID NO:2-6X variant, as described in detail in Example 2, below.

High Throughput Assay Development:

Cultures of SEQ ID NO:2 and SEQ ID NO:2-6× were grown in 384 well microtiter plates were tested in an automated robotic assay format for SGF stability. The plates were heat treated at 65 C for 30 minutes to lyse the cells. The cultures were then split into an untreated control plate and a SGF-treated plate. The activities of the SGF-treated samples were compared to the untreated control samples. Time points were taken at 10, 20, 30, and 40 minutes (FIG. 14). The parental phytase's (whole cell lysate) SGF profile from the automated assay mirrored the purified bench scale SGF assay.

High Throughput Assay Results

The entire parental sequence (SEQ ID NO:2, except the start codon), 432 codons, were mutated, expressed (in *E. coli*, as described below), and screened for SGF degradation improvements utilizing the developed Phytase SGF high throughput assay. One hundred and thirty two novel mutations were confirmed for SGF lability at 69 different residue locations (Table 5). At least eight single-site mutations met the SGF requirement of complete protein degradation in 10 minutes. However, most of these mutants fall short of the parental phytase's thermal tolerance properties by 4° C. or more. Only one mutant, Q247H, had thermotolerance equal to or slightly greater than the parental phytase and full degradation in SGF within 10 minutes.

Figure 15:
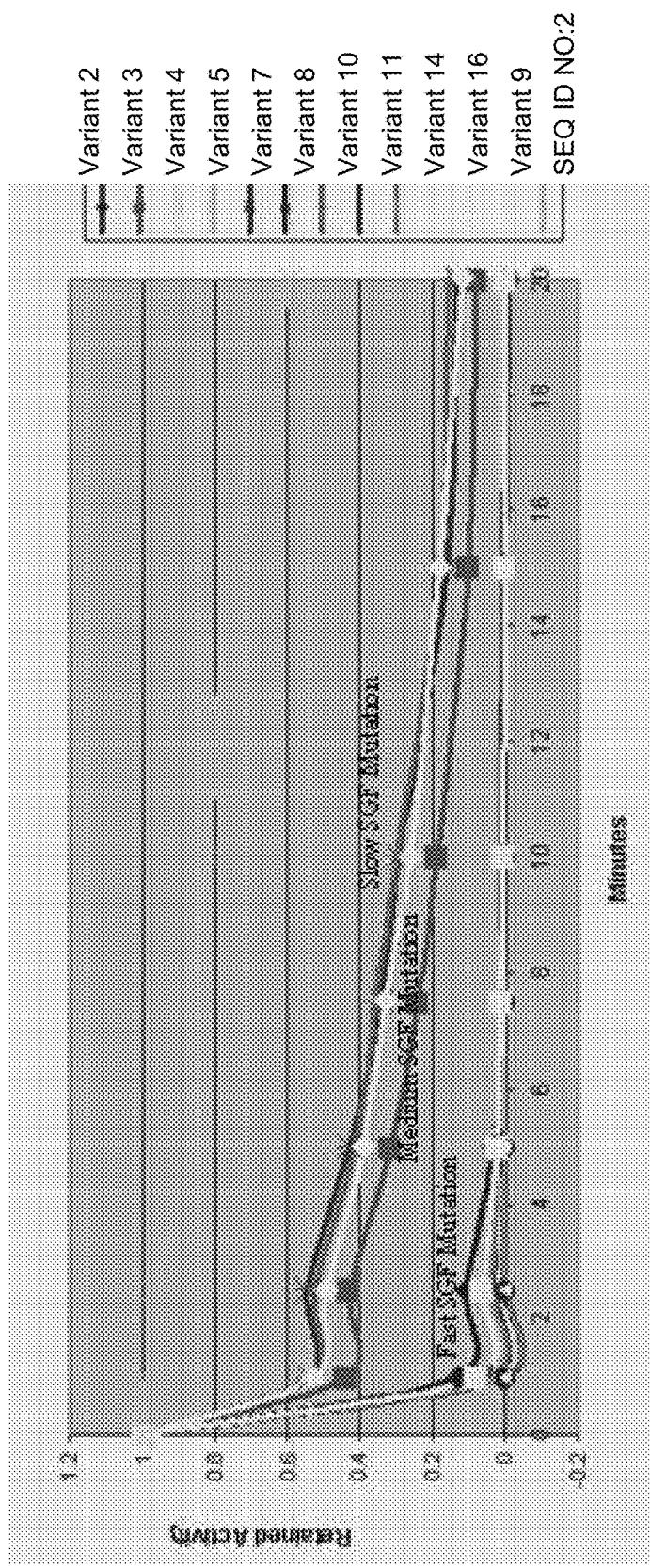
FIG. 15 illustrates the SGF activity loss of select mutants from GSSM evolution of SEQ ID NO:2, as described in detail in Example 2, below.

SGF activity loss of select mutants from the GSSM screen was determined over a twenty minute time course study (FIG. 15), on difluoro-4-methylumbelliferyl phosphate (DiFMUP), 50 mM Na-Acetate, pH 5.5, 0.75 mg/mL pepsin. The characterization of these SGF mutations showed that the rate for complete degradation fell into three categories, fast (less than 2 minutes), medium (~10-15 minutes), and slow (>20 minutes); slow SGF mutants showed just a slight improvement over the parental phytase (SEQ ID NO:2). The data suggest that the activity analysis is a more sensitive method to determine phytase decay; at 20% residual activity the phytase band is not detectable on the SDS-Page gel (data not shown).

The SGF mutants were tested for thermotolerance by two methods; a) 65° C. thirty minute heat treatment and b) thirty minute 50-70° C. gradient. The thermotolerance data suggest that most of the SGF mutations lost ≥4° C. with the exception of variant I427T and variant Q247H. To quickly overcome the thermotolerance deficiencies, a fast track strategy was developed; several very promising SGF mutations were incorporated into more thermotolerant phytase backbones (from Example 1, above) to test if thermotolerance can be regained (discussed in depth under title Fast Track Strategy).

All mutations were compared and the top 48 were ranked (Table 6) by a Fitness Value FT (Thermotolerance %–SGF %=FT). The top single-site mutations were considered for combination in the Tailored Multi-Site Combinatorial Assembly$^{SM}$ (TMCA$^{SM}$) phase (see below).

Figure 16:
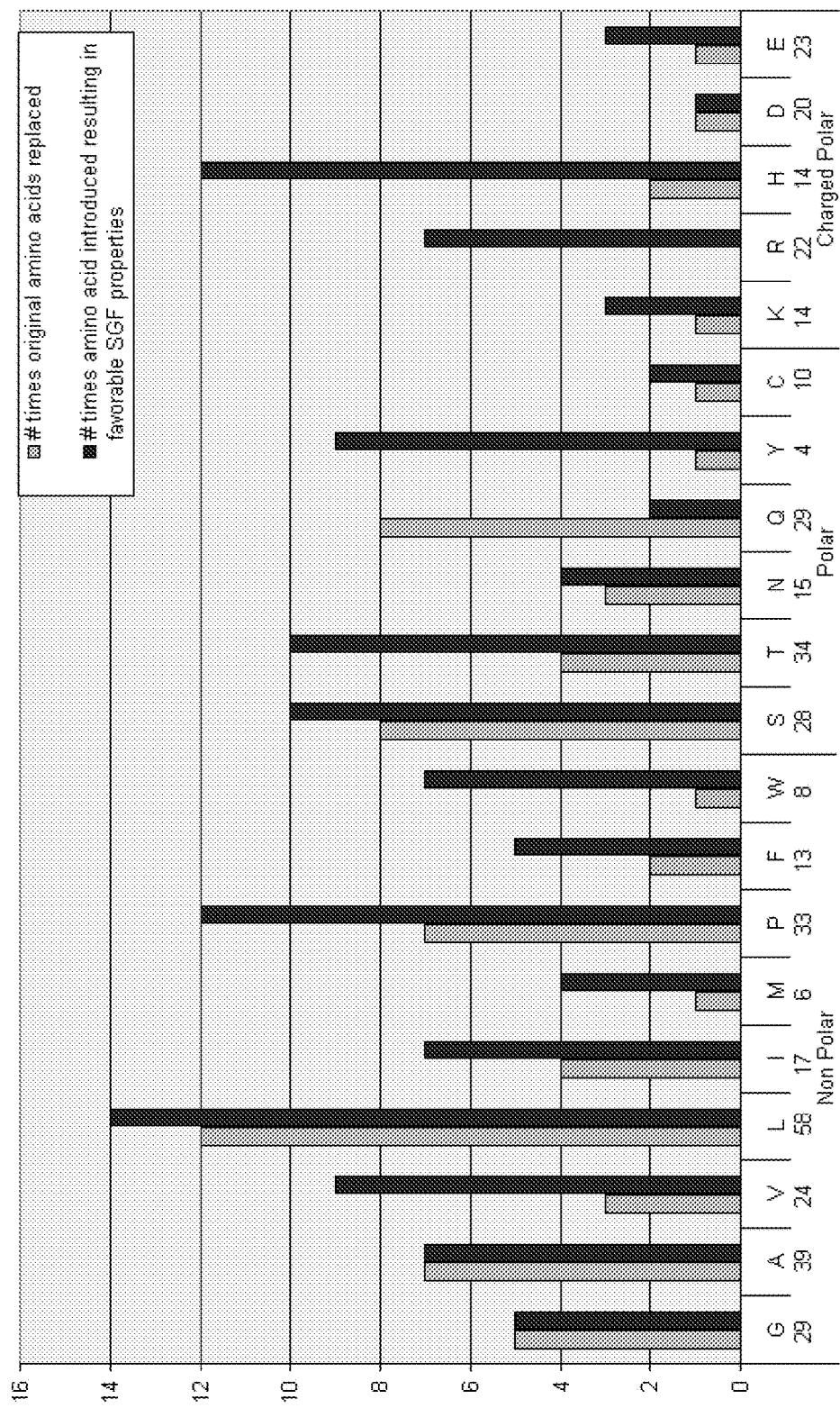
FIG. 16 illustrates the effect of different amino acids on SGF lability, as described in detail in Example 2, below.
Figure 17:
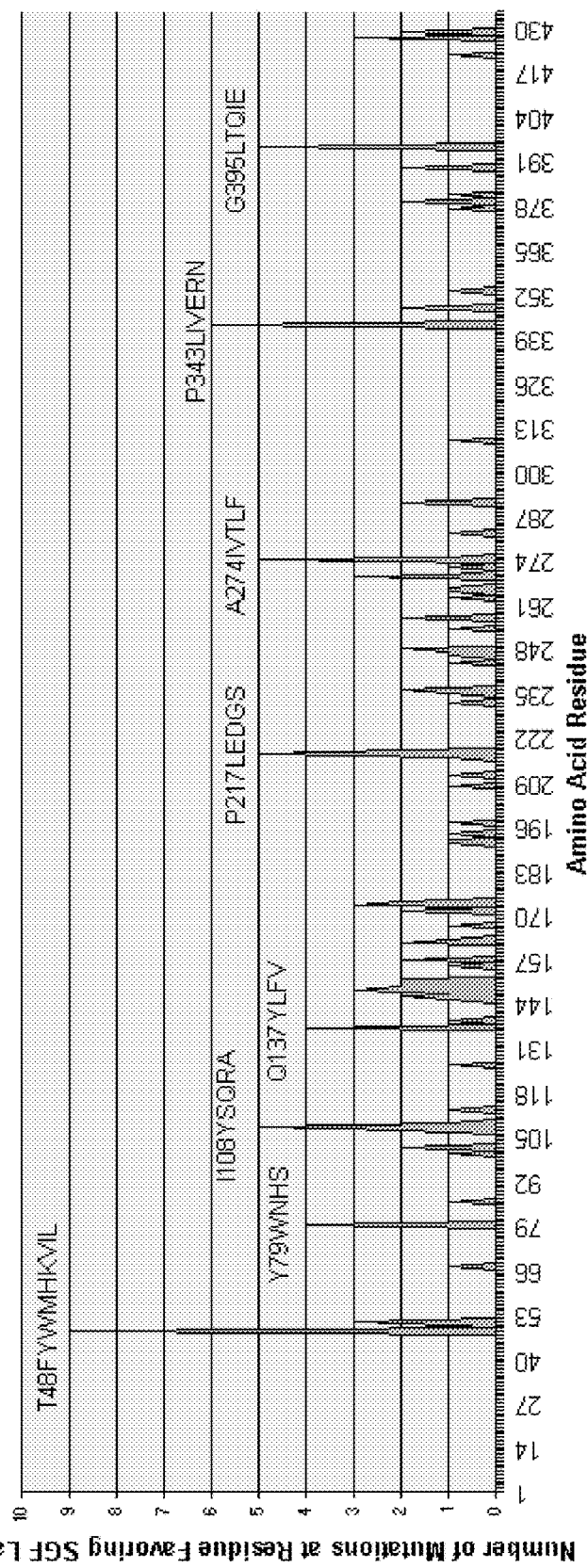
FIG. 17 illustrates SGF mutation hot spots, as described in detail in Example 2, below.

Based on the data, there were certain amino acid substitutions and residue positions, when changed in the parental phytase (SEQ ID NO:2) molecule, which were more favorable for SGF lability improvements than others (FIG. 16). In FIG. 16, the number below the amino acid symbol indicates how many times the molecule is represented in the original protein. For example, residue position 48, a Threonine, could be changed to nine other amino acids (FYWMHK-VIL). The three amino acid additions that most frequently increased SGF lability were Leucine (14 times), Proline (12 times), and Histidine (12 times). As a further example, Arginines which were in the original protein (22 times in SEQ ID NO:2) were never replaced with another amino acid where an accompanying increase in SFG lability was observed. However, when Arginine was substituted for another amino acid in the original protein (7 times), in each instance, SGF lability was increased. The SGF GSSM data suggested that hot spots for SGF mutations occurred in the phytase molecule (FIG. 17). The largest series of mutations, seven in row, occurred between residues 145-151. There were also three sets where three residues in a row could be mutated. Several amino acid residues were promiscuous to amino acid substitutions favoring SGF lability, the most extreme being T48, which was replaced by nine different amino acids (F, Y, W, M, H, K, V, I, and L). For position 48 and 79, H was the best mutation and selected as a candidate for the TMCA library.

TABLE 5

Variant names and mutations of the hits discovered from the GSSM screen which have SGF degradation improvements.

| Variant | Mutation |
| --- | --- |
| 1 | P 100 A |
| 2 | P 149 L |
| 3 | I 427 T |
| 4 | T 291 W |
| 5 | T 291 V |
| 6 | L 126 R |
| 7 | P 254 S |
| 8 | L 192 F |
| 9 | Q 377 R |
| 10 | V 422 M |
| 11 | L 157 P |
| 12 | I 107 H |
| 13 | I 108 R |
| 14 | Q 309 P |
| 15 | I 108 A |
| 16 | I 108 S |
| 17 | I 107 P |
| 18 | C 155 Y |
| 19 | I 108 Q |
| 20 | A 236 T |
| 21 | S 208 P |
| 22 | A 109 V |
| 23 | G 171 M |
| 24 | S 173 G |
| 25 | V 162 L |
| 26 | D 139 Y |
| 27 | L 146 R |
| 28 | Q 137 Y |
| 29 | Q 137 L |
| 30 | L 146 T |
| 31 | K 151 P |
| 32 | N 148 K |
| 33 | K 151 H |
| 34 | Q 137 F |
| 35 | L 157 C |
| 36 | L 150 Y |
| 37 | V 162 T |
| 38 | I 174 P |
| 39 | G 353 C |
| 40 | L 150 T |
| 41 | S 102 A |
| 42 | I 174 F |
| 43 | G 171 S |
| 44 | N 148 M |
| 45 | Q 137 V |
| 46 | P 145 L |
| 47 | I 108 Y |
| 48 | E 113 P |
| 49 | F 147 Y |
| 50 | S 173 H |
| 51 | T 163 P |
| 52 | N 148 R |
| 53 | S 173 V |
| 54 | A 248 L |
| 55 | A 248 T |
| 56 | Q 247 H |
| 57 | A 236 H |
| 58 | L 269 I |
| 59 | S 197 G |
| 60 | L 235 I |
| 61 | S 211 H |
| 62 | T 282 H |
| 63 | Q 246 W |
| 64 | G 257 R |
| 65 | L 269 T |
| 66 | G 257 A |
| 67 | F 194 L |
| 68 | H 272 W |
| 69 | V 191 A |
| 70 | S 218 Y |
| 71 | P 217 S |
| 72 | P 217 D |
| 73 | P 217 G |
| 74 | S 102 Y |
| 75 | S 218 I |
| 76 | A 232 P |
| 77 | W 265 L |
| 78 | N 266 P |
| 79 | L 167 S |

TABLE 5-continued

Variant names and mutations of the hits discovered from the GSSM screen which have SGF degradation improvements.

| Variant | Mutation |
|---|---|
| 80 | L 216 T |
| 81 | P 217 L |
| 82 | L 244 S |
| 83 | P 269 L |
| 84 | T 48 F |
| 85 | T 48 W |
| 86 | T 48 M |
| 87 | T 48 H |
| 88 | T 48 K |
| 89 | T 48 Y |
| 90 | T 48 V |
| 91 | M 51 A |
| 92 | M 51 L |
| 93 | T 48 I |
| 94 | M 51 G |
| 95 | T 48 L |
| 96 | L 50 W |
| 97 | G 67 A |
| 98 | Y 79 W |
| 99 | Y 79 N |
| 100 | P 149 N |
| 101 | Y 79 H |
| 102 | Q 86 H |
| 103 | Q 275 H |
| 104 | A 274 I |
| 105 | A 274 T |
| 106 | Y 79 S |
| 107 | H 263 P |
| 108 | A 274 V |
| 109 | A 274 L |
| 110 | A 274 F |
| 111 | S 389 V |
| 112 | G 395 T |
| 113 | G 395 Q |
| 114 | G 395 L |
| 115 | G 395 I |
| 116 | G 395 E |
| 117 | S 389 H |
| 118 | I 427 G |
| 119 | I 427 S |
| 120 | A 429 P |
| 121 | P 343 E |
| 122 | P 343 V |
| 123 | P 343 R |
| 124 | P 343 L |
| 125 | P 343 V |
| 126 | N 348 K |
| 127 | P 343 I |
| 128 | N 348 W |
| 129 | P 343 N |
| 130 | L 379 V |
| 131 | Q 381 S |
| 132 | L 379 S |

A significant number of the GSSM variants met the SGF requirements (Fast Degradation <10% after 10 Min SGF survival), but are short on the thermotolerance properties (<75% survival after 65° C. 30 min heat treatment). The Medium and Slow degrading mutants met the thermotolerance requirements, but not SGF requirements. From the GSSM screen, only Variant 56 (Q247H) met both SGF and Thermotolerance properties.

TABLE 6

Ranking Top SGF mutants.

| Rank | Mutation | 65C HT % | SGF % | Fitness Value |
|---|---|---|---|---|
| 1 | Q247H | 76 | 3 | 0.73 |
| 2 | I427T | 99 | 37 | 0.62 |
| 3 | Q246W | 76 | 23 | 0.53 |
| 4 | L157P | 46 | 2 | 0.44 |
| 5 | Q377R | 47 | 3 | 0.44 |
| 6 | T48M | 66 | 24 | 0.42 |
| 7 | A274V | 60 | 17 | 0.42 |
| 8 | A236T | 47 | 5 | 0.42 |
| 9 | Q275H | 77 | 35 | 0.41 |
| 10 | T48W | 56 | 15 | 0.41 |
| 11 | I174P | 44 | 4 | 0.41 |
| 12 | T48H | 50 | 10 | 0.40 |
| 13 | Y79H | 67 | 27 | 0.40 |
| 14 | A232P | 41 | 1 | 0.40 |
| 15 | T48K | 53 | 13 | 0.40 |
| 16 | T48Y | 63 | 24 | 0.39 |
| 17 | ? | 45 | 7 | 0.38 |
| 18 | P217D | 40 | 3 | 0.37 |
| 19 | P217G | 43 | 7 | 0.37 |
| 20 | P217S | 42 | 5 | 0.37 |
| 21 | T48I | 70 | 34 | 0.36 |
| 22 | P343V | 41 | 5 | 0.36 |
| 23 | S211H | 67 | 31 | 0.35 |
| 24 | T291V | 36 | 2 | 0.34 |
| 25 | A274I | 51 | 16 | 0.34 |
| 26 | L50W | 58 | 26 | 0.33 |
| 27 | P343E | 40 | 7 | 0.33 |
| 28 | M51L | 60 | 28 | 0.33 |
| 29 | G257A | 36 | 3 | 0.32 |
| 30 | H263P | 60 | 29 | 0.32 |
| 31 | Y79S | 67 | 36 | 0.31 |
| 32 | Y79N | 68 | 38 | 0.30 |
| 33 | T48F | 50 | 21 | 0.29 |
| 34 | L296T | 62 | 34 | 0.29 |
| 35 | S218Y | 30 | 2 | 0.28 |
| 36 | P343R | 32 | 6 | 0.26 |
| 37 | T48L | 48 | 24 | 0.24 |
| 38 | P149L | 36 | 12 | 0.24 |
| 39 | L167S | 42 | 18 | 0.23 |
| 40 | G67A | 59 | 36 | 0.23 |
| 41 | P343N | 47 | 25 | 0.22 |
| 42 | P343L | 26 | 6 | 0.20 |
| 43 | A236H | 19 | 0 | 0.19 |
| 44 | ? | 36 | 20 | 0.15 |
| 45 | T291W | 18 | 3 | 0.14 |
| 46 | SEQ ID NO: 2 | 74 | 64 | 0.10 |
| 47 | SEQ ID NO: 2 | 70 | 61 | 0.09 |
| 48 | S208P | 11 | 2 | 0.08 |
| 49 | L192F | 22 | 13 | 0.08 |
| 50 | SEQ ID NO: 2 | 64 | 57 | 0.07 |
| 51 | SEQ ID NO: 2 | 66 | 59 | 0.07 |
| 52 | SEQ ID NO: 2 | 63 | 56 | 0.07 |
| 53 | SEQ ID NO: 2 | 67 | 62 | 0.50 |
| 54 | Q377R | 7 | 3 | 0.04 |
| 55 | Q309P | 1 | 2 | -0.01 |
|  | SEQ ID NO: 2 AVERAGE | 67 | 60 | 0.07 |

All 132 mutants were compared side by side to determine the best mutants from the SGF screen. The top 49 SGF mutants ranked and compared with six separate controls (parental phytase SEQ ID NO: 2). Variants were ranked on their thermotolerance properties (% survival at 65° C. HT %) and SGF lability (SGF survival SGF %). An arbitrary Fitness Value (FV) = (65° C. HT %) − (SGF %) was established and the variants with the higher FV, highlighted in orange, were considered for further evolution using the TMCA technology.

Two of the top three mutations (Q246W and Q247H) showed thermotolerance properties similar to the parental phytase (SEQ ID NO:2) and significant improvements in SGF lability. Using 3-D modeling, it was observed that W246 is predicted to be buried beneath the surface of the protein, necessitating the protein to adapt to a larger tryptophan side chain in what was a tightly packed environment around a glutamine side chain. Also, the protein must adapt to the loss of the hydrogen bond between the epsilon oxygen of the Q246 side chain with the main chain nitrogen of G255 as there is no side chain oxygen in tryptophan residues.

Structural analysis also indicated that while the main chain of H247 would be buried, the imidizole side chain would snorkel to the surface. Although glutamine to histidine is a relatively conservative change, this creates a new surface accessible group in this region that is available for protonation at lower pH which would clearly alter the local hydrogen bonding network, potentially acting as a acidic switch for disrupting the local protein structure in this region leaving the protein more susceptible to acid and pepsin degradation.

Fast Track Strategy

To overcome the thermotolerance properties which were lost in the lead SGF labile variants (except Q247H), a Fast Track Strategy was initiated to design phytase molecules which have both the desired properties; SGF and thermotolerance. Thermotolerant phytases (SEQ ID NO:2-N159V, SEQ ID NO:2-6X and SEQ ID NO:2-9X) from the earlier evolution work (see Example 1, above) were selected as the backbones for two rounds of Site Directed Mutagenesis (SDM).

The first SDM incorporated each of the single SGF mutations (T291V, A236T, or L157P) into each of the three thermotolerant backbones as shown in the table below (Table 7).

TABLE 7

SDM Round I variants
SDM round I

| Variant | Parent (backbone) | His Tag | Host - TOP 10 | Additional Mutations |
|---|---|---|---|---|
| A | SEQ ID NO: 2-6X | x | x | T291V |
| B | SEQ ID NO: 2-6X | x | x | A236T |
| C | SEQ ID NO: 2-6X | x | x | L157P |
| D | SEQ ID NO: 2-N159V | x | x | L157P |
| E | SEQ ID NO: 2-N159V | x | x | A236T |
| F | SEQ ID NO: 2-N159V | x | x | T291V |
| G | SEQ ID NO: 2-9X | x | x | L157P |
| H | SEQ ID NO :2-9X | x | x | A236T |
| I | SEQ ID NO: 2-9X | x | x | T291V |

The data from this first round of SDM suggested that improvements in SGF lability was made to the variants made from backbone SEQ ID NO:2-N159V. However, those SGF mutations also decreased the thermotolerance properties below the objective. The variants of the other two thermotolerant backbones (SEQ ID NO:2-6X and SEQ ID NO:2-9X) showed only minimal improvements in SGF degradation. It was also observed that adding more SGF mutations to the SEQ ID NO:2-N159V backbone reduced the thermotolerance below the thermotolerance objective.

A second round of SDM adding more SGF mutations to the other two thermotolerant variants was performed by incorporating up to two SGF mutations (T291V and/or L192F) into SEQ ID NO:2-6X and SEQ ID NO:2-9X, both with or without the A236T mutation (see Table 8 below).

TABLE 8

SDM Round II variants
SDM round II

| Variant | Parent (backbone) | His Tag | Host - TOP 10 | Additional Mutations |
|---|---|---|---|---|
| J | SEQ ID NO: 2-6X | x | x | L192F |
| K | SEQ ID NO: 2-6X | x | x | T291V |
| L | SEQ ID NO: 2-6X | x | x | T291V + L192F |
| M | SEQ ID NO: 2-9X | x | x | L192F |
| N | SEQ ID NO: 2-9X | x | x | T291V |
| O | SEQ ID NO: 2-9X | x | x | T291V + L192F |
| P | SEQ ID NO: 2-6X + (A236T) | x | x | L192F |
| Q | SEQ ID NO: 2-6X + (A236T) | x | x | T291V |
| R | SEQ ID NO: 2-6X + (A236T) | x | x | T291V + L192F |
| S | SEQ ID NO: 2-9X + (A236T) | x | x | L192F |
| T | SEQ ID NO: 2-9X + (A236T) | x | x | T291V |
| U | SEQ ID NO: 2-9X + (A236T) | x | x | T291V + L192F |

The result from this SDM produced a variant, Variant O, with slightly better thermal tolerance than the parental phytase (SEQ ID NO:2) and full degradation in less than 10 min in SGF. For example, at T-0 and T-10 (min) time points using different SGF pepsin dosages (0.3, 0.2, 0.1, 0.05, 0.025 and 0 mg/mL pepsin), SDS-PAGE gels dyed with Simply Blue™ SafeStain, showed that Variant O was fully degraded within 10 minutes at 0.3 mg/mL and 0.2 mg/mL pepsin. A twenty minute SGF time course (at 0.3 mg/mL pepsin), again run on SDS-PAGE gels, showed that SEQ ID NO:2-HIS is not degraded after 20 minutes, while Variant O is fully degraded around 7.5 minutes.

Figure 18:
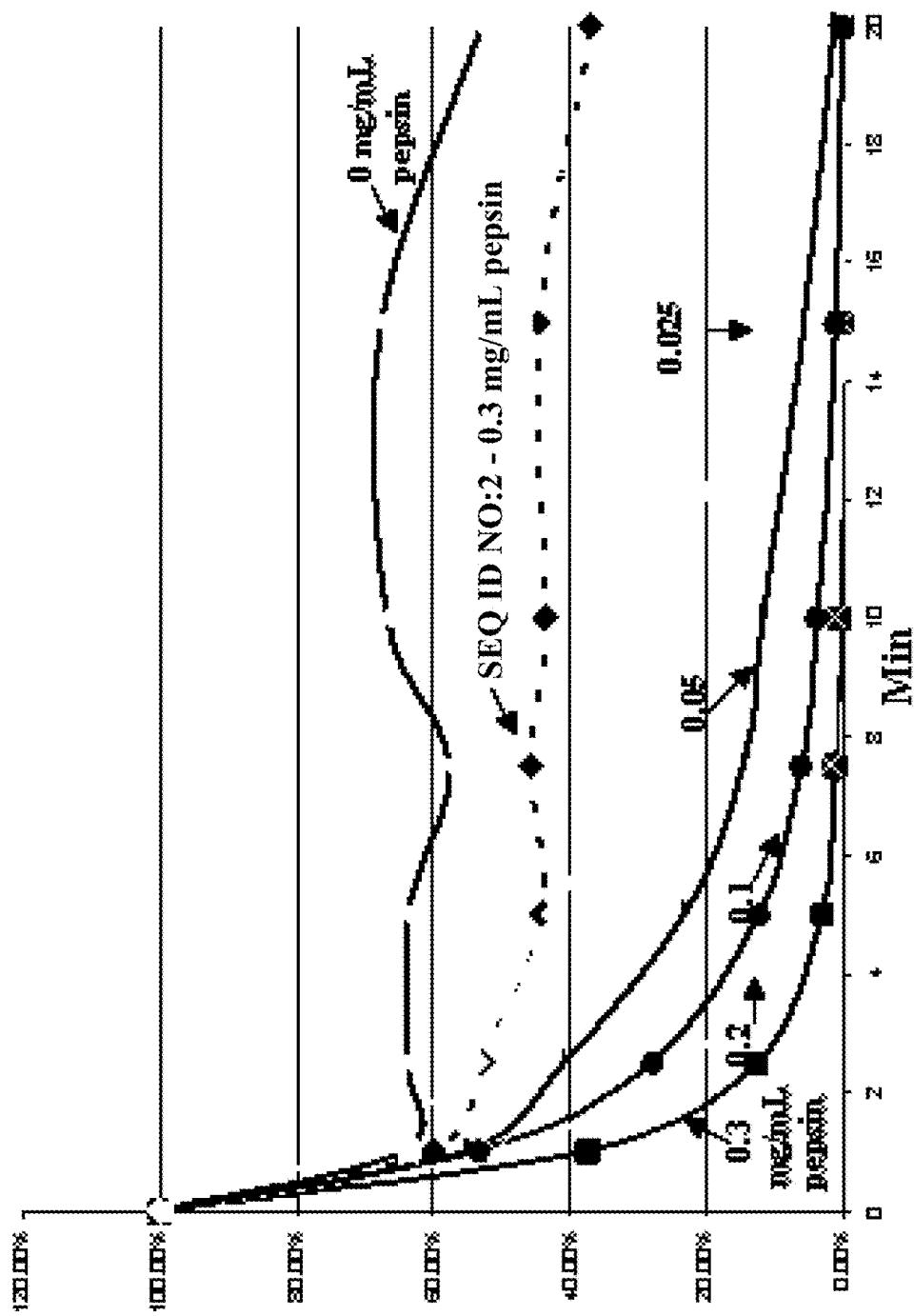
FIG. 18 illustrates SGF lability of SEQ ID NO:2-HIS and Variant O at different pepsin dosages, as described in detail in Example 2, below.

SGF stability of Variant O and SEQ ID NO:2-HIS was determined at different pepsin dosages: 0.3, 0.2, 0.1, 0.05, 0.025, and 0.0 mg/mL Pepsin (FIG. 18). In FIG. 18, the 0.3 mg/mL pepsin dose for SEQ ID NO:2-HIS is graphed as a benchmark. The dosage response experiments indicated that pepsin is required for complete degradation and that it is not just a function of the acidic treatment (FIG. 18).

Figure 19:
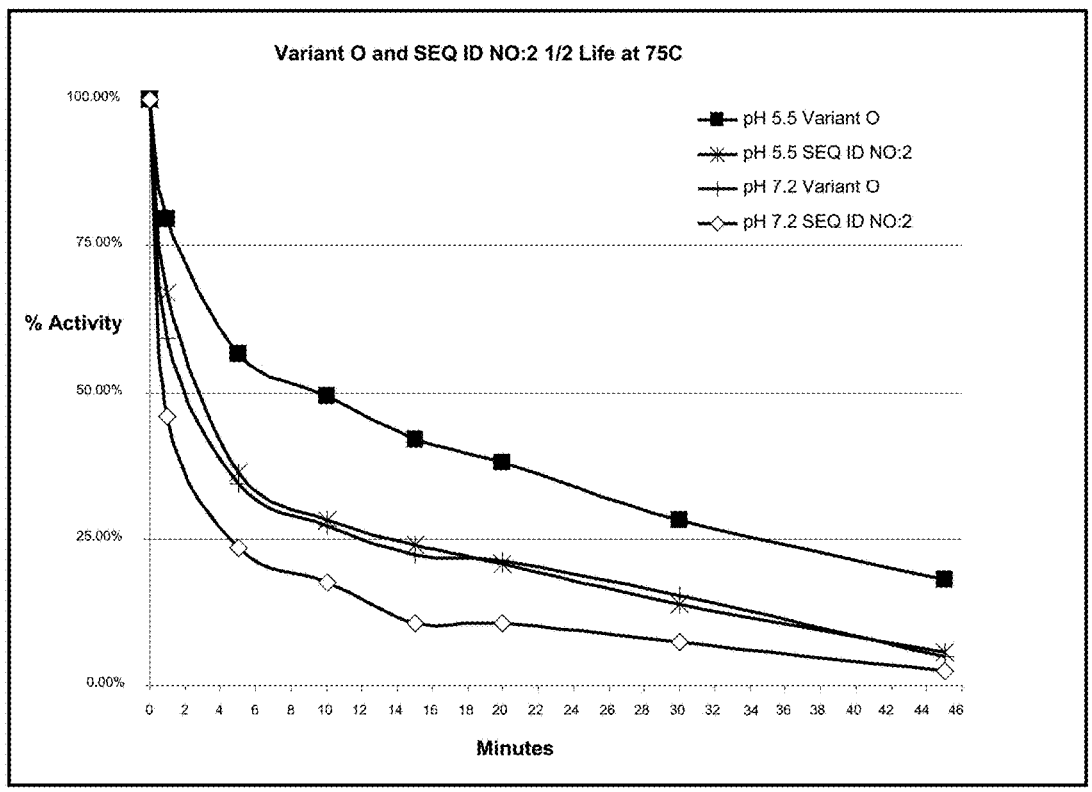
FIG. 19 illustrates the ½ life of SEQ ID NO:2-HIS and Variant O, as described in detail in Example 2, below.

The ½ Life of Variant O and SEQ ID NO:2-HIS was determined at 75° C. (FIG. 19). Purified parental phytase (SEQ ID NO:2-HIS) and phytase variant Variant O, in two different buffers (100 mM Citrate pH 5.5 and 100 mM Tris pH 7.2), were heat treated at 75 C° up to 45 minutes (T-0, 5, 10, 15, 20, 30, 45 min). Ten microliters of the heat treated samples were assayed for activity in 100 µL 100 µM DiFMUP, 50 mM Citrate pH 5.5. Activity was compared to T-0 activity. Variant O met the SGF and thermotolerance requirements, however, specific activity was lower than desired (FIG. 19). Loss of specific activity was expected because of previous knowledge from the earlier evolution work (Example 1) indicating that the SEQ ID NO:2-6X backbone only had ⅔ of the specific activity of the parental phytase (SEQ ID NO:2).

To maximize the TMCA strategy, and overcome Variant O deficiencies, the approach was to blend thermotolerant mutations that maintained specific activity with SGF mutations using the parental phytase (SEQ ID NO:2-HIS) as the template.

TMCA<sup>SM</sup> Evolution

The high throughput assay was modified to include a heat treatment step in order to select for variants that desired thermotolerant as well as the SGF properties. Two libraries were created utilizing the Tailored Multi-Site Combinatorial Assembly (TMCA) technology (see PCT Publication No. WO 09/018449). TMCA evolution comprises a method for producing a plurality of progeny polynucleotides having different combinations of various mutations at multiple sites. The method can be performed, in part, by a combination of at least one or more of the following steps:

Obtaining Sequence Information of a ("First" or "Template") Polynucleotide.

For example, the first or template sequence can be a wild type (e.g. SEQ ID NO:2-N159V) or mutated (e.g. the "D164R template", described below) sequence. The sequence information can be of the complete polynucleotide (e.g., a gene or an open reading frame) or of partial regions of interest, such as a sequence encoding a site for binding, binding-specificity, catalysis, or substrate-specificity.

Identifying Three or More Mutations of Interest Along the First or Template Polynucleotide Sequence.

For example, mutations can be at 3, 4, 5, 6, 8, 10, 12, 20 or more positions within the first or template sequence. The positions can be predetermined by absolute position or by the context of surrounding residues or homology. For TMCA of phytase polypeptides, the top SGF and thermotolerant amino acid changes that resulted in improved enzyme performance were included as mutations of interest. The sequences flanking the mutation positions on either side can be known. Each mutation position may contain two or more mutations, such as for different amino acids. Such mutations can be identified by using Gene Site Saturation Mutagenesis$^{SM}$ (GSSM$^{SM}$) technology, as described herein and in U.S. Pat. Nos. 6,171,820; 6,562,594; and 6,764,835.

Providing Primers (e.g., Synthetic Oligonucleotides) Comprising the Mutations of Interest.

In one embodiment, a primer is provided for each mutation of interest. Thus, a first or template polynucleotide having 3 mutations of interest can use 3 primers at that position. The primer also can be provided as a pool of primers containing a degenerate position so that the mutation of interest is the range of any nucleotide or naturally occurring amino acid, or a subset of that range. For example, a pool of primers can be provided that favor mutations for aliphatic amino acid residues.

The primers can be prepared as forward or reverse primers, or the primers can be prepared as at least one forward primer and at least one reverse primer. When mutations are positioned closely together, it can be convenient to use primers that contain mutations for more than one position or different combinations of mutations at multiple positions.

Providing a Polynucleotide Containing the Template Sequence.

The first or template polynucleotide can be circular, or can be supercoiled, such as a plasmid or vector for cloning, sequencing or expression. The polynucleotide may be single-stranded ("ssDNA"), or can be double-stranded ("dsDNA"). For example, the TCMA method subjects the supercoiled ("sc") dsDNA template to a heating step at 95° C. for 1 min (see Levy, Nucleic Acid Res., 28(12):e57(i-vii) (2000)).

Adding the Primers to the Template Polynucleotide in a Reaction Mixture.

The primers and the template polynucleotide are combined under conditions that allow the primers to anneal to the template polynucleotide. In one embodiment of the TMCA protocol, the primers are added to the polynucleotide in a single reaction mixture, but can be added in multiple reactions.

Performing a Polymerase Extension Reactions.

The extension products (e.g., as a "progeny" or "modified extended polynucleotide") may be amplified by conventional means. The products may be analyzed for length, sequence, desired nucleic acid properties, or expressed as polypeptides. Other analysis methods include in-situ hybridization, sequence screening or expression screening. The analysis can include one or more rounds of screening and selecting for a desired property.

The products can also be transformed into a cell or other expression system, such as a cell-free system. The cell-free system may contain enzymes related to DNA replication, repair, recombination, transcription, or for translation. Exemplary hosts include bacterial, yeast, plant and animal cells and cell lines, and include *E. coli, Pseudomonas fluorescens, Pichia pastoris* and *Aspergillus niger*. For example, XL1-Blue or Stb12 strains of *E. coli* can be used as hosts.

The method of the invention may be used with the same or different primers under different reaction conditions to promote products having different combinations or numbers of mutations.

By performing the exemplary method described above, this protocol also provides one or more polynucleotides produced by this TMCA evolution method, which then can be screened or selected for a desired property. One or more of the progeny polynucleotides can be expressed as polypeptides, and optionally screened or selected for a desired property. Thus, this embodiment of the TMCA evolution protocol provides polynucleotides and the encoded polypeptides, as well as libraries of such polynucleotides encoding such polypeptides. This embodiment of the TMCA evolution protocol further provides for screening the libraries by screening or selecting the library to obtain one or more polynucleotides encoding one or more polypeptides having the desired activity.

Another embodiment of the TMCA evolution protocol described in PCT Publication No. WO 2009/018449 comprises a method of producing a plurality of modified polynucleotides. Such methods generally include (a) adding at least three primers to a double stranded template polynucleotide in a single reaction mixture, wherein the at least three primers are not overlapping, and wherein each of the at least three primers comprise at least one mutation different from the other primers, wherein at least one primer is a forward primer that can anneal to a minus strand of the template and at least one primer is a reverse primer that can anneal to a plus strand of the template, and (b) subjecting the reaction mixture to a polymerase extension reaction to yield a plurality of extended modified polynucleotides from the at least three primers.

Another embodiment of the TMCA evolution protocol described in PCT Publication No. WO 2009/018449 comprises a method wherein a cell is transformed with the plurality of extended products that have not been treated with a ligase. In another embodiment of the invention, the plurality of extended modified polynucleotides is recovered from the cell. In another embodiment, the recovered plurality of extended modified polynucleotides is analyzed, for example, by expressing at least one of the plurality of extended modified polynucleotides and analyzing the polypeptide expressed therefrom. In another embodiment, the plurality of extended modified polynucleotides comprising the mutations of interest is selected.

In another embodiment of the TMCA evolution protocol, sequence information regarding the template polynucleotide is obtained, and three or more mutations of interest along the template polynucleotide can be identified. In another embodiment, products obtained by the polymerase extension can be analyzed before transforming the plurality of extended modified products into a cell.

In one embodiment of the TMCA evolution protocol, products obtained by the polymerase extension are treated with an enzyme, e.g., a restriction enzyme, such as a DpnI restriction enzyme, thereby destroying the template polynucleotide sequence. The treated products can be transformed into a cell, e.g., an *E. coli* cell.

In one embodiment of the TMCA evolution protocol, at least two, or at least three, or at least four, or at least five, or at least six, or at least seven, or at least eight, or at least nine, or at least ten, or at least eleven, or at least twelve, or more primers can be used. In one embodiment, each primer comprises a single point mutation. In another embodiment, two forward or two reverse primers comprise a different change in the same position on the template polynucleotide. In another embodiment, at least one primer comprises at least two changes in different positions on the template polynucleotide. In yet another embodiment, at least one primer comprises at least two changes in different positions and at least two forward or two reverse primers comprise a different change in the same position on the template polynucleotide.

In one embodiment of the TMCA evolution protocol, the forward primers are grouped into a forward group and the reverse primers are grouped into a reverse group, and the primers in the forward group and the primers in the reverse group, independent of one another, are normalized to be equal concentration in the corresponding group regardless of positions on the template polynucleotide, and wherein after the normalization an equal amount of the forward and reverse primers is added to the reaction. In this normalization method, a combination of some positions may be biased. The bias can be due to, for example, a relatively low primer concentration at one position containing a single primer compared to a position containing multiple primers. "Positional bias" refers to resulting polynucleotides which show a strong preference for the incorporation of primers at a single position relative to the other positions within its forward or reverse primer group. This results in a combination of modified polynucleotides which may have a high percentage of mutations within a single primer position but a low percentage of mutations at another position within its forward or reverse primer group. This bias is unfavorable when the goal of the TMCA is to generate progeny polynucleotides comprising all possible combinations of changes to the template. The bias can be corrected, for example, by normalizing the primers as a pool at each position to be equal.

In one embodiment of the TMCA evolution protocol, the primer normalization is performed by organizing the primers into multiple groups depending on their location on the template polynucleotide, wherein the primers covering the same selected region on the template are in one group; normalizing the grouped primers within each group to be equal concentration; pooling the forward primers within one group into a forward group and normalizing concentration between each group of the forward primers to be equal; pooling the reverse primers within one group into a reverse group and normalizing concentration between each group of the reverse primers to be equal; and adding an equal amount of the pooled forward and reversed primers into the reaction. No bias has been observed for position combinations.

In one embodiment of the TMCA evolution protocol, a set of degenerate primers each comprising a degenerate position is provided, wherein the mutation of interest is a range of different nucleotides at the degenerate position. In another embodiment, a set of degenerate primers is provided comprising at least one degenerate codon corresponding to at least one codon of the template polynucleotide and at least one adjacent sequence that is homologous to a sequence adjacent to the codon of the template polynucleotide sequence. In another embodiment, the degenerated codon is N,N,N and encodes any of 20 naturally occurring amino acids. In another embodiment, the degenerated codon encodes less than 20 naturally occurring amino acids.

Another embodiment of the TMCA evolution protocol described in PCT Publication No. WO 2009/018449 comprises a method of producing a plurality of modified polynucleotides comprising the mutations of interest. Such methods generally include (a) adding at least two primers to a double stranded template polynucleotide in a single reaction mixture, wherein the at least two primers are not overlapping, and wherein each of the at least two primers comprise at least one mutation different from the other primer(s), wherein at least one primer is a forward primer that can anneal to a minus strand of the template and at least one primer is a reverse primer that can anneal to a plus strand of the template, (b) subjecting the reaction mixture to a polymerase extension reaction to yield a plurality of extended modified polynucleotides from the at least two primers, (c) treating the plurality of extended modified polynucleotides with an enzyme, thereby destroying the template polynucleotide, (d) transforming the treated extended modified polynucleotides that have not been treated with a ligase into a cell, (e) recovering the plurality of extended modified polynucleotides from the cell, and (f) selecting the plurality of extended modified polynucleotides comprising the mutations of interest.

Using the TMCA technology, a small library, Library A, was created for quick turn around and to simplify the process (96 different variants containing up to five SGF mutations and two thermotolerance mutations, see Table 9). Library A used a single template, SEQ ID NO:2-N159V and the oligoes listed in Table 10, below. A second more extensive library, Library B, was also created using TMCA technology in order to increase the potential of creating a very thermotolerant variant with the required SGF properties (4096 different variants containing up to seven SGF mutations and five thermotolerance mutations, see Table 9). Library B used two templates, SEQ ID NO:2-N159V and "D164R template", in two separate TMCA reactions each using the oligoes listed in Table 11, creating two sub-libraries. The "D164R template" was generated in Library A and consisted of the SEQ ID NO:2-N159V backbone with the D164R mutation incorporated. Both libraries were amplified into the pQE60 vector (Qiagen, Valencia, Calif.) and then transformed into host PHY635 (described below) to confirm primary and secondary phytase activity.

A total of eight promising thermotolerant SGF labile hits were discovered by screening the libraries. Five thermotolerant (Tm ~5° C. greater than the parental phytase, SEQ ID NO:2, Table 13) SGF labile variants were discovered in the small library (Variants AA-EE, Table 12). The larger TMCA library produced ten candidates, however, only three had greater thermotolerance than Variants AA-EE (Variants FF-HH, Table 13, had Tm ~7.5° C. greater than the parental phytase, SEQ ID NO:2). For characterization screening, these variants, along with the best single-site SGF mutation (Variant 56), all as glycosylated and glycosylation minus versions, were expressed in *Pichia pastoris*, (glycosylation minus versions included the two mutations, T163R and N339E, from the N-glycosylation removal research, see above).

Figure 20:
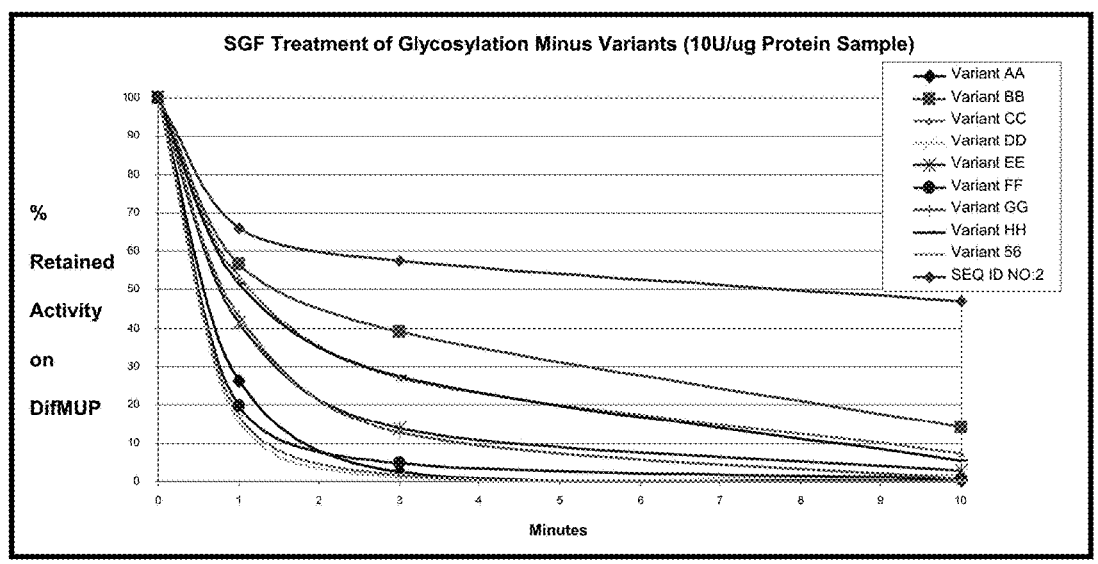
FIG. 20 illustrates the residual activity of SGF labile phytase variants, as described in detail in Example 2, below.
Figure 21:
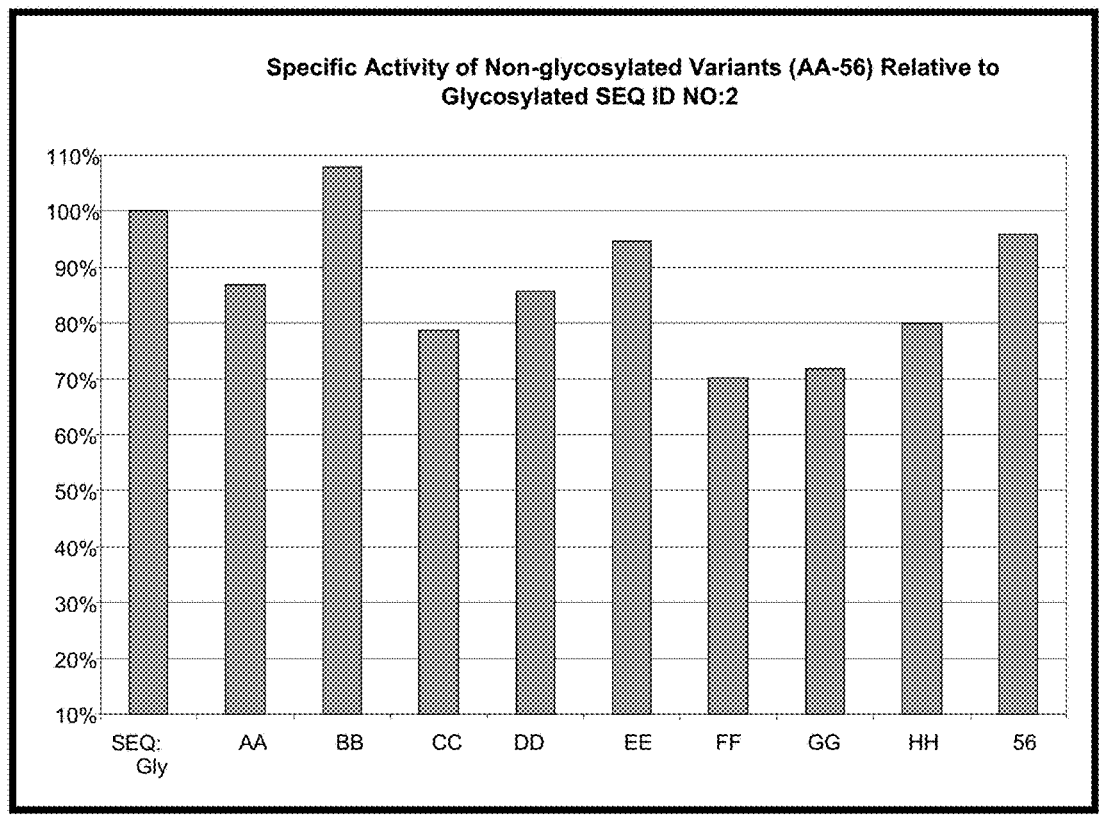
FIG. 21 illustrates the specific activity of SGF label variant phytases as compared to SEQ ID NO:2, as described in detail in Example 2, below.

Residual activity of SGF labile phytase variants during SGF treatment was determined (FIG. 20). Purified parental phytase (SEQ ID NO:2), Variant 56 and Variant AA-HH were treated with SGF (pH 1.2) with pepsin (10 U/µg phytase) over a 10.0 minute time course. Phytase stability was determined by activity on DiFMUP. The specific activity of SGF labile phytase variants compared to SEQ ID NO:2 phytase (FIG. 21). Purified parental phytase (SEQ ID NO:2) and lead phytase variants were tested for activity on phytate. Purified protein was assayed in 4 mM phytate, 100 mM Na-Acetate pH 4.5 at 37° C. There was not any significant change in SGF and thermotolerance properties between the glycosylated and non-glycosylated *Pichia* expressed lead variants (FIGS. 20 and 21). Previous work predicted that the glycosylated variants would have a higher thermotolerance and be more tolerant to SGF; our data suggested otherwise.

Also, a pH profile of glycosylated, glycosylation-minus variants, and the parental phytase (SEQ ID NO:2) was generated for phytase activity on phytate at pH 2, 2.5, 3, 4, 5, and 6 at 37° C. All phytases assayed had very similar pH profiles (data not shown).

TABLE 9

Mutations selected for TMCA evolution. Thermotolerance mutations and SGF mutations were blended utilizing TMCA technology, using SEQ ID NO: 2-N159V as the backbone.

| Library A | | Library B | |
|---|---|---|---|
| SGF Mutations | Thermotolerant Mutations | SGF Mutations | Thermotolerant Mutations |
| Q247H | Q275V | Q247H | G179R |
| I427T | D164R | I427T | Q275V |
| L157P | | L157P | T349Y |
| Q275H | | Q275H | C226D |
| T48M | | T48M | D164R |
| | | Q246W | |
| | | Q377R | |
| | | Y79H | |

TABLE 10

Oligoes used in Library A

| Oligo name | Oligo sequence - 5' - 3' | |
|---|---|---|
| T48M_F | TGCGTGCTCCAACCAAGGCCATGCAACTGATGCAGGATGTCAC | SEQ ID NO: 3 |
| L157P_F | TAAAAACTGGCGTTTGCCAACCGGATGTGGCGAACGTGACTGACGCGATCCTCGAGAGGGCAGGA | SEQ ID NO: 4 |
| D164R_F | TAAAAACTGGCGTTTGCCAACTGGATGTGGCGAACGTGACTCGTGCGATCCTCGAGAGGGCAGGA | SEQ ID NO: 5 |
| L157P-D164_R | TAAAAACTGGCGTTTGCCAACCGGATGTGGCGAACGTGACTCGTGCGATCCTCGAGAGGGCAGGA | SEQ ID NO: 6 |
| Q247H_R | GAGATATTTCTCCTGCAACATGCACAGGGAATGCCGGAGCC | SEQ ID NO: 7 |
| Q275H_R | TGCTAAGTTTGCATAACGCGCATTTTGATTTGCTACAACGCAC | SEQ ID NO: 8 |
| Q275V_R | TGCTAAGTTTGCATAACGCGGTGTTTGATTTGCTACAACGCAC | SEQ ID NO: 9 |
| I427T_R | AATCGTGAATGAAGCACGCACACCGGCGTGCAGTTTGAGAT | SEQ ID NO: 10 |

TABLE 11

Oligoes used in Library B

| Oligo name | Oligo sequence - 5' - 3' | |
|---|---|---|
| T48M_F | TGCGTGCTCCAACCAAGGCCATGCAACTGATGCAGGATGTCAC | SEQ ID NO: 11 |
| Y79H_F | GCGGTGGTGAGCTAATCGCCCATCTCGGACATTACTGGCGTCA | SEQ ID NO: 12 |
| L157P_F | TAAAAACTGGCGTTTGCCAACCGGATGTGGCGAACGTGACTGA | SEQ ID NO: 13 |
| G179R_F | GGTCAATTGCTGACTTTACCCGCCATTATCAAACGGCGTTTCG | SEQ ID NO: 14 |
| C226D_F | AACTCAAGGTGAGCGCCGACGATGTCTCATTAACCGGTGCGGT | SEQ ID NO: 15 |

TABLE 11-continued

Oligoes used in Library B

| Oligo name | Oligo sequence - 5' - 3' | |
|---|---|---|
| Q246W_R | TGACGGAGATATTTCTCCTGTGGCAAGCACAG GGAATGCCGGA | SEQ ID NO: 16 |
| Q246W + Q247H_R | TGACGGAGATATTTCTCCTGTGGCATGCACAG GGAATGCCGGAGCC | SEQ ID NO: 17 |
| Q247H_R | CGGAGATATTTCTCCTGCAACATGCACAGGGA ATGCCGGAGCC | SEQ ID NO: 18 |
| Q275V_R | TGCTAAGTTTGCATAACGCGGTGTTTGATTTG CTACAACGCAC | SEQ ID NO: 19 |
| T349Y_R | TTCCCGGTCAGCCGGATAACTATCCGCCAGGT GGTGAACTGGT | SEQ ID NO: 20 |
| Q377R_R | TTCAGGTTTCGCTGGTCTTCCGCACTTTACAGC AGATGCGTGA | SEQ ID NO: 21 |
| I427T_R | AATCGTGAATGAAGCACGCACACCGGCGTGC AGTTTGAGAT | SEQ ID NO: 22 |

TABLE 12

Sequence of Lead SGF Labile Thermotolerant Phytase variants

| Variant | SGF T48M | SGF Y79H | SGF L157P | Thermo N159V | Glycos T163R | Thermo D164R | Thermo G179R | Thermo C226D | SGF Q246W |
|---|---|---|---|---|---|---|---|---|---|
| AA |  |  |  | X | X | X |  |  |  |
| BB | X |  |  | X | X |  |  |  |  |
| CC | X |  |  | X | X | X |  |  |  |
| DD | X |  |  | X | X | X |  |  |  |
| EE | X |  |  | X | X |  |  |  |  |
| FF | X | X |  | X | X | X |  |  |  |
| GG | X | X |  | X | X | X | X | X |  |
| HH | X |  |  | X | X | X | X | X | X |
| 56 |  |  |  |  | X |  |  |  |  |

| Variant | SGF Q247H | Thermo Q275V | SGF Q275H | Glycos N339E | Thermo T349Y | SGF Q377R | SGF I427T |
|---|---|---|---|---|---|---|---|
| AA | X |  | X | X |  |  |  |
| BB | X | X |  | X |  |  |  |
| CC | X | X |  | X |  |  | X |
| DD | X |  |  | X |  |  |  |
| EE | X | X |  | X |  |  |  |
| FF | X | X |  | X | X |  |  |
| GG | X | X |  | X |  |  |  |
| HH | X | X |  | X |  |  |  |
| 56 | X |  |  | X |  |  |  |

Variant AA is SEQ ID NO:28 (encoded by SEQ ID NO:27), Variant BB is SEQ ID NO:32 (encoded by SEQ ID NO:31), Variant CC is SEQ ID NO:34 (encoded by SEQ ID NO:33), Variant DD is SEQ ID NO:36 (encoded by SEQ ID NO:35), Variant EE is SEQ ID NO:38 (encoded by SEQ ID NO:37), Variant FF is SEQ ID NO:24 (encoded by SEQ ID NO:23), Variant GG is SEQ ID NO:26 (encoded by SEQ ID NO:25), Variant HH is SEQ ID NO:40 (encoded by SEQ ID NO:39), and Variant 56 is SEQ ID NO:30 (encoded by SEQ ID NO:29). Note, however, that SEQ ID NOs:23, 25, 27, 29, 31, 33, 35, 37, and 39, do not include the nucleic acids encoding the native signal sequence and that SEQ ID NOs:24, 26, 28, 30, 32, 34, 36, 38, and 40, do include the native signal sequence amino acids (amino acids 1-22 of SEQ ID NO:2). A start Methionine (ATG) is added in each of the referenced sequences. The positions of the point mutations for these variants (listed e.g. in Table 12) are counted as if the native signal sequence is present.

TABLE 13

Melting Temperature (Tm) of SEQ ID NO: 2 and Lead SGF Candidates. Purified parental phytase (SEQ ID N0: 2) and the nine lead SGF phytase candidates were expressed in *Pichia pastoris*, purified, dialyzed in 100 mM Citrate pH 5.5, and tested for Tm utilizing the Applied Thermodynamics N-DSCII.

| DSC Tm | Library | Glycosylated (Tm in Celsius) | Glycosylation Minus (Tm in Celsius) |
|---|---|---|---|
| SEQ ID NO:2 |   | 79.8 | N/A |
| Variant AA (SEQ ID NO: 28) | A | 85.2 | 85.8 |
| Variant BB (SEQ ID NO: 32) | A | 84.2 | 85.8 |
| Variant CC (SEQ ID NO: 34) | A | 85.6 | 85.2 |
| Variant DD (SEQ ID NO: 36) | A | 83.8 | 84.2 |
| Variant EE (SEQ ID NO: 38) | A | 85.4 | 84.6 |
| Variant FF (SEQ ID NO: 24) | B | 87.5 | 87.6 |
| Variant GG (SEQ ID NO: 26) | B | 87.3 | 87.0 |
| Variant HH (SEQ ID NO: 40) | B | 87.4 | 86.2 |
| Variant 56 (SEQ ID NO: 30) |   | 81.0 | 81.3 |

Selection of Top Four Variants for Animal Studies

SGF SDS-PAGE analysis at nine time points (0, 0.5, 1.0, 1.5, 2.0, 3.0, 4.0, 5.0, and 10 minutes), with pepsin dosage of 10 U per μg phytase, four variants were selected based on this characterization data (not shown) for large scale fermentation to be used in animal trials. The four selected leads showed complete protein degradation within five minutes.

Selected leads:

Variant 56 (SEQ ID NO:30, encoded by SEQ ID NO:29) is the closest variant to the original parental phytase (SEQ ID NO:2) molecule, having one SGF mutation and two glycosylation-minus mutations.

Variant AA (SEQ ID NO:28, encoded by SEQ ID NO:27) has two SGF mutations, two thermotolerant mutations and two glycosylation-minus mutations.

Variant FF (SEQ ID NO:24, encoded by SEQ ID NO:23) has three SGF mutations, four thermotolerant mutations and two glycosylation-minus mutations.

Variant GG (SEQ ID NO:26, encoded by SEQ ID NO:25) has three SGF mutations, five thermotolerant mutations, two glycosylation-minus mutations.

Fermentation of Lead Candidates:

The leads (Variant 56, Variant AA, Variant FF, and Variant GG) were selected for animal trials and scaled up for 30 L fermentations to produce at least 5 g of each protein. Based on activity and Bradford Protein analysis ≥than 16 g of protein for each variant was produced. Recovered samples were lyophilized, then resuspended and heat treated to kill potential microbial growth and then re-lyophilized. These samples (Table 14) were used for animal trials. Along with the four selected variants, a small sample (15-50 mg) of the other SGF labile variants (Table 12) were used for bench scale evaluation.

TABLE 14

Specifications of samples used for animal trials and for bench scale evaluation. The lyophilized product was quantified by both activity and Bradford Protein Assay.

| Variant | Solid (g) | Protein (g) | Units Activity |
|---|---|---|---|
| 56 (SEQ ID NO: 30) | 106.2 | 8.34 | $1.37 \times 10^7$ |
| AA (SEQ ID NO: 28) | 98.9 | 10.9 | $1.72 \times 10^7$ |
| FF (SEQ ID NO: 24) | 132.0 | 14.2 | $2.16 \times 10^7$ |
| GG (SEQ ID NO: 26) | 109.6 | 17.4 | $3.09 \times 10^7$ |

| Variant | Protein (mg) |
|---|---|
| BB (SEQ ID NO: 32) | 30 |
| DD (SEQ ID NO: 36) | 50 |
| CC (SEQ ID NO: 34) | 20 |
| EE (SEQ ID NO: 38) | 40 |
| HH (SEQ ID NO: 40) | 15 |
| SEQ ID NO: 2 | 30 |

Methods

Growth, Induction, and Purification

*E. coli* Phytase Expression (2 L Scale)

All phytase variants, except of those in the glycosylation studies, were expressed in *E. coli*; strain PHY635 (phy-strain; created by making *E. coli* strain CU1867 (ATCC 47092; appA deficient) Rec A-through P1 phage transduction). Starting cultures of the phytase variants were grown in 5 mL LBcarb100 at 37 C for ~18 hrs. 2 L of LBcarb100 were inoculated with the overnight starting cultures, culture was induced with 1 mM IPTG when the culture reached ~$OD_{600}$ 0.5. After 24 hrs of induction, the cultures were harvested by pelleting the culture by centrifugation (Sorvall RC 5C Plus Centrifuge; SLC-4000 rotor, 7000 RPM; 9220 RCF) for 20 minutes. The cells were resuspended in 50 mM Tris pH 8.0 and lysed utilizing the microfluidizer (Microfluidics Model 110L). To remove cellular debris the whole cell lysate was centrifuged (Sorvall RC 5C Plus; F13S-14X50 Rotor, 12500 RPM; 25642 RCF) for 30 minutes. The clear lysate was sterile filtered and the phytase protein was purified across a HisTrap FF 5 mL column on an AKTA FPLC. Phytase was eluted off with a 2 M Immidizole, 50 mM Tris pH 8.0 gradient. Fractions were tested for activity on 100 uM DiFMUP, 100 mM Na-Acetate (pH 5.5) and SDS-gel analysis for protein purity.

*Pichia Pastoris* Phytase Expression (1 L Scale)

The characterization of the final lead phytase variants (glycosylation-plus and glycosylation-minus versions of Variants AA-HH and Variant 56), along with the glycosylation-minus versions of SEQ ID NO:2 (Variants GLY1-GLY4) were expressed in *Pichia pastoris* (X-33). Starting cultures of the phytase variants were grown in 10 mL BMGYzeo100 at 30° C. for ~18 hrs (~OD60015-20), cells were pelleted and resuspended in 10 mL MES* medium with 0.5% MeOH. 1 L of MES* medium with 0.5% MeOH was inoculated with the starting culture and incubated for three-four days at 30° C. (5 mL MeOH added every 24 hrs for protein induction). The secreted protein separated from the cell mass by centrifugation (Sorvall RC 5C Plus Centrifuge; SLC-4000 rotor, 7000 RPM; 9220 RCF), concentrated and buffer exchanged (100 mM Na Acetate pH 5.5)

using the MiniKros Tangential Flow Separation Module (SpectrumLabs M215-600-01P). To improve purity the sample was passed across a HiTrap™ Q FF 5 mL column on an AKTA FPLC. Phytase was eluted off with a 1 M NaCl, 100 mM Na-Acetate pH 5.5 gradient. Fractions were tested for activity on 100 uM DiFMUP, 100 mM Na-Acetate (pH 5.5) and SDS-gel analysis for protein purity.

Phytase Characterization

Protein Thermotolerance

Differential Scanning calorimetry (DSC)—Protein melting temperature (Tm) of the *Pichia* expressed phytase variants were determined by utilizing the Applied Thermodynamics N-DSC II. Protein samples (~1.0 mg/mL) were dialyzed in 100 mM Citrate pH 5.5, loaded into the test chamber (600 uL) and compared to the control sample (600 ul of 100 mM Citrate pH 5.5) and scanned from 60 to 100° C. and back to 60° C. (to assess protein refolding).

Modified Tm determination—Quick thermotolerance tool developed to evaluate whole cell lysate and non purified protein samples during the preliminary characterization to compare thermotolerance of SGF labile phytases to the parental phytase (SEQ ID NO:2). The protein sample was arrayed across a row on a 96 well PCR plate (20 uL per well) and heat treated across a gradient (60-80° C.) on the PCR machine for 30 minutes. Heat treated protein samples (10 uL) were mixed with fluorescence substrate (190 uL of 100 uM DiFMUP, 50 mM Na-Acetate pH 5.5) measuring florescence change (EX360 nm/EM465 nm) over a five minute time course. The temperature at which 50% activity remained was compared to the parental phytase (SEQ ID NO:2) performance (50% activity temperature).

SGF Assay (Modified-Scaled Down)

Multiple mini reactions, quenched at different time points were established to determine SGF lability of phytase molecule. As a control T-0 reference, a pre-quenched SGF reaction was also run similar to the actual experiment. Ten uL of the protein sample was incubated in 50 uL of pH 1.2 SGF (2 mg/mL NaCl, 7 uL/mL concentrated HCl) with pepsin (dosed at 0.15, 0.30, and 0.75 mg/mL) over a time course at 37° C. The reaction was quenched by adding 10 uL of pH 10.0, 200 mM Na-Carbonate buffer (this step was performed prior to adding protein sample for the T-0 reference).

SGF SDS Gel Analysis—Removed 20 uL of the quenched SGF reaction and mixed with 210 uL SDS sample buffer, boiled for 10 minutes, and loaded 15 uL onto a Tris-Gly SDS Page gel. Applied 180V, 250 mA, through SDS sample running buffer for ~1 hour, or until complete.

SGF Activity Analysis—Removed 10 uL of the quenched SGF reaction and mixed with substrate (190 uL of 100 uM DiFMUP, 50 mM Na-Acetate pH 5.5) measuring florescence change (EX360 nm/EM465 nm) over a five minute time course.

SGF Assay (adapted from The United States Pharmacopeia 24, 2000. Simulated gastric fluid, TS, In The National Formulary 19; Board of Trustees, Eds.; United States Pharmacopeial Convention, Inc., Rockville, Md., p. 2235)

Incubate 50 uL of 5 mg/mL phytase in pre-heated 37° C. 950 uL SGF (2 mg/mL NaCl, titrated to pH 1.2 with HCl) with 10 U pepsin/ug test protein (760 ug/mL SGF) over a 10 minute time course at 37° C. Time points were taken by removing 50 uL of reaction and mixing with 50 uL termination solution (200 mM Na-Carbonate, pH 10.0). Time points (terminated samples) were kept on ice until assay was complete and ready for analysis (in compliance with *SGF SDS Gel Analysis and SGF Activity Analysis* outlined under SGF Assay (Modified-Scaled Down)).

Phytase Specific Activity Analysis

Phytase samples (50 uL) were assayed for relative activity in pre heated 37° C., 950 uL, 4.0 mM Phytate, 100 mM acetic acid, titrated to pH 4.5 with NaOH. Reaction was quenched by removing 50 uL reaction and mixing with the 50 uL color/stop solution (20 mM Ammonium molybdate/5 mM Ammonium vanadate/10% Nitric acid solution). After 10 minute color development time points were measure at 415 nm and results were plotted against time. The reaction rate was compared to the phosphate standard to determine relative rate.

The specific activity was determined by calculating relative rated based on protein concentration. Protein concentration was determined by 260 nm/280 nm analysis (1A $OD_{280}$ correlates to 0.93 mg/mL). A secondary comparison was performed by loading equal phytase activities on SDS gel and quantifying protein band intensities using GelPro gel densiotometry analysis to compare activity relationship of phytase leads and the parental phytase (SEQ ID NO:2).

Phytase pH Profile Analysis

Same as the above specific activity protocol, except substrate was modified with a broader buffer capacity (pH 2-6). Substrate: 4 mM Phytate, 80 mM Malic acid, 80 mM Formic acid, and 80 mM Na-Acetate titrated to different pH (2, 2.5, 3, 4, 5, and 6 pH Units). Relative rated for each variant were compared to the activity optimum which was pH 4.

Materials:

SGF Assay

Pepsin from porcine stomach mucosa (Sigma P-6887)
HCl (Fisher UN1789)
Sodium Chloride (Fisher S-271-1)
6,8-difluoro-4-methylumbelliferyl phosphate (DiFMUP) (Invitrogen-D22068)
4-20% Tris-Glycine SDS PAGE Gels (Invitrogen EC60255BOX)
Novex Tris-Glycine SDS Sample Buffer (InvitrogenNovex LC2676)
Novex SDS Running Buffer (Invitrogen LC2675)
Simply Blue™ SafeStain (Invitrogen LC6065)

Phytase Specific Activity Analysis

Dodecasodium phytate from rice (Sigma P-3168)
Ammonium metavanadate (Acros Organics 194910500)
Ammonium molybdate (Sigma A-7302)
Potassium Phosphate, dibasic (Fisher P288-500)
70% Nitric Acid (Sigma 380091)
25% Ammonium Solution (Atlas Chemical AA-3060)

Protein Purification

HisTrap™ FF 5 mL Ni-Sepharose Column (GE Healthcare 17-5255-01)
HiTrap™ Q FF 5 mL Anion Exchange Column (GE Healthcare 17-5156-01)
Immidizole (Sigma 1-0125)

A number of embodiments as provided herein have been described. Nevertheless, it will be understood that various modifications may be made without departing from the spirit and scope as provided herein. Accordingly, other embodiments are within the scope of the following claims.

What is claimed:

1. A transgenic plant comprising an isolated, synthetic or recombinant polynucleotide encoding a variant polypeptide of the amino acid sequence of SEQ ID NO: 2, wherein the variant polypeptide comprises at least one amino acid mutation selected from the group consisting of: T48F; T48H; T48I; T48K; T48L; T48M; T48V; T48W; T48Y; L50W; M51A; M51G; M51L; G67A; Y79H; Y79N; Y79S; Y79W; Q86H; P100A; S102A; S102Y; I107H; I107P; I108A; I108Q; I108R; I108S; I108Y; A109V; E113P; L126R; Q137F; Q137L; Q137V; Q137Y; D139Y; P145L; L146R; L146T; F147Y; N148K; N148M; N148R; P149N; L150T; L150Y; K151H; K151P; C155Y; L157C; L157P; V162L; V162T; T163P; L167S; G171M; G171S; S173G; S173H; S173V; I174F; I174P; V191A; L192F; F194L; S197G; S211 H; L216T; P217D; P217G; P217L; P217S; S218I; S218Y; A232P; L235I; A236H; A236T; L244S; Q246W; Q247H; A248L; A248T; P254S; G257A; G257R; H263P; W265L; N266P; L269I; L269T; H272W; A274F; A274I; A274L; A274T; A274V; Q275H; T282H; T291V; T291W; Q309P; P343E; P343I; P343L; P343N; P343R; P343V; N348K; N348W; G353C; Q377R; L379S; L379V; Q381S; S389H; S389V; G395E; G395I; G395L; G395Q; G395T; V422M; I427G; I427S; I427T; and A429P; and wherein the variant polypeptide comprising the at least one amino acid mutation is an amino acid sequence at least 95% identical to the amino acid sequence as set forth in SEQ ID NO:2; and wherein the variant polypeptide has phytase activity and has decreased gastric stability when compared to the parent polypeptide of the amino acid sequence of SEQ ID NO: 2.

2. The plant of claim 1, wherein the plant is a corn plant, a potato plant, a tomato plant, a wheat plant, an oilseed plant, a rapeseed plant, a soybean plant, a tobacco plant, or a forage or feed plant.

3. The plant of claim 1, wherein the plant is an alfalfa plant, a sunflower plant, a *Brassica* plant, a sugar cane plant, a cotton plant, a safflower plant, a peanut plant, a sorghum plant, an oat plant, a rye plant, a millet plant, a barley plant, a rice plant, a conifer plant, a pea plant, a bean plant, a sweet potato plant, a cassava plant, a taro plant, a canna plant or a sugar beet plant.

4. The plant of claim 2, wherein the forage or feed plant is or comprises hay, millet, buckwheat, barley, alfalfa, rye, an annual grass, sorghum, sudangrass, veldt grass or buffel grass.

5. The plant of claim 1, wherein the plant is a corn plant.

6. A plant product of the plant of claim 1, wherein the plant product comprises the isolated, synthetic or recombinant polynucleotide encoding the variant polypeptide.

7. The plant product of claim 6, wherein the plant product is an oil, seed, leaf, or extract.

8. The transgenic plant comprising an isolated, synthetic or recombinant polynucleotide encoding a variant polypeptide of claim 1, wherein the variant polypeptide is the amino acid sequence as set forth in SEQ ID NO: 2 comprising one amino acid mutation selected from the group consisting of: T48F; T48H; T48I ; T48K; T48L; T48M; T48V; T48W; T48Y; L50W; M51A; M51G; M51L; G67A; Y79H; Y79N; Y79S; Y79W; Q86H; P100A; S102A; S102Y; I107H; I107P; I108A; I108Q; I108R; I108S; I108Y; A109V; E113P; L126R; Q137F; Q137L; Q137V; Q137Y; D139Y; P145L; L146R; L146T; F147Y; N148K; N148M; N148R; P149N; L150T; L150Y; K151H; K151P; C155Y; L157C; L157P; V162L; V162T; T163P; L167S; G171M; G171S; S173G; S173H; S173V; I174F; I174P; V191A; L192F; F194L; S197G; S211H; L216T; P217D; P217G; P217L; P217S; S218I; S218Y; A232P; L235I ; A236H; A236T; L244S; Q246W; Q247H; A248L; A248T; P254S; G257A; G257R; H263P; W265L; N266P; L269I ; L269T; H272W; A274F; A274I; A274L; A274T; A274V; Q275H; T282H; T291V; T291W; 0309P; P343E; P343I; P343L; P343N; P343R; P343V; N348K; N348W; G353C; Q377R; L379S; L379V; Q381S; S389H; S389V; G395E; G395I ; G395L; G395Q; G395T; V422M; I427G; I427S; I427T; and A429P; and wherein the variant polypeptide has phytase activity and has gastric stability when compared to the parent polypeptide of the amino acid sequence of SEQ ID NO: 2.

9. The plant of claim 8, wherein the plant is a corn plant, a potato plant, a tomato plant, a wheat plant, an oilseed plant, a rapeseed plant, a soybean plant, a tobacco plant, or a forage or feed plant.

10. The plant of claim 8, wherein the plant is an alfalfa plant, a sunflower plant, a *Brassica* plant, a sugar cane plant, a cotton plant, a safflower plant, a peanut plant, a sorghum plant, an oat plant, a rye plant, a millet plant, a barley plant, a rice plant, a conifer plant, a pea plant, a bean plant, a sweet potato plant, a cassava plant, a taro plant, a canna plant or a sugar beet plant.

11. The plant of claim 9, wherein the forage or feed plant is or comprises hay, millet, buckwheat, barley, alfalfa, rye, an annual grass, sorghum, sudangrass, veldt grass or buffel grass.

12. The plant of claim 8, wherein the plant is a corn plant.

13. A plant product of the plant of claim 8, wherein the plant product comprises the isolated, synthetic or recombinant polynucleotide encoding the variant polypeptide.

14. The plant product of claim 13, wherein the plant product is an oil, seed, leaf, or extract.

15. A transgenic seed comprising an isolated, synthetic or recombinant polynucleotide encoding a variant polypeptide of the amino acid sequence of SEQ ID NO: 2, wherein the variant polypeptide comprises at least one amino acid mutation selected from the group consisting of: T48F; T48H; T48I; T48K; T48L; T48M; T48V; T48W; T48Y; L50W; M51A; M51G; M51L; G67A; Y79H; Y79N; Y79S; Y79W; Q86H; P100A; S102A; S102Y; I107H; I107P; I108A; I108Q; I108R; I108S; I108Y; A109V; E113P; L126R; Q137F; Q137L; Q137V; Q137Y; D139Y; P145L; L146R; L146T; F147Y; N148K; N148M; N148R; P149N; L150T; L150Y; K151H; K151P; C155Y; L157C; L157P; V162L; V162T; T163P; L167S; G171M; G171S; S173G; S173H; S173V; I174F; I174P; V191A; L192F; F194L; S197G; S211 H; L216T; P217D; P217G; P217L; P217S; S218I ; S218Y; A232P; L235I ; A236H; A236T; L244S; Q246W; Q247H; A248L; A248T; P254S; G257A; G257R; H263P; W265L; N266P; L269I ; L269T; H272W; A274F; A274I; A274L; A274T; A274V; Q275H; T282H; T291V; T291W; Q309P; P343E; P343I; P343L; P343N; P343R; P343V; N348K; N348W; G353C; Q377R; L379S; L379V; Q381S; S389H; S389V; G395E; G395I ; G395L; G395Q; G395T; V422M; I427G; I427S; I427T; and A429P; and wherein the variant polypeptide comprising the at least one amino acid mutation is an amino acid sequence at least 95% identical to the amino acid sequence as set forth in SEQ ID NO:2; and wherein the variant polypeptide has phytase activity and has decreased gastric stability when compared to the parent polypeptide of the amino acid sequence of SEQ ID NO: 2.

16. The seed of claim 15, wherein the seed is a corn seed, a wheat kernel, an oilseed, a rapeseed, a soybean seed, a palm kernel, a sunflower seed, a sesame seed, a peanut or peanut seed, an alfalfa seed, a cotton seed, a safflower seed, a sorghum seed, an oat kernel, a rye seed, a millet seed, a barley seed, a rice kernel, a pea seed, or a tobacco seed.

17. The seed of claim 15, wherein the seed is a corn seed.

18. The transgenic seed comprising an isolated, synthetic or recombinant polynucleotide encoding a variant polypeptide of claim 15, wherein the variant polypeptide is the amino acid sequence as set forth in SEQ ID NO: 2 comprising one amino acid mutation selected from the group consisting of: T48F; T48H; T48I; T48K; T48L; T48M; T48V; T48W; T48Y; L50W; M51A; M51G; M51L; G67A; Y79H; Y79N; Y79S; Y79W; Q86H; P100A; S102A; S102Y; I107H; I107P; I108A; I108Q; I108R; I108S; I108Y; A109V; E113P; L126R; Q137F; Q137L; Q137V; Q137Y; D139Y; P145L; L146R; L146T; F147Y; N148K; N148M; N148R; P149N; L150T; L150Y; K151H; K151P; C155Y; L157C; L157P; V162L; V162T; T163P; L167S; G171M; G171S; S173G; S173H; S173V; I174F; I174P; V191A; L192F; F194L; S197G; S211 H; L216T; P217D; P217G; P217L; P217S; S218I; S218Y; A232P; L235I ; A236H; A236T; L244S; Q246W; Q247H; A248L; A248T; P254S; G257A; G257R; H263P; W265L; N266P; L269I ; L269T; H272W; A274F; A274I; A274L; A274T; A274V; Q275H; T282H; T291V; T291W; Q309P; P343E; P343I; P343L; P343N; P343R; P343V; N348K; N348W; G353C; Q377R; L379S; L379V; Q381S; S389H; S389V; G395E; G395I ; G395L; G395Q; G395T; V422M; I427G; I427S; I427T; and A429P; and wherein the variant polypeptide has phytase activity and has gastric stability when compared to the parent polypeptide of the amino acid sequence of SEQ ID NO: 2.

19. The seed of claim 18, wherein the seed is a corn seed, a wheat kernel, an oilseed, a rapeseed, a soybean seed, a palm kernel, a sunflower seed, a sesame seed, a peanut or peanut seed, an alfalfa seed, a cotton seed, a safflower seed, a sorghum seed, an oat kernel, a rye seed, a millet seed, a barley seed, a rice kernel, a pea seed, or a tobacco seed.

20. The seed of claim 18, wherein the seed is a corn seed.

\* \* \* \* \*

SEQUENCE LISTING

<160> NUMBER OF SEQ ID NOS: 40

<210> SEQ ID NO 1
<211> LENGTH: 1299
<212> TYPE: DNA
<213> ORGANISM: Artificial sequence
<220> FEATURE:
<223> OTHER INFORMATION: Synthetically generated

<400> SEQUENCE: 1

```
atgaaagcga tcttaatccc attttatct cttctgattc cgttaacccc gcaatctgca      60
ttcgctcaga gtgagccgga gctgaagctg gaaagtgtgg tgattgtcag tcgtcatggt    120
gtgcgtgctc caaccaaggc cacgcaactg atgcaggatg tcaccccaga cgcatggcca    180
acctggccgg taaaactggg tgagctgaca ccgcgcggtg gtgagctaat cgcctatctc    240
ggacattact ggcgtcagcg tctggtagcc gacggattgc tgcctaaatg ggctgcccg    300
cagtctggtc aggtcgcgat tattgctgat gtcgacgagc gtacccgtaa acaggcgaa    360
gccttcgccg ccgggctggc acctgactgt gcaataaccg tacataccca ggcagatacg    420
tccagtcccg atccgttatt taatcctcta aaaactggcg tttgccaact ggataacgcg    480
aacgtgactg acgcgatcct cgagagggca ggagggtcaa ttgctgactt taccgggcat    540
tatcaaacgc cgtttcgcga actggaacgg gtgcttaatt tccgcaatc aaacttgtgc    600
cttaaacgtg agaaacagga cgaaagctgt tcattaacgc aggcattacc atcggaactc    660
aaggtgagcg ccgactgtgt ctcattaacc ggtgcggtaa gcctcgcatc aatgctgacg    720
gagatatttc tcctgcaaca agcacaggga atgccggagc cggggtgggg aaggatcacc    780
gattcacacc agtggaacac cttgctaagt ttgcataacg cgcaatttga tttgctacaa    840
cgcacgccag aggttgcccg cagccgcgcc accccgttat tagatttgat caagacagcg    900
ttgacgcccc atccaccgca aaacaggcg tatggtgtga cattacccac ttcagtgctg    960
tttatcgccg gacacgatac taatctggca atctcggcg gcgcactgga gctcaactgg   1020
acgcttcccg gtcagccgga taacacgccc ccaggtggtg aactggtgtt tgaacgctgg   1080
cgtcggctaa gcgataacag ccagtggatt caggtttcgc tggtcttcca gactttacag   1140
cagatgcgtg ataaaacgcc gctgtcatta aatacgccgc ccggagaggt gaaactgacc   1200
ctggcaggat gtgaagagcg aaatgcgcag ggcatgtgtt cgttggcagg ttttacgcaa   1260
atcgtgaatg aagcacgcat accggcgtgc agtttgtaa                         1299
```

<210> SEQ ID NO 2
<211> LENGTH: 432
<212> TYPE: PRT
<213> ORGANISM: Artificial sequence
<220> FEATURE:
<223> OTHER INFORMATION: Synthetically generated
<220> FEATURE:
<221> NAME/KEY: SIGNAL
<222> LOCATION: (1)..(22)

<400> SEQUENCE: 2

Met Lys Ala Ile Leu Ile Pro Phe Leu Ser Leu Leu Ile Pro Leu Thr
1               5                   10                  15

Pro Gln Ser Ala Phe Ala Gln Ser Glu Pro Glu Leu Lys Leu Glu Ser
            20                  25                  30

Val Val Ile Val Ser Arg His Gly Val Arg Ala Pro Thr Lys Ala Thr
        35                  40                  45

Gln Leu Met Gln Asp Val Thr Pro Asp Ala Trp Pro Thr Trp Pro Val

```
              50                  55                  60
Lys Leu Gly Glu Leu Thr Pro Arg Gly Gly Glu Leu Ile Ala Tyr Leu
 65                  70                  75                  80

Gly His Tyr Trp Arg Gln Arg Leu Val Ala Asp Gly Leu Leu Pro Lys
                     85                  90                  95

Cys Gly Cys Pro Gln Ser Gly Gln Val Ala Ile Ile Ala Asp Val Asp
                    100                 105                 110

Glu Arg Thr Arg Lys Thr Gly Glu Ala Phe Ala Ala Gly Leu Ala Pro
                115                 120                 125

Asp Cys Ala Ile Thr Val His Thr Gln Ala Asp Thr Ser Ser Pro Asp
130                 135                 140

Pro Leu Phe Asn Pro Leu Lys Thr Gly Val Cys Gln Leu Asp Asn Ala
145                 150                 155                 160

Asn Val Thr Asp Ala Ile Leu Glu Arg Ala Gly Gly Ser Ile Ala Asp
                165                 170                 175

Phe Thr Gly His Tyr Gln Thr Ala Phe Arg Glu Leu Glu Arg Val Leu
                180                 185                 190

Asn Phe Pro Gln Ser Asn Leu Cys Leu Lys Arg Glu Lys Gln Asp Glu
                195                 200                 205

Ser Cys Ser Leu Thr Gln Ala Leu Pro Ser Glu Leu Lys Val Ser Ala
210                 215                 220

Asp Cys Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
                260                 265                 270

Asn Ala Gln Phe Asp Leu Leu Gln Arg Thr Pro Glu Val Ala Arg Ser
                275                 280                 285

Arg Ala Thr Pro Leu Leu Asp Leu Ile Lys Thr Ala Leu Thr Pro His
                290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
                340                 345                 350

Gly Glu Leu Val Phe Glu Arg Trp Arg Leu Ser Asp Asn Ser Gln
                355                 360                 365

Trp Ile Gln Val Ser Leu Val Phe Gln Thr Leu Gln Gln Met Arg Asp
370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
                420                 425                 430
```

<210> SEQ ID NO 3
<211> LENGTH: 43
<212> TYPE: DNA
<213> ORGANISM: Artificial sequence
<220> FEATURE:
<223> OTHER INFORMATION: Oligonucleotide sequence

<400> SEQUENCE: 3
tgcgtgctcc aaccaaggcc atgcaactga tgcaggatgt cac            43

<210> SEQ ID NO 4
<211> LENGTH: 65
<212> TYPE: DNA
<213> ORGANISM: Artificial sequence
<220> FEATURE:
<223> OTHER INFORMATION: Oligonucleotide sequence

<400> SEQUENCE: 4
taaaaactgg cgtttgccaa ccggatgtgg cgaacgtgac tgacgcgatc ctcgagaggg    60
cagga                                                               65

<210> SEQ ID NO 5
<211> LENGTH: 65
<212> TYPE: DNA
<213> ORGANISM: Artificial sequence
<220> FEATURE:
<223> OTHER INFORMATION: Oligonucleotide sequence

<400> SEQUENCE: 5
taaaaactgg cgtttgccaa ctggatgtgg cgaacgtgac tcgtgcgatc ctcgagaggg    60
cagga                                                               65

<210> SEQ ID NO 6
<211> LENGTH: 65
<212> TYPE: DNA
<213> ORGANISM: Artificial sequence
<220> FEATURE:
<223> OTHER INFORMATION: Oligonucleotide sequence

<400> SEQUENCE: 6
taaaaactgg cgtttgccaa ccggatgtgg cgaacgtgac tcgtgcgatc ctcgagaggg    60
cagga                                                               65

<210> SEQ ID NO 7
<211> LENGTH: 41
<212> TYPE: DNA
<213> ORGANISM: Artificial sequence
<220> FEATURE:
<223> OTHER INFORMATION: Oligonucleotide sequence

<400> SEQUENCE: 7
gagatatttc tcctgcaaca tgcacaggga atgccggagc c               41

<210> SEQ ID NO 8
<211> LENGTH: 43
<212> TYPE: DNA
<213> ORGANISM: Artificial sequence
<220> FEATURE:
<223> OTHER INFORMATION: Oligonucleotide sequence

<400> SEQUENCE: 8
tgctaagttt gcataacgcg cattttgatt tgctacaacg cac             43

<210> SEQ ID NO 9
<211> LENGTH: 43
<212> TYPE: DNA
<213> ORGANISM: Artificial sequence
<220> FEATURE:
<223> OTHER INFORMATION: Oligonucleotide sequence

<400> SEQUENCE: 9
tgctaagttt gcataacgcg gtgtttgatt tgctacaacg cac              43

<210> SEQ ID NO 10
<211> LENGTH: 41
<212> TYPE: DNA
<213> ORGANISM: Artificial sequence
<220> FEATURE:
<223> OTHER INFORMATION: Oligonucleotide sequence

<400> SEQUENCE: 10
aatcgtgaat gaagcacgca caccggcgtg cagtttgaga t                41

<210> SEQ ID NO 11
<211> LENGTH: 43
<212> TYPE: DNA
<213> ORGANISM: Artificial sequence
<220> FEATURE:
<223> OTHER INFORMATION: Oligonucleotide sequence

<400> SEQUENCE: 11
tgcgtgctcc aaccaaggcc atgcaactga tgcaggatgt cac              43

<210> SEQ ID NO 12
<211> LENGTH: 43
<212> TYPE: DNA
<213> ORGANISM: Artificial sequence
<220> FEATURE:
<223> OTHER INFORMATION: Oligonucleotide sequence

<400> SEQUENCE: 12
gcggtggtga gctaatcgcc catctcggac attactggcg tca              43

<210> SEQ ID NO 13
<211> LENGTH: 43
<212> TYPE: DNA
<213> ORGANISM: Artificial sequence
<220> FEATURE:
<223> OTHER INFORMATION: Oligonucleotide sequence

<400> SEQUENCE: 13
taaaaactgg cgtttgccaa ccggatgtgg cgaacgtgac tga              43

<210> SEQ ID NO 14
<211> LENGTH: 43
<212> TYPE: DNA
<213> ORGANISM: Artificial sequence
<220> FEATURE:
<223> OTHER INFORMATION: Oligonucleotide sequence

<400> SEQUENCE: 14
ggtcaattgc tgactttacc cgccattatc aaacggcgtt tcg              43

<210> SEQ ID NO 15
<211> LENGTH: 43
<212> TYPE: DNA
<213> ORGANISM: Artificial sequence
<220> FEATURE:
<223> OTHER INFORMATION: Oligonucleotide sequence

<400> SEQUENCE: 15
aactcaaggt gagcgccgac gatgtctcat taaccggtgc ggt              43

<210> SEQ ID NO 16
<211> LENGTH: 43
<212> TYPE: DNA

```
<213> ORGANISM: Artificial sequence
<220> FEATURE:
<223> OTHER INFORMATION: Oligonucleotide sequence

<400> SEQUENCE: 16
tgacggagat atttctcctg tggcaagcac agggaatgcc gga                43

<210> SEQ ID NO 17
<211> LENGTH: 46
<212> TYPE: DNA
<213> ORGANISM: Artificial sequence
<220> FEATURE:
<223> OTHER INFORMATION: Oligonucleotide sequence

<400> SEQUENCE: 17
tgacggagat atttctcctg tggcatgcac agggaatgcc ggagcc             46

<210> SEQ ID NO 18
<211> LENGTH: 43
<212> TYPE: DNA
<213> ORGANISM: Artificial sequence
<220> FEATURE:
<223> OTHER INFORMATION: Oligonucleotide sequence

<400> SEQUENCE: 18
cggagatatt tctcctgcaa catgcacagg gaatgccgga gcc                43

<210> SEQ ID NO 19
<211> LENGTH: 43
<212> TYPE: DNA
<213> ORGANISM: Artificial sequence
<220> FEATURE:
<223> OTHER INFORMATION: Oligonucleotide sequence

<400> SEQUENCE: 19
tgctaagttt gcataacgcg gtgtttgatt tgctacaacg cac                43

<210> SEQ ID NO 20
<211> LENGTH: 43
<212> TYPE: DNA
<213> ORGANISM: Artificial sequence
<220> FEATURE:
<223> OTHER INFORMATION: Oligonucleotide sequence

<400> SEQUENCE: 20
ttcccggtca gccggataac tatccgccag gtggtgaact ggt                43

<210> SEQ ID NO 21
<211> LENGTH: 43
<212> TYPE: DNA
<213> ORGANISM: Artificial sequence
<220> FEATURE:
<223> OTHER INFORMATION: Oligonucleotide sequence

<400> SEQUENCE: 21
ttcaggtttc gctggtcttc cgcactttac agcagatgcg tga                43

<210> SEQ ID NO 22
<211> LENGTH: 41
<212> TYPE: DNA
<213> ORGANISM: Artificial sequence
<220> FEATURE:
<223> OTHER INFORMATION: Oligonucleotide sequence

<400> SEQUENCE: 22
aatcgtgaat gaagcacgca caccggcgtg cagtttgaga t                  41
```

<210> SEQ ID NO 23
<211> LENGTH: 1236
<212> TYPE: DNA
<213> ORGANISM: Artificial sequence
<220> FEATURE:
<223> OTHER INFORMATION: Synthetically generated

<400> SEQUENCE: 23

```
atgcagagtg agccggagct gaagctggaa agtgtggtga ttgtcagtcg tcatggtgtg      60
cgtgctccaa ccaaggccat gcaactgatg caggatgtca ccccagacgc atggccaacc     120
tggccggtaa aactgggtga gctgacaccg cgcggtggtg agctaatcgc ccatctcgga     180
cattactggc gtcagcgtct ggtagccgac ggattgctgc ctaaatgtgg ctgcccgcag     240
tctggtcagg tcgcgattat tgctgatgtc gacgagcgta cccgtaaaac aggcgaagcc     300
ttcgccgccg gctggcacc tgactgtgca ataaccgtac atacccaggc agatacgtcc     360
agtcccgatc cgttatttaa tcctctaaaa actggcgttt gccaactgga tgtggcgaac     420
gtgagacgtg cgatcctcga gaggcagga gggtcaattg ctgactttac cgggcattat     480
caaacggcgt ttcgcgaact ggaacgggtg cttaattttc cgcaatcaaa cttgtgcctt     540
aaacgtgaga acaggacga agctgttca ttaacgcagg cattaccatc ggaactcaag     600
gtgagcgccg actgtgtctc attaaccggt gcggtaagcc tcgcatcaat gctgacggag     660
atatttctcc tgcaacatgc acaggaatg ccggagccgg ggtggggaag gatcaccgat     720
tcacaccagt ggaacaccttt gctaagtttg cataacgcgg tgtttgattt gctacaacgc     780
acgccagagg ttgcccgcag ccgcgccacc ccgttattag atttgatcaa gacagcgttg     840
acgccccatc caccgcaaaaa acaggcgtat ggtgtgacat acccacttc agtgctgttt     900
atcgccggac acgatactaa tctggcaaat ctcggcggcg cactggagct cgaatggacg     960
cttcccggtc agccggataa ctatccgcca ggtggtgaac tggtgtttga acgctggcgt    1020
cggctaagcg ataacagcca gtggattcag gtttcgctgg tcttccagac tttacagcag    1080
atgcgtgata aaacgccgct gtcattaaat acgccgcccg gagaggtgaa actgaccctg    1140
gcaggatgtg aagagcgaaa tgcgcagggc atgtgttcgt tggcaggttt tacgcaaatc    1200
gtgaatgaag cacgcatacc ggcgtgcagt ttgtaa                                1236
```

<210> SEQ ID NO 24
<211> LENGTH: 411
<212> TYPE: PRT
<213> ORGANISM: Artificial sequence
<220> FEATURE:
<223> OTHER INFORMATION: Synthetically generated

<400> SEQUENCE: 24

Met Gln Ser Glu Pro Glu Leu Lys Leu Glu Ser Val Val Ile Val Ser
1               5                   10                  15

Arg His Gly Val Arg Ala Pro Thr Lys Ala Met Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala His Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys

```
                          85                  90                  95
Thr Gly Glu Ala Phe Ala Ala Gly Leu Ala Pro Asp Cys Ala Ile Thr
                100                 105                 110

Val His Thr Gln Ala Asp Thr Ser Ser Pro Asp Pro Leu Phe Asn Pro
                115                 120                 125

Leu Lys Thr Gly Val Cys Gln Leu Asp Val Ala Asn Val Arg Arg Ala
            130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
    210                 215                 220

Gln His Ala Gln Gly Met Pro Glu Pro Gly Trp Gly Arg Ile Thr Asp
225                 230                 235                 240

Ser His Gln Trp Asn Thr Leu Leu Ser Leu His Asn Ala Val Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Glu Trp Thr
305                 310                 315                 320

Leu Pro Gly Gln Pro Asp Asn Tyr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 25
<211> LENGTH: 1236
<212> TYPE: DNA
<213> ORGANISM: Artificial sequence
<220> FEATURE:
<223> OTHER INFORMATION: Synthetically generated

<400> SEQUENCE: 25
atgcagagtg agccggagct gaagctggaa agtgtggtga ttgtcagtcg tcatggtgtg    60
cgtgctccaa ccaaggccat gcaactgatg caggatgtca ccccagacgc atggccaacc   120
tggccggtaa aactgggtga gctgacaccg cgcgtggtg agctaatcgc ccatctcgga    180
cattactggc gtcagcgtct ggtagccgac ggattgctgc ctaaatgtgg ctgcccgcag   240
```

```
tctggtcagg tcgcgattat tgctgatgtc gacgagcgta cccgtaaaac aggcgaagcc      300
ttcgccgccg ggctggcacc tgactgtgca ataaccgtac atacccaggc agatacgtcc      360
agtcccgatc cgttatttaa tcctctaaaa actggcgttt gccaactgga tgtggcgaac      420
gtgagacgtg cgatcctcga gagggcagga gggtcaattg ctgactttac ccgccattat      480
caaacggcgt ttcgcgaact ggaacgggtg cttaattttc gcaatcaaa cttgtgcctt       540 aaacgtgaga acaggacga aagctgttca ttaacgcagg cattaccatc ggaactcaag       600
gtgagcgccg acgatgtctc attaaccggt gcggtaagcc tcgcatcaat gctgacggag      660
atatttctcc tgcaacatgc acagggaatg ccggagccgg ggtggggaag gatcaccgat      720
tcacaccagt ggaacacctt gctaagtttg cataacgcgg tgtttgattt gctacaacgc      780
acgccagagg ttgcccgcag ccgcgccacc ccgttattag atttgatcaa gacagcgttg      840
acgccccatc caccgcaaaa acaggcgtat ggtgtgacat acccacttc agtgctgttt       900 atcgccggac acgatactaa tctggcaaat ctcggcggcg cactggagct cgaatggacg      960
cttcccggtc agccggataa cacgccgcca ggtggtgaac tggtgtttga acgctggcgt     1020
cggctaagcg ataacagcca gtggattcag gtttcgctgg tcttccagac tttacagcag     1080
atgcgtgata aaacgccgct gtcattaaat acgccgcccg gagaggtgaa actgaccctg     1140
gcaggatgtg aagagcgaaa tgcgcagggc atgtgttcgt tggcaggttt tacgcaaatc     1200
gtgaatgaag cacgcatacc ggcgtgcagt ttgtaa                              1236
```

<210> SEQ ID NO 26
<211> LENGTH: 411
<212> TYPE: PRT
<213> ORGANISM: Artificial sequence
<220> FEATURE:
<223> OTHER INFORMATION: Synthetically generated

<400> SEQUENCE: 26

```
Met Gln Ser Glu Pro Glu Leu Lys Leu Glu Ser Val Val Ile Val Ser
1               5                   10                  15

Arg His Gly Val Arg Ala Pro Thr Lys Ala Met Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala His Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Val Ala Asn Val Arg Arg Ala
    130                 135                 140

Ile Leu Glu Arg Ala Gly Gly Ser Ile Ala Asp Phe Thr Arg His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
```

|  |  |  | 180 |  |  |  | 185 |  |  |  | 190 |
|---|---|---|---|---|---|---|---|---|---|---|---|

Gln Ala Leu Pro Ser Glu Leu Lys Val Ser Ala Asp Asp Val Ser Leu
            195                 200                 205

Thr Gly Ala Val Ser Leu Ala Ser Met Leu Thr Glu Ile Phe Leu Leu
        210                 215                 220

Gln His Ala Gln Gly Met Pro Glu Pro Gly Trp Gly Arg Ile Thr Asp
225                 230                 235                 240

Ser His Gln Trp Asn Thr Leu Leu Ser Leu His Asn Ala Val Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Glu Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 27
<211> LENGTH: 1236
<212> TYPE: DNA
<213> ORGANISM: Artificial sequence
<220> FEATURE:
<223> OTHER INFORMATION: Synthetically generated

<400> SEQUENCE: 27

| atgcagagtg | agccggagct | gaagctggaa | agtgtggtga | ttgtcagtcg | tcatggtgtg | 60 |
| cgtgctccaa | ccaaggccac | gcaactgatg | caggatgtca | ccccagacgc | atggccaacc | 120 |
| tggccggtaa | aactgggtga | gctgacaccg | cgcggtggtg | agctaatcgc | ctatctcgga | 180 |
| cattactggc | gtcagcgtct | ggtagccgac | ggattgctgc | ctaaatgtgg | ctgcccgcag | 240 |
| tctggtcagg | tcgcgattat | tgctgatgtc | gacgagcgta | cccgtaaaac | aggcgaagcc | 300 |
| ttcgccgccg | ggctggcacc | tgactgtgca | ataaccgtac | atacccaggc | agatacgtcc | 360 |
| agtcccgatc | cgttatttaa | tcctctaaaa | actggcgttt | gccaactgga | tgtggcgaac | 420 |
| gtgagacgtg | cgatcctcga | gagggcagga | gggtcaattg | ctgactttac | cgggcattat | 480 |
| caaacggcgt | tcgcgaact  | ggaacgggtg | cttaatttc  | cgcaatcaaa | cttgtgcctt | 540 |
| aaacgtgaga | aacaggacga | agctgttca  | ttaacgcagg | cattaccatc | ggaactcaag | 600 |
| gtgagcgccg | actgtgtctc | attaaccggt | gcggtaagcc | tcgcatcaat | gctgacggag | 660 |
| atatttctcc | tgcaacatgc | acagggaatg | ccggagccgg | ggtggggaag | gatcaccgat | 720 |
| tcacaccagt | ggaacaccctt | gctaagtttg | cataacgcgc | attttgattt | gctacaacgc | 780 |

```
acgccagagg ttgcccgcag ccgcgccacc ccgttattag atttgatcaa gacagcgttg    840
acgccccatc caccgcaaaa acaggcgtat ggtgtgacat tacccacttc agtgctgttt    900
atcgccggac acgatactaa tctggcaaat ctcggcggcg cactggagct cgaatggacg    960
cttcccggtc agccggataa cacgccgcca ggtggtgaac tggtgtttga acgctggcgt   1020
cggctaagcg ataacagcca gtggattcag gtttcgctgg tcttccagac tttacagcag   1080
atgcgtgata aaacgccgct gtcattaaat acgccgcccg agaggtgaa actgaccctg    1140 gcaggatgtg aagagcgaaa tgcgcagggc atgtgttcgt tggcaggttt tacgcaaatc   1200
gtgaatgaag cacgcatacc ggcgtgcagt ttgtaa                             1236
```

<210> SEQ ID NO 28
<211> LENGTH: 411
<212> TYPE: PRT
<213> ORGANISM: Artificial sequence
<220> FEATURE:
<223> OTHER INFORMATION: Synthetically generated

<400> SEQUENCE: 28

```
Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Val Ala Asn Val Arg Arg Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
    210                 215                 220

Gln His Ala Gln Gly Met Pro Glu Pro Gly Trp Gly Arg Ile Thr Asp
225                 230                 235                 240

Ser His Gln Trp Asn Thr Leu Leu Ser Leu His Asn Ala His Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
```

```
                275                 280                 285
Ala Tyr Gly Val Thr Leu Pro Thr Ser Val Leu Phe Ile Ala Gly His
            290                 295                 300
Asp Thr Asn Leu Ala Asn Leu Gly Gly Ala Leu Glu Leu Glu Trp Thr
305                 310                 315                 320
Leu Pro Gly Gln Pro Asp Asn Thr Pro Pro Gly Gly Glu Leu Val Phe
                325                 330                 335
Glu Arg Trp Arg Arg Leu Ser Asp Asn Ser Gln Trp Ile Gln Val Ser
            340                 345                 350
Leu Val Phe Gln Thr Leu Gln Gln Met Arg Asp Lys Thr Pro Leu Ser
            355                 360                 365
Leu Asn Thr Pro Pro Gly Glu Val Lys Leu Thr Leu Ala Gly Cys Glu
        370                 375                 380
Glu Arg Asn Ala Gln Gly Met Cys Ser Leu Ala Gly Phe Thr Gln Ile
385                 390                 395                 400
Val Asn Glu Ala Arg Ile Pro Ala Cys Ser Leu
                405                 410
```

<210> SEQ ID NO 29
<211> LENGTH: 1236
<212> TYPE: DNA
<213> ORGANISM: Artificial sequence
<220> FEATURE:
<223> OTHER INFORMATION: Synthetically generated

<400> SEQUENCE: 29

```
atgcagagtg agccggagct gaagctggaa agtgtggtga ttgtcagtcg tcatggtgtg      60
cgtgctccaa ccaaggccac gcaactgatg caggatgtca ccccagacgc atggccaacc     120
tggccggtaa aactgggtga gctgacaccg cgcggtggtg agctaatcgc ctatctcgga     180
cattactggc gtcagcgtct ggtagccgac ggattgctgc taaatgtgg ctgcccgcag     240
tctggtcagg tcgcgattat tgctgatgtc gacgagcgta cccgtaaaac aggcgaagcc     300
ttcgccgccg ggctggcacc tgactgtgca ataaccgtac atcccaggc agatacgtcc      360
agtcccgatc cgttatttaa tcctctaaaa actggcgttt gccaactgga taacgcgaac     420
gtgagagacg cgatcctcga gagggcagga gggtcaattg ctgactttac cgggcattat     480
caaacggcgt ttcgcgaact ggaacgggtg cttaattttc gcaatcaaa cttgtgcctt      540
aaacgtgaga acaggacga agctgttca ttaacgcagg cattaccatc ggaactcaag       600
gtgagcgccg actgtgtctc attaaccggt gcggtaagcc tcgcatcaat gctgacggag     660
atatttctcc tgcaacatgc acagggaatg ccggagccgg ggtggggaag gatcaccgat     720
tcacaccagt ggaacacctt gctaagtttg cataacgcgc aatttgattt gctacaacgc     780
acgccagagg ttgcccgcag ccgcgccacc ccgttattag atttgatcaa gacagcgttg     840
acgccccatc caccgcaaaa acaggcgtat ggtgtgacat acccacttc agtgctgttt       900
atcgccggac acgatactaa tctggcaaat ctcggcggcg cactgagct cgaatggacg      960
cttccccggtc agccggataa cacgccgcca ggtggtgaac tggtgtttga acgctggcgt    1020
cggctaagcg ataacagcca gtggattcag gtttcgctgg tcttccagac tttacagcag    1080
atgcgtgata aacgccgct gtcattaaat acgccgcccg gagaggtgaa actgaccctg     1140
gcaggatgtg aagagcgaaa tgcgcagggc atgtgttcgt tggcaggttt tacgcaaatc    1200
gtgaatgaag cacgcatacc ggcgtgcagt ttgtaa                              1236
```

<210> SEQ ID NO 30
<211> LENGTH: 411
<212> TYPE: PRT
<213> ORGANISM: Artificial sequence
<220> FEATURE:
<223> OTHER INFORMATION: Synthetically generated

<400> SEQUENCE: 30

```
Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Cys Gly Cys Pro Gln
65              70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Asn Val Arg Asp Ala
    130                 135                 140

Ile Leu Glu Arg Ala Gly Gly Ser Ile Ala Asp Phe Thr Gly His Tyr
145             150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
    210                 215                 220

Gln His Ala Gln Gly Met Pro Glu Pro Gly Trp Gly Arg Ile Thr Asp
225             230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Glu Trp Thr
305             310                 315                 320

Leu Pro Gly Gln Pro Asp Asn Thr Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
```

```
                    370                 375                 380
Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 31
<211> LENGTH: 1236
<212> TYPE: DNA
<213> ORGANISM: Artificial sequence
<220> FEATURE:
<223> OTHER INFORMATION: Synthetically generated

<400> SEQUENCE: 31
atgcagagtg agccggagct gaagctggaa agtgtggtga ttgtcagtcg tcatggtgtg      60
cgtgctccaa ccaaggccat gcaactgatg caggatgtca ccccagacgc atggccaacc     120
tggccggtaa aactgggtga gctgacaccg cgcggtggtg agctaatcgc ctatctcgga     180
cattactggc gtcagcgtct ggtagccgac ggattgctgc taaatgtggg ctgccgcag      240
tctggtcagg tcgcgattat tgctgatgtc gacgagcgta cccgtaaaac aggcgaagcc     300
ttcgccgccg gctggcacc tgactgtgca ataaccgtac ataccaggc agatacgtcc       360
agtcccgatc cgttatttaa tcctctaaaa actggcgttt gccaactgga tgtggcgaac     420
gtgagagacg cgatcctcga gagggcagga gggtcaattg ctgactttac cgggcattat     480
caaacggcgt ttcgcgaact ggaacgggtg cttaattttc gcaatcaaa cttgtgcctt      540
aaacgtgaga acaggacga agctgttca ttaacgcagg cattaccatc ggaactcaag       600
gtgagcgccg actgtgtctc attaaccggt gcggtaagcc tcgcatcaat gctgacggag     660
atatttctcc tgcaacatgc acagggaatg ccggagccgg ggtggggaag gatcaccgat     720
tcacaccagt ggaacacctt gctaagtttg cataacgcgg tgtttgattt gctacaacgc     780
acgccagagg ttgcccgcag ccgcgccacc ccgttattag atttgatcaa gacagcgttg     840
acgccccatc caccgcaaaa acaggcgtat ggtgtgacat acccacttc agtgctgttt      900
atcgccggac acgatactaa tctggcaaat ctcggcggcg cactggagct cgaatggacg     960
cttcccggtc agccggataa cacgccgcca ggtggtgaac tggtgtttga acgctggcgt    1020
cggctaagcg ataacagcca gtggattcag gtttcgctgg tcttccagac tttacagcag    1080
atgcgtgata aaacgccgct gtcattaaat acgccgcccg gagaggtgaa actgaccctg    1140
gcaggatgtg aagagcgaaa tgcgcagggc atgtgttcgt tggcaggttt tacgcaaatc    1200
gtgaatgaag cacgcatacc ggcgtgcagt ttgtaa                              1236

<210> SEQ ID NO 32
<211> LENGTH: 411
<212> TYPE: PRT
<213> ORGANISM: Artificial sequence
<220> FEATURE:
<223> OTHER INFORMATION: Synthetically generated

<400> SEQUENCE: 32

Met Gln Ser Glu Pro Glu Leu Lys Leu Glu Ser Val Val Ile Val Ser
1               5                   10                  15

Arg His Gly Val Arg Ala Pro Thr Lys Ala Met Gln Leu Met Gln Asp
                20                  25                  30

Val Thr Pro Asp Ala Trp Pro Thr Trp Pro Val Lys Leu Gly Glu Leu
        35                  40                  45
```

```
Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Val Ala Asn Val Arg Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
    210                 215                 220

Gln His Ala Gln Gly Met Pro Glu Pro Gly Trp Gly Arg Ile Thr Asp
225                 230                 235                 240

Ser His Gln Trp Asn Thr Leu Leu Ser Leu His Asn Ala Val Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Glu Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 33
<211> LENGTH: 1236
<212> TYPE: DNA
<213> ORGANISM: Artificial sequence
<220> FEATURE:
<223> OTHER INFORMATION: Synthetically generated

<400> SEQUENCE: 33
```

```
atgcagagtg agccggagct gaagctggaa agtgtggtga ttgtcagtcg tcatggtgtg      60
cgtgctccaa ccaaggccat gcaactgatg caggatgtca ccccagacgc atggccaacc     120
tggccggtaa aactgggtga gctgacaccg cgcggtggtg agctaatcgc ctatctcgga     180
cattactggc gtcagcgtct ggtagccgac ggattgctgc ctaaatgtgg ctgcccgcag     240
tctggtcagg tcgcgattat tgctgatgtc gacgagcgta cccgtaaaac aggcgaagcc     300
ttcgccgccg gctggcacc tgactgtgca ataaccgtac atacccaggc agatacgtcc      360
agtcccgatc cgttatttaa tcctctaaaa actggcgttt gccaactgga tgtggcgaac     420
gtgagacgtg cgatcctcga gagggcagga gggtcaattg ctgactttac cgggcattat     480
caaacggcgt ttcgcgaact ggaacgggtg cttaattttc gcaatcaaa cttgtgcctt      540
aaacgtgaga acaggacga aagctgttca ttaacgcagg cattaccatc ggaactcaag      600
gtgagcgccg actgtgtctc attaaccggt gcggtaagcc tcgcatcaat gctgacggag     660
atatttctcc tgcaacatgc acagggaatg ccggagccgg ggtggggaag gatcaccgat     720
tcacaccagt ggaacaccctt gctaagtttg cataacgcgg tgtttgattt gctacaacgc    780
acgccagagg ttgcccgcag ccgcgccacc ccgttattag atttgatcaa gacagcgttg     840
acgcccatc caccgcaaaa acaggcgtat ggtgtgacat acccacttc agtgctgttt       900
atcgccggac acgatactaa tctggcaaat ctcggcggcg cactggagct cgaatggacg     960
cttcccggtc agccggataa cacgccgcca ggtggtgaac tggtgtttga acgctggcgt    1020
cggctaagcg ataacagcca gtggattcag gtttcgctgg tcttccagac tttacagcag    1080
atgcgtgata aaacgccgct gtcattaaat acgccgcccg agaggtgaa actgaccctg     1140
gcaggatgtg aagagcgaaa tgcgcagggc atgtgttcgt tggcaggttt tacgcaaatc    1200
gtgaatgaag cacgcacacc ggcgtgcagt ttgtaa                              1236
```

<210> SEQ ID NO 34
<211> LENGTH: 411
<212> TYPE: PRT
<213> ORGANISM: Artificial sequence
<220> FEATURE:
<223> OTHER INFORMATION: Synthetically generated

<400> SEQUENCE: 34

```
Met Gln Ser Glu Pro Glu Leu Lys Leu Glu Ser Val Val Ile Val Ser
1               5                   10                  15

Arg His Gly Val Arg Ala Pro Thr Lys Ala Met Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Val Ala Asn Val Arg Arg Ala
    130                 135                 140
```

```
Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
            165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
            195                 200                 205

Thr Gly Ala Val Ser Leu Ala Ser Met Leu Thr Glu Ile Phe Leu Leu
210                 215                 220

Gln His Ala Gln Gly Met Pro Glu Pro Gly Trp Gly Arg Ile Thr Asp
225                 230                 235                 240

Ser His Gln Trp Asn Thr Leu Leu Ser Leu His Asn Ala Val Phe Asp
            245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
            275                 280                 285

Ala Tyr Gly Val Thr Leu Pro Thr Ser Val Leu Phe Ile Ala Gly His
290                 295                 300

Asp Thr Asn Leu Ala Asn Leu Gly Gly Ala Leu Glu Leu Glu Trp Thr
305                 310                 315                 320

Leu Pro Gly Gln Pro Asp Asn Thr Pro Pro Gly Gly Glu Leu Val Phe
            325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
            355                 360                 365

Leu Asn Thr Pro Pro Gly Glu Val Lys Leu Thr Leu Ala Gly Cys Glu
            370                 375                 380

Glu Arg Asn Ala Gln Gly Met Cys Ser Leu Ala Gly Phe Thr Gln Ile
385                 390                 395                 400

Val Asn Glu Ala Arg Thr Pro Ala Cys Ser Leu
            405                 410

<210> SEQ ID NO 35
<211> LENGTH: 1236
<212> TYPE: DNA
<213> ORGANISM: Artificial sequence
<220> FEATURE:
<223> OTHER INFORMATION: Synthetically generated

<400> SEQUENCE: 35
atgcagagtg agccggagct gaagctggaa agtgtggtga ttgtcagtcg tcatggtgtg      60
cgtgctccaa ccaaggccat gcaactgatg caggatgtca ccccagacgc atggccaacc     120
tggccggtaa aactgggtga gctgacaccg cgcggtggtg agctaatcgc ctatctcgga     180
cattactggc gtcagcgtct ggtagccgac ggattgctgc taaatgtggc tgcccgcag     240 tctggtcagg tcgcgattat tgctgatgtc gacgagcgta cccgtaaaac aggcgaagcc     300
ttcgccgccg ggctggcacc tgactgtgca ataaccgtac ataccaggc agatacgtcc     360 agtcccgatc cgttatttaa tcctctaaaa actggcgttt gccaactgga tgtggcgaac     420
gtgagacgtg cgatcctcga gagggcagga gggtcaattg ctgactttac cgggcattat     480
caaacggcgt tcgcgaact ggaacgggtg cttaattttc cgcaatcaaa cttgtgcctt     540
```

```
aaacgtgaga aacaggacga aagctgttca ttaacgcagg cattaccatc ggaactcaag   600
gtgagcgccg actgtgtctc attaaccggt gcggtaagcc tcgcatcaat gctgacggag   660
atatttctcc tgcaacatgc acagggaatg ccggagccgg ggtggggaag gatcaccgat   720
tcacaccagt ggaacacctt gctaagtttg cataacgcgc aatttgattt gctacaacgc   780
acgccagagg ttgcccgcag ccgcgccacc ccgttattag atttgatcaa gacagcgttg   840
acgccccatc caccgcaaaa acaggcgtat ggtgtgacat tacccacttc agtgctgttt   900
atcgccggac acgatactaa tctggcaaat ctcggcggcg cactggagct cgaatggacg   960
cttcccggtc agccggataa cacgccgcca ggtggtgaac tggtgtttga acgctggcgt  1020
cggctaagcg ataacagcca gtggattcag gtttcgctgg tcttccagac tttacagcag  1080
atgcgtgata aaacgccgct gtcattaaat acgccgcccg agaggtgaa actgaccctg  1140 gcaggatgtg aagagcgaaa tgcgcagggc atgtgttcgt tggcaggttt tacgcaaatc  1200
gtgaatgaag cacgcatacc ggcgtgcagt ttgtaa                            1236
```

<210> SEQ ID NO 36
<211> LENGTH: 411
<212> TYPE: PRT
<213> ORGANISM: Artificial sequence
<220> FEATURE:
<223> OTHER INFORMATION: Synthetically generated

<400> SEQUENCE: 36

```
Met Gln Ser Glu Pro Glu Leu Lys Leu Glu Ser Val Val Ile Val Ser
1               5                   10                  15

Arg His Gly Val Arg Ala Pro Thr Lys Ala Met Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Val Ala Asn Val Arg Arg Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
    210                 215                 220

Gln His Ala Gln Gly Met Pro Glu Pro Gly Trp Gly Arg Ile Thr Asp
225                 230                 235                 240
```

```
Ser His Gln Trp Asn Thr Leu Leu Ser Leu His Asn Ala Gln Phe Asp
            245                 250                 255

Leu Leu Gln Arg Thr Pro Glu Val Ala Arg Ser Arg Ala Thr Pro Leu
        260                 265                 270

Leu Asp Leu Ile Lys Thr Ala Leu Thr Pro His Pro Pro Gln Lys Gln
            275                 280                 285

Ala Tyr Gly Val Thr Leu Pro Thr Ser Val Leu Phe Ile Ala Gly His
        290                 295                 300

Asp Thr Asn Leu Ala Asn Leu Gly Gly Ala Leu Glu Leu Glu Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 37
<211> LENGTH: 1236
<212> TYPE: DNA
<213> ORGANISM: Artificial sequence
<220> FEATURE:
<223> OTHER INFORMATION: Synthetically generated

<400> SEQUENCE: 37
atgcagagtg agccggagct gaagctggaa agtgtggtga ttgtcagtcg tcatggtgtg      60
cgtgctccaa ccaaggccat gcaactgatg caggatgtca ccccagacgc atggccaacc     120
tggccggtaa aactgggtga gctgacaccg cgcggtggtg agctaatcgc ctatctcgga     180
cattactggc gtcagcgtct ggtagccgac ggattgctgc ctaaatgtgg ctgcccgcag     240
tctggtcagg tcgcgattat tgctgatgtc gacgagcgta cccgtaaaac aggcgaagcc     300
ttcgccgccg ggctggcacc tgactgtgca ataaccgtac atacccaggc agatacgtcc     360
agtcccgatc cgttatttaa tcctctaaaa actggcgttt gccaactgga tgtggcgaac     420
gtgagagacg cgatcctcga gagggcagga gggtcaattg ctgactttac cgggcattat     480
caaacggcgt ttcgcgaact ggaacgggtg cttaattttc gcaatcaaa cttgtgcctt      540 aaacgtgaga acaggacga agctgttca ttaacgcagg cattaccatc ggaactcaag      600
gtgagcgccg actgtgtctc attaaccggt gcggtaagcc tcgcatcaat gctgacggag     660
atatttctcc tgcaacatgc acagggaatg ccggagccgg ggtggggaag gatcaccgat     720
tcacaccagt ggaacaccctt gctaagtttg cataacgcgg tgtttgattt gctacaacgc     780
acgccagagg ttgcccgcag ccgcgccacc ccgttattag atttgatcaa gacagcgttg     840
acgccccatc caccgcaaaa acaggcgtat ggtgtgacat acccacttc agtgctgttt     900 atcgccggac acgatactaa tctggcaaat ctcggcggcg cactggagct cgaatggacg     960
cttcccggtc agccgataaa cacgccgcca ggtggtgaac tggtgtttga acgctggcgt    1020
cggctaagcg ataacagcca gtggattcag gtttcgctgg tcttccagac tttacagcag    1080
```

```
atgcgtgata aaacgccgct gtcattaaat acgccgcccg gagaggtgaa actgaccctg    1140
gcaggatgtg aagagcgaaa tgcgcagggc atgtgttcgt tggcaggttt tacgcaaatc    1200
gtgaatgaag cacgcacacc ggcgtgcagt ttgtaa                              1236
```

<210> SEQ ID NO 38
<211> LENGTH: 411
<212> TYPE: PRT
<213> ORGANISM: Artificial sequence
<220> FEATURE:
<223> OTHER INFORMATION: Synthetically generated

<400> SEQUENCE: 38

| Met | Gln | Ser | Glu | Pro | Glu | Leu | Lys | Leu | Glu | Ser | Val | Val | Ile | Val | Ser |
|---|---|---|---|---|---|---|---|---|---|---|---|---|---|---|---|
| 1 | | | | 5 | | | | | 10 | | | | | 15 | |

Arg His Gly Val Arg Ala Pro Thr Lys Ala Met Gln Leu Met Gln Asp
                20                  25                  30

Val Thr Pro Asp Ala Trp Pro Thr Trp Pro Val Lys Leu Gly Glu Leu
            35                  40                  45

Thr Pro Arg Gly Gly Glu Leu Ile Ala Tyr Leu Gly His Tyr Trp Arg
        50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Val Ala Asn Val Arg Asp Ala
130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
210                 215                 220

Gln His Ala Gln Gly Met Pro Glu Pro Gly Trp Gly Arg Ile Thr Asp
225                 230                 235                 240

Ser His Gln Trp Asn Thr Leu Leu Ser Leu His Asn Ala Val Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Gln Lys Gln
        275                 280                 285

Ala Tyr Gly Val Thr Leu Pro Thr Ser Val Leu Phe Ile Ala Gly His
        290                 295                 300

Asp Thr Asn Leu Ala Asn Leu Gly Gly Ala Leu Glu Leu Glu Trp Thr
305                 310                 315                 320

Leu Pro Gly Gln Pro Asp Asn Thr Pro Pro Gly Gly Glu Leu Val Phe
                325                 330                 335

-continued

```
Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Thr Pro Ala Cys Ser Leu
                405                 410

<210> SEQ ID NO 39
<211> LENGTH: 1236
<212> TYPE: DNA
<213> ORGANISM: Artificial sequence
<220> FEATURE:
<223> OTHER INFORMATION: Synthetically generated

<400> SEQUENCE: 39
atgcagagtg agccggagct gaagctggaa agtgtggtga ttgtcagtcg tcatggtgtg      60
cgtgctccaa ccaaggccat gcaactgatg caggatgtca ccccagacgc atggccaacc     120
tggccggtaa aactgggtga gctgacaccg cgcggtggtg agctaatcgc ctatctcgga     180
cattactggc gtcagcgtct ggtagccgac ggattgctgc ctaaatgtgg ctgcccgcag     240
tctggtcagg tcgcgattat tgctgatgtc gacgagcgta cccgtaaaac aggcgaagcc     300
ttcgccgccg ggctggcacc tgactgtgca ataaccgtac ataccaggc agatacgtcc      360 agtcccgatc cgttatttaa tcctctaaaa actggcgttt gccaactgga tgtggcgaac     420
gtgagacgtg cgatcctcga gagggcagga gggtcaattg ctgactttac ccgccattat    480
caaacggcgt ttcgcgaact ggaacgggtg cttaattttc gcaatcaaa cttgtgcctt     540 aaacgtgaga acaggacga agctgttca ttaacgcagg cattaccatc ggaactcaag     600
gtgagcgccg acgatgtctc attaaccggt gcggtaagcc tcgcatcaat gctgacggag     660
atatttctcc tgtggcatgc acagggaatg ccggagccgg ggtggggaag gatcaccgat     720
tcacaccagt ggaacaccct gctaagtttg cataacgcgg tgtttgattt gctacaacgc     780
acgccagagg ttgcccgcag ccgcgccacc ccgttattag atttgatcaa gacagcgttg     840
acgccccatc caccgcaaaa acaggcgtat ggtgtgacat acccacttc agtgctgttt     900 atcgccggac acgatactaa tctggcaaat ctcggcggcg cactggagct cgaatggacg     960
cttcccggtc agccggataa cacgccgcca ggtggtgaac tggtgtttga acgctggcgt    1020
cggctaagcg ataacagcca gtggattcag gtttcgctgg tcttccagac tttacagcag    1080
atgcgtgata aaacgccgct gtcattaaat acgccgcccg agaggtgaa actgaccctg    1140 gcaggatgtg aagagcgaaa tgcgcagggc atgtgttcgt tggcaggttt tacgcaaatc    1200
gtgaatgaag cacgcatacc ggcgtgcagt ttgtaa                              1236

<210> SEQ ID NO 40
<211> LENGTH: 411
<212> TYPE: PRT
<213> ORGANISM: Artificial sequence
<220> FEATURE:
<223> OTHER INFORMATION: Synthetically generated

<400> SEQUENCE: 40

Met Gln Ser Glu Pro Glu Leu Lys Leu Glu Ser Val Val Ile Val Ser
1               5                   10                  15
```

```
Arg His Gly Val Arg Ala Pro Thr Lys Ala Met Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Val Ala Asn Val Arg Arg Ala
    130                 135                 140

Ile Leu Glu Arg Ala Gly Gly Ser Ile Ala Asp Phe Thr Arg His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asp Val Ser Leu
        195                 200                 205

Thr Gly Ala Val Ser Leu Ala Ser Met Leu Thr Glu Ile Phe Leu Leu
    210                 215                 220

Trp His Ala Gln Gly Met Pro Glu Pro Gly Trp Gly Arg Ile Thr Asp
225                 230                 235                 240

Ser His Gln Trp Asn Thr Leu Leu Ser Leu His Asn Ala Val Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Glu Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410
```